United States Patent
Granger et al.

(10) Patent No.: US 11,668,481 B2
(45) Date of Patent: Jun. 6, 2023

(54) SYSTEMS, METHODS AND ARTICLES FOR ASSESSING AND/OR IMPROVING HEALTH AND WELL-BEING

(71) Applicant: Delos Living LLC, New York, NY (US)

(72) Inventors: Trevor Granger, New York, NY (US); Jennifer Lan-Anh Nguyen, New York, NY (US); Dana Pillai, New York, NY (US); Regina Vaicekonyte-Peters, New York, NY (US); Jie Zhao, New York, NY (US)

(73) Assignee: Delos Living LLC, New York, NY (US)

( * ) Notice: Subject to any disclaimer, the term of this patent is extended or adjusted under 35 U.S.C. 154(b) by 308 days.

(21) Appl. No.: 16/639,217

(22) PCT Filed: Aug. 30, 2018

(86) PCT No.: PCT/US2018/048853
§ 371 (c)(1),
(2) Date: Feb. 14, 2020

(87) PCT Pub. No.: WO2019/046580
PCT Pub. Date: Mar. 7, 2019

(65) Prior Publication Data
US 2020/0200416 A1     Jun. 25, 2020

Related U.S. Application Data

(60) Provisional application No. 62/634,608, filed on Feb. 23, 2018, provisional application No. 62/593,678, (Continued)

(51) Int. Cl.
G05B 21/00     (2006.01)
G01M 1/38      (2006.01)
(Continued)

(52) U.S. Cl.
CPC .............. *F24F 11/30* (2018.01); *F24F 11/56* (2018.01); *G06F 1/163* (2013.01); *G06F 16/9035* (2019.01); *F24F 2110/50* (2018.01)

(58) Field of Classification Search
CPC ........ F24F 11/30; F24F 11/56; F24F 2110/50; F24F 2110/10; F24F 2120/14;
(Continued)

(56) References Cited

U.S. PATENT DOCUMENTS

| 628,351 A | 7/1899 | Gibson |
| 828,733 A | 8/1906 | Fuller |

(Continued)

FOREIGN PATENT DOCUMENTS

| CA | 2307458 | 11/2001 |
| CA | 2740939 | 3/2010 |

(Continued)

OTHER PUBLICATIONS

International Search Report for PCT/US2018/048853 dated Nov. 21, 2018.
(Continued)

*Primary Examiner* — Zhipeng Wang
(74) *Attorney, Agent, or Firm* — Fitch, Even, Tabin & Flannery LLP

(57) ABSTRACT

In some embodiments, apparatuses and methods are provided herein useful to assess monitor, improve, and/or modify health and well-being as it relates to people associated with a habitable or other built environments or spaces therein. In some embodiments, an intervention assessment system and methods include one or more sensors for measuring aspects related to the built environment, a personal user device, and a control circuit configured to receive one or more measurements form the sensor(s), identify a problem with the built environment, and identify potential inter-
(Continued)

ventions based on the indicators associated with the problem. By one approach, a plurality of potential interventions may be ranked based on, for example, the ability to reduce the prevalence of the problem or indicator in the built environment, feasibility, cost, and timeliness. In some approaches, the system and method also select and may implement one or more interventions.

16 Claims, 19 Drawing Sheets

Related U.S. Application Data filed on Dec. 1, 2017, provisional application No. 62/552,189, filed on Aug. 30, 2017.

(51) Int. Cl.

| | | |
|---|---|---|
| G05B 13/00 | (2006.01) | |
| G05B 15/00 | (2006.01) | |
| G05D 23/00 | (2006.01) | |
| F24F 11/30 | (2018.01) | |
| F24F 11/56 | (2018.01) | |
| G06F 16/9035 | (2019.01) | |
| G06F 1/16 | (2006.01) | |
| F24F 110/50 | (2018.01) | |

(58) Field of Classification Search
CPC .............. F24F 2120/20; F24F 2130/10; F24F 2130/20; F24F 11/00; G06F 1/163; G06F 16/9035; G16H 40/67; G16H 10/60; G16H 50/30; G06Q 10/06; G06Q 10/04; G06Q 50/16; Y02B 30/70; Y02A 90/10
See application file for complete search history.

(56) References Cited

U.S. PATENT DOCUMENTS

| | | |
|---|---|---|
| 853,033 A | 5/1907 | Roberts |
| 1,648,277 A | 11/1927 | Korb |
| 1,856,969 A | 5/1932 | Reiter |
| 2,184,644 A | 12/1939 | Homberger |
| 3,483,302 A | 12/1969 | Ashkenas |
| RE27,027 E | 1/1971 | Cristofv |
| 3,621,838 A | 11/1971 | Harding |
| 3,678,337 A | 7/1972 | Grauvogel |
| 3,782,006 A | 1/1974 | Symmes |
| 3,901,215 A | 8/1975 | John |
| 3,910,701 A | 10/1975 | Henderson |
| 4,074,124 A | 2/1978 | Maute |
| 4,122,334 A | 10/1978 | Owens |
| 4,135,116 A | 1/1979 | Smith |
| 4,233,545 A | 11/1980 | Webster |
| 4,236,101 A | 11/1980 | Luchaco |
| 4,247,766 A | 1/1981 | Warren |
| 4,273,999 A | 6/1981 | Pierpoint |
| 4,308,911 A | 1/1982 | Mandl |
| 4,587,459 A | 5/1986 | Blake |
| 4,638,853 A | 1/1987 | Papak |
| 4,701,669 A | 10/1987 | Head |
| 4,717,343 A | 1/1988 | Densky |
| D295,934 S | 5/1988 | Dyrhood |
| 4,755,140 A | 7/1988 | Rimland |
| 4,770,636 A | 9/1988 | Buschke |
| 4,803,625 A | 2/1989 | Fu |
| 4,828,609 A | 5/1989 | Anderson |
| 4,853,854 A | 8/1989 | Behar |
| 4,858,609 A | 8/1989 | Cole |
| 4,882,166 A | 11/1989 | Graham |
| 4,893,291 A | 1/1990 | Bick |
| 4,911,166 A | 3/1990 | Leighton |
| 4,911,737 A | 3/1990 | Yehl |
| 4,916,642 A | 4/1990 | Kaiser |
| 4,930,505 A | 6/1990 | Hatje |
| 4,938,582 A | 7/1990 | Leslie |
| 4,947,928 A | 8/1990 | Parker |
| 4,953,784 A | 9/1990 | Yasufuku |
| 4,962,687 A | 10/1990 | Belliveau |
| D312,018 S | 11/1990 | Giesy |
| 5,006,985 A | 4/1991 | Ehret |
| 5,010,777 A | 4/1991 | Yehl |
| 5,017,142 A | 5/1991 | Bemis |
| 5,043,840 A | 8/1991 | Yehl |
| 5,079,682 A | 1/1992 | Roberts |
| 5,079,726 A | 1/1992 | Keller |
| 5,082,173 A | 1/1992 | Poehlman |
| 5,086,385 A | 2/1992 | Launey |
| 5,092,669 A | 3/1992 | Anderson |
| 5,103,391 A | 4/1992 | Barrett |
| 5,103,408 A | 4/1992 | Greenberg |
| 5,121,030 A | 6/1992 | Schott |
| 5,176,133 A | 1/1993 | Czeisler |
| 5,193,900 A | 3/1993 | Yano |
| 5,197,941 A | 3/1993 | Whitaker |
| 5,207,580 A | 5/1993 | Strecher |
| 5,214,736 A | 5/1993 | Uemiya |
| D335,978 S | 6/1993 | Grahn |
| 5,230,629 A | 7/1993 | Buschke |
| 5,250,799 A | 10/1993 | Werner |
| 5,259,553 A | 11/1993 | Shyu |
| 5,285,356 A | 2/1994 | Skene |
| 5,285,430 A | 2/1994 | Decker |
| D345,071 S | 3/1994 | Gould |
| 5,290,200 A | 3/1994 | Kiser |
| 5,292,345 A | 3/1994 | Gerardo |
| 5,295,491 A | 3/1994 | Gevins |
| 5,304,212 A | 4/1994 | Czeisler |
| 5,343,121 A | 8/1994 | Terman |
| 5,344,068 A | 9/1994 | Haessig |
| 5,344,324 A | 9/1994 | O'Donnell et al. |
| 5,350,977 A | 9/1994 | Hamamoto |
| 5,357,170 A | 10/1994 | Luchaco |
| 5,374,876 A | 12/1994 | Horibata |
| 5,377,258 A | 12/1994 | Bro |
| 5,395,042 A | 3/1995 | Riley |
| 5,433,923 A | 7/1995 | Wolverton |
| 5,436,535 A | 7/1995 | Yang |
| 5,462,485 A | 10/1995 | Kinkead |
| D364,762 S | 12/1995 | Compton |
| D365,484 S | 12/1995 | Trattner, Jr. |
| 5,473,537 A | 12/1995 | Glazfr |
| 5,503,637 A | 4/1996 | Kyricos |
| 5,545,192 A | 8/1996 | Czeisler |
| 5,589,741 A | 12/1996 | Terman |
| 5,596,994 A | 1/1997 | Bro |
| 5,648,656 A | 7/1997 | Begemann |
| 5,692,501 A | 12/1997 | Minturn |
| 5,721,471 A | 2/1998 | Begemann |
| 5,722,418 A | 3/1998 | Bro |
| 5,724,987 A | 3/1998 | Gevins |
| 5,742,516 A | 4/1998 | Olcerst |
| 5,749,365 A | 5/1998 | Magill |
| D396,581 S | 8/1998 | Schubert |
| 5,791,982 A | 8/1998 | Curry |
| 5,805,267 A | 9/1998 | Goldman |
| 5,813,863 A | 9/1998 | Sloane |
| D401,085 S | 11/1998 | Grant |
| 5,833,466 A | 11/1998 | Borg |
| 5,861,717 A | 1/1999 | Begemann |
| 5,892,690 A | 4/1999 | Boatman |
| 5,908,301 A | 6/1999 | Lutz |
| 5,911,581 A | 6/1999 | Reynolds |
| 5,919,217 A | 7/1999 | Hughes |
| 5,937,387 A | 8/1999 | Summerell |
| 5,954,510 A | 9/1999 | Merrill |
| 5,963,294 A | 10/1999 | Schiffer |
| 5,967,789 A | 10/1999 | Segel |
| 5,976,010 A | 11/1999 | Reese |
| 6,053,936 A | 4/2000 | Koyama |
| 6,055,480 A | 4/2000 | Nevo |
| D424,356 S | 5/2000 | Hahn |

(56) References Cited

U.S. PATENT DOCUMENTS

| | | |
|---|---|---|
| 6,118,230 A | 9/2000 | Fleischmann |
| 6,135,970 A | 10/2000 | Kadhiresan |
| 6,166,496 A | 12/2000 | Lys |
| 6,170,318 B1 | 1/2001 | Lewis |
| 6,197,094 B1 | 3/2001 | Thofelt |
| 6,208,905 B1 | 3/2001 | Giddings |
| 6,235,046 B1 | 5/2001 | Gerdt |
| 6,238,337 B1 | 5/2001 | Kambhatla |
| 6,269,339 B1 | 7/2001 | Silver |
| 6,280,198 B1 | 8/2001 | Calhoun |
| 6,290,140 B1 | 9/2001 | Pesko |
| 6,331,160 B1 | 12/2001 | Bardy |
| 6,340,864 B1 | 1/2002 | Wacyk |
| 6,340,868 B1 | 1/2002 | Lys |
| 6,344,641 B1 | 2/2002 | Blalock |
| 6,348,867 B1 | 2/2002 | Myllymaki |
| 6,350,275 B1 | 2/2002 | Vreman |
| 6,369,716 B1 | 4/2002 | Abbas |
| 6,387,844 B1 | 5/2002 | Fujishima |
| 6,411,046 B1 | 6/2002 | Muthu |
| 6,416,472 B1 | 7/2002 | Cady |
| 6,417,019 B1 | 7/2002 | Mueller |
| 6,419,629 B1 | 7/2002 | Balkin |
| 6,435,878 B1 | 8/2002 | Reynolds |
| 6,439,893 B1 | 8/2002 | Byrd |
| 6,441,558 B1 | 8/2002 | Muthu |
| 6,448,550 B1 | 9/2002 | Nishimura |
| 6,448,978 B1 | 9/2002 | Salvador |
| 6,459,919 B1 | 10/2002 | Lys |
| 6,488,698 B1 | 12/2002 | Hyman |
| 6,498,440 B2 | 12/2002 | Stam |
| 6,503,462 B1 | 1/2003 | Michalakos |
| 6,507,159 B2 | 1/2003 | Muthu |
| 6,507,709 B2 | 1/2003 | Hirai |
| 6,525,658 B2 | 2/2003 | Streetman |
| 6,535,190 B2 | 3/2003 | Evanicky |
| 6,553,252 B2 | 4/2003 | Balkin |
| 6,554,439 B1 | 4/2003 | Teicher |
| 6,565,359 B2 | 5/2003 | Calhoun |
| 6,567,009 B2 | 5/2003 | Ohishi |
| 6,582,380 B2 | 6/2003 | Kazlausky |
| 6,583,573 B2 | 6/2003 | Bierman |
| 6,583,720 B1 | 6/2003 | Quigley |
| D477,158 S | 7/2003 | Calcerano |
| 6,589,912 B2 | 7/2003 | Kawai |
| 6,607,484 B2 | 8/2003 | Suzuki |
| 6,608,453 B2 | 8/2003 | Morgan |
| 6,610,127 B2 | 8/2003 | Lu |
| 6,614,013 B2 | 9/2003 | Pitigoi-Aron |
| 6,618,723 B1 | 9/2003 | Smith |
| 6,623,512 B1 | 9/2003 | Heller |
| 6,632,174 B1 | 10/2003 | Breznitz |
| 6,661,798 B2 | 12/2003 | Sano |
| 6,666,567 B1 | 12/2003 | Feldman |
| 6,669,481 B2 | 12/2003 | Winter |
| 6,683,419 B2 | 1/2004 | Kriparos |
| 6,691,070 B1 | 2/2004 | Williams |
| 6,711,470 B1 | 3/2004 | Hartenstein |
| 6,712,615 B2 | 3/2004 | Martin |
| 6,720,745 B2 | 4/2004 | Lys |
| 6,727,091 B2 | 4/2004 | Darlington |
| 6,738,551 B2 | 5/2004 | Noda |
| 6,743,171 B1 | 6/2004 | Bowles |
| 6,755,783 B2 | 6/2004 | Cosentino |
| 6,756,998 B1 | 6/2004 | Bilger |
| 6,757,710 B2 | 6/2004 | Reed |
| 6,769,915 B2 | 8/2004 | Murgia |
| 6,772,016 B1 | 8/2004 | Oern |
| 6,774,802 B2 | 8/2004 | Bachinski |
| 6,782,351 B2 | 8/2004 | Reichel |
| 6,806,659 B1 | 10/2004 | Mueller |
| 6,834,208 B2 | 12/2004 | Gonzales |
| 6,862,529 B2 | 3/2005 | Brown |
| 6,865,428 B2 | 3/2005 | Gonzales |
| 6,872,221 B2 | 3/2005 | Lytle |
| 6,878,191 B2 | 4/2005 | Escaffre |
| 6,879,451 B1 | 4/2005 | Hewlett |
| 6,884,078 B2 | 4/2005 | Wiig |
| 6,888,453 B2 | 5/2005 | Lutz |
| 6,888,779 B2 | 5/2005 | Mollicone |
| 6,904,508 B2 | 6/2005 | Selkirk |
| 6,912,429 B1 | 6/2005 | Bilger |
| 6,923,653 B2 | 8/2005 | Ito |
| 6,933,486 B2 | 8/2005 | Pitigoi-Aron |
| 6,955,684 B2 | 10/2005 | Savage, Jr. |
| 6,964,638 B2 | 11/2005 | Theodoracopulos |
| 6,967,565 B2 | 11/2005 | Lingemann |
| 6,991,029 B2 | 1/2006 | Orfield |
| 6,992,803 B2 | 1/2006 | Chang |
| 7,004,606 B2 | 2/2006 | Schofield |
| 7,014,336 B1 | 3/2006 | Ducharme |
| 7,024,256 B2 | 4/2006 | Krzyzanowski |
| 7,038,399 B2 | 5/2006 | Lys |
| 7,065,280 B2 | 6/2006 | Ogawa |
| 7,067,995 B2 | 6/2006 | Gunter |
| 7,081,128 B2 | 7/2006 | Hart |
| D526,512 S | 8/2006 | Hahn |
| 7,092,101 B2 | 8/2006 | Brady |
| 7,095,056 B2 | 8/2006 | Vitta |
| 7,097,111 B2 | 8/2006 | Riley |
| 7,099,723 B2 | 8/2006 | Gonzales |
| 7,113,086 B2 | 9/2006 | Shorrock |
| D530,940 S | 10/2006 | Raile |
| 7,129,855 B2 | 10/2006 | Krzyzanowski |
| 7,145,295 B1 | 12/2006 | Lee |
| 7,145,614 B2 | 12/2006 | Lee |
| 7,173,384 B2 | 2/2007 | Ploetz |
| 7,190,126 B1 | 3/2007 | Paton |
| 7,196,619 B2 | 3/2007 | Perlman |
| 7,202,613 B2 | 4/2007 | Morgan |
| 7,204,611 B2 | 4/2007 | Lukas |
| 7,213,940 B1 | 5/2007 | Van De Ven |
| 7,215,086 B2 | 5/2007 | Maxik |
| 7,224,282 B2 | 5/2007 | Terauchi |
| 7,234,943 B1 | 6/2007 | Aleali |
| 7,256,554 B2 | 8/2007 | Lys |
| 7,260,950 B2 | 8/2007 | Choi |
| 7,274,160 B2 | 9/2007 | Mueller |
| 7,288,902 B1 | 10/2007 | Melanson |
| 7,294,107 B2 | 11/2007 | Simon |
| 7,298,871 B2 | 11/2007 | Lee |
| 7,302,313 B2 | 11/2007 | Sharp |
| 7,308,296 B2 | 12/2007 | Lys |
| 7,319,298 B2 | 1/2008 | Jungwirth |
| 7,324,874 B2 | 1/2008 | Jung |
| 7,327,337 B2 | 2/2008 | Callahan |
| 7,328,243 B2 | 2/2008 | Yeager |
| 7,347,818 B2 | 3/2008 | Simon |
| 7,348,949 B2 | 3/2008 | Lee |
| D566,428 S | 4/2008 | Kester |
| 7,354,172 B2 | 4/2008 | Chemel |
| 7,358,679 B2 | 4/2008 | Lys |
| 7,364,583 B2 | 4/2008 | Rose |
| 7,366,989 B2 | 4/2008 | Naik |
| 7,369,903 B2 | 5/2008 | Diederiks |
| 7,387,405 B2 | 6/2008 | Ducharme |
| 7,415,310 B2 | 8/2008 | Bovee |
| 7,446,303 B2 | 11/2008 | Maniam |
| 7,453,217 B2 | 11/2008 | Lys |
| 7,457,834 B2 | 11/2008 | Jung |
| 7,507,091 B1 | 3/2009 | Aleali |
| 7,520,634 B2 | 4/2009 | Ducharme |
| 7,524,279 B2 | 4/2009 | Auphan |
| 7,534,255 B1 | 5/2009 | Streeter |
| 7,536,388 B2 | 5/2009 | Jung |
| 7,545,267 B2 | 6/2009 | Stortoni |
| 7,553,039 B2 | 6/2009 | Harris |
| 7,556,604 B2 | 7/2009 | Murata |
| 7,557,521 B2 | 7/2009 | Lys |
| 7,558,546 B2 | 7/2009 | Johnson |
| 7,567,956 B2 | 7/2009 | Yu |
| 7,572,028 B2 | 8/2009 | Mueller |
| 7,573,210 B2 | 8/2009 | Ashdown |
| 7,574,320 B2 | 8/2009 | Corwin |

(56) References Cited

U.S. PATENT DOCUMENTS

| | | |
|---|---|---|
| 7,577,915 B2 | 8/2009 | Hunter |
| 7,621,871 B2 | 11/2009 | Downs, III |
| 7,624,028 B1 | 11/2009 | Brown |
| 7,647,285 B2 | 1/2010 | Heckerman |
| 7,652,582 B2 | 1/2010 | Littell |
| 7,659,673 B2 | 2/2010 | Lys |
| 7,676,280 B1 | 3/2010 | Bash |
| 7,679,281 B2 | 3/2010 | Kim |
| 7,680,745 B2 | 3/2010 | Hunter |
| 7,689,437 B1 | 3/2010 | Teller |
| 7,725,842 B2 | 5/2010 | Bronkema |
| 7,759,854 B2 | 7/2010 | Miller |
| 7,766,503 B2 | 8/2010 | Heiking |
| 7,767,280 B2 | 8/2010 | Klasen-Memmer |
| 7,772,965 B2 | 8/2010 | Farhan |
| 7,779,097 B2 | 8/2010 | Lamkin |
| 7,792,920 B2 | 9/2010 | Istvan |
| 7,827,039 B2 | 11/2010 | Butcher |
| 7,828,205 B2 | 11/2010 | Cronin |
| 7,837,472 B1 | 11/2010 | Elsmore |
| 7,839,275 B2 | 11/2010 | Spalink |
| 7,840,310 B2 | 11/2010 | Orfield |
| 7,843,353 B2 | 11/2010 | Pan |
| 7,845,823 B2 | 12/2010 | Mueller |
| 7,848,945 B2 | 12/2010 | Rozell |
| D632,102 S | 2/2011 | Sato |
| 7,878,810 B2 | 2/2011 | Kuntz |
| D634,952 S | 3/2011 | Gile |
| 7,901,071 B1 | 3/2011 | Kulas |
| 7,906,789 B2 | 3/2011 | Jung |
| 7,914,172 B2 | 3/2011 | Nagara |
| 7,918,406 B2 | 4/2011 | Rosen |
| 7,918,407 B2 | 4/2011 | Patch |
| 7,925,673 B2 | 4/2011 | Beard |
| 7,953,678 B2 | 5/2011 | Hunter |
| 7,967,731 B2 | 6/2011 | Kil |
| 7,973,759 B2 | 7/2011 | Huang |
| 7,977,904 B2 | 7/2011 | Berman |
| 7,987,490 B2 | 7/2011 | Ansari |
| 8,025,687 B2 | 9/2011 | Streeter |
| 8,028,706 B2 | 10/2011 | Skene |
| 8,035,320 B2 | 10/2011 | Sibert |
| 8,038,615 B2 | 10/2011 | Gobeyn |
| 8,042,049 B2 | 10/2011 | Killian |
| 8,064,295 B2 | 11/2011 | Palmer |
| 8,066,405 B2 | 11/2011 | Simon |
| 8,081,216 B2 | 12/2011 | Cheung |
| 8,083,675 B2 | 12/2011 | Robinson |
| 8,086,407 B2 | 12/2011 | Chan |
| 8,095,153 B2 | 1/2012 | Jenkins |
| 8,100,552 B2 | 1/2012 | Spero |
| 8,100,746 B2 | 1/2012 | Heidel |
| 8,137,108 B2 | 3/2012 | Hamway |
| 8,140,391 B2 | 3/2012 | Jacobi |
| 8,143,792 B2 | 3/2012 | Joo |
| 8,147,302 B2 | 4/2012 | Desrochers |
| 8,150,707 B2 | 4/2012 | Hayet |
| 8,154,398 B2 | 4/2012 | Rolf |
| 8,159,150 B2 | 4/2012 | Ashdown |
| 8,172,153 B1 | 5/2012 | Kennedy |
| 8,188,873 B2 | 5/2012 | Barth |
| 8,200,744 B2 | 6/2012 | Jung |
| 8,202,095 B2 | 6/2012 | Shankle |
| 8,219,115 B1 | 7/2012 | Nelissen |
| 8,226,418 B2 | 7/2012 | Lycas |
| D666,123 S | 8/2012 | Sichello |
| 8,253,349 B2 | 8/2012 | Shteynberg |
| 8,271,575 B2 | 9/2012 | Hunter |
| 8,292,468 B2 | 10/2012 | Narendran |
| 8,296,408 B2 | 10/2012 | Anke |
| 8,301,482 B2 | 10/2012 | Reynolds |
| 8,308,784 B2 | 11/2012 | Streeter |
| 8,321,192 B2 | 11/2012 | Boyce |
| 8,344,665 B2 | 1/2013 | Verfuerth |
| 8,352,408 B2 | 1/2013 | Guillama |
| 8,358,214 B2 | 1/2013 | Amigo |
| 8,359,208 B2 | 1/2013 | Slutzky |
| 8,380,359 B2 | 2/2013 | Duchene |
| 8,385,812 B2 | 2/2013 | Bertelsen |
| 8,392,025 B2 | 3/2013 | Orfield |
| 8,429,223 B2 | 4/2013 | Gilley |
| 8,436,556 B2 | 5/2013 | Eisele |
| 8,446,275 B2 | 5/2013 | Utter, II |
| 8,449,300 B2 | 5/2013 | Lycas |
| 8,454,729 B2 | 6/2013 | Mittelmark |
| 8,469,547 B2 | 6/2013 | Paolini |
| 8,484,153 B2 | 7/2013 | Mott |
| 8,490,006 B1 | 7/2013 | Reeser |
| 8,497,871 B2 | 7/2013 | Zulch |
| 8,506,612 B2 | 8/2013 | Ashdown |
| 8,508,169 B2 | 8/2013 | Zaharchuk |
| 8,515,785 B2 | 8/2013 | Clark |
| 8,527,213 B2 | 9/2013 | Kailas |
| 8,540,515 B2 | 9/2013 | Williams |
| 8,543,244 B2 | 9/2013 | Keeling |
| 8,543,665 B2 | 9/2013 | Ansari |
| 8,558,466 B2 | 10/2013 | Curasi |
| 8,558,687 B2 | 10/2013 | Haupt |
| 8,560,344 B2 | 10/2013 | Earles |
| 8,609,121 B2 | 12/2013 | Averett |
| 8,622,560 B2 | 1/2014 | Di Trapani |
| 8,630,741 B1 | 1/2014 | Matsuoka |
| 8,632,209 B2 | 1/2014 | Graeber |
| 8,640,038 B1 | 1/2014 | Reeser |
| 8,655,717 B2 | 2/2014 | Schwarzberg |
| 8,660,861 B2 | 2/2014 | Chun |
| 8,662,897 B2 | 3/2014 | Sims, Jr. |
| 8,666,666 B2 | 3/2014 | Bassa |
| 8,674,608 B2 | 3/2014 | Holland |
| 8,674,842 B2 | 3/2014 | Zishaan |
| 8,690,771 B2 | 4/2014 | Wekell |
| 8,707,619 B2 | 4/2014 | Edwards |
| 8,716,952 B2 | 5/2014 | Van De Ven |
| 8,740,623 B2 | 6/2014 | Walker |
| 8,755,942 B2 | 6/2014 | Bonilla |
| 8,760,370 B2 | 6/2014 | Maxik |
| 8,783,902 B2 | 7/2014 | Takakura |
| 8,795,169 B2 | 8/2014 | Cosentino |
| 8,801,636 B2 | 8/2014 | Lewicke |
| 8,823,507 B1 | 9/2014 | Touloumtzis |
| 8,827,489 B2 | 9/2014 | Li |
| 8,836,243 B2 | 9/2014 | Eisele |
| 8,843,484 B2 | 9/2014 | Gu |
| 8,852,254 B2 | 10/2014 | Moscovici |
| 8,855,757 B2 | 10/2014 | Kapoor |
| 8,862,532 B2 | 10/2014 | Beaulieu |
| 8,870,740 B2 | 10/2014 | Clegg |
| 8,896,427 B1 | 11/2014 | Ramirez |
| 8,907,803 B2 | 12/2014 | Martin |
| 8,924,026 B2 | 12/2014 | Federspiel |
| 8,939,885 B2 | 1/2015 | Martin |
| 8,941,500 B1 | 1/2015 | Faaborg |
| 8,952,626 B2 | 2/2015 | Huang |
| 8,961,414 B2 | 2/2015 | Teller |
| 8,975,827 B2 | 3/2015 | Chobot |
| 8,979,913 B2 | 3/2015 | D Ambrosio |
| 8,986,204 B2 | 3/2015 | Pacey |
| 8,986,427 B2 | 3/2015 | Hauville |
| 9,007,877 B2 | 4/2015 | Godlieb |
| 9,010,019 B2 | 4/2015 | Mittelmark |
| 9,015,610 B2 | 4/2015 | Hunter |
| 9,020,647 B2 | 4/2015 | Johnson |
| 9,032,097 B2 | 5/2015 | Albanese |
| 9,032,215 B2 | 5/2015 | Kalofonos |
| 9,041,530 B2 | 5/2015 | Sprigg |
| 9,044,567 B2 | 6/2015 | Poirrier |
| 9,063,739 B2 | 6/2015 | Ward |
| 9,066,405 B2 | 6/2015 | Van De Ven |
| 9,068,887 B1 | 6/2015 | Bennouri |
| D734,958 S | 7/2015 | Gosling |
| 9,095,029 B2 | 7/2015 | Lu |
| D737,078 S | 8/2015 | Mckinney |
| 9,098,114 B2 | 8/2015 | Potter |
| 9,104,183 B2 | 8/2015 | Zheng |

(56) References Cited

U.S. PATENT DOCUMENTS

| | | |
|---|---|---|
| 9,110,958 B2 | 8/2015 | Brust |
| 9,118,499 B2 | 8/2015 | Hunter |
| 9,125,257 B2 | 9/2015 | Eisele |
| 9,125,274 B1 | 9/2015 | Brunault |
| 9,131,573 B2 | 9/2015 | Maxik |
| 9,147,296 B2 | 9/2015 | Ricci |
| 9,154,559 B1 | 10/2015 | Bovee |
| 9,155,165 B2 | 10/2015 | Chobot |
| 9,204,518 B2 | 12/2015 | Jung |
| 9,220,202 B2 | 12/2015 | Maxik |
| 9,226,371 B2 | 12/2015 | Mohan |
| 9,230,064 B2 | 1/2016 | Yanev |
| 9,230,560 B2 | 1/2016 | Ehsani |
| 9,235,978 B1 | 1/2016 | Charlton |
| 9,236,026 B2 | 1/2016 | Jia |
| 9,248,309 B2 | 2/2016 | Pugh |
| 9,251,716 B2 | 2/2016 | Drane |
| 9,286,442 B2 | 3/2016 | Csoma |
| 9,297,748 B2 | 3/2016 | Risk |
| 9,306,763 B2 | 4/2016 | Tatzel |
| 9,307,608 B2 | 4/2016 | Maxik |
| 9,326,363 B2 | 4/2016 | Godlieb |
| 9,339,227 B2 | 5/2016 | D'Arcy et al. |
| 9,345,091 B2 | 5/2016 | Pickard |
| 9,360,364 B2 | 6/2016 | Hingorani |
| 9,360,731 B2 | 6/2016 | Berman |
| 9,370,689 B2 | 6/2016 | Guillama |
| D761,598 S | 7/2016 | Goodman |
| 9,380,978 B2 | 7/2016 | Reiner |
| 9,392,665 B2 | 7/2016 | Eisele |
| 9,401,098 B2 | 7/2016 | Ellis |
| 9,410,664 B2 | 8/2016 | Krames |
| 9,420,667 B2 | 8/2016 | Mohan |
| 9,420,671 B1 | 8/2016 | Sugimoto |
| 9,426,867 B2 | 8/2016 | Beghelli |
| 9,429,009 B2 | 8/2016 | Paulk |
| 9,430,617 B2 | 8/2016 | Brust |
| 9,430,927 B2 | 8/2016 | Yu |
| 9,450,904 B2 | 9/2016 | Wheeler |
| 9,456,482 B1 | 9/2016 | Pope |
| 9,465,392 B2 | 10/2016 | Bradley |
| 9,471,751 B1 | 10/2016 | Kahn |
| 9,473,321 B1 | 10/2016 | Bazar |
| 9,480,115 B2 | 10/2016 | Bradford |
| 9,493,112 B2 | 11/2016 | Thomas |
| 9,500,325 B2 | 11/2016 | Tong et al. |
| 9,501,049 B2 | 11/2016 | Rajalakshmi |
| 9,510,426 B2 | 11/2016 | Chemel |
| 9,526,455 B2 | 12/2016 | Horseman |
| 9,528,876 B2 | 12/2016 | Micheels |
| 9,562,702 B2 | 2/2017 | Law |
| 9,576,939 B2 | 2/2017 | Roth |
| 9,589,475 B2 | 3/2017 | Lycas |
| 9,589,480 B2 | 3/2017 | Ellis |
| 9,593,861 B1 | 3/2017 | Burnett |
| 9,595,118 B2 | 3/2017 | Maxik |
| 9,609,724 B2 | 3/2017 | Bulut |
| 9,615,429 B2 | 4/2017 | Roosli |
| 9,636,520 B2 | 5/2017 | Pedersen |
| 9,642,209 B2 | 5/2017 | Eisele |
| 9,655,195 B2 | 5/2017 | Tseng |
| 9,659,150 B2 | 5/2017 | Greene |
| 9,661,715 B2 | 5/2017 | Van De Ven |
| RE46,430 E | 6/2017 | Sibert |
| 9,672,335 B2 | 6/2017 | Shuart |
| 9,672,472 B2 | 6/2017 | Snyder |
| 9,687,187 B2 | 6/2017 | Dagum |
| 9,693,724 B2 | 7/2017 | Dagum |
| 9,694,496 B2 | 7/2017 | Martinson |
| 9,696,052 B2 | 7/2017 | Malchiondo |
| 9,699,874 B2 | 7/2017 | Phillips |
| 9,703,931 B2 | 7/2017 | Hinkel |
| 9,715,242 B2 | 7/2017 | Pillai |
| 9,717,459 B2 | 8/2017 | Sereno |
| 9,730,298 B2 | 8/2017 | Vangeel |
| 9,734,293 B2 | 8/2017 | Collins, Jr. |
| 9,734,542 B2 | 8/2017 | Ji |
| 9,737,842 B2 | 8/2017 | Matlin |
| 9,750,116 B2 | 8/2017 | Witzgall |
| 9,763,592 B2 | 9/2017 | Le |
| 9,774,697 B2 | 9/2017 | Li |
| 9,788,373 B1 | 10/2017 | Chowdhury |
| 9,791,129 B2 | 10/2017 | Dennis |
| 9,794,355 B2 | 10/2017 | Moghaddam |
| 9,801,259 B2 | 10/2017 | Rasmussen |
| 9,820,656 B2 | 11/2017 | Olivier |
| 9,827,439 B2 | 11/2017 | Maxik |
| 9,839,083 B2 | 12/2017 | Van De Ven |
| 9,842,313 B2 | 12/2017 | B'Far et al. |
| 9,848,811 B2 | 12/2017 | Yasumura |
| 9,870,449 B2 | 1/2018 | Rajan |
| 9,874,317 B2 | 1/2018 | Dijken |
| 9,875,667 B2 | 1/2018 | Thompson |
| 9,881,511 B1 | 1/2018 | Srinivasan |
| 9,883,563 B2 | 1/2018 | Bosua |
| 9,887,854 B2 | 2/2018 | Park |
| 9,890,969 B2 | 2/2018 | Martin |
| 9,894,729 B2 | 2/2018 | Forbis |
| 9,907,149 B1 | 2/2018 | Dolan |
| 9,909,772 B2 | 3/2018 | Bazar |
| 9,913,583 B2 | 3/2018 | Smith, Sr. |
| 9,915,438 B2 | 3/2018 | Cheatham, III |
| 9,916,474 B2 | 3/2018 | Tribble |
| 9,924,243 B2 | 3/2018 | Lupien |
| 9,933,182 B2 | 4/2018 | Alfakhrany |
| 9,939,823 B2 | 4/2018 | Ovadia |
| 9,944,519 B2 | 4/2018 | Bohler |
| 9,949,074 B2 | 4/2018 | Austraat |
| 9,952,614 B2 | 4/2018 | Hunter |
| 9,954,147 B2 | 4/2018 | Pentlehner |
| 9,955,423 B2 | 4/2018 | Kates |
| 9,955,550 B2 | 4/2018 | Baek |
| 9,958,180 B2 | 5/2018 | Mahar |
| 9,959,997 B2 | 5/2018 | Bailey |
| 9,984,590 B2 | 5/2018 | Stevens |
| 9,986,313 B2 | 5/2018 | Schwarzkopf |
| 9,992,292 B2 | 6/2018 | Gunnarsson |
| 9,993,198 B2 | 6/2018 | Dugan |
| 10,001,789 B2 | 6/2018 | Hunka |
| 10,015,865 B2 | 7/2018 | Engelen |
| 10,019,690 B2 | 7/2018 | Oobayashi |
| 10,022,556 B1 | 7/2018 | Holbert |
| 10,024,699 B2 | 7/2018 | Rapetti Mogol |
| 10,030,833 B2 | 7/2018 | Adler |
| 10,031,973 B2 | 7/2018 | Dey |
| 10,039,169 B2 | 7/2018 | Chen |
| 10,042,336 B2 | 8/2018 | Cipollo |
| 10,047,971 B2 | 8/2018 | Nyamjav |
| 10,051,707 B2 | 8/2018 | Deixler |
| 10,052,061 B2 | 8/2018 | Raymann |
| 10,054,534 B1 | 8/2018 | Nourbakhsh |
| 10,057,963 B2 | 8/2018 | Mead |
| 10,060,787 B2 | 8/2018 | Balooch |
| 10,064,255 B2 | 8/2018 | Barroso |
| 10,068,297 B2 | 9/2018 | Hull Roskos |
| 10,072,866 B2 | 9/2018 | Bazar |
| 10,075,757 B2 | 9/2018 | Ugan |
| 10,078,865 B2 | 9/2018 | Joshi |
| 10,088,577 B2 | 10/2018 | Klein |
| 10,091,017 B2 | 10/2018 | Landow |
| 10,091,303 B1 | 10/2018 | Ledvina |
| 10,092,772 B1 | 10/2018 | Makesh |
| 10,129,367 B2 | 11/2018 | Yan |
| 10,139,118 B2 | 11/2018 | Law |
| 10,154,574 B2 | 12/2018 | Yeh |
| 10,178,972 B2 | 1/2019 | Raymann |
| 10,203,267 B2 | 2/2019 | D'Orlando et al. |
| 10,230,538 B2 | 3/2019 | Killian |
| 10,234,162 B2 | 3/2019 | Lu |
| 10,242,757 B2 * | 3/2019 | Baughman ............ A61B 5/1171 |
| 10,244,606 B2 | 3/2019 | Wingren |
| 10,265,011 B2 | 4/2019 | Garnavi |
| 10,271,400 B2 | 4/2019 | Parker |
| 10,304,249 B2 | 5/2019 | Cronin |

(56) References Cited

U.S. PATENT DOCUMENTS

| | | |
|---|---|---|
| 10,420,912 B2 | 9/2019 | Lütz |
| 10,527,490 B2 | 1/2020 | Dumont |
| 10,561,376 B1 | 2/2020 | Kahn |
| 10,602,599 B2 | 3/2020 | Wouhaybi |
| 10,709,899 B1 | 7/2020 | Maa |
| 10,775,068 B2 | 9/2020 | Lee |
| 10,845,829 B2 | 11/2020 | Pillai |
| 10,917,259 B1* | 2/2021 | Chein .................. H04L 12/282 |
| 10,948,348 B2 | 3/2021 | Rountree |
| 10,972,360 B2 | 4/2021 | Cahill |
| 10,976,065 B2 | 4/2021 | Kohn |
| 10,980,096 B2 | 4/2021 | Summers |
| 11,078,899 B2 | 8/2021 | Mou |
| 11,137,163 B2 | 10/2021 | Nasis |
| 11,141,688 B2 | 10/2021 | Hur |
| 11,187,419 B2 | 11/2021 | Aleti |
| 2002/0072322 A1 | 6/2002 | Sharp |
| 2002/0072859 A1 | 6/2002 | Kajimoto |
| 2002/0096121 A1 | 7/2002 | Ingman |
| 2002/0119281 A1 | 8/2002 | Higgins |
| 2002/0128864 A1 | 9/2002 | Maus |
| 2002/0163529 A1 | 11/2002 | Evanicky |
| 2002/0187082 A1 | 12/2002 | Wu |
| 2002/0192624 A1 | 12/2002 | Darby |
| 2003/0100837 A1 | 5/2003 | Lys |
| 2003/0133292 A1 | 7/2003 | Mueller |
| 2003/0199244 A1 | 10/2003 | Siddaramanna |
| 2003/0209140 A1 | 11/2003 | Kutt |
| 2003/0209501 A1 | 11/2003 | Leung |
| 2004/0002792 A1 | 1/2004 | Hoffknecht |
| 2004/0052076 A1 | 3/2004 | Mueller |
| 2004/0060677 A1 | 4/2004 | Huang |
| 2004/0065098 A1 | 4/2004 | Choi |
| 2004/0105264 A1 | 6/2004 | Spero |
| 2004/0111036 A1 | 6/2004 | Nissila |
| 2004/0152995 A1 | 8/2004 | Cox |
| 2004/0160199 A1 | 8/2004 | Morgan |
| 2004/0176666 A1 | 9/2004 | Chait |
| 2004/0178751 A1 | 9/2004 | Mueller |
| 2004/0212321 A1 | 10/2004 | Lys |
| 2004/0222307 A1 | 11/2004 | Deluca |
| 2004/0245351 A1 | 12/2004 | Orfield |
| 2004/0264193 A1 | 12/2004 | Okumura |
| 2004/0267385 A1 | 12/2004 | Lingemann |
| 2005/0004942 A1 | 1/2005 | Madsen |
| 2005/0053904 A1 | 3/2005 | Shephard |
| 2005/0057158 A1 | 3/2005 | Chang |
| 2005/0110416 A1 | 5/2005 | Veskovic |
| 2005/0125275 A1 | 6/2005 | Wright |
| 2005/0142524 A1 | 6/2005 | Simon |
| 2005/0151489 A1 | 7/2005 | Lys |
| 2005/0177957 A1 | 8/2005 | Long |
| 2005/0191505 A1 | 9/2005 | Akarsu |
| 2005/0200578 A1 | 9/2005 | Lee |
| 2005/0213353 A1 | 9/2005 | Lys |
| 2005/0214533 A1 | 9/2005 | Shimosaki |
| 2005/0218870 A1 | 10/2005 | Lys |
| 2005/0225976 A1 | 10/2005 | Zampini |
| 2005/0231133 A1 | 10/2005 | Lys |
| 2005/0236998 A1 | 10/2005 | Mueller |
| 2005/0253533 A1 | 11/2005 | Lys |
| 2005/0281531 A1 | 12/2005 | Unmehopa |
| 2006/0000257 A1 | 1/2006 | Samadpour |
| 2006/0002110 A1 | 1/2006 | Dowling |
| 2006/0017928 A1 | 1/2006 | Crowther |
| 2006/0018118 A1 | 1/2006 | Lee |
| 2006/0018428 A1 | 1/2006 | Li |
| 2006/0026972 A1 | 2/2006 | Masui |
| 2006/0074340 A1 | 4/2006 | Murata |
| 2006/0092520 A1 | 5/2006 | Buchsbaum |
| 2006/0103728 A1 | 5/2006 | Ishigami |
| 2006/0106437 A1 | 5/2006 | Czeisler |
| 2006/0111944 A1 | 5/2006 | Sirmans |
| 2006/0154596 A1 | 7/2006 | Meneely |
| 2006/0162552 A1 | 7/2006 | Yost |
| 2006/0172579 A1 | 8/2006 | Murphy |
| 2006/0173580 A1 | 8/2006 | Desrochers |
| 2006/0184283 A1 | 8/2006 | Lee |
| 2006/0207730 A1 | 9/2006 | Berman |
| 2006/0246149 A1 | 11/2006 | Buchholz |
| 2006/0252014 A1 | 11/2006 | Simon |
| 2007/0001617 A1 | 1/2007 | Pogodayev |
| 2007/0024210 A1 | 2/2007 | Zwanenburg |
| 2007/0084937 A1 | 4/2007 | Ahmed |
| 2007/0115665 A1 | 5/2007 | Mueller |
| 2007/0162858 A1 | 7/2007 | Hurley |
| 2007/0166676 A1 | 7/2007 | Bird |
| 2007/0198226 A1 | 8/2007 | Lee |
| 2007/0240437 A1 | 10/2007 | Yonezawa |
| 2007/0276270 A1 | 11/2007 | Tran |
| 2007/0288247 A1 | 12/2007 | Mackay |
| 2008/0031832 A1 | 2/2008 | Wakefield |
| 2008/0103561 A1 | 5/2008 | Moscovici |
| 2008/0116780 A1 | 5/2008 | Kupper |
| 2008/0129174 A1 | 6/2008 | Schafer |
| 2008/0146892 A1 | 6/2008 | Leboeuf |
| 2008/0182506 A1 | 7/2008 | Jackson |
| 2008/0187894 A1 | 8/2008 | Cady |
| 2008/0224121 A1 | 9/2008 | Bose |
| 2008/0225021 A1 | 9/2008 | Hekstra |
| 2008/0246629 A1 | 10/2008 | Tsui |
| 2008/0277486 A1 | 11/2008 | Seem |
| 2008/0294012 A1 | 11/2008 | Kurtz |
| 2008/0297027 A1 | 12/2008 | Miller |
| 2009/0015403 A1 | 1/2009 | Kuris |
| 2009/0053989 A1 | 2/2009 | Lunde |
| 2009/0065596 A1 | 3/2009 | Seem |
| 2009/0068089 A1 | 3/2009 | Hussain |
| 2009/0104086 A1 | 4/2009 | Zax |
| 2009/0115597 A1 | 5/2009 | Giacalone |
| 2009/0126382 A1 | 5/2009 | Rubino |
| 2009/0128044 A1 | 5/2009 | Nevins |
| 2009/0169425 A1 | 7/2009 | Park |
| 2009/0177613 A1 | 7/2009 | Martinez |
| 2009/0223126 A1 | 9/2009 | Garner |
| 2009/0241496 A1 | 10/2009 | Pintault |
| 2009/0242485 A1 | 10/2009 | Cabados |
| 2009/0243517 A1 | 10/2009 | Verfuerth |
| 2009/0273470 A1 | 11/2009 | Sinkevicius |
| 2009/0278464 A1 | 11/2009 | Chung |
| 2009/0287064 A1 | 11/2009 | Dougherty, Jr. |
| 2009/0292180 A1 | 11/2009 | Mirow |
| 2009/0300673 A1 | 12/2009 | Bachet |
| 2010/0021710 A1 | 1/2010 | Hunt |
| 2010/0084996 A1 | 4/2010 | Van De Sluis |
| 2010/0119461 A1 | 5/2010 | Bicard-Benhamou |
| 2010/0146855 A1 | 6/2010 | Ma |
| 2010/0169108 A1 | 7/2010 | Karkanias |
| 2010/0185064 A1 | 7/2010 | Bandic |
| 2010/0197495 A1 | 8/2010 | Filippini |
| 2010/0217099 A1 | 8/2010 | Leboeuf |
| 2010/0265803 A1 | 10/2010 | Lee |
| 2010/0277106 A1 | 11/2010 | Baaijens |
| 2010/0289643 A1 | 11/2010 | Trundle |
| 2010/0295244 A1 | 11/2010 | Stut |
| 2010/0298981 A1 | 11/2010 | Chamorro |
| 2010/0301776 A1 | 12/2010 | Feri |
| 2011/0010014 A1 | 1/2011 | Oexman |
| 2011/0066465 A1 | 3/2011 | Orfield |
| 2011/0084614 A1 | 4/2011 | Eisele |
| 2011/0178977 A1* | 7/2011 | Drees ................ H02J 13/00002<br>706/52 |
| 2011/0186644 A1 | 8/2011 | Yoshii |
| 2011/0190913 A1 | 8/2011 | Van De Sluis |
| 2011/0190945 A1 | 8/2011 | Yoshii |
| 2011/0237905 A1 | 9/2011 | Kutzik |
| 2011/0270446 A1 | 11/2011 | Scharf |
| 2011/0307112 A1 | 12/2011 | Barrilleaux |
| 2012/0003198 A1 | 1/2012 | Barker |
| 2012/0011033 A1 | 1/2012 | Salgia |
| 2012/0019386 A1 | 1/2012 | Doraiswami |
| 2012/0031984 A1 | 2/2012 | Feldmeier |
| 2012/0064818 A1 | 3/2012 | Kurelowech |
| 2012/0072032 A1 | 3/2012 | Powell |

(56) References Cited

U.S. PATENT DOCUMENTS

| | | |
|---|---|---|
| 2012/0139720 A1 | 6/2012 | Mazar |
| 2012/0158203 A1 | 6/2012 | Feldstein |
| 2012/0176041 A1 | 7/2012 | Birru |
| 2012/0190001 A1 | 7/2012 | Knight |
| 2012/0206726 A1 | 8/2012 | Pervez |
| 2012/0214143 A1 | 8/2012 | Severson |
| 2012/0235579 A1 | 9/2012 | Chemel |
| 2012/0241633 A1 | 9/2012 | Smith |
| 2012/0279120 A1 | 11/2012 | Prescott |
| 2012/0298599 A1 | 11/2012 | Sichello |
| 2013/0027637 A1 | 1/2013 | Hosoki |
| 2013/0035208 A1 | 2/2013 | Dalebout |
| 2013/0065098 A1 | 3/2013 | Ohkawa |
| 2013/0073093 A1 | 3/2013 | Songkakul |
| 2013/0081541 A1 | 4/2013 | Hasenoehrl |
| 2013/0090562 A1 | 4/2013 | Ryan |
| 2013/0102852 A1 | 4/2013 | Kozloski |
| 2013/0119891 A1 | 5/2013 | Herremans |
| 2013/0134962 A1 | 5/2013 | Kamel |
| 2013/0141235 A1 | 6/2013 | Utter, II |
| 2013/0144537 A1 | 6/2013 | Schalk |
| 2013/0208576 A1 | 8/2013 | Loree, IV |
| 2013/0229114 A1 | 9/2013 | Eisele |
| 2013/0262357 A1 | 10/2013 | Amarasingham |
| 2013/0276371 A1 | 10/2013 | Birru |
| 2013/0331727 A1 | 12/2013 | Zhang |
| 2013/0342111 A1 | 12/2013 | Mohan |
| 2014/0039685 A1 | 2/2014 | Blount |
| 2014/0046193 A1 | 2/2014 | Stack |
| 2014/0052220 A1 | 2/2014 | Pedersen |
| 2014/0058566 A1 | 2/2014 | Rains, Jr. |
| 2014/0067130 A1 | 3/2014 | Pillai |
| 2014/0089836 A1 | 3/2014 | Damani |
| 2014/0093551 A1 | 4/2014 | Averett |
| 2014/0099348 A1 | 4/2014 | Averett |
| 2014/0107846 A1 | 4/2014 | Li |
| 2014/0114889 A1 | 4/2014 | Dagum |
| 2014/0125225 A1 | 5/2014 | Calame |
| 2014/0142760 A1 | 5/2014 | Drees |
| 2014/0155705 A1 | 6/2014 | Papadopoulos |
| 2014/0168636 A1 | 6/2014 | Funamoto |
| 2014/0222210 A1 | 8/2014 | Agarwal |
| 2014/0222241 A1 | 8/2014 | Ols |
| 2014/0243935 A1 | 8/2014 | Brainard |
| 2014/0249447 A1 | 9/2014 | Sereno |
| 2014/0249760 A1 | 9/2014 | Proud |
| 2014/0266669 A1 | 9/2014 | Fadell |
| 2014/0277757 A1 | 9/2014 | Wang |
| 2014/0283450 A1 | 9/2014 | Darlington |
| 2014/0298719 A1 | 10/2014 | Mackin |
| 2014/0318011 A1 | 10/2014 | Järvinen et al. |
| 2014/0343380 A1 | 11/2014 | Carter |
| 2014/0375230 A1 | 12/2014 | Liu |
| 2015/0015152 A1 | 1/2015 | Aboulnaga |
| 2015/0027879 A1 | 1/2015 | Myre |
| 2015/0048742 A1 | 2/2015 | Wingren |
| 2015/0052975 A1 | 2/2015 | Martin |
| 2015/0066578 A1* | 3/2015 | Manocchia .......... G16H 50/30 |
| | | 705/7.28 |
| 2015/0088786 A1 | 3/2015 | Anandhakrishnan |
| 2015/0102730 A1 | 4/2015 | Eisele |
| 2015/0119731 A1 | 4/2015 | Yasumura |
| 2015/0126806 A1 | 5/2015 | Barroso |
| 2015/0134123 A1 | 5/2015 | Obinelo |
| 2015/0154523 A1 | 6/2015 | Oobayashi |
| 2015/0174361 A1 | 6/2015 | Baaijens |
| 2015/0196232 A1 | 7/2015 | Mitsi |
| 2015/0204551 A1 | 7/2015 | Nair |
| 2015/0204561 A1 | 7/2015 | Sadwick |
| 2015/0212057 A1 | 7/2015 | Darveau |
| 2015/0221233 A1 | 8/2015 | Couriol |
| 2015/0227870 A1* | 8/2015 | Noboa ............... G06Q 10/0635 |
| | | 705/7.28 |
| 2015/0234369 A1 | 8/2015 | Wen |
| 2015/0289347 A1 | 10/2015 | Baaijens |
| 2015/0309484 A1 | 10/2015 | Lyman |
| 2015/0312696 A1 | 10/2015 | Ribbich |
| 2015/0317592 A1 | 11/2015 | Oobayashi |
| 2015/0338117 A1 | 11/2015 | Henneberger |
| 2015/0382427 A1 | 12/2015 | Eisele |
| 2016/0007905 A1 | 1/2016 | Milner |
| 2016/0019813 A1 | 1/2016 | Mullen |
| 2016/0125758 A1 | 5/2016 | Hong |
| 2016/0139576 A1 | 5/2016 | Aiken |
| 2016/0151603 A1 | 6/2016 | Shouldice |
| 2016/0203700 A1 | 7/2016 | Bruhn |
| 2016/0206898 A1 | 7/2016 | Brainard |
| 2016/0213946 A1 | 7/2016 | Brainard |
| 2016/0231014 A1 | 8/2016 | Ro |
| 2016/0253802 A1 | 9/2016 | Venetianer |
| 2016/0284172 A1 | 9/2016 | Weast |
| 2016/0313245 A1 | 10/2016 | Sato |
| 2016/0316543 A1 | 10/2016 | Liu |
| 2016/0339203 A1 | 11/2016 | Krames |
| 2016/0341436 A1 | 11/2016 | Parker |
| 2016/0377305 A1 | 12/2016 | Kwa |
| 2017/0023225 A1 | 1/2017 | Chen |
| 2017/0023269 A1 | 1/2017 | Gevelber |
| 2017/0038787 A1 | 2/2017 | Baker |
| 2017/0050561 A1 | 2/2017 | Lickfelt |
| 2017/0053068 A1 | 2/2017 | Pillai |
| 2017/0065792 A1 | 3/2017 | Bonvallet |
| 2017/0068782 A1 | 3/2017 | Pillai |
| 2017/0080373 A1 | 3/2017 | Engelhard |
| 2017/0105666 A1 | 4/2017 | Lee |
| 2017/0123440 A1 | 5/2017 | Mangsuli |
| 2017/0136206 A1 | 5/2017 | Pillai |
| 2017/0139386 A1 | 5/2017 | Pillai |
| 2017/0162548 A1 | 6/2017 | Roth |
| 2017/0181685 A1 | 6/2017 | Lee |
| 2017/0188926 A1 | 7/2017 | Oobayashi |
| 2017/0189640 A1 | 7/2017 | Sadwick |
| 2017/0191695 A1 | 7/2017 | Bruhn |
| 2017/0196510 A1 | 7/2017 | Ouwerkerk |
| 2017/0200389 A1 | 7/2017 | Yigal |
| 2017/0208021 A1 | 7/2017 | Ingram |
| 2017/0232225 A1 | 8/2017 | Pedersen |
| 2017/0238401 A1 | 8/2017 | Sadwick |
| 2017/0259079 A1 | 9/2017 | Grajcar |
| 2017/0299210 A1 | 10/2017 | Nyamjav |
| 2017/0300647 A1 | 10/2017 | Goldberg |
| 2017/0300651 A1 | 10/2017 | Strobridge |
| 2017/0300655 A1 | 10/2017 | Lane |
| 2017/0301255 A1 | 10/2017 | Lee |
| 2017/0307243 A1 | 10/2017 | Burt |
| 2017/0319816 A1 | 11/2017 | Sokol |
| 2017/0321923 A1* | 11/2017 | Wiens-Kind ......... G08B 27/005 |
| 2017/0325310 A1 | 11/2017 | Chen |
| 2017/0326380 A1 | 11/2017 | Moore-Ede |
| 2017/0347907 A1 | 12/2017 | Le |
| 2017/0348506 A1 | 12/2017 | Berman |
| 2017/0350610 A1 | 12/2017 | Michielsen |
| 2017/0356602 A1 | 12/2017 | Lin |
| 2017/0356670 A1 | 12/2017 | Zhang |
| 2017/0359879 A1 | 12/2017 | Eisele |
| 2017/0363314 A1 | 12/2017 | Barber |
| 2018/0011978 A1 | 1/2018 | Reeckmann |
| 2018/0012242 A1 | 1/2018 | Phan |
| 2018/0025125 A1 | 1/2018 | Crane |
| 2018/0025126 A1 | 1/2018 | Barnard |
| 2018/0042077 A1 | 2/2018 | Riley |
| 2018/0043130 A1 | 2/2018 | Moore Ede |
| 2018/0077767 A1 | 3/2018 | Soler |
| 2018/0082261 A1 | 3/2018 | Hendriks |
| 2018/0082393 A1 | 3/2018 | Ahrens |
| 2018/0107962 A1 | 4/2018 | Lundin |
| 2018/0108442 A1 | 4/2018 | Börve |
| 2018/0119973 A1 | 5/2018 | Rothman |
| 2018/0120161 A1 | 5/2018 | Qiu |
| 2018/0120162 A1 | 5/2018 | Qiu |
| 2018/0149802 A1 | 5/2018 | Krames |
| 2018/0154297 A1 | 6/2018 | Maletich |
| 2018/0157864 A1 | 6/2018 | Tribble |
| 2018/0160944 A1 | 6/2018 | Aubert |

(56) References Cited

U.S. PATENT DOCUMENTS

| | | |
|---|---|---|
| 2018/0165588 A1 | 6/2018 | Saxena |
| 2018/0166171 A1 | 6/2018 | Pulitzer |
| 2018/0178063 A1 | 6/2018 | Silver |
| 2018/0182472 A1 | 6/2018 | Preston |
| 2018/0188701 A1 | 7/2018 | Billings |
| 2018/0193589 A1 | 7/2018 | Mclaughlin |
| 2018/0196925 A1 | 7/2018 | Mukherjee |
| 2018/0197625 A1 | 7/2018 | Lobach |
| 2018/0197637 A1 | 7/2018 | Chowdhury |
| 2018/0197638 A1 | 7/2018 | Blanshard |
| 2018/0206783 A1 | 7/2018 | Yoon |
| 2018/0207445 A1 | 7/2018 | Maxik |
| 2018/0209683 A1 | 7/2018 | Cho |
| 2018/0216843 A1 | 8/2018 | Zhou |
| 2018/0218289 A1 | 8/2018 | Albrecht |
| 2018/0226158 A1 | 8/2018 | Fish |
| 2018/0240274 A1 | 8/2018 | Cronin |
| 2018/0247029 A1 | 8/2018 | Fish |
| 2018/0250430 A1 | 9/2018 | Machovina |
| 2018/0264224 A1 | 9/2018 | Gronfier |
| 2018/0266718 A1 | 9/2018 | Gillette |
| 2018/0285934 A1 | 10/2018 | Baughman |
| 2018/0295696 A1 | 10/2018 | Li |
| 2018/0295704 A1 | 10/2018 | Haverlag |
| 2018/0308390 A1 | 10/2018 | Moser |
| 2018/0311464 A1 | 11/2018 | Krames |
| 2018/0318602 A1 | 11/2018 | Ciccarelli |
| 2018/0320919 A1 | 11/2018 | Tang |
| 2018/0322240 A1 | 11/2018 | Goyal |
| 2018/0322253 A1 | 11/2018 | Goyal |
| 2018/0322255 A1 | 11/2018 | Connell, II |
| 2018/0330626 A1 | 11/2018 | Donadio |
| 2018/0331845 A1 | 11/2018 | Warren |
| 2018/0336500 A1 | 11/2018 | Pinho |
| 2018/0336530 A1 | 11/2018 | Johnson |
| 2018/0339127 A1 | 11/2018 | Van Reen |
| 2018/0342327 A1 | 11/2018 | Madan |
| 2018/0349689 A1 | 12/2018 | Lee |
| 2018/0349945 A1 | 12/2018 | Jayaraman |
| 2018/0350455 A1 | 12/2018 | Rosen |
| 2018/0350456 A1 | 12/2018 | Kendrick |
| 2018/0351758 A1 | 12/2018 | Becker |
| 2018/0351761 A1 | 12/2018 | Li |
| 2018/0353073 A1 | 12/2018 | Boucher |
| 2018/0353108 A1 | 12/2018 | Prate |
| 2018/0358117 A1 | 12/2018 | Neagle |
| 2018/0358129 A1 | 12/2018 | Gorzelniak |
| 2018/0358130 A1 | 12/2018 | Schmidt |
| 2018/0369637 A1 | 12/2018 | Hoang |
| 2018/0373843 A1* | 12/2018 | Baughman ............. G16H 20/00 |
| 2018/0374053 A1 | 12/2018 | Willamowski |
| 2018/0374572 A1 | 12/2018 | Ackerman |
| 2018/0374586 A1 | 12/2018 | Baughman |
| 2019/0001059 A1 | 1/2019 | Handler |
| 2019/0005844 A1 | 1/2019 | Dragicevic |
| 2019/0007424 A1 | 1/2019 | Ford |
| 2019/0007927 A1 | 1/2019 | Blahnik |
| 2019/0010603 A1 | 1/2019 | Boughton |
| 2019/0011146 A1 | 1/2019 | Seo |
| 2019/0013960 A1 | 1/2019 | Sadwick |
| 2019/0014643 A1 | 1/2019 | Gharabegian |
| 2019/0024926 A1 | 1/2019 | Kim |
| 2019/0028549 A1 | 1/2019 | Ledvina |
| 2019/0041080 A1 | 2/2019 | Higuchi |
| 2019/0046109 A1 | 2/2019 | Lewis |
| 2019/0056126 A1 | 2/2019 | Law |
| 2019/0057615 A1 | 2/2019 | Mullen |
| 2019/0075687 A1 | 3/2019 | Brunstetter |
| 2019/0091700 A1 | 3/2019 | Hilbig |
| 2019/0107267 A1 | 4/2019 | Luo |
| 2019/0193508 A1 | 6/2019 | Ganem |
| 2019/0209806 A1 | 7/2019 | Allen |
| 2019/0215184 A1 | 7/2019 | Emigh |
| 2019/0224445 A1 | 7/2019 | Fernandes |
| 2019/0268999 A1 | 8/2019 | Oobayashi |
| 2019/0281681 A1 | 9/2019 | De Bries |
| 2019/0297700 A1 | 9/2019 | Gal |
| 2019/0309975 A1 | 10/2019 | Salem |
| 2019/0320516 A1 | 10/2019 | Parker |
| 2019/0350066 A1 | 11/2019 | Herf |
| 2019/0366032 A1 | 12/2019 | Lockley |
| 2020/0011563 A1 | 1/2020 | Jeong |
| 2020/0101893 A1 | 4/2020 | Studeny |
| 2020/0103841 A1 | 4/2020 | Pillai |
| 2020/0182495 A1 | 6/2020 | Park |
| 2020/0224915 A1 | 7/2020 | Nourbakhsh |
| 2020/0229289 A1 | 7/2020 | Cahill |
| 2020/0298168 A1 | 9/2020 | Lee |
| 2020/0340700 A1 | 10/2020 | Park |
| 2021/0116144 A1 | 4/2021 | Morgan |
| 2021/0207833 A1 | 7/2021 | Dameno |
| 2021/0239339 A1 | 8/2021 | Morgan |
| 2021/0379524 A1 | 12/2021 | Prigge |

FOREIGN PATENT DOCUMENTS

| | | |
|---|---|---|
| CN | 1150882 | 5/1997 |
| CN | 1544222 | 11/2004 |
| CN | 1971268 | 5/2007 |
| CN | 101421558 | 4/2009 |
| CN | 201414191 Y | 2/2010 |
| CN | 101963607 | 2/2011 |
| CN | 101976063 | 2/2011 |
| CN | 102073935 | 5/2011 |
| CN | 102262710 | 11/2011 |
| CN | 202075431 | 12/2011 |
| CN | 102305451 | 1/2012 |
| CN | 202551821 | 11/2012 |
| CN | 103040443 A | 4/2013 |
| CN | 103197659 A | 7/2013 |
| CN | 103277870 | 9/2013 |
| CN | 203175090 U | 9/2013 |
| CN | 103531174 A | 1/2014 |
| CN | 103604198 A | 2/2014 |
| CN | 203454309 U | 2/2014 |
| CN | 204759076 | 11/2015 |
| EP | 0710804 | 5/1996 |
| EP | 1067825 | 1/2001 |
| EP | 1271442 | 1/2003 |
| EP | 1511218 | 3/2005 |
| EP | 1821582 | 8/2007 |
| EP | 2016879 | 1/2009 |
| EP | 2132960 | 12/2009 |
| EP | 2296448 | 3/2011 |
| EP | 2431541 | 3/2012 |
| EP | 2488912 | 8/2012 |
| EP | 3297218 | 10/2020 |
| JP | S60110520 A | 6/1985 |
| JP | H04341243 | 11/1992 |
| JP | H0552361 A | 3/1993 |
| JP | H0658593 | 3/1994 |
| JP | H0658593 A | 3/1994 |
| JP | H06159763 A | 6/1994 |
| JP | H06225858 A | 8/1994 |
| JP | H09303842 A | 11/1997 |
| JP | H10238089 A | 9/1998 |
| JP | 2000130828 | 5/2000 |
| JP | 2000294388 | 10/2000 |
| JP | 2001224078 | 8/2001 |
| JP | 2001286226 | 10/2001 |
| JP | 2001314882 | 11/2001 |
| JP | 2002042546 A | 2/2002 |
| JP | 2002059152 A | 2/2002 |
| JP | 2003042507 | 2/2003 |
| JP | 2003042509 | 2/2003 |
| JP | 2003083590 | 3/2003 |
| JP | 2003232559 | 8/2003 |
| JP | 2004005313 A | 1/2004 |
| JP | 2004053130 A | 2/2004 |
| JP | 2005040769 A | 2/2005 |
| JP | 2005177726 | 7/2005 |
| JP | 2005211319 | 8/2005 |
| JP | 2005235634 | 9/2005 |
| JP | 2006210045 | 8/2006 |

(56) References Cited

FOREIGN PATENT DOCUMENTS

| | | |
|---|---|---|
| JP | 2006522699 | 10/2006 |
| JP | 2006321721 | 11/2006 |
| JP | 2006348600 | 12/2006 |
| JP | 2007170761 | 7/2007 |
| JP | 2007184436 | 7/2007 |
| JP | 2008125541 | 6/2008 |
| JP | 2008157548 | 7/2008 |
| JP | 2008204640 | 9/2008 |
| JP | 2010119563 | 6/2010 |
| JP | 2010182661 | 8/2010 |
| JP | 2010239878 | 10/2010 |
| JP | 2011146137 | 7/2011 |
| JP | 2012001931 | 1/2012 |
| JP | 2012149839 A | 8/2012 |
| JP | 2013140523 A | 7/2013 |
| KR | 20000009824 A | 2/2000 |
| KR | 20010048235 | 6/2001 |
| KR | 20030074107 A | 9/2003 |
| KR | 20050003899 | 1/2005 |
| KR | 100771486 | 10/2007 |
| KR | 100804892 | 2/2008 |
| KR | 101102733 | 1/2012 |
| KR | 20120004243 | 1/2012 |
| KR | 101135926 | 4/2012 |
| KR | 20120039359 A | 4/2012 |
| KR | 20130108709 | 10/2013 |
| KR | 20130124184 | 11/2013 |
| WO | 0039964 | 7/2000 |
| WO | 2000058873 | 10/2000 |
| WO | 2004037301 | 5/2004 |
| WO | 2007026387 | 3/2007 |
| WO | 2008043396 | 4/2008 |
| WO | 2008051222 | 5/2008 |
| WO | 2008102308 | 8/2008 |
| WO | 2008120127 | 10/2008 |
| WO | 2008135093 | 11/2008 |
| WO | 2009030641 | 3/2009 |
| WO | 2009044330 | 4/2009 |
| WO | 2009044330 A1 | 4/2009 |
| WO | 2010046875 | 4/2010 |
| WO | 2010087386 | 8/2010 |
| WO | 2010115720 | 10/2010 |
| WO | 2011033377 | 3/2011 |
| WO | 2011046875 | 4/2011 |
| WO | 2012104773 | 8/2012 |
| WO | 2012151407 | 11/2012 |
| WO | 2013014337 | 1/2013 |
| WO | 2013049297 | 4/2013 |
| WO | 2013175348 | 11/2013 |
| WO | 2014013376 | 1/2014 |
| WO | 2014036133 | 3/2014 |
| WO | 2014071046 | 5/2014 |
| WO | 2015130786 | 9/2015 |
| WO | 2015200730 A1 | 12/2015 |
| WO | 2016019005 A1 | 2/2016 |
| WO | 2016115230 | 7/2016 |
| WO | 2016154320 | 9/2016 |
| WO | 2017008321 | 1/2017 |
| WO | 2018039433 | 3/2018 |
| WO | 2018157063 | 8/2018 |
| WO | 2019046580 | 3/2019 |
| WO | 2019151684 | 8/2019 |
| WO | 2019204779 | 10/2019 |
| WO | 2020014688 | 1/2020 |
| WO | 2020073723 | 4/2020 |
| WO | 2020075189 | 4/2020 |
| WO | 2020104878 | 5/2020 |
| WO | 2020146315 | 7/2020 |
| WO | 2020189819 | 9/2020 |
| WO | 2021011822 | 1/2021 |
| WO | 2021249653 | 12/2021 |
| WO | 2021252439 | 12/2021 |

OTHER PUBLICATIONS

"Adolescent Psychology Around the World", Edited by Jeffrey Jensen Arnett, Ph.D., Clark University, Worcester, MA, 2012, (30 pages).

"ANSI/ASAS12.60-2010/Part 1 American National Standard Acoustical Performance Criteria, Design Requirements, and Guidelines for Schools, Part 1: Permanent Schools", Acoustical Society of America, 2010, 44 pgs.

"Cochrane Handbook for Systematic Reviews of Interventions", Cochrane Book Series, Edited by Julian PT Higgins and Sally Green, 2008, 17 pgs.

"Daylight Metrics: Pier Daylighting Plus Research Program", Public Interest Energy Research (PIER) Program Final Project Report, Feb. 2012, 387 pgs.

"Depression and Other Common Mental Disorders", Global Health Estimates, World Health Organization, 2017, 24 pgs.

"Depression: A Global CrisisWorld Mental Health Day, Oct. 10, 2012", World Federation for Mental Health, (2012), (32 pages).

"Ergonomics of the thermal environment—Analytical determination and interpretation of thermal comfort using calculation of the PMV and PPD indices and local thermal comfort criteria", International Standard, Third edition, Nov. 15, 2005, 11 pgs.

"Evidence-based methodologies for public health—How to assess the best available evidence when time is limited and there is lack of sound evidence", European Centre for Disease Prevention and Control, Stockholm: ECDC; 2011, 67 pgs.

"Global Burden of Disease Study 2015 provides GPS for global health 2030", www.thelancet.com, vol. 388, Octobers, 2016, pp. 1448-1449.

"Global status report on alcohol and health 2014", World Health Organization, 2014, 392 pgs.

"Global, regional, and national age-sex specific all-cause and cause-specific mortality for 240 causes of death, 1990-2013: a systematic analysis for the Global Burden of Disease Study 2013", www.thelancet.com, vol. 385, Jan. 10, 2015, pp. 117-171.

"Global, regional, and national life expectancy, all-cause mortality, and cause-specific mortality for 249 causes of death, 1980-2015: a systematic analysis for the Global Burden of Disease Study 2015", www.thelancet.com, vol. 388, Oct. 8, 2016, pp. 1459-1544.

"Haemoglobin concentrations for the diagnosis of anaemia and assessment of severity", Vitamin and Mineral Nutrition Information System. Geneva, World Health Organization, 2011, pp. 1-6.

"Hazard Prevention and Control in the Work Environment: Airborne Dust", Occupational and Environmental Health Series, Department of Protection of the Human Environment, World Health Organization, Geneva, Dec. 1999, 224 pgs.

"IARC Monographs on the Evaluation of Carcinogenic Risks to Humans" vol. 90 Human papillomaviruses, World Health Organization International Agency for Research on Cancer, Lyon, France, 2007, 690 pgs.

"Light and Lighting—Basic terms and criteria for specifying lighting requirements", The National Standards Authority of Ireland. (2011), (7 pages).

"My Plate My Wins, Make half your grains whole grains", Center for Nutrition Policy and Promotion. United States Department of Agriculture, Oct. 2016, (1 page).

"Progress on Drinking Water, Sanitation and Hygiene, 2017, Update and SDG Baselines", World Health Organization (WHO) and the United Nations Children's Fund (UNICEF), 2017, 116 pgs.

"Sodium in Your Diet Use the Nutrition Facts Label and Reduce Your Intake", U.S. Food and Drug Administration. Mar. 2020, (4 pages).

"State Council Air Pollution Prevention and Control Action Plan, China Clean Air Updates", Clean Air Alliance of China, Issue II, 2013, English Translation, 20 pgs.

"WHO Framework Convention on Tobacco Control," World Health Organization 2003, updated reprint 2004, 2005, (44 pages).

(56) References Cited

OTHER PUBLICATIONS

Ahmed, Tahmeed, et al.; "Global Burden of Maternal and Child Undernutrition and Micronutrient Deficiencies", Ann Nutr Metab 2012;61(suppl 1):8-17.
Ajzen, I. "Nature and operation of attitudes", Annual review of psychology vol. 52: 27-58 (2001).
Alfano, Francesca Romana d'Ambrosio et al. "On the measurement of the mean radiant temperature and its influence on the indoor thermal environment assessment", Building and Environment 63: 79-88, (2013).
Alonso-Coello, Pablo, et al.; "Grade Evidence to Decision (EtD) frameworks: a systematic and transparent approach to making well informed healthcare choices. 1: Introduction"; BMJ 2016; 353:12016, http://dx.doi.org/10.1136/bmj.i2016, 10 pgs.
Arnett, Jeffrey J. "The neglected 95%: why American psychology needs to become less American." The American psychologist vol. 63, 7 : 602-14, (2008).
Arundel, Anthongy V., et al.; "Indirect Health Effects of Relative Humidity in Indoor Environments", Environmental Health Perspectives vol. 65, pp. 351-361, 1986.
Astolfi, Arianna, and Franco Pellerey. "Subjective and objective assessment of acoustical and overall environmental quality in secondary school classrooms." The Journal of the Acoustical Society of America vol. 123,1: 163-73, (2008).
Atmaca, Ibrahim, et al.; "Effects of radiant temperature on thermal comfort", Building and Environment 42 (2007) 3210-3220.
Bandura, A. "Self-efficacy", In V. S. Ramachaudran (Ed.), Encyclopedia of human behavior (vol. 4, pp. 71-81) (1994). New York: Academic Press. (Reprinted in H. Friedman [Ed.], Encyclopedia of mental health. San Diego: Academic Press, (1998).
Barclay, Laurie, J., et al.; "Healing the Wounds of Organizational Injustice: Examining the Benefits of Expressive Writing", Journal of Applied Psychology 2009, vol. 94, No. 2, 511-523.
Bornehag, C. G., et al.; "Dampness in Buildings and Health: Nordic Interdisciplinary Review of the Scientific Evidence on Associations between Exposure to "Dampness" in Buildings and Health Effects (NORDDAMP)", Indoor Air 2001; 11: 72-86.
Bradley, J. S., et al.; "Describing Levels of Speech Privacy in Open-Plan Offices", NRC Publications Archive, National Research Council of Canada, Sep. 12, 2003, 29 pgs.
Cavanaugh, William J. et al. "Speech Privacy in Buildings." Journal of the Acoustical Society of America 34: 475-492, (1962).
D. A. Mcintyre, "Response to Atmospheric Humidity at Comfortable Air Temperature: A Comparison of Three Experiments", The Annals of Occupational Hygiene, vol. 21, Issue 2, Aug. 1978, pp. 177-190.
Edgerton, V. R., et al.; "Elevation of Hemoglobin and Work Tolerance in Iron-Deficient Subjects", J. Nutr. Sci. Vitaminol., 27, 77-86, 1981.
Evans, G W, and D Johnson. "Stress and open-office noise." The Journal of applied psychology vol. 85,5: 779-83, (2000).
Fanger, P. O.; "Assessment of man's thermal comfort in practice", British Journal of Industrial Medicine, 1973, 30, 313-324.
Fanger, PO; "Olf and decipol: New units for perceived air quality," Building Serv. Eng. Res. Technol. 9(4) 155-157 (1988), (3 pages).
Fanger, PO; "Local Discomfort to the Human Body Caused by Non-Uniform Thermal Environments", Annals of Occupational Hygiene 20: 285-291 (1977).
Fitzgerald, Sarah, et al.; "A cost-analysis of complex workplace nutrition education and environmental dietary modification interventions", BMC Public Health (2017) 17:49, 10 pgs.
Fox, Marilyn L., et al.; "Effects of Stressful Job Demands and Control on Physiological and Attitudinal Outcomes in a Hospital Setting", The Academy of Management Journal, Apr., 1993, vol. 36, No. 2 (Apr. 1993), pp. 289-318.
GBD 2015 Tobacco Collaborators. "Smoking prevalence and attributable disease burden in 195 countries and territories, 1990-2015: a systematic analysis from the Global Burden of Disease Study 2015." Lancet (London, England) vol. 389,10082: 1885-1906, (2017).

Global, regional, and national disability-adjusted life-years (DALYs) for 315 diseases and injuries and healthy life expectancy (HALE), 1990-2015: a systematic analysis for the Global Burden of Disease Study 2015, www.thelancet.com, vol. 388, Oct. 8, 2016, pp. 1603-1658.
Greenwald, Anthony G et al. "Understanding and using the Implicit Association Test: III. Meta-analysis of predictive validity." Journal of personality and social psychology vol. 97,1: 17-41, (2009), (25 pages).
Gunnar, Megan, and Karina Quevedo. "The neurobiology of stress and development." Annual review of psychology vol. 58: 145-73, (2007), (33 pages).
Henrich, J., Heine, S. & Norenzayan, A. "Most people are not Weird", Nature 466, 29 (2010), (1 Page).
Hertenstein, Matthew J et al. "The communication of emotion via touch." Emotion (Washington, D.C.) vol. 9,4: 566-73, (2009), (8 pages).
Hoffman, Steven J, and Charlie Tan. "Overview of systematic reviews on the health-related effects of government tobacco control policies", BMC public health vol. 15 744. Aug. 5, 2015, (11 pages).
Humphreys, Michael A., "Quantifying occupant comfort: are combined indices of the indoor environment practicable?", Building Research & Information, 33:4, 317-325, (2005), (10 pages).
Jensen, KL, et al.; "Acoustical Quality in Office Workstations, as Assessed by Occupant Surveys", Proceedings: Indoor Air (2002) UC Berkeley Indoor Environmental Quality (IEQ), Sep. 4, 2005, 6 pgs.
Kaplan, Seth, et al. "Measurement of Emotions." Research Methods in Occupational Health Psychology: Measurement, Design, and Data Analysis, 1st ed., Routledge, New York, New York, 2012, pp. 61-75.
Lai et al., "An evaluation model for indoor environmental quality (IEQ) acceptance in residential buildings," 2009, vol. 41, pp. 930-9636.
Lai, A.C.K, et al.; "An evaluation model for indoor environmental quality (IEQ) acceptance in residential buildings", Energy and Buildings 41 (2009) 930-936.
Lai, H. K., and Yik, F. W. H., "Perception of importance and performance of the indoor environmental quality of high-rise residential buildings", Building and Environment, 44(2), 352-360 (2009).
Lai, Joseph H. K. and Francis W.H. Yik. "Perceived Importance of the Quality of the Indoor Environment in Commercial Buildings." Indoorand Built Environment 16: 311-321, (2007).
Leavitt, Keith, et al.; "Asking about well-being gets you half an answer: Intra-individual processes of implicit and explicit job attitudes", Journal of Organizational Behavior, J. Organiz. Behav. 32, 672-687 (2011).
Li, Danny H. W., et al.; "A simplified procedure for determining indoor daylight illuminance using daylight coefficient concept", Building and Environment 41 (2006) 578-589.
Mardaljevic, J., et al.; "Daylighting Metrics: Is There a Relation Between Useful Daylight Illuminance and Daylight Glare Probability?", First Building Simulation and Optimization Conference Loughborough, UK, Sep. 10-11, 2012, 189-196.
Moya-Albiol, Luis et al. "Job satisfaction and cortisol awakening response in teachers scoring high and low on burnout." The Spanish journal of psychology vol. 13,2: 629-36, (2010).
Nabil, A. and Mardaljevic, John, "Useful daylight illuminance: A new paradigm for assessing daylight in buildings", Lighting Research & Technology—Lighting Res Technol. 37. 41-59, (2005).
Nabil, Azza and John Mardaljevic. "Useful daylight illuminances: A replacement for daylight factors." Energy and Buildings 38: 905-913, (2006).
Newsham, Guy R.; "Clothing as a thermal comfort moderator and the effect on energy consumption", Energy and Buildings 26 (1997) 283-291.
Oberg, Mattias et al. "Worldwide burden of disease from exposure to second-hand smoke: a retrospective analysis of data from 192 countries." Lancet (London, England) vol. 377,9760: 139-46, (2011).
Oxizidis, S., et al.; "Typical Weather Years and the Effect of Urban Microclimate on the Energy Behaviour of Buildings and HVAC Systems", Advances in Building Energy Research, 2007, vol. 1, 26 pages.

(56) References Cited

OTHER PUBLICATIONS

Pattakos, Alex, et al.; "Discovering Meaning Through the Lens of Work", Journal of Constructivist Psychology, 30:1, 42-49 (2017), (9 pages).
Pennebaker, James W. "Writing about Emotional Experiences as a Therapeutic Process." Psychological Science 8, No. 3: 162-66, (1997).
Pennebaker, James W., et al.; "Accelarating the Coping Process", Journal of Personality and Social Psychology, 1990, vol. 58, No. 3, 528-537.
Pruessner, Jens C., et al.; "Burnout, Perceived Stress, and Cortisol Responses to Awakening", Psychosomatic Medicine 61:197-204 (1999).
Rocha, Maria C. et al., "Stress among nurses: An examination of salivary cortisol levels on work and day off", Revista da Escola de Enfermagem da U S p. 47. 1187-1194 (2013).
Safizadeh, M. Reza, et al.; "Evaluation of Radiant Ceiling Heating Systems for Renovated Buildings based on Thermal Comfort Criteria", Windsor Conference Rethinking comfort, Apr. 12-15, 2018, 16 pgs.
Salter, Charles M. et al.; "Case studies of a method for predicting speech privacy in the contemporary workplace", UC Berkeley Indoor Environmental Quality (IEQ), Center for the Build Environment, 2003, 48 pgs.
Schlegel, Jay C., "The Relative Effects of Convection and Radiation Heat Transfer on The Thermal Sensations of Sedentary Objects", Kansas State University, (1968), (73 pages).
Shea, Beverley J., et al.; "Development of AMSTAR: a measurement tool to assess the methodological quality of systematic reviews", BMC Medical Research Methodology 2007, 7:10, 7 pgs.
Smith, Emma et al. "The global burden of other musculoskeletal disorders: estimates from the Global Burden of Disease 2010 study." Annals of the rheumatic diseases vol. 73,8: 1462-9, (2014).
Song, Gook-Sup; "Could sperm quality be affected by a building environment? A literature review", Building and Environment 45 (2010) 936-943.
Steger, Michael, et al. "Measuring meaningful work: The Work as Meaning Inventory (WAMI)", Journal of Career Assessment—J Career Assessment. 20. 322-337,(2012).
Strauss, Richard. H., et al.; "Influence of Heat and Humidity on the Airway Obstruction Induced by Exercise in Asthma", The Journal of Clinical Investigation, vol. 61, Feb. 1978, 433-440.
Tracy, Jessica L., and Richard W. Robins, "Show Your Pride: Evidence for a Discrete Emotion Expression", Psychological Science 15, No. 3:194-97, (2004).
Vining, R F et al. "Salivary cortisol: a better measure of adrenal cortical function than serum cortisol", Annals of clinical biochemistry vol. 20 (Pt 6): 329-35, (1983).
Wang, Jiandong et al. "Particulate matter pollution over China and the effects of control policies." The Science of the total environment vol. 584-585: 426-447, (2017).
Weibel, Laurence et al. "Work-related stress in an emergency medical dispatch center." Annals of emergency medicine vol. 41,4: 500-506, (2003), (7 pages).
Wong et al., "A multivariate-logistic model for acceptance of indoor environmental quality (IEQ) in offices," 2007, Building and Environment, vol. 48, pp. 1-6.
Wong, L. T., et al.; "A multivariate-logistic model for acceptance of indoor environmental quality (IEQ) in offices", Building and Environment 43 (2008) 1-6.
World Health Organization. (2019). Nutrition Landscape Information System (NLiS) country profile indicators: interpretation guide, 2nd ed. World Health Organization, https://apps.who.int/iris/handle/10665/332223. License: CC BY-NC-SA 3.0 IGO.
Zakowski, Sandra G et al. "Written emotional disclosure buffers the effects of social constraints on distress among cancer patients." Health psychology : official journal of the Division of Health Psychology, American Psychological Association vol. 23,6: 555-63, (2004).

American Society of Heating, Refrigerating and Air-Conditioning Engineers (ASHRAE), "Indoor Air Quality Guide, Best Practices for Design, Construction and Commissioning", ASHRAE Philadelphia Chapter, May 14, 2009, http://ashraephilly.org/images/downloads/Presentation_Archives/0509.pdf, Accessed Nov. 27, 2017 (19 pages).
Fanger, P.O., "Introduction of the olf and the decipol units to quantify air pollution perceived by humans indoors and outdoors", Building Serv. Eng. Res. Technol. 9(4), 1988, pp. 155-157 (3 pages).
Hastings, R., "Accommodating Seasonal Affective Disorder", https://www.shrm.org/resourcesandtools/hr-topics/employeerelations/pages/accommodatingsad.aspx. Dec. 21, 2009, Accessed Oct. 27, 2017 (3 pages).
Hu, Yi-meng et al., "Effects of probiotics supplement in patients with type 2 diabetes mellitus: A meta-analysis of randomized trials", Medicina Clinica (English Edition), vol. 148, Issue 8, Apr. 21, 2017, pp. 362-370 (6 pages).
National Center for Health Statistics (CDC), National Health Interview Survey (Adult Physical Activity Information; Glossary), https://www.cdc.gov/nchs/nhis/physical_activity/pa_glossary.htm, 2017 (2 pages).
Thompson, J. et al., "Effects of daily iron supplementation in 2- to 5-year-old children: systematic review and meta-analysis", Pediatrics. 2013; vol. 131, No. 4, pp. 739-753 (16 pages).
Trust for America'S Health, "A healthier America 2013: strategies to move from sick care to health care in the next four years", Issue Report, Jan. 2013, http://healthyamericans.org/assets/files/TFAH2013HealthierAmericaFnlRv.pdf, Accessed Nov. 30, 2017 (100 pages).
US Environmental Protection Agency, National Oceanic and Atmospheric Administration, National Park Service, et al., "Extremely high levels of PM2.5: steps to reduce your exposure", AirNow, https://airnow.gov/index.cfm?action=aqibasics.pmhilevels, Accessed Nov. 27, 2017 (4 pages).
Van Der Scheer J.W., et al., "Effects of exercise on fitness and health of adults with spinal cord injury: A systematic review", Neurology, 2017 (34 pages).
World Health Organization, "Nutritional Anaemias: Tools for Effective Prevention and Control", Geneva: World Health Organization; 2017, available online: http://apps.who.int/iris/bitstream/10665/66914/1/WHO_NHD_01,3.pdf (96 pages).
"Active Design Guidelines: Promoting Physical Activity and Health in Design," New York City Departments of Design and Construction, 2010.
"Assembly: Civic Design Guidelines," Center for Active Design, 2018.
"Leed Reference Guide for Building Design and Construction," U.S. Green Building Council, 2013, (67 pages).
"Policy recommendations on protection from exposure to second-hand tobacco smoke," World Health Organization, 2007, pp. 1-50 (56 pages).
"Preventing Diarrhoea Through Better Water, Sanitation and Hygiene: Exposures and impacts in low- and middle-income countries," World Health Organization, 2014, pp. 1-33 (48 pages).
"Proceedings: vol. 1—Indoor Air Quality (IAQ), building related diseases and human response," Healthy Buildings, 2006 (361 pages).
"Social determinants of mental health," World Health Organization and Calouste Gulbenkian Foundation, 2014, pp. 1-52 (54 pages).
Abrahamsson et al., "Impairment of Contrast Sensitivity Function (CSF) as a Measure of Disability Glare," Investigative Ophthalmology & Visual Science, 1986, vol. 27, pp. 1131-1136.
Abt et al., "Characterization of Indoor Particle Sources: A Study Conducted in the Metropolitan Boston Area," Environmental Health Perspectives, 2000, vol. 108, No. 1, pp. 35-44.
Advances in Building Energy Research, 2007, vol. 1 (263 pages).
Ahn, "Synthesis and Characterization of Nanostructured ZnO and SnOx for VOC Sensor Devices," 2011 (204 pages).
Akacem et al., "Bedtime and evening light exposure influence circadian timing in preschoolage children," Neurobiology of Sleep and Circadian Rhythms, 2016, vol. 1, pp. 27-31.
Akacem et al., "Sensitivity of the circadian system to evening bright light in preschool-age children," Physiological Reports, 2018, vol. 6, No. 5, pp. 1-10.

(56) References Cited

OTHER PUBLICATIONS

Al Horr et al., "Occupant productivity and office indoor environment quality: A review of the literature," Building and Environment, 2016, vol. 105, pp. 369-389.
Allen, Michele L. et al., "Effective Parenting Interventions to Reduce Youth Substance Use: A Systematic Review," Pediatrics, 2016, vol. 138, No. 2 (19 pages).
Allergy Buyers Club, "Philips Wake Up Light Dawn Simulators Alarm Clocks," retrieved from http://www.allergybuyersclub.com/philips-wake-up-light-dawn-simulator-alarm-clocks.html, retrieved on Aug. 13, 2012, 2 pages.
Amaral et al., "An Overview of Particulate Matter Measurement Instruments," Atmosphere, 2015, vol. 6, pp. 1327-1345.
Amendment, filed Jan. 25, 2018, for U.S. Appl. No. 15/421,046, Eisele et al., "LED Lighting System," 6 pages.
American Diabetes Association, "Standards of Medical Care in Diabetes—2017 Abridged for Primary Care Providers," Clinical Diabetes, 2017, vol. 35, No. 1, pp. 5-26 (22 pages).
American Society of Heating, Refrigerating and Air-Conditioning Engineers et al., "Indoor Air Quality Guide: Best Practices for Design, Construction and Commissioning," 2009 (198 pages).
American Society of Heating, Refrigerating and Air-Conditioning Engineers, "Indoor Air Quality Guide: Best Practices for Design, Construction and Commissioning," 2009 (19 pages).
American Society of Heating, Refrigerating and Air-Conditioning Engineers, Inc., ASHRAE Standard 55-2010: Thermal Environmental Conditions for Human Occupancy (44 pages).
American Ultraviolet, "Handheld Germicidal Fixtures," retrieved from http://americanultraviolet.com/germicidal_solutions/commercial_products/handheld..., retrieved on Aug. 13, 2012, 1 page.
American Ultraviolet, "In Room Germicidal Solutions," HVAC MRS (0810/2.5M), retrieved from http://www.americanultraviolet.com, 2 pages.
Anderson et al., "Clearing the Air: A Review of the Effects of Particulate Matter Air Pollution on Human Health," Journal of Medical Toxicology, 2012, vol. 8, pp. 166-175.
Apaydin, Erica A. et al., "Asystematic review of St. John's wort for major depressive disorder," Systematic Reviews, 2016, vol. 5, No. 148 (25 pages).
Aries et al., "Daylight and health: A review of the evidence and consequences forthe built environment," Lighting Research & Technology, 2015, vol. 47, pp. 6-27.
Aries et al., "Windows, view, and office characteristics predict physical and psychological discomfort," Journal of Environmental Psychology, 2010, vol. 30, pp. 533-541.
Aries, "Human lighting demands: healthy lighting in an office environment," thesis, 2005 (159 pages).
Arrington et al., "Voluntary Task Switching: Chasing the Elusive Homunculus," Journal of Experimental Psychology: Learning, Memory, and Cognition, 2005, vol. 31, No. 4, pp. 683-702.
Arundel et al., "Indirect Health Effects of Relative Humidity in Indoor Environments," Environmental Health Perspectives, 1986, vol. 65, pp. 351-361.
Astolfi et al., "Subjective and objective assessment of acoustical and overall environmental quality in secondary school classrooms," The Journal of the Acoustical Society of America, 2008, vol. 123, No. 1, pp. 163-173.
Atmaca et al., "Effects of radiant temperature on thermal comfort," Building and Environment, 2007, vol. 42, pp. 3210-3220.
Atmaca et al., "Predicting the effect of relative humidity on skin temperature and skin wettedness," Journal of Thermal Biology, 2006, vol. 31, pp. 442-452.
Australian Examination report No. 1, dated Dec. 13, 2017, for Australian Application No. 2017200995, 6 pages.
Australian Patent Examination Report, dated Sep. 14, 2016, for Australian Application No. 2013308871, 5 pages.
Averett et al., "Titanium Dioxide Photocatalytic Compositions and Uses Thereof," U.S. Appl. No. 61/482,393, filed May 4, 2011, 26 pages.

Babyak, Richard J., "Ready to roll," Appliance Manufacturer, 2000, vol. 48, No. 9, pp. 40-42.
Bakker et al., "User satisfaction and interaction with automated dynamic facades: a pilot study," Building and Environment, 2014, vol. 78, pp. 44-52.
Beauchemin et al., "Sunny hospital rooms expedite recovery from severe and refractory depressions," Journal of Affective Disorders, 1996, vol. 40, pp. 49-51.
Beaven et al., "A Comparison of Blue Light and Caffeine Effects on Cognitive Function and Alertness in Humans," PLoS One, 2013, vol. 8, No. 10 (7 pages).
Bekö et al., Ventilation rates in the bedrooms of 500 Danish children, Building and Environment, 2010, vol. 45, pp. 2289-2295.
Bell et al., "The Exposure-Response Curve for Ozone and Risk of Mortality and the Adequacy of Current Ozone Regulations," Environmental Health Perspectives, 2006, vol. 114, No. 4, pp. 532-536.
Bellicha, Alice et al., "A multistage controlled intervention to increase stair climbing at work: effectiveness and process evaluation," International Journal of Behavioral Nutrition and Physical Activity, 2016, vol. 13, No. 47, pp. 1-9 (9 pages).
Benedetti, "Morning sunlight reduces length of hospitalization in bipolar depression," Journal of Affective Disorders, 2001, vol. 62, pp. 221-223.
Berman et al., "The Cognitive Benefits of Interacting With Nature," Psychological Science, 2008, vol. 19, No. 12, pp. 1207-1212.
Berto, "Exposure to restorative environments helps restore attentional capacity," Journal of Environmental Psychology, 2005, vol. 25, pp. 249-259.
Berto, "The Role of Nature in Coping with Psycho-Physiological Stress: A Literature Review on Restorativeness," Behavioral Sciences, 2014, vol. 4, pp. 394-409.
Besner et al., "The Stroop effect and the myth of automaticity," Psychonomic Bulletin & Review, 1997, vol. 4, No. 2, pp. 221-225.
Bhutta, Zulfiqar A. et al., "Evidence-based interventions for improvement of maternal and child nutrition: what can be done and at what cost?," The Lancet, 2013, vol. 382, pp. 452-447.
Bidonde, J. et al., "Aerobic exercise training for adults with fibromyalgia (Review)," Cochrane Database of Systematic Reviews, 2017, Issue 6 (130 pages).
Bierman et al., "Characterizing Daylight Photosensor System Performance to Help Overcome Market Barriers," Journal of the Illuminating Engineering Society, 2000, vol. 29, No. 1, pp. 101-115.
Bohn, Hendrik et al., "SIRENA—Service Infrastructure for Real-time Embedded Networked Devices: A service oriented framework for different domains," 2006 (7 pages).
Borisuit et al., "Effects of realistic office daylighting and electric lighting conditions on visual comfort, alertness and mood," Lighting Research and Technology, 2015, vol. 47, pp. 192-209.
Boubekri et al., "Impact of Windows and Daylight Exposure on Overall Health and Sleep Quality of Office Workers: A Case-Control Pilot Study," Journal of Clinical Sleep Medicine, 2014, vol. 10, No. 6, pp. 603-611.
Boubekri et al., "The Impact of Optimized Daylight and Views on the Sleep Duration and Cognitive Performance of Office Workers," International Journal of Environmental Research and Public Health, 2020, vol. 17, No. 3219, pp. 1-16.
Boubekri et al., "Windows and Environmental Satisfaction: A Survey Study of an Office Building," Indoor Environment, 1993, vol. 2, pp. 164-172.
Bourcier, Johann et al., "A Dynamic-SOA Home Control Gateway," 2006 (9 pages).
Brager, Gail S., et al., "Thermal adaptation in the built environment: a literature review," Energy and Buildings, 1998, vol. 27, pp. 83-96 (15 pages).
Braniš et al., "The effect of outdoor air and indoor human activity on mass concentrations of PM10, PM2.5, and PM1 in a classroom," Environmental Research, 2005, vol. 99, pp. 143-149.
Brook et al., "Particulate Matter Air Pollution and Cardiovascular Disease: An Update to the Scientific Statement From the American Heart Association," Circulation: Journal of the American Heart Association, 2010, vol. 121, pp. 2331-2378.

(56) References Cited

OTHER PUBLICATIONS

Brookstone, "Tranquil Moments® Advanced Sleep Sounds," 2012, retrieved from http://www.brookstone.com/tranquil-moments-advanced-sleep-sound . . . , retrieved on Apr. 28, 2014, 3 pages.
Brown et al., "Interventions to Reduce Harm from Smoking with Families in Infancy and Early Childhood: A Systematic Review," International Journal of Environmental Research and Public Health, 2015, vol. 12, pp. 3091-3119 (29 pages).
Brown et al., "Recommendations for healthy daytime, evening, and night-time indoor light exposure," Preprints, 2020 (21 pages).
Brown, Nicola et al., "Interventions to Reduce Harm from Smoking with Families in Infancy and Early Childhood: A Systematic Review ," International Journal of Environmental Research and Public Health, 2015, vol. 12, pp. 3091-3119, (29 pages).
Buchanan et al., "Air filter materials, outdoor ozone and building-related symptoms in the BASE study," Indoor Air, 2008, vol. 18, pp. 144-155.
Burge et al., "Sick Building Syndrome: A Study of 4373 Office Workers," Annals of Occupational Hygiene, 1987, vol. 31, No. 4A, pp. 493-504.
Bussières, André E., et al., "The Treatment of Neck Pain-Associated Disorders and Whiplash-Associated Disorders: A Clinical Practice Guideline,"Journal of Manipulative and Physiological Therapeutics, 2016, vol. 39, No. 8, pp. 523-564.e27 (69 pages).
Butler et al., "Effects of Setting on Window Preferences and Factors Associated With Those Preferences," Environment and Behavior, 1989, vol. 21, No. 1, pp. 17-31.
Byrne, Daniel W. et al., "Seven-Year Trends in Employee Health Habits From a Comprehensive Workplace Health Promotion Program at Vanderbilt University," Journal of Occupational and Environmental Medicine, Dec. 2011, vol. 53, No. 12, pp. 1372-1381 (10 pages).
Cairncross, Sandy, et al., "Water, sanitation and hygiene for the prevention of diarrhoea," International Journal of Epidemiology, 2010, vol. 39, pp. :i193-i205 (14 pages).
California Energy Commission, 2013 Building Energy Efficiency Standards for Residential and Nonresidential Buildings, CEC400-2012-004-CMF-REV2 (268 pages).
Campanella et al., "Well Living Lab: A New Tool for Measuring the Human Experience in the Built Environment," Conscious Cities Journal No. 2, Conscious Cities Anthology 2017: Bridging Neuroscience, Architecture and Technology, 2017 (5 pages).
Canadian Office Action, dated Jul. 18, 2017, for Canadian Application No. 2,946,367, 3 pages.
Canadian Office Action, dated Jul. 25, 2017, for Canadian Application No. 2,940,766, 6 pages.
Cao, Chunmei et al., "Effect of Active Workstation on Energy Expenditure and Job Performance: A Systematic Review and Meta-analysis," Journal of Physical Activity and Health, 2016, vol. 13, No. 5, pp. 562-571.
Carlucci, Salvatore et al., "A review of indices for assessing visual comfort with a view to their use in optimization processes to support building integrated design," Renewable and Sustainable Energy Reviews, 2015, vol. 47, pp. 1016-1033.
Carr et al., "Interventions for tobacco cessation in the dental setting (Review)," Cochrane Database of Systematic Reviews, 2012, Issue 6, pp. 1-38 (40 pages).
Carrer et al., "Assessment through Environmental and Biological Measurements of Total Daily Exposure to Volatile Organic Compounds of Office Workers in Milan, Italy," Indoor Air, 2000, vol. 10, pp. 258-268.
Center for Disease Control and Prevention, "Steps to Wellness: A Guide to Implementing the 2008 Physical Activity Guidelines for Americans in the Workplace" U.S. Department of Health Services, 2012, (120 pages).
Centers for Disease Control and Prevention, "Strategies to Prevent Obesity and Other Chronic Diseases: The CDC Guide to Strategies to Increase the Consumption of Fruits and Vegetables.," U.S. Department of Health and Human Services, 2011, pp. 1-60 (68 pages).

Chellappa et al., "Can light make us bright? Effects of light on cognition and sleep," Progress in Brain Research, 2011, vol. 190, 119-133.
Chellappa et al., "Non-Visual Effects of Light on Melatonin, Alertness and Cognitive Performance: Can Blue-Enriched Light Keep Us Alert?," PLoS One, 2011, vol. 6, No. 1 (11 pages).
Chellappa et al., "Sex differences in light sensitivity impact on brightness perception, vigilant attention and sleep in humans," Scientific Reports, 2017, vol. 7, No. 14215, pp. 1-9.
Chellappa, "Individual differences in light sensitivity affect sleep and circadian rhythms," Sleep, 2021, vol. 44, No. 2, pp. 1-10.
Chen et al., "The Effect of Blue-Enriched Lighting on Medical Error Rate in a University Hospital ICU," The Joint Commission Journal on Quality and Patient Safety, 2021, vol. 47, No. 3, pp. 165-175.
Chen, Chun-Yuan, "A MOM-based Home Automation Platform in Heterogeneous Environments," A Thesis Submitted to Institute of Computer Science and Engineering College of Computer Science National Chiao Tung University, 2006 (93 pages).
Chinese Office Action, dated May 5, 2016, for Chinese Application No. 201380051774.0, 10 pages.
Cho et al., "Effects of artificial light at night on human health: A literature review of observational and experimental studies applied to exposure assessment," Chronobiology International: The Journal of Biological and Medical Rhythm Research, 2015, pp. 1-17.
Choi et al., "Impacts of indoor daylight environments on patient average length of stay (ALOS) in a healthcare facility," Building and Environment, 2012, vol. 50, pp. 65-75.
Chou, "A Practical Guide to Hazardous Gas Monitors" Occupational Hazards, 2000, vol. 62, No. 9, pp. 61-66.
Christoffersen et al., "Windows and Daylight—A post-occupancy evaluation of Danish offices," 2000 (9 pages).
Chun et al., "Thermal diary: Connecting temperature history to indoor comfort," Building and Environment, 2008, vol. 43, pp. 877-885.
Clasen et al., "Interventions to improve water quality for preventing diarrhoea (Review)," Cochrane Database of Systematic Reviews, 2015, Issue 10, pp. 1-175 (178 pages).
Clements-Croome, "Work performance, productivity and indoor air," Scandinavian Journal of Work Environment & Health, 2008, pp. 69-78.
Communication pursuant to Article 94(3) EPC issued in EP Application No. 20191237.5 on Jun. 14, 2021 (13 pages).
Communication pursuant to Article 94(3) EPC, dated Mar. 15, 2018, for European Application No. 15 754 628.4-1222, 9 pages.
Communication pursuant to Article 94(3) EPC, dated Nov. 23, 2016, for European Application No. 13833105.3, 8 pages.
Communication pursuant to Rule 164(1) EPC, dated Mar. 30, 2016, for European Application No. 13833105.3-1853 / 2891019, 9 pages.
Corbijn Van Willenswaard, Kyrsten et al., "Music interventions to reduce stress and anxiety in pregnancy: a systematic review and meta-analysis," BMC Psychiatry, 2017, vol. 17, No. 271, pp. 1-9 (9 pages).
Corrected Notice of Allowance, dated Jun. 26, 2017, for U.S. Appl. No. 14/012,444, Pillai et al, "Systems, Methods and Articles for Enhancing Wellness Associated With Habitable Environments," 2 pages.
Corrected Notice of Allowance, dated Jun. 6, 2017, for U.S. Appl. No. 14/012,444, Pillai et al, "Systems, Methods and Articles for Enhancing Wellness Associated With Habitable Environments," 2 pages.
Coury, Helenice J.C.G et al., "Evaluation of the effectiveness of workplace exercise in controlling neck, shoulder and low back pain: a systematic review," Brazilian Journal of Physical Therapy, 2009, vo. 13, No. 6, pp. 461-479.
D'Ambrosio Alfano et al., "On the measurement of the mean radiant temperature and its influence on the indoor thermal environment assessment," Building and Environment, 2013, vol. 63, pp. 79-88.
Dalager et al., "Implementing intelligent physical exercise training at the workplace: health effects among office workers—a randomized controlled trial," European Journal of Applied Physiology, 2016, vol. 116, pp. 1433-1442 (10 pages).
Dalal, Reeshad S., "Job Attitudes: Cognition and Affect," Handbook of Psychology, Second Edition, 2013, pp. 341-366 (26 pages).

(56) References Cited

OTHER PUBLICATIONS

Darvesh, Nazia, et al., "Water, sanitation and hygiene interventions for acute childhood diarrhea: a systematic review to provide estimates for the Lives Saved Tool," BMC Public Health, 2017, vol. (Suppl 4), Article 776, pp. 101-111 (11 pages).
De Dear et al., "Developing an Adaptive Model of Thermal Comfort and Preference," Ashrae Transactions, 1998, vol. 104, part 1 (19 pages).
Delos, "Delos and MGM Grand Las Vegas Introduce First-Ever Stay Well Rooms," Sep. 20, 2012, retrieved from http://delosliving.com/staywell/delos-mgm-grand-las-vegas-introduce-first-ever-stay-well- . . . retrieved on May 14, 2014, 4 pages.
Delos, "Delos Announces First-Ever Well™ Certified Office At CBRE Headquarters in Los Angeles," Nov. 19, 2013, retrieved from http://delosliving.com/press-release/delos-the-pioneer-of-wellness-real-estate-announces-fi . . . , retrieved on May 14, 2014, 4 pages.
Delos, "MGM Grand and Delos Complete Expansion of Stay Well Experience and Introduce New Stay Well Lounge," Feb. 26, 2014, retrieved from http://delosliving.com/press-release/mgm-grand-and-delos-complete-expansion-of-stay-we . . . , retrieved on May 14, 2014, 4 pages.
Delos, "World's First Well® Certified Restaurants Introduced by Delos and LYFE Kitchen," Dec. 4, 2013, retrieved from http://delosliving.com/press-release/worlds-first-well-certified-restaurants-introduced-by-d . . . retrieved on May 14, 2014, 4 pages.
Delos, "World's First Wellness-Infused Student Housing Model in Philadelphia For St. Joseph's University Introduced by Delos and Cross Properties," Nov. 25, 2013, retrieved from http://delosliving.com/press-release/delos-the-pioneer-of-wellness-real-estate-and-cross-pr . . . , retrieved on May 14, 2014, 4 pages.
Delos, "Introducing Wellness Real Estate—Can Your Home Actually Improve Your Health?," May 1, 2012, retrieved from http://delosliving.com/press-release/can-your-home-actually-improve-your-health/, retrieved on May 14, 2014, 3 pages.
Destaillats et al., "Indoor pollutants emitted by office equipment: A review of reported data and information needs," Atmospheric Environment, 2008, vol. 42, pp. 1371-1388.
Diamond, "Executive Functions," Annual Review of Psychology, 2013, vol. 64, pp. 135-168.
Dijk et al., "Light, Sleep, and Circadian Rhythms: Together Again," PLoS Biology, 2009, vol. 7, No. 6, pp. 1-4.
Dingle et al., "Formaldehyde Levels and the Factors Affecting These Levels in Homes in Perth, Western Australia," Indoor Built Environment, 2002, vol. 11, pp. 111-116.
Domanico et al., "Documenting the NICU design dilemma: comparative patient progress in openward and single family room units," Journal of Perinatology, 2011, vol. 31, pp. 281-288.
Dong et al., "A review of smart building sensing system for better indoor environment control," Energy and Buildings, 2019, vol. 199, pp. 29-46.
Dounis et al., "Design of a fuzzy system for living space thermal-comfort regulation," Applied Energy, 2001, vol. 69, pp. 119-144.
Duckitt, Kirsten et al., "Menorrhagia," BMJ Clinical Evidence, 2012, pp. 1-69 (69 pages).
Dueñas, Juan C. et al., "An End-to-End Service Provisioning Scenario forthe Residential Environment," IEEE Communications Magazine, 2005, pp. 94-100.
Dussault et al., "Office buildings with electrochromic windows: A sensitivity analysis of design parameters on energy performance, and thermal and visual comfort," Energy and Building, 2017, vol. 153, pp. 50-62.
Ebbert et al., "Interventions for smokeless tobacco use cessation (Review)," Cochrane Database of Systematic Reviews, 2015, No. 10 (56 pages).
Eisele et al., "LED Lighting System," Notice of Allowance, dated Apr. 21, 2015, for U.S. Appl. No. 14/486,753, 9 pages.
Eisele et al., "LED Lighting System," Notice of Allowance, dated Mar. 14, 2016, for U.S. Appl. No. 14/805,243, 6 pages.
Eisele et al., "LED Lighting System," Notice of Allowance, dated May 13, 2014, for U.S. Appl. No. 13/863,589, 6 pages.
Eisele et al., "LED Lighting System," Office Action dated Oct. 22, 2015, for USAN U.S. Appl. No. 14/805,243, 14 pages.
Eisele et al., "LED Lighting System," Office Action, dated Feb. 4, 2015, for U.S. Appl. No. 14/486,753, 7 pages.
Eisele et al., "LED Lighting System," Office Action, dated Jul. 26, 2012, for U.S. Appl. No. 12/900,158, 13 pages.
Eisele et al., "LED Lighting System," Office Action, dated Jun. 5, 2013, for U.S. Appl. No. 13/863,589, 5 pages.
Eisele et al., "LED Lighting System," Office Action, dated Nov. 1, 2013, for U.S. Appl. No. 13/863,589, 6 pages.
Eisele et al, "LED Lighting System," Office Action, dated Oct. 22, 2015, for U.S. Appl. No. 14/805,243, 18 pages.
Eisele et al, "LED Lighting System," Preliminary Amendment, filed Dec. 30, 2014, for U.S. Appl. No. 14/486,753.
Eisele et al, "LED Lighting System," Preliminary Amendment, filed Sep. 15, 2015, for U.S. Appl. No. 14/805,243, 9 pages.
Eisele et al, "LED Lighting System," Preliminary Amendment, filed Sep. 8, 2016, for U.S. Appl. No. 15/187,317, 9 pages.
Eisele et al, "LED Lighting System," Response, filed Jan. 27, 2014, for U.S. Appl. No. 13/863,589, 3 pages.
Eisele et al, "LED Lighting System," Response, filed Jan. 5, 2016, for U.S. Appl. No. 14/805,243, 3 pages.
Eisele et al, "LED Lighting System," Response, filed Mar. 6, 2015, for U.S. Appl. No. 14/486,753, 3 pages.
Eisele et al, "LED Lighting System," Response, filed Sep. 4, 2013, for U.S. Appl. No. 13/863,589, 3 pages.
Eisele et al., "LED Lighting System," Amendment, filed Oct. 24, 2012, for U.S. Appl. No. 12/900,158, 12 pages.
Eisele et al., "LED Lighting System," Second Preliminary Amendment filed Dec. 30, 2014, for U.S. Appl. No. 14/486,753, 9 pages.
Eisele et al., "LED Lighting System," U.S. Appl. No. 61/249,858, filed Oct. 8, 2009, 58 pages.
Eisele et al., "LED Lighting System," Notice of Allowance dated Jan. 9, 2013, for U.S. Appl. No. 12/900,158, 9 pages.
Engvall et al., "Sick building syndrome in relation to building dampness in multi-family residential buildings in Stockholm," International Archives of Occupational and Environmental Health, 2001, vol. 74, pp. 270-278.
Epstein et al., "Thermal Comfort and the Heat Stress Indices," Industrial Health, 2006, vol. 44, pp. 388-398.
European Agency for Safety and Health at Work, et al., "Work-related musculoskeletal disorders: back to work report," Luxembourg: Office for Official Publications of the European Communities, 2007. pp. 3-100 (100 pages).
European Search Report for EP Application No. 15160578.9, dated Aug. 11, 2015, 8 pages.
Examination Report issued in AU Application No. 2016202287 dated May 8, 2020.
Examiner's Report issued in CA Application No. 2,940,766 dated Jan. 11, 2019.
Exelmans et al., "Bedtime mobile phone use and sleep in adults," Social Science & Medicine, 2016, vol. 148, pp. 93-101.
Extended European Search Report and Lack of Unity of Invention Sheet B, dated Jul. 28, 2016, for European Application No. 13833105.3, 17 pages.
Extended European Search Report issued in EP Application No. 17844397.4 dated Jun. 17, 2020 (8 pages).
Extended European Search report issued in EP Application No. 20152815.5 dated Aug. 4, 2020.
Extended European Search Report issued in EP Application No. 20191237.5 dated Sep. 21, 2020.
Extended European Search Report, dated Feb. 1, 2018, for European Application No. 17167920.2-1213, 10 pages.
Extended European Search Report, dated Jul. 12, 2017, for European Application No. 15754628.4-1958, 11 pages.
Extended European Search Report, dated May 28, 2018, for European Application No. 16737803.3-1222/3245631, 7 pages.
Extended European Search Report, dated Nov. 5, 2014, for European Application No. 12779504.5-1352, 6 pages.
Fabrictech International, "PureCare™ Antibacterial Silver," retrieved from http://www.fabrictech.com/shop/purecaresilver.html, retrieved on Aug. 13, 2012, 1 page.

(56) References Cited

OTHER PUBLICATIONS

Fabrictech International, "Total Health & Wellness Protection Package-Save 25%," retrieved from http://www.fabrictech.com/shop/custom-package/total-healthawellness-protection.html, retrieved on Aug. 13, 2012, 3 pages.

Farzaneh et al., "Controlling automobile thermal comfort using optimized fuzzy controller," Applied Thermal Engineering, 2008, vol. 28, pp. 1906-1917.

Felleman et al., "Distributed Hierarchical Processing in the Primate Cerebral Cortex," Cerebral Corte, 1991, vol. 1, No. 1, pp. 1-47.

Ferguson MA et al., "Hearing aids for mild to moderate hearing loss in adults (Review)," Cochrane Database of Systematic Reviews, 2017, Issue 9, pp. 1-46 (48 pages).

Fewtrell, Lorna, et al., "Water, sanitation, and hygiene interventions to reduce diarrhoea in less developed countries: a systematic review and meta-analysis," The Lancet Infect Diseases, 2005, vol. 5, pp. 42-52 (11 pages).

Figueiro et al., "Daylight and Productivity—A Field Study," Panel 8. Human and Social Dimensions of Energy Use: Understanding Markets and Demand, 2002 (10 pages).

Finnegan et al., "Work Attitudes in Windowed vs. Windowless Environments," The Journal of Social Psychology, 1981, vol. 115, pp. 291-292.

First Examination Report issued in IN Application No. 201617032677 dated Jul. 30, 2020.

Fisk et al., "Age-Related Impairment in Executive Functioning: Updating, Inhibition, Shifting, and Access," Journal of Clinical and Experimental Neuropsychology, 2004, vol. 26, No. 7, pp. 874-890.

Fisk, "Estimates of Potential Nationwide Productivity and Health Benefits From Better Indoor Environments: An Update," Indoor Air Quality Handbook, 1999 (38 pages).

Fisk, William J. et al., "Estimates of Potential Nationwide Productivity And Health Benefits From Better Indoor Environments: An Update," 1999 (38 pages).

Fisk, William, "How IEQ Affects Health, Productivity," ASHRAE Journal, 2002, vol. 44, No. 5, pp. 56-60 (4 pages).

Földváry et al., "Effect of energy renovation on indoor air quality in multifamily residential buildings in Slovakia," Building and Environment, 2017, vol. 122, pp. 363-372.

Fonken et al., "Dim Light at Night Disrupts Molecular Circadian Rhythms and Affects Metabolism," Journal of Biological Rhythms, Author Manuscript, 2013, vol. 28, No. 4 (15 pages).

Food Service Guidelines Federal Workgroup, "Food Service Guidelines for Federal Facilities," 2017, U.S. Department of Health and Human Services, Washington, DC (30 pages).

Fossum et al., "The Association Between Use of Electronic Media in Bed Before Going to Sleep and Insomnia Symptoms, Daytime Sleepiness, Morningness, and Chronotype," Behavioral Sleep Medicine, 2014, vol. 12, pp. 343-357.

Foster et al., "Shortened complex span tasks can reliably measure working memory capacity," Memory & Cognition, 2015, vol. 43, pp. 226-236.

Foster, "Fundamentals of circadian entrainment by light," Lighting Research & Technology, 2021, vol. 53, pp. 377-393.

Frazer K et al., "Impact of institutional smoking bans on reducing harms and secondhand smoke exposure (Review)," Cochrane Database of Systematic Reviews, 2016, Issue 5, pp. 1-85 (87 pages).

Frazer, K et al., "Legislative smoking bans for reducing harms from secondhand smoke exposure, smoking prevalence and tobacco consumption (Review)," Cochrane Database of Systematic Reviews, 2016, Issue 2, pp. 1-192 (194 pages).

Frontczak et al., "Literature survey on how different factors influence human comfort in indoor environments," Building and Environment, 2011, vol. 46, pp. 922-937.

Frontczak, Monika et al., "Literature survey on how different factors influence human comfort in indoor environments," Building and Environment, vol. 46, 2011, pp. 922-937 (16 pages).

Galasiu et al., "Occupant preferences and satisfaction with the luminous environment and control systems in daylit offices: a literature review," Energy and Buildings, 2006, vol. 38, pp. 728-742.

Garn, Joshua V., et al., "The impact of sanitation interventions on latrine coverage and latrine use: A systematic review and meta-analysis," International Journal of Hygiene and Environmental Health, 2017, vol. 220, pp. 329-340 (12 pages).

GBD 2016 Risk Factors Collaborators, "Global, regional, and national comparative risk assessment of 84 behavioural, environmental and occupational, and metabolic risks or clusters of risks, 1990-2016: a systematic analysis for the Global Burden of Disease Study 2016," The Lancet, 2017, vol. 390, pp. 1345-1422 (78 pages).

Geaney, F., et al., "The effectiveness of workplace dietary modification interventions: Asystematic review," Preventive Medicine, 2013, vol. 57, pp. 438-447, 10 pages.

General Services Administration, "Sound Matters: How to achieve accoustic comfort in the contemporary office," 2011, pp. 1-42 (42 pages).

Goodman, "Measurement and specification of lighting: A look at the future," Lighting Research and Technology, 2009, vol. 41, pp. 229-243.

Goodman, "Green Wall Frame," Amendment After Allowance, filed May 11, 2016, for U.S. Appl. No. 29/528,147, 8 pages.

Goodman, "Green Wall Frame," Notice of Allowance, dated Feb. 11, 2016, for U.S. Appl. No. 29/528,147, 11 pages.

Goodnough, L.T. et al., "Detection, evaluation, and management of preoperative anaemia in the elective orthopaedic surgical patient: NATA guidelines," British Journal of Anaesthesia, 2011, vol. 106, No. 1, pp. 13-22.

Grant et al., "Daytime Exposure to Short Wavelength-Enriched Light Improves Cognitive Performance in Sleep-Restricted College-Aged Adults," Frontier in Neurology, 2021, vol. 12, pp. 1-10.

Graves, Lee E.F. et al., "Evaluation of sit-stand workstations in an office setting: a randomised controlled trial," BMC Public Health, 2015, vol. 15, No. 1145 (14 pages).

Grønli et al., "Reading from an iPad or from a book in bed: the impact on human sleep. A randomized controlled crossover trial," Sleep Medicine, 2016, vol. 21, pp. 86-92.

GSky Plant Systems, Inc., "Smart Wall Cabinet," 2012, retrieved from http://gsky.com/green-walls/smartwall/, retrieved on Apr. 29, 2015, 3 pages.

Gueymard, "Turbidity Determination from Broadband Irradiance Measurements: A Detailed Multicoefficient Approach," Journal of Applied Meteorology, 1998, vol. 37, pp. 414-435.

Guirao, "Average Optical Performance of the Human Eye as a Function of Age in a Normal Population," Investigative Ophthalmology & Visual Science, 1999, vol. 40, No. 1, pp. 203-213.

Guyatt et al., "Grade: an emerging consensus on rating quality of evidence and strength of recommendations," BMJ, Apr. 26, 2008, vol. 336, pp. 924-926 (3 pages).

Hafner et al., Why sleep matters—the economic costs of insufficient sleep: A cross-country comparative analysis, 2016 (101 pages).

Haider, B.A et al., "Anaemia, prenatal iron use, and risk of adverse pregnancy outcomes: systematic review and meta-analysis," BMJ, 2013, pp. 1-19.

Haider, BA et al., "Multiple-micronutrient supplementation for women during pregnancy (Review)," Cochrane Database of Systematic Reviews, 2015, Issue 11, pp. 1-100 (103 pages).

Hajdukiewicz, Magdalena et al., "Calibrated CFD simulation to evaluate thermal comfort in a highly-glazed naturally ventilated room," Building and Environment, 2013, vol. 70, pp. 73-89.

Hajdukiewicz, Magdalena et al., "Formal calibration methodology for CFD models of naturally ventilated indoor environments," Building and Environment, 2012, vol. 59 (28 pages).

Hannibal et al., "Melanopsin is Expressed in PACAP-Containing Retinal Ganglion Cells of the Human Retinohypothalamic Tract," Investigative Ophthalmology & Visual Science, 2004, vol. 45, No. 11, pp. 4202-4209.

Haq et al., "A review on lighting control technologies in commercial buildings, their performance and affecting factors," Renewable and Sustainable Energy Reviews, 2014, vol. 33, pp. 268-279.

(56) References Cited

OTHER PUBLICATIONS

Hasan et al., "Sensitivity study forthe PMV thermal comfort model and the use of wearable devices biometric data for metabolic rate estimation," Building and Environment, 2016, vol. 110, pp. 173-183.
Hasan, Mohammad H., et al. "Sensitivity study forthe PMV thermal comfort model and the use of wearable devices biometric data for metabolic rate estimation," Building and Environment, 2016, vol. 110, pp. 173-183 (11 pages).
Heijnen, Marieke et al., "Shared Sanitation versus Individual Household Latrines: A Systematic Review of Health Outcomes," PLoS One, 2014, vol. 9, Issue 4, pp. 1-9 (9 pages).
Hensen, "Literature Review on Thermal Comfort in Transient Conditions," Building and Environment, 1990, vol. 25, No. 4, pp. 309-316.
Higuchi et al., "Influence of eye colors of Caucasians and Asians on suppression of melatonin secretion by light," American Journal of Physiology: Regulatory, Integrative and Comparative Physiology, 2007, vol. 292, pp. R2352-R2356.
Hiscocks, "Measuring Light," 2008 (9 pages).
Hiscocks, "Measuring Luminance with a Digital Camera: Case History," 2013 (10 pages).
Hoisington et al., "Ten questions concerning the built environment and mental health," Building and Environment, 2019, vol. 155, pp. 58-69.
Horne et al., "A Self-Assessment Questionnaire to Determine Morningness-Eveningness in Human Circadian Rhythms," International Journal of Chronobiology, 1976, vol. 4, pp. 97-110.
Hossain, Muttaquina et al., "Evidence-based approaches to childhood stunting in low and middle income countries: a systematic review," Archives of Disease in Childhood, 2017, vol. 102, pp. 903-909.
Hou, Can et al., "Do Mobile Phone Applications Improve Glycemic Control (HbA1c) in the Self-management of Diabetes? A Systematic Review, Meta-analysis, and Grade of 14 Randomized Trials," Diabetes Care, 2016, vol. 39, pp. 2089-2095.
Howieson et al., "Building tight—ventilating right? How are new air tightness standards affecting indoor air quality in dwellings?" Journal of Building Services Engineering Research & Technology, 2014, vol. 35, No. 5, pp. 475-487.
Huang et al., "A study about the demand for air movement in warm environment," Building and Environment, 2013, vol. 61, pp. 27-33.
Huizenga et al., "Air Quality and Thermal Comfort in Office Buildings: Results of a Large Indoor Environmental Quality Survey," Proceedings of Healthy Buildings, 2006, vol. 3, pp. 393-397.
Huizenga, C. et al., "Air Quality and Thermal Comfort in Office Buildings: Results of a Large Indoor Environmental Quality Survey," Proceeding of Healthy Buildings, 2006, vol. 3 (6 pages).
Humphreys, "Quantifying occupant comfort: are combined indices of the indoor environment practicable?" Building Research & Information, 2005, vol. 33, No. 4, pp. 317-325.
Huo, Jun Sheng et al., "Effect of NaFeEDTA-Fortified Soy Sauce on Anemia Prevalence in China: A Systematic Review and Meta-analysis of Randomized Controlled Trials," Biomedical and Environmental Science, 2015, vol. 28, No. 11, pp. 788-798.
Hutchinson, et al. "Improving nutrition and physical activity in the workplace: a meta-analysis of intervention studies," Health Promotion International, 2012, vol. 27, No. 2, pp. 238-249 (12 pages).
Hysing et al., "Sleep and use of electronic devices in adolescence: results from a large populationbased study," BMJ Open, 2015, vol. 5, pp. 1-7.
International Commission on Illumination, Technical Report: Guide on the Limitation of the Effects of Obtrusive Light From outdoor Lighting Installations, 2003 (46 pages).
International Organization for Standardization, "Ergonomics of the thermal environment—Instruments for measuring physical quantities," BS EN ISO 7726, 2nd Edition, 2001 (62 pages).
International Organization for Standardization, "Ergonomics of the thermal environment—Analytical determination and interpretation of thermal comfort using calculation of the PMV and PPD indices and local thermal comfort criteria," ISO 7730, 3rd Edition, 2005 (11 pages).
International Search Report and the Written Opinion of the International Searching Authority, dated Jun. 8, 2015, for International Application No. PCT/US2015/017528, 20 pages.
International Search Report and Written Opinion for PCT/US2022/020903, dated Jul. 12, 2022 (17 pages).
International Search Report and Written Opinion of the International Searching Authority, dated Aug. 29, 2016, for International Application No. PCT/US2016/034416, 22 pages.
International Search Report for International Application No. PCT/US2019/050339, dated Nov. 27, 2019 (2 pages).
International Search Report for PCT/JUS2020/019697, dated Jul. 14, 2020 (4 pages).
International Search Report for PCT/US2017/048382 dated Jan. 4, 2018 (4 pages).
International Search Report issued in International Application No. PCT/US2019/50416, dated Nov. 27, 2019, 1 p.
International Search Report, dated Apr. 28, 2016, for International Application No. PCT/US2016/013215, 5 pages.
International Search Report, dated Dec. 26, 2013, for International Application No. PCT/US2013/057070, 4 pages.
International Search Report, dated Feb. 4, 2011, for International Application No. PCT/US2010/051791, 2 pages.
International Well Building Institute, "The Well Building Standard: Version 1.0," 2015 (220 pages).
Ishihara et al., "Metabolic responses to polychromatic LED and OLED light at night," Scientific Reports, 2021, vol. 11, pp. 1-11.
Jammes, François et al., "Service-Oriented Device Communications Using the Devices Profile for Web Services," 2005 (8 pages).
Jamrozik et al., "A novel methodology to realistically monitor office occupant reactions and environmental conditions using a living lab," Building and Environment, 2018, vol. 130, pp. 190-199.
Japanese Office Action dated Apr. 25, 2017 for JP Application No. 2015-529995, with English summary, 14 pages.
Jenkins et al., "A practical approach to glare assessment fortrain cabs," Applied Ergonomics, 2015, vol. 47, pp. 170-180.
Jernigan, "Light studies focus on circadian rhythms," BioPhotonics, Jul. 2009, retrieved from http://www.photonics.com/Article.aspx?PID=I&VID=43&IID=396&AID=38995, retrieved on Nov. 3, 2014, 2 pages.
Jernigan, R., "Light Studies Focus on Circadian Rhythms," Photonics Showcase, Nov. 2009, p. 12.
Job Accommodation Network, "Accommodation and Compliance Series: Employees with Hearing Loss," available at https://askjan.org/media/Hearing.html, accessed Oct. 31, 2017 (25 pages).
Jones, "Chapter 4—Acoustical Treatment for Indoor Areas," in Handbook for Sound Engineers, Ballou (ed.), Burlington, MA, Focal Press, 2008, 65-94.
Jonsson, Ulf et al., "Psychological Treatment of Depression in People Aged 65 Years and Over: A Systematic Review of Efficacy, Safety, and Cost Effectiveness," PLoS One, 2016, vol. 11, No. 8, pp. 1-20 (20 pages).
Joshi et al., "The importance of temperature and thermoregulation for optimal human sleep," Energy and Buildings, 2016, vol. 131, pp. 153-157.
Kahn-Marshall, Jennifer L. et al., "Making Healthy Behaviors the Easy Choice for Employees: A Review of the Literature on Environmental and Policy Changes in Worksite Health Promotion," Health Education & Behavior, 2012, vol. 39, No. 6, pp. 752-776, (25 pages).
Kakde, S. et al., "Asystematic review on the social context of smokeless tobacco use in the South Asian population: Implications for public health," Public Health, 2012, vol. 126, No. 8, pp. 635-645.
Kaplan et al., "Directed Attention as a Common Resource for Executive Functioning and Self-Regulation," Perspectives on Psychological Science, 2010, vol. 5, No. 1, pp. 43-57.
Kaplan, "The Restorative Benefits of Nature: Toward an Integrative Framework," Journal of Environmental Psychology, 1995, vol. 15, pp. 169-182.

(56) References Cited

OTHER PUBLICATIONS

Karjalainen et al., "User problems with individual temperature control in offices," Building and Environment, 2007, vol. 42, pp. 2880-2887.

Karjalainen, "Thermal comfort and gender: a literature review," Indoor Air, 2012, vol. 22, pp. 96-109.

Kastner, Wolfgang et al., "Communication Systems for Building Automation and Control," Proceedings of the IEEE, 2005, vol. 93, No. 6, pp. 1178-1203.

Kennedy et al., "Smoke-Free Policies in U.S. Prisons and Jails: A Review of the Literature," (Author Manuscript) Nicotine & Tobacco Research, 2015, vol. 17, No. 6 (14 pages).

Khunti, Kamlesh et al., "Association Between Adherence to Pharmacotherapy and Outcomes in Type 2 Diabetes: A Meta-analysis," Diabetes Care, 2017, vol. 40, pp. 1588-1596.

Kinney, "Climate Change, Air Quality, and Human Health," American Journal of Preventive Medicine, 2008, vol. 35, No. 5, pp. 459-467.

Klein, Laura et al., "Coordinating occupant behavior for building energy and comfort management using multi-agent systems," Automation in Construction, vol. 22, Mar. 2012, pp. 525-536.

Klepeis et al., "The National Human Activity Pattern Survey (NHAPS): a resource for assessing exposure to environmental pollutants," Journal of Exposure Analysis and Environmental Epidemiology, 2001, vol. 11, No. 3, pp. 231-252.

Knai, Cécile C. et al., "Are the Public Health Responsibility Deal alcohol pledges likely to improve public health? An evidence synthesis," Addiction, 2015, vol. 110, No. 8 (29 pages).

Knudsen et al., "Sensory and chemical characterization of VOC emissions from building products: impact of concentration and air velocity," Atmospheric Environment, 1999, vol. 33, pp. 1217-1230.

Kong et al., "The impact of interior design on visual discomfort reduction: A field study integrating lighting environments with POE survey," Building and Environment, 2018, vol. 138, pp. 135-148.

Konstantzos et al., "The effect of lighting environment on task performance in buildings—A review," Energy & Buildings, 2020, vol. 226, pp. 1-14.

Kool et al., "Decision Making and the Avoidance of Cognitive Demand," Journal of Experimental Psychology: General, 2010, vol. 139, No. 4, pp. 665-682.

Korotcenkov et al., "In2O3- and SnO2-Based Thin Film Ozone Sensors: Fundamentals," Journal of Sensors, 2016, vol. 2016 (32 pages).

Kota, Sandeep et al., "Historical Survey of Daylighting Calculations Methods and Their Use in Energy Performance Simulations," Proceedings of the Ninth International Conference for Enhanced Building Operations, Nov. 17-19, 2009, Austin, Texas (9 pages).

LaCaille et al., "Go!: results from a quasi-experimental obesity prevention trial with hospital employees," BMC Public Health, 2016, vol. 17, No. 171, pp. 1-16 (16 pages).

Lai et al., "An evaluation model for indoor environmental quality (IEQ) acceptance in residential buildings," Energy and Buildings, 2009, vol. 41, pp. 930-936.

Lai et al., "Perceived Importance of the Quality of the Indoor Environment in Commercial Buildings," Indoor and Built Environment, 2007, vol. 16, No. 4, pp. 311-321.

Lai et al., "Perception of importance and performance of the indoor environmental quality of high-rise residential buildings," Building and Environment, 2009, vol. 44, pp. 352-360.

Lal, Avtar, et al., "The Effect of Physical Exercise After a Concussion: A Systematic Review and Meta-analysis," The American Journal of Sports Medicine, 2018, vol. 43, Issue 3, pp. 743-752 (10 pages).

Lan et al., "Ten questions concerning thermal environment and sleep quality," Building and Environment, 2016, vol. 99, pp. 252-259.

Land, "Using Vitamin C To Neutralize Chlorine in Water Systems," Recreation Management Tech Tips, Apr. 2005, retrieved from http://www.fs.fed.us/t-d/pubs/html/05231301/05231301.html, retrieved on Mar. 1, 2016, 6 pages.

Landrigan, Phillip J., "Air pollution and health," The Lancet Public Health, 2017, vol. 2, No. 1, pp. e4-e5.

Larson, Nicole et al., "A Review of Environmental Influences on Food Choices," Annals of Behavioral Medicine : A Publication of the Society of Behavioral Medicine, 2009, vol. 38 Suppl 1, pp. S56-73.

Lassi et al., "Impact of education and provision of complementary feeding on growth and morbidity in children less than 2 years of age in developing countries: a systematic review," BMC Public Health, 2013, vol. 13, pp. 1-10 (10 pages).

Leather et al., "Windows in the Workplace: Sunlight, View, and Occupational Stress," Environment and Behavior, 1998, vol. 30, No. 6, pp. 739-762.

Leder et al., "Effects of office environment on employee satisfaction: a new analysis," Building Research and Information, 2015 (22 pages).

Lee, Courtney, et al., "The effectiveness of acupuncture research across components of the trauma spectrum response (tsr): a systematic review of reviews," Systematic Reviews, 2012, vol. 1, Article 46, pp. 1-18 (18 pages).

Leech et al., "It's about time: A comparison of Canadian and American time-activity patterns," Journal of Exposure Analysis and Environmental Epidemiology, 2002, vol. 12, No. 6, pp. 427-432.

Leidinger et al., "Selective detection of hazardous VOCs for indoor air quality applications using a virtual gas sensor array," Journal of Sensors and Sensor Systems, 2014, vol. 3, pp. 253-263.

Levy et al., "Ozone Exposure and Mortality: An Empiric Bayes Metaregression Analysis," Epidemiology, 2005, vol. 16, No. 4, pp. 458-468.

Lewtas, "Air pollution combustion emissions: Characterization of causative agents and mechanisms associated with cancer, reproductive, and cardiovascular effects," Reviews in Mutation Research, 2007, vol. 636, pp. 95-133.

Li et al., "Health promotion interventions and policies addressing excessive alcohol use: Asystematic review of national and global evidence as a guide to health-care reform in China," HHS Public Access, Author Manuscript, 2015, vol. 110, No. 1, pp. 1-18 (18 pages).

Licht.wissen 19: Impact of Light on Human Beings, licht.de, Mar. 2014 (56 pages).

Licina et al., "Concentrations and Sources of Airborne Particles in a Neonatal Intensive Care Unit," PLOS One, 2016 (17 pages).

Licina et al., "Emission rates and the personal cloud effect associated with particle release from the perihuman environment," Indoor Air, 2017, vol. 27, pp. 791-802.

Liu et al.,"Human thermal adaptive behaviour in naturally ventilated offices for different outdoor air temperatures: A case study in Changsha China," Building and Environment, 2012, vol. 50, pp. 76-89.

Liu et al., "A Survey on Gas Sensing Technology," Sensors, 2012, vol. 12, pp. 9635-9665.

Löndahl et al., "A set-up for field studies of respiratory tract deposition of fine and ultrafine particles in humans," Journal of Aerosol Science, 2006, vol. 37, pp. 1152-1163.

Luedtke, Kerstin et al., "Efficacy of interventions used by physiotherapists for patients with headache and migraine—Systematic review and meta-analysis," Cephalalgia, 2015 (20 pages).

Luke, "Evaluating significance in linear mixed-effects models in R," Behavior Research Methods, 2017, vol. 49, pp. 1494-1502.

Luttmann, Alwin et al., "Preventing Musculoskeletal Disorders in the Workplace," World Health Organization, Protecting Workers' Health Series No. 5, 2003 (40 pages).

MacArthur, Georgie J. et al., "Peer-led interventions to prevent tobacco, alcohol and/or drug use among young people aged 11-21 years: a systematic review and meta-analysis," 2016, Addiction, vol. 111, pp. 391-407 (17 pages).

Macary et al., "Systems, Methods and Articles for Monitoring and Enhancing Human Wellness," U.S. Appl. No. 15/543,114, filed Jul. 12, 2017, 113 pages.

Maes, Lea et al., "Effectiveness of workplace interventions in Europe promoting healthy eating: a systematic review," European Journal of Public Health, 2012, vol. 22, No. 5, pp. 677-683.

(56) References Cited

OTHER PUBLICATIONS

Mahyuddin et al., "The spatial distribution of carbon dioxide in rooms with particular application to classrooms," Indoor and Built Environment, 2014, vol. 23, No. 3, pp. 433-448.
Marinelli et al., "Hours of Television Viewing and Sleep Duration in Children: A Multicenter Birth Cohort Study," JAMA Pediatrics, 2014, vol. 168, No. 5, pp. 458-464.
Markus, "The Function of Windows—A Reappraisal," Building Science, 1967, vol. 2, pp. 97-121.
Massey et al., "Emission and Formation of Fine Particles from Hardcopy Devices: the Cause of Indoor Air Pollution," Monitoring, Control and Effects of Air Pollution, 2001, pp. 121-134.
McCullough et al., "Determining temperature ratings for children's cold weather clothing," Applied Ergonomics, 2009, vol. 40, pp. 870-877.
McIntyre, "Response to Atmospheric Humidity at Comfortable Air Temperature: A Comparison of Three Experiments," Annals of Occupational Hygiene, 1978, vol. 21, pp. 177-190.
McKay, Alisa J. et al,, "Strategies for Tobacco Control in India: A Systematic Review," PLOS One, 2015, vol. 4. pp 1-34 (34 pages).
Meerbeek et al., "Impact of blinds usage on energy consumption: automatic versus manual control," conference paper, 2014 (17 pages).
Meister et al., "Low-Level Visual Processing: The Retina," Chapter 26, Principles of Neural Science, 2014, pp. 577-601.
Mendell et al., "Improving the Health of Workers in Indoor Environments: Priority Research Needs for a National Occupational Research Agenda," American Journal of Public Health, 2002, vol. 92, No. 9, pp. 1430-1440.
Mendell, et al. "Improving the Health of Workers in Indoor Environments: Priority Research Needs for a National Occupational Research Agenda," American Journal of Public Health, 2002, vol. 92, No. 9, pp. 1430-1440 (11 pages).
Merz, Victoire et al., "Brief interventions to prevent recurrence and alcohol-related problems in young adults admitted to the emergency ward following an alcohol-related event: a systematic review," Journal of Epidemiology and Community Health, 2015, vol. 69, No. 9, pp. 912-917.
Messer, Alan et al., "InterPlay: A Middleware for Seamless Device Integration and Task Orchestration in a Networked Home," Proceedings of the Fourth Annual IEEE International Conference on Pervasive Computing and Communications, 2006 (10 pages).
Mingkhwan, A. et al., "Dynamic service composition in home appliance networks," Multimedia Tools and Applications, 2006, vol. 29, pp. 257-284.
Minichiello, Alexa et al., "Effective strategies to reduce commercial tobacco use in Indigenous communities globally: A systematic review," BMC Public Health, 2016, vol. 16, No. 21 (25 pages).
Mitchell, Lana J. et al., "Effectiveness of dietetic consultations in primary health care: A systematic review of randomized controlled trials," Journal of the Academy of Nutrition and Dietetics, 2017 (41 pages).
Miyake et al., "The Unity and Diversity of Executive Functions and Their Contributions to Complex "Frontal Lobe" Tasks: A Latent Variable Analysis," Cognitive Psychology, 2000, vol. 41, pp. 49-100.
Mold Inspection California, "Killing Mold With Ozone & Thermal Heat," retrieved from http://moldinspectioncalifornia.com/kill_mold_with_ozone.html, 3 pages.
Monson, Eva et al., "Effects of Enactment of Legislative (Public) Smoking Bans on Voluntary Home Smoking Restrictions: A Review," Nicotine & Tobacco Research, 2017, vol. 19, No. 2, pp. 141-148.
Moore-Ede et al., "Circadian Potency Spectrum with Extended Exposure to Polychromatic White LED Light under Workplace Conditions," Journal of Biological Rhythms, 2020, vol. 35, No. 4, pp. 405-415.
Moore-Ede et al., "LEDs must spectrally balance illumination, circadian health, productivity, and energy efficiency," LEDs Magazine, available at least as early as Aug. 2021 at https://www.ledsmagazine.com/lighting-health-wellbeing/article/14199941/ideal-led-lighting-must-balance-multiple-objectives-magazine (14 pages).
Myhren, Jonn Are et al., "Flow patterns and thermal comfort in a room with panel, floor and wall heating," Energy and Buildings, 2008, vol. 40, 524-536.
Nabil et al., "Useful daylight illuminances: A replacement for daylight factors," Energy and Buildings, 2006, vol. 38, pp. 905-913.
Nair, Natasha K. et al., "A Systematic Review of Digital and Computer-Based Alcohol Intervention Programs in Primary Care," Current Drug Abuse Reviews, 2015, vol. 8, No. 2, pp. 1-8.
National Center for Chronic Disease Prevention and Health Promotion, Division for Heart Disease and Stroke Prevention, "Under Pressure: Strategies for Sodium Reduction in Worksites ," Centers for Disease Control and Prevention, 2012, pp. 1-9 (12 pages).
National Lighting Product Information Program, "Photosensors: Dimming and Switching Systems for Daylight Harvesting," Specifier Reports, 2007, vol. 11, No. 1 (54 pages).
Naturvention, "Science," URL=https://www.naturvention.com/technology-and-science/science/, download date Apr. 5, 2016, 4 pages.
Naturvention, "Technology," URL=https://www.naturvention.com/technology-and-science/, download date Apr. 5, 2016, 6 pages.
Ne'eman et al., "Office Worker Response to Lighting and Daylighting Issues in Workspace Environments: A Pilot Survey," Energy and Buildings, 1984, vol. 6, pp. 159-171.
Newsham, "Clothing as a thermal comfort moderator and the effect on energy consumption," Energy and Buildings, 1997, vol. 26, pp. 283-291.
Ni Mhurchu, Cliona et al., "Effects of worksite health promotion interventions on employee diets: a systematic review," BMC Public Health, 2010, vol. 10, No. 62, (7 pages).
Nicol et al., "A critique of European Standard EN 15251: strengths, weaknesses and lessons for future standards," Building Research & Information, 2011, vol. 39, No. 2, pp. 183-193.
Nie et al., "The effects of dynamic daylight-like light on the rhythm, cognition, and mood of irregular shift workers in closed environment," Scientific Reports, 2021, vol. 11, No. 13059, pp. 1-11.
Nieuwenhuijsen, K. et al., "Interventions to improve return to work in depressed people (Review)," The Cochrane Library, 2014, Issue 12, pp. 1-140 (143 pages).
Ning, Mao et al., "Experimental and numerical studies on the performance evaluation of a bed-based task/ambient air conditioning (TAC) system," Applied Sciences, 2014, vol. 136, pp. 956-967.
Novoselac et al., "A critical review on the performance and design of combined cooled ceiling and displacement ventilation systems," Energy and Buildings, 2002, vol. 34, pp. 497-509.
O'Brien et al., "Manually-operated window shade patterns in office buildings: A critical review," Building and Environment, 2013, vol. 60, pp. 319-338.
Obiltschnig, Günter, "Automatic Configuration and Service Discovery for Networked Smart Devices," Electronica Embedded Conference Munich, 2006 (8 pages).
Office Action issued in CN Application No. 201580021358.5 dated Feb. 2, 2019.
Office Action issued in CN Application No. 201680009629.X dated Jul. 23, 2020.
Office Action issued in MX Application No. MX/a/2016/011107.
Office Action, dated May 21, 2018, for U.S. Appl. No. 15/121,953, Pillai et al., "Systems and Articles for Enhancing Wellness Associated With Habitable Environments," 38 pages.
Office Action, dated May 31, 2018, for United States U.S. Appl. No. 15/421,046, Eisele et al., "LED Lighting System," 9 pages.
Office Action, dated Oct. 27, 2017, for U.S. Appl. No. 15/421,046, Eisele et al., "LED Lighting System," 8 pages.
Ormandy et al., "Health and thermal comfort: From WHO guidance to housing strategies," Energy Policy, 2012, vol. 49, pp. 116-121 (6 pages).
Osilla, Karen Chan, et al., "Systematic review of the Impact of Worksite Wellness Programs," The American Journal of Managed Care, 2012, vol. 18, No. 2, pp. e68-e81, (14 pages).
OxiTitan, "Light Powered Protection," retrieved from http://www.oxititan.com, retrieved on Aug. 13, 2012, 2 pages.
Pachón, Helena et al., "Evidence of the effectiveness of flour fortification programs on iron status and anemia: a systematic review," Nutrition Reviews, 2015, vol. 73, No. 11, pp. 780-795.

(56) References Cited

OTHER PUBLICATIONS

Painter et al., "Practical application of a sensor overlay system for building monitoring and commissioning," Energy and Buildings, 2012, vol. 48, pp. 29-39.
Panda et al., "Coordinated Transcription of Key Pathways in the Mouse by the Circadian Clock," Cell, 2002, vol. 109, pp. 307-320.
Park et al., "Variations of formaldehyde and VOC levels during 3 years in new and older homes," Indoor Air, 2006, vol. 16, pp. 129-135.
Park, "Are Humans Good Sensors? Using Occupants as Sensors for Indoor Environmental Quality Assessment and for Developing Thresholds that Matter," thesis, 2015 (274 pages).
Pasricha, Sant-Ryan et al., "Effect of daily iron supplementation on health in children aged 4-23 months: a systematic review and meta-analysis of randomised controlled trials," The Lancet Global Health, 2013, vol. 1, pp. e77-e86.
Passey, Megan E. et al., "Smoke-free homes: what are the barriers, motivators and enablers? A qualitative systematic review and thematic synthesis," BMJ Open, 2016, vol. 6, pp. 1-16 (16 pages).
Pasut, Wilmer et al., "Energy-efficient comfort with a heated/cooled chair: Results from human subject tests," Building and Environment, 2015, vol. 84, pp. 10-21.
Peña-Rosas et al. "Intermittent oral iron supplementation during pregnancy (Review)," Cochrane Database of Systematic Reviews, 2015, Issue 10, pp. 1-186 (193 pages).
Perez et al., "All-Weather Model For Sky Luminance Distribution—Preliminary Configuration and Validation," Solar Energy, 1993. vol. 50, No. 3, pp. 235-245.
Persily, "Evaluating Building IAQ and Ventilation with Indoor Carbon Dioxide," ASHRAE Transactions, 1997, vol. 103 (12 pages).
Pervez et al., "Photonic Crystal Spectrometer," U.S. Appl. No. 61/278,773, filed Oct. 12, 2009, 78 pages.
Pervez et al., "Photonic Crystal Spectrometer," U.S. Appl. No. 61/349,570, filed May 28, 2010, 52 pages.
Peuhkuri et al., "Diet promotes sleep duration and quality," Nutrition Research, 2012, vol. 32, pp. 309-319.
Phillips et al., "High sensitivity and interindividual variability in the response of the human circadian system to evening light," Proceedings of the National Academy of Sciences of the United States of America, 2019, vol. 116, No. 24, pp. 12019-12024.
Phipps-Nelson et al., "Daytime Exposure to Bright Light, as Compared to Dim Light, Decreases Sleepiness and Improves Psychomotor Vigilance Performance," Sleep, 2003, vol. 26, No. 6, pp. 695-700.
Piccolo et al., "Effect of switchable glazing on discomfort glare from windows," Building and Environment, 2009, vol. 44, pp. 1171-1180.
Pillai et al., "Systems, Methods and Articles for Enhancing Wellness Associated With Habitable Environments," Amendment, filed Jul. 21, 2016, for U.S. Appl. No. 14/012,444, 25 pages.
Pillai et al., "Systems, Methods and Articles for Enhancing Wellness Associated With Habitable Environments," Office Action, dated Mar. 22, 2016, for U.S. Appl. No. 14/012,444, 29 pages.
Pillai et al., "Systems, Methods and Articles for Enhancing Wellness Associated With Habitable Environments," Preliminary Amendment, filed Mar. 25, 2015, for U.S. Appl. No. 14/012,444, 149 pages.
Pillai et al., "Systems, Methods and Articles for Enhancing Wellness Associated With Habitable Environments," U.S. Appl. No. 15/409,233, filed Jan. 18, 2017, 84 pages.
Pillai et al., "Systems, Methods and Articles for Enhancing Wellness Associated With Habitable Environments," U.S. Appl. No. 15/421,022, filed Jan. 31, 2017, 84 pages.
Plotnikoff, Ronald et al., "Effectiveness of Interventions Targeting Health Behaviors in University and College Staff: A Systematic Review," American Journal of Health Promotion, 2015, vol. 29, No. 5 (20 pages).
Potter et al., "Circadian Rhythm and Sleep Disruption: Causes, Metabolic Consequences, and Countermeasures," Endocrine Reviews, 2016, vol. 37, No. 6, pp. 584-608.
Preliminary Amendment, filed Jul. 12, 2017, for U.S. Appl. No. 15/543,114, Macary et al., "Systems, Methodsand Articles for Monitoring and Enhancing Human Wellness," 10 pages.
Preto et al., "Lighting in the Workplace: Recommended Illuminance (lux) at Workplace Environs," Advances in Design for Inclusion, 2019, pp. 180-191.
Provencio et al., "A Novel Human Opsin in the Inner Retina," The Journal of Neuroscience, 2000, vol. 20, No. 2, pp. 600-605.
Prudhon, Claudine et al., "WHO, UNICEF, and SCN Informal Consultation on Community-Based Management of Severe Malnutrition in Children," SCN Nutrition Policy Paper No. 21, Food and Nutrition Bulletin, 2006, vol. 27, No. 3 (supplement), The United Nations University, pp. s3-s108 (108 pages).
Rabbie, Harold M., "Distributed Processing Using Local Operating Networks," Assembly Automation, 1992, vol. 12, No. 1 (7 pages).
Rea, "Window Blind Occlusion: a Pilot Study," Building and Environment, 1984, vol. 19, No. 2, pp. 133-137.
Reinhart et al., "Monitoring manual control of electric lighting and blinds," Lighting Research & Technology, 2003, vol. 35, No. 3, pp. 243-260.
Revel et al., "Integration of real-time metabolic rate measurement in a low-cost tool forthe thermal comfort monitoring in AAL environments," Ambient Assisted Living , 2015 (11 pages).
Roberge et al., Operational Amplifiers: Theory and Practice, Second Edition, 2007 (104 pages).
Romm et al., Greening the Building and the Bottom Line: Increasing Productivity Through Energy-Efficient Design, 1994 (17 pages).
Rosen, Laura J. et al., "Effectiveness of Interventions to Reduce Tobacco Smoke Pollution in Homes: A Systematic Review and Meta-Analysis," International Journal of Environmental Research and Public Health, 2015, vol. 12, pp. 16043-16059.
Rubin et al., "Window Blinds as a Potential Energy Saver—A Case Study," National Bureau of Standards Building Science Series 112, 1978 (89 pages).
Saif, Umar, "Architectures for ubiquitous systems," University of Cambridge Computer Laboratory Technical Report No. 527, 2002 (271 pages).
Saini et al., "The Mammalian Circadian Timing System: Synchronization of Peripheral Clocks," Cold Spring Harbor Symposia on Quantitative Biology, 2011, vol. 76 (10 pages).
Salthammer et al. "Formaldehyde in the Indoor Environment," Chemical Reviews, 2010, vol. 110, No. 4, pp. 2536-2572.
Sandberg et al., "Experimental Methods in Ventilation," Advances in Building Energy Research, 2008,vol. 2, No. 1, pp. 159-210.
Sarigiannis et al., "Multi-objective optimization of air quality monitoring," Environmental Monitoring Assessment, 2008, vol. 136, pp. 87-99.
Satish et al., "Is CO2 an Indoor Pollutant? Direct Effects of Low-to-Mode rate CO2 Concentrations on Human Decision-Making Performance," Environmental Health Perspectives, 2012, vol. 120, No. 12, pp. 1671-1677.
Sbar et al., "Electrochromic dynamic windows for office buildings," International Journal of Sustainable Built Environment, 2012, vol. 1, pp. 125-139.
Schellen et al., "Differences between young adults and elderly in thermal comfort, productivity, and thermal physiology in response to a moderate temperature drift and a steady-state condition," Indoor Air, 2010, vol. 20, pp. 273-283.
Schlegel, "The Relative Effects of Convection And Radiation Heat Transfer on the Thermal Sensations of Sedentary Subjects," 1968 (73 pages).
Schröer, S. et al., "Evidence-based lifestyle interventions in the workplace—an overview," Occupational Medicine, 2014, vol. 64, pp. 8-12.
Schweizer et al., "Indoor time—microenvironment—activity patterns in seven regions of Europe," Journal of Exposure Analysis and Environmental Epidemiology, 2007, vol. 17, No. 2, pp. 170-181.
Semenova et al., "Association of the melatonin circadian rhythms with clock 3111T/C gene polymorphism in Caucasian and Asian menopausal women with insomnia," Chronobiology International, 2018 (12 pages).

(56) References Cited

OTHER PUBLICATIONS

Seppänen et al., "Association of Ventilation Rates and CO2 Concentrations with Health and Other Responses in Commercial and Institutional Buildings," Indoor Air, 1999, vol. 9, pp. 226-252.
Seppänen et al., "Summary of human responses to ventilation," Indoor Air, 2004, vol. 14, pp. 102-118.
Seppänen, O.A., et al., "Summary of human responses to ventilation," Indoor Air, 2004, vol. 14, SuppL 7, pp. 102-118 (17 pages).
Shearer, Jane et al., "Nutra-ergonomics: influence of nutrition on physical employment standards and the health of workers," Applied Physiology, Nutrition, and Metabolism, 2016, vol. 41, pp. S165-S174 (10 pages).
Siemens, "Demand-controlled ventilation: Control strategy and applications for energy-efficient operation," publicly available at least as early as May 21, 2018 (72 pages).
Smith-McLallen, Aaron et al., "Comparative Effectiveness of Two Walking Interventions on Participation, Step Counts, and Health," American Journal of Health Promotion, 2016 (9 pages).
Smith, GA et al., "Oral or parenteral iron supplementation to reduce deferral, iron deficiency and/or anaemia in blood donors (Review)," Cochrane Database of Systematic Reviews, 2014, Issue 7, pp. 1-120 (124 pages).
Song, "Could sperm quality be affected by a building environment? A literature review," Building and Environment, 2010, vol. 45, pp. 936-943.
Sorensen, Glorian, et al., "Worksite-based research and initiatives to increase fruit and vegetable consumption," Preventive Medicine, 2004, vol. 39, pp. S94-S100 (7 pages).
Spinellis, "The information furnace: consolidated home control," Personal and Ubiquitous Computing, 2003, vol. 7, pp. 53-69.
Storch et al., "Extensive and divergent circadian gene expression in liver and heart," Nature, 2002, vol. 417 (8 pages).
Strauss et al., "Influence of Heat and Humidity on the Airway Obstruction Induced by Exercise in Asthma," The Journal of Clinical Investigation, 1978, vol. 61, pp. 433-440.
Strøm-Tejsen et al., "The effects of bedroom air quality on sleep and next-day performance," Indoor Air, 2016, vol. 26, pp. 679-686.
Summons to attend oral proceedings issued in EP Application No. 15754628.4 on Sep. 10, 2018.
Sunde et al., "Blue-Enriched White Light Improves Performance but Not Subjective Alertness and Circadian Adaptation During Three Consecutive Simulated Night Shifts," Frontiers in Psychology, 2020, vol. 11, No. 2172, pp. 1-16.
Suryadevara, N.K. et al., "Sensor data fusion to determine wellness of an elderly in intelligent home monitoring environment", Instrumentation and Measurement Technology Conference, Graz: IEEE, (2012), ISSN 1091-5281, pp. 947-952, XP032451677.
Sutter et al., "The use of shading systems in VDU task offices: A pilot study," Energy and Buildings, 2006, vol. 38, pp. 780-789.
Swaminathan et al., "Are Individual Differences in Sleep and Circadian Timing Amplified by Use of Artificial Light Sources?," Journal of Biological Rhythms, 2017, vol. 32, No. 2, pp. 165-176.
Szigeti et al., "Spatial and temporal variation of particulate matter characteristics within office buildings—The OFFICAIR study," Science of the Total Environment, 2017, vol. 587-588, pp. 59-67.
Tähkämö et al., "Systematic review of light exposure impact on human circadian rhythm," Chronobiology International: The Journal of Biological and Medical Rhythm Research, 2019, vol. 36, No. 2, pp. 151-170.
Tan, Ai May et al., "Efficacy of a workplace osteoporosis prevention intervention: a cluster randomized trial," BMC Public Health, 2016, vol. 16, No. 859 (14 pages).
Tansil, Kristin A. et al., "Alcohol Electronic Screening and Brief Intervention: A Community Guide Systematic Review," American Journal of Preventative Medicine Author Manuscript, 2016 (19 pages).
Taylor et al., "Impact of Booster Breaks and Computer Prompts on Physical Activity and Sedentary Behavior Among Desk-Based Workers: A Cluster-Randomized Controlled Trial," Preventing Chonic Disease Public Health Research, Practice, and Policy, Centers for Disease Control and Prevention, Nov. 2016, vol. 13, E155, pp. 1-15 (16 pages).
Te Kulve et al., "Early evening light mitigates sleep compromising physiological and alerting responses to subsequent late evening light," Scientific Reports, 2019, vol. 9, No. 16064, pp. 1-12.
Tebb et al., "Use of theory in computer-based interventions to reduce alcohol use among adolescents and young adults: a systematic review," BMC Public Health, 2016, vol. 16, No. 517, pp. 1-33.
Techau, David et al. "Buildings, Brains and Behaviour: Towards an affective neuroscience of architecture: The Hedonic Impact of Sustainable Work Environments on Occupant Well-being," World Health Design, 2016, pp. 24-37.
Tennessen et al., "Views to Nature: Effects on Attention," Journal of Environmental Psychology, 1995, vol. 15, pp. 77-85.
Third Examination Report issued in AU Application No. 2016202287 on Feb. 15, 2021.
Third Office Action issued in MX Application No. MX/a/2016/011107.
Tong, Van T. et al., "Clinical interventions to reduce secondhand smoke exposure among pregnant women: a systematic review," Tobacco Control, Author Manuscript, 2015 (17 pages).
U.S. Green Building Council, "Daylight and views—daylight," 2009, available at https://www.usgbc.org/credits/schools/v2009/ieqc81.
Uğursal et al., "The effect of temperature, metabolic rate and dynamic localized airflow on thermal comfort," Applied Energy, 2013, vol. 111, pp. 64-73.
Uğursal, Ahmet, et al., "The effect of temperature, metabolic rate and dynamic localized airflow on thermal comfort," Applied Energy, 2013, vol. 111, pp. 64-73 (10 pages).
Ulrich, "View Through a Window May Influence Recovery from Surgery," Science, 1984, vol. 224, pp. 420-421.
Unswodh et al., "An automated version of the operation span task," Behavior Research Methods, 2005, vol. 37, No. 3, pp. 498-505.
US Department of Health and Human Services, 2008 Physical Activity Guidelines for Americans, Oct. 2008, available at https://health.gov/paguidelines/pdf/paguide.pdf (76 pages).
US Department of Justice Civil Rights Division, 2010 ADA Standards for Accessible Design, available at https://www.ada.gov/regs2010/2010ADAStandards/2010ADAStandards.pdf, accessed Oct. 31, 2017 (279 pages).
Van Den Wymelenberg, "Patterns of occupant interaction with window blinds: A literature review," Energy and Buildings, 2012, vol. 51, pp. 165-176.
Van Eerd, D. et al., "Effectiveness of workplace interventions in the prevention of upper extremity musculoskeletal disorders and symptoms: an update of the evidence," Occupational and Environmental Medicine, 2016, vol. 73, pp. 62-70.
Vandewalle et al., "Daytime Light Exposure Dynamically Enhances Brain Responses," Current Biology, 2006, vol. 16, pp. 1616-1621.
Vastamäki et al., "A behavioural model of temperature controller usage and energy saving," Personal and Ubiquitous Computing, 2005, vol. 9, pp. 250-259.
Veitch et al., "A model of satisfaction with open-plan office conditions: Cope field findings," Journal of Environmental Psychology, 2007, vol. 27, pp. 177-189.
Veitch et al., "Assessing Beliefs about Lighting Effects on Health, Performance, Mood, and Social Behavior," Environment and Behavior, 1996, vol. 28, No. 4, pp. 446-470.
Veitch et al., "Determinants of Lighting Quality II: Research and Recommendations," presented at the 104th Annual Convention of the American Psychological Association, 1996 (57 pages).
Verlarde et al., "Health effects of viewing landscapes—Landscape types in environmental psychology," Urban Forestry & Urban Greening, 2007, vol. 6, pp. 199-212.
Viola et al., "Blue-enriched white light in the workplace improves self-reported alertness, performance and sleep quality," Scandinavian Journal of Work, Environment & Health, 2008, vol. 34, No. 4, pp. 294-306.
VitashowerCorp., "Products," retrieved from http://www.vitashowercorp.com/products.html, retrieved on May 13, 2014, 8 pages.

(56) References Cited

OTHER PUBLICATIONS

Vitashower Corporation, "Ascorbic Acid Reduction of Residual Active Chlorine in Potable Water Prior to Halocarboxylate Determination," from Urbansky et al., Journal of Environmental Monitoring 2(3):253-256, 2000, retrieved from http://www.vitashowercorp.com/research.html, retrieved on May 13, 2014, 2 pages.
Vitashower Corporation, "Frequently Asked Questions," 2003, retrieved from http://www.vitashowercorp.com/FAQs.html, retrieved on May 13, 2014, 3 pages.
Vitashower Corporation, "Vitamin C Shower Filter SF-2000," 2003, retrieved from http://www.vitashowercorp.com/products.html, retrieved on May 13, 2014, 8 pages.
Vitashower Corporation, "Welcome to Vitashower Corporation," 2003, retrieved from http://www.vitashowercorp.com/index.html, retrieved on May 13, 2014, 4 pages.
Wargocki et al., "Ten questions concerning thermal and indoor air quality effects on the performance of office work and schoolwork," Building and Environment, 2017, vol. 112, pp. 359-366.
Wargocki et al., "The Effects of Outdoor Air Supply Rate in an Office on Perceived Air Quality, Sick Building Syndrome (SBS) Symptoms and Productivity," Indoor Air, 2000, vol. 10, pp. 222-236.
Watson et al., "Recommended Amount of Sleep for a Healthy Adult: A Joint Consensus Statement of the American Academy of Sleep Medicine and Sleep Research Society," Sleep, 2015, vol. 38, No. 6, pp. 843-844.
Wells et al., "Subjective Responses to the Lighting Installation in a Modern Office Building and their Design Implications," Building Science, 1965, vol. 1, pp. 57-68.
Weschler, "Ozone in Indoor Environments: Concentration and Chemistry," Indoor Air, 2000, vol. 10, pp. 269-288.
Weschler, "Ozone's Impact on Public Health: Contributions from Indoor Exposures to Ozone and Products of Ozone-Initiated Chemistry," Environmental Health Perspectives, 2006, vol. 114, No. 10, pp. 1489-1496.
West et al., "Blue light from light-emitting diodes elicits a dose-dependent suppression of melatonin in humans," Journal of Applied Physiology, 2011, vol. 110, pp. 619-626.
Wikipedia, "Home automation," Jan. 17, 2014, URL: https://en.wikipedia.org/w/index.php?title=Home_automation&oldid=591169195, retreived on Sep. 2, 2020, (11 pages).
Wikipedia, "Thermostat," as archived on Jan. 24, 2014, URL=https://en.wikipedia.org/w/index.php?title=Thermostat&oldid=592239648, download date Jun. 30, 2017, 10 pages.
Williams et al., Next Generation Air Monitor (NGAM) VOC Sensor Evaluation Report, EPA/600/R-15/122,2015 (71 pages).
Wisthaler et al., "Reactions of ozone with human skin lipids: Sources of carbonyls, dicarbonyls, and hydroxycarbonyls in indoor air," Proceedings of the National Academy of Sciences, 2010, vol. 107, No. 15, pp. 6568-6575.
Wolkoff, "Impact of Air Velocity, Temperature, Humidity, and Air on Long-Term VOC Emissions From Building Products," Atmospheric Environment, 1998, vol. 32, No. 14/15, pp. 2659-2668.
Won et al., "The State-of-the-Art in Sensor Technology for Demand-Controlled Ventilation, PERD S5-42: Final Report," IRC-RR-243, NRC Publications Archive, 2005 (89 pages).
Wong et al., "A multivariate-logistic model for acceptance of indoor environmental quality (IEQ) in offices," Building and Environment, 2008, vol. 48, pp. 1-6.
World Health Organization, "Global Nutrition Targets 2025: Low Birth Weight policy Brief," 2014, Geneva (8 pages).
World Health Organization, "Guideline: Daily iron supplementation in adult women and adolescent girls," 2016, Geneva (34 pages).
World Health Organization, "Guideline: Daily iron supplementation in infants and children," 2016, Geneva (54 pages).
World Health Organization, "WHO Recommendations for the Prevention and Management of tobacco use and second-hand smoke exposure in pregnancy," 2013 (104 pages).
Written Opinion of the International Searching Authority, dated Apr. 28, 2016, for International Application No. PCT/US2016/013215, 16 pages.
Written Opinion of the International Searching Authority, dated Dec. 26, 2013, for International Application No. PCT/US2013/057070, 5 pages.
Xiong et al., "Potential indicators for the effect of temperature steps on human health and thermal comfort," Energy and Buildings, 2016, vol. 113, pp. 87-98.
Yadlapalli et al., "Circadian clock neurons constantly monitor environmental temperature to set sleep timing," Nature, 2018, vol. 555 (21 pages).
Yetish et al., "Natural sleep and its seasonal variations in three pre-industrial societies," Current Biology, Author Manuscript, 2015, vol. 25, No. 21 (19 pages).
Yu et al., "People who live in a cold climate: thermal adaptation differences based on availability of heating," Indoor Air, 2013, vol. 23, pp. 303-310.
Zhai et al., "Human comfort and perceived air quality in warm and humid environments with ceiling fans," Building and Environment, 2015, vol. 90, pp. 178-185 (8 pages).
Zhai, Yongchao et al., "Comfort under personally controlled air movement in warm and humid environments," Building and Environment, 2013 (16 pages).
Zhai, Yongchao, et al., "Using air movement for comfort during moderate exercise," Building and Environment, 2015, vol. 24, pp. 344-352 (9 pages).
Zhang et al., "Study on TVOCs concentration distribution and evaluation of inhaled air quality under a re-circulated ventilation system," Building and Environment, 2007, vol. 42, pp. 1110-1118.
Zhang et al., "Thermal comfort in naturally ventilated buildings in hot-humid area of China," Building and Environment, 2010, vol. 45, pp. 2562-2570.
Zhang, Hui, "Human Thermal Sensation and Comfort in Transient and Non-Uniform Thermal Environments," Dissertation, 2003, University of California, Berkeley (436 pages).
Zhang, Yu F, et al., "The influence of heated or cooled seats on the acceptable ambient temperature range," Ergonomics, 2007, vol. 50, No. 4, pp. 586-600 (16 pages).
Zhao et al., "Effect of particle spatial distribution on particle deposition in ventilation rooms," Journal of Hazardous Materials, 2009, vol. 170, pp. 449-456.
Zhou et al., "Experimental study of the influence of anticipated control on human thermal sensation and thermal comfort," Indoor Air, 2014, vol. 24, pp. 171-177.
Zhu, Hongmei et al., "Is self-monitoring of blood glucose effective in improving glycaemic control in type 2 diabetes without insulin treatment: a meta-analysis of randomised controlled trials," BMJ Open, 2016, vol. 6, pp. 1-9 (9 pages).
Zhuang et al., "Haze insights and mitigation in China: an overview," Journal of Environmental Sciences, 2014, vol. 26, pp. 2-12 (11 pages).
Zinzi, "Office worker preferences of electrochromic windows: a pilot study," Building and Environment, 2006, vol. 41, pp. 1262-1273.

\* cited by examiner

SYSTEMS, METHODS AND ARTICLES FOR ASSESSING AND/OR IMPROVING HEALTH AND WELL-BEING

CROSS-REFERENCE TO RELATED APPLICATIONS

This application is a U.S. national phase application filed under 35 U.S.C. § 371 of International Application No. PCT/US2018/048853, filed Aug. 30, 2018, designating the United States, which claims priority from U.S. Provisional Application No. 62/634,608, filed Feb. 23, 2018, and from U.S. Provisional Application No. 62/593,678, filed Dec. 1, 2017, and from U.S. Provisional Application No. 62/552,189, filed Aug. 30, 2017, all of which are incorporated herein by references in their entirety.

TECHNICAL FIELD

This invention relates generally to assessing, monitoring, improving and/or modifying health and well-being for one or more people, and/or one or more factors that may improve and/or modify health and well-being for one or more people, wherein the one or more people may or may not be associated with a habitable or other built environment and/or spaces therein.

BACKGROUND

Most people spend significant amounts of time indoors or in habitable or other built environments, such as, for example, partially or completely enclosed spaces associated with homes, apartments, condominium units, hotels rooms, hospitals, spas, and other public and private facilities. While some of these spaces are typically controlled (and/or owned) by the principal occupants, other spaces are typically controlled by others such as, for example, a facility owner or operator, building manager, rental agent, etc.

Significant time in these spaces exposes the occupant to a wide range of environmental factors, some of which may have either adverse or beneficial effects on the occupant's health, well-being or sense thereof. Minimizing exposure to environmental or other factors that tend to have an adverse effect is desirable, as is increasing exposure to environmental or other factors that tend to have a beneficial effect.

More particularly, various problems may be associated with a built environment that may impact occupants or users of the built environment, or one or more other people associated with the built environment, such as, for example, poor lighting, poor air quality or ventilation, lack of ergonomic furniture, lack of a sick leave policy, etc. A built environment may include any type of building or occupiable space. In many situations, multiple problems may exist and the priorities or ranking of them may vary by location, use, budget availability, impact metric number and type of occupants, etc. As a result, one or more interventions may be used to help mitigate or otherwise resolve the problem. In some cases, while a problem may be known or suspected, an intervention which may help mitigate or otherwise resolve the problem may not be known or might be difficult to predict. Thus, an indicator that can predict the success of one or more interventions to one or more problems may be very helpful if one can be found or determined.

Further, researchers have begun to identify increasingly more aspects of our environment that have an impact on our health and well-being, and large databases of health-related data are being compiled. Nonetheless, consistent and feasible application of this information poses some difficulties, especially in certain types of buildings or in certain circumstances. For example, though certain air flow or natural light parameters may be preferable for certain spaces, the project's budgets, current building design, available materials, surrounding buildings, geography, among numerous other factors, may render some environmental interventions impractical or unworkable. Further, the wide array of health-related environmental aspects means evaluating extensive amounts of ever-growing research such that implementing the suggestions would be incredibly time consuming. Accordingly, many builders, homeowners, architects, and many others, are interested in having a manner of evaluating the environmental research and helping individuals apply this information to their spaces in a manner that works for the space, the individuals using the space, and those funding the project.

In other situations, a problem may exist independently of a built environment. For example, a person, a group of people, a neighborhood, or other community may have to deal with social, cultural, economic, family, educational, physical, mental, environmental, traffic, pollution, national, global, political, or other issues or problems that may impact their health and well-being. As a result, one or more interventions may be used to help mitigate or otherwise resolve the problem. In some cases, in a manner similar to problems with a built environment, while a problem may be known or suspected, an intervention which may help mitigate or otherwise resolve the problem may not be known or might be difficult to predict. Thus, an indicator that can predict the success of one or more interventions regarding one or more problems may be very helpful if one can be found or determined.

BRIEF DESCRIPTION OF THE DRAWINGS

Disclosed herein are embodiments of systems, apparatus, methods pertaining to assessing and/or improving human health and well-being in a built environment. This description includes drawings, wherein.

Figure 1:
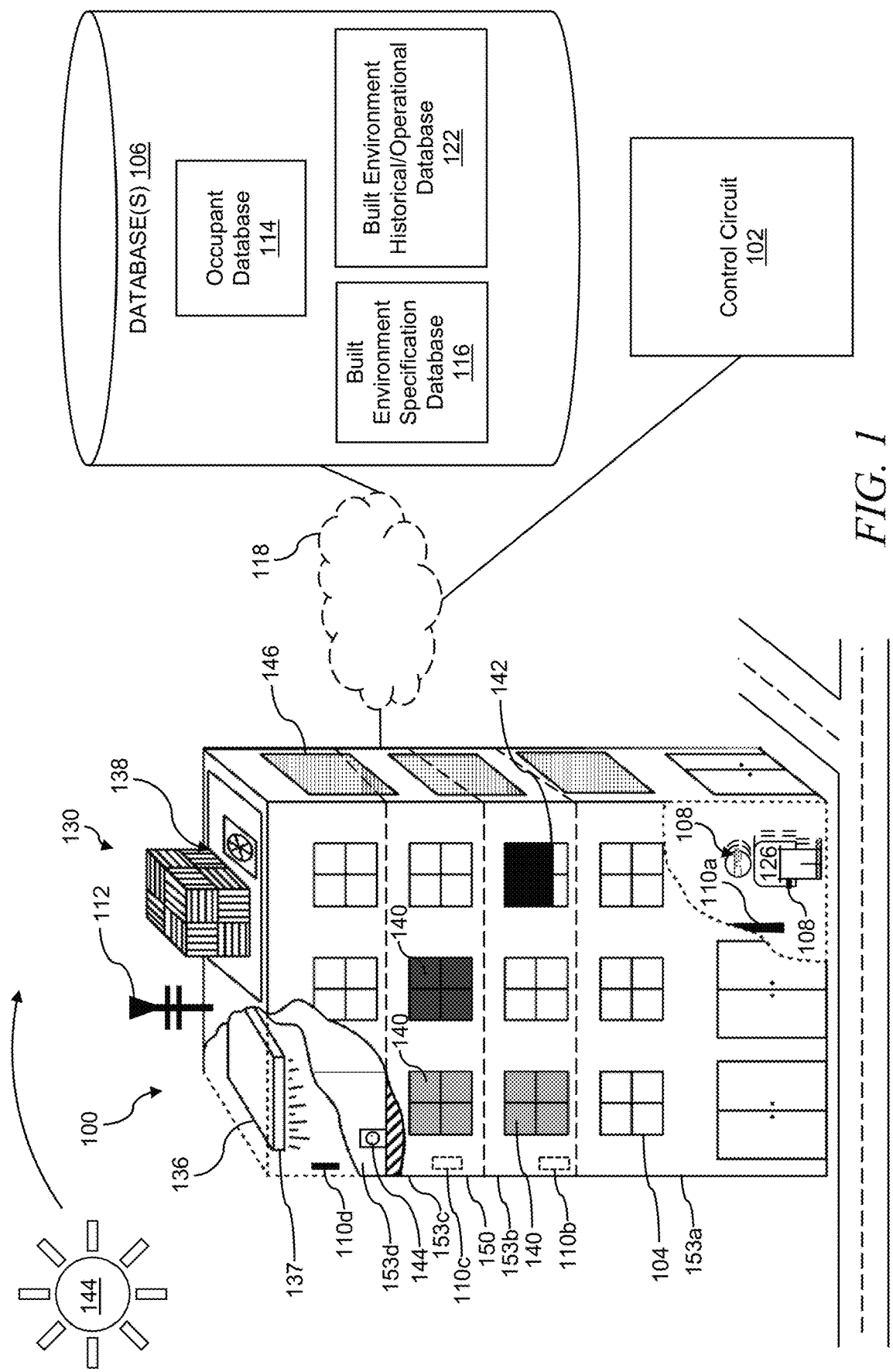
FIG. 1 is a block diagram of an exemplary smart building system in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

BRIEF SUMMARY

Many of the building systems, apparatus, and methods for controlling indoor environments in built structures are designed to manage building systems in the most energy efficient manner. These systems generally do not account for individual needs or preferences in a systemic or organized manner, except to permit individuals to manually override normal system operation, such as, for example, by manually adjusting settings. Further, these systems fail to respond to the dynamic needs of those occupying a space.

Thus, generally speaking, pursuant to various embodiments, systems, apparatuses and methods are provided herein useful to provide shelter to occupants in a built structure with environmentally-controllable zones with sensors (detecting lighting, temperature, and air quality) therein, wearable sensor(s), a built environment operation database with target operation parameters, and a control circuit that analyzes information from the sensors and the database to automatically manage the environment in the built environment. In one illustrative embodiment, these teachings employ wearable sensor(s) associated with occupants that can detect, for example, biometric information of the wearer/occupant, ambient lighting, temperature, and air quality levels. By one approach, biometric information may include, for example, heart rate, glucose levels, body temperature, heart-rate variability, sleep phase, sleep length, or respiration, motion or walking steps, body weight, or BMI. In operation, these teachings employ a building or built structure environmental control system that adjust at least one of lighting, temperature, or air quality and may include, for example, a lighting system, an HVAC system, a water system, and/or an air remediation system. The control circuit is generally in communication with the built environment sensors, wearable sensor(s), database(s), and the built environmental control system. In operation, the control circuit is configured to, receive sensor measurements, determine whether the measurements received fall within target operational parameters of the built environment, and if the measurements fall out of the target operational parameters, and/or send instructions to the built structure environmental control system to adjust lighting, temperature, and air quality.

Further, in some embodiments, the system includes an occupant health database with profiles of occupants associated with wearable devices having sensors. In some configurations, the system includes an occupant health database that the control circuit may be configured to query prior to sending instructions to the building environment control remediation system to determine adjustment parameters.

In operation, these teachings provide a method for regulating an occupied space by receiving measurements from a plurality of sensors in an environmentally-controllable built environment and wearable sensors associated with an occupant of the built environment, comparing measurements received with target operational parameters and personal target parameters in an occupant database, and, upon detection of either of the received measurements being outside of the target operational parameters or the personal target parameters, determining a location of the occupant within the built environment. The method then instructs a built environmental control system to adjust lighting, temperature, or air quality proximate the location of the occupant within the built environment.

In another aspect, these teachings may be configured to provide a smart building with sensors and databases that can identify and rank potential interventions. In one illustrative approach, a smart building system includes an environmentally-controllable built structure, installed sensors configured to detect environmental parameters in the interior of the built structure, wearable sensors associated with the occupants, a building environmental control system, and a built environment operational database with target operational parameters, and an intervention assessment engine. In operation, the intervention assessment engine is configured to receive sensor measurements from the installed sensors and the wearable sensors, detect whether the received sensor measurements fall within the target operational parameters, and, upon detection of measurements outside of the target operational parameters, analyze at least one of a health outcomes database or a scientific literature database to identify a plurality of potential interventions and indexing those potential interventions based on effectiveness, implementability, timelines, feasibility, impact metrics, and/or expense to identify a preferred intervention. Then, the intervention assessment engine can instruct the built environmental control system to adjust the lighting, temperature, or air quality based on the preferred intervention identified. As described below, the health outcomes database or the scientific literature database may include, for example, information on optimal performance ranges for occupants, circadian rhythm-based operational parameters, and health outcomes, among many other data sets.

As noted above, organizations are currently compiling data regarding a number of associations between one's environment and its aspects impact on human health. Considering the time spent indoors for many people, this is a significant area of interest and many different researches are examining various aspects of our personal environment's health impact. Accordingly, an ever-increasing amount of data about environmental health and wellness impacts is available for review and consideration. The teachings described herein assist with evaluating the information and applying it in a workable manner.

Further, implementing some of the suggestions gleaned from the research may be expensive, impractical, and/or logistically difficult, especially under certain conditions. Using these teachings, one of skill in the art may select environmental interventions based on efficacy, temporality, compatibility, adaptability, permanence, relevance, feasibility, geography, intended user, and/or cost, among other factors. For example, ordering the preference of indoor environmental quality (IEQ) related comfort conditions or identifying amenities that contribute to workplace satisfaction (sometimes using different budget scenarios) provide guidance to those tasked with improving workplace environments.

In one illustrative approach, a weighting system is used to help evaluate a space, a population or the needs of a group of people, and/or a geography to analyze the features or environmental aspects that have the most profound impact, provide the greatest felt improvement to the space, or otherwise improve the health and well-being or one or more people. These teachings also are customizable so that the weighting system can generate a personalized health and wellness attribute system, such as for a given demographic that might typically use a space, such as a nursing home, hospital, college dorm, or elementary school, among numerous options.

In some embodiments, a method for intervention assessment, such as evaluating an intervention or determining what interventions to employ, may include determining or identifying at least one problem associated with a built environment and determining at least one potential intervention based on the identified problem, wherein the potential intervention can reduce the prevalence of the identified problem in the built environment. In some embodiments, the method also may include one or more of the following: ranking one or more indicators of one or more potential interventions, ranking one or more interventions, implementing one or more interventions, identifying or otherwise determining one or more people associated with the built environment, identifying or otherwise determining one or more indicators associated with the at least one problem, identifying or otherwise determining a relationship between one or more indicators and one or more interventions, and/or using one or more indicators of the at least one problem to identify or otherwise determine the at least one intervention.

In some embodiments, a method for evaluating an intervention or determining whether an intervention should be incorporated or employed may include determining or identifying at least one problem associated with a built environment, determining or identifying at least one indicator associated with the problem, and determining at least one potential intervention based on the identified indicator, wherein the at least one potential intervention can reduce the prevalence of the identified problem in the built environment. In some embodiments, the method also may include one or more of the following: ranking one or more indicators, ranking one or more interventions, implementing one or more interventions, identifying or otherwise determining one or more people associated with the built environment, or other steps.

In some embodiments, a method for evaluating an intervention or determining whether to incorporate or employ an intervention may include determining or identifying a plurality of problems associated with a built environment; ranking the identified problems, selecting one of the identified problems based at least in part on the ranking, determining or identifying a plurality of indicators associated with the one of the identified problems, ranking the plurality of indicators, selecting one of the plurality of indicators based at least in part on the ranking, determining or identifying a plurality of potential interventions based on the one of the plurality of indicators, wherein each of the at plurality of potential interventions can reduce the prevalence of one or more of the identified problems in the built environment, ranking the plurality of potential interventions, and selecting at least one of the plurality of potential interventions based at least in part on the ranking of the plurality of potential interventions. In some embodiments, the method also may include one or more of the following: implementing one or more interventions, identifying or otherwise determining one or more people associated with the built environment, identifying or otherwise determining a characteristic of one or more people or community associated with the built environment, or other steps.

In some embodiments, a method for evaluating an intervention or determining whether to incorporate or employ an intervention may include determining or identifying at least one problem associated with a person or a group of people, a neighborhood or other community, determining or identifying at least one indicator associated with the identified problem, and determining or identifying at least one potential intervention based on the at least one indicator, wherein the at least one potential intervention can reduce the prevalence of the at least one problem for the person or a group of people. Such a group of people may include, for example, a neighborhood or other community. In some embodiments, the method also may include one or more of the following: ranking one or more indicators, ranking one or more interventions, implementing one or more interventions, identifying or otherwise determining one or more built environments associated with the person, a group of people, a neighborhood or other community, identifying or otherwise determining a characteristic of the person or a group of people that includes the person, or other steps.

In some embodiments, a method of operation of an intervention assessment system (which includes at least one processor, at least one non-transitory processor-readable medium communicatively coupled to the at least one processor and which stores at least one of instructions or data executable by the at least one processor) may include determining or identifying at least one problem associated with a built environment and determining or identifying at least one potential intervention based on the at least one problem. In such a configuration, the at least one potential intervention typically reduces the prevalence of the identified problem in the built environment.

In some embodiments, a method of operation of an intervention assessment system (which includes at least one processor, at least one non-transitory processor-readable medium communicatively coupled to the at least one processor and which stores at least one of instructions or data executable by the at least one processor) may include determining or identifying at least one problem associated with a built environment, determining or identifying at least one indicator associated with the at least one problem, and determining or identifying at least one potential intervention based on the at least one indicator, wherein the at least one potential intervention can reduce the prevalence of the at least one problem in the built environment.

In some embodiments, a method of operation of an intervention assessment system (which includes at least one processor, at least one non-transitory processor-readable medium communicatively coupled to the at least one processor and which stores at least one of instructions or data executable by the at least one processor) may include determining or identifying at least one problem associated with a person, determining or identifying at least one indicator associated with the at least one problem, and determining or identifying at least one potential intervention based on the at least one indicator, wherein the at least one potential intervention can reduce the prevalence of the at least one problem for the person.

In some embodiments, an intervention assessment system may include at least one processor; at least one non-transitory processor-readable medium communicatively coupled to the at least one processor and which stores at least one of instructions or data executable by the at least one processor for implementing a method, the method may include determining or identifying at least one problem associated with a built environment and determining or identifying at least one potential intervention associated with the identified problem, wherein the at least one potential intervention can reduce the prevalence of the at least one problem in the built environment.

In some embodiments, a system may include at least one non-transitory processor-readable medium communicatively coupled to the at least one processor and which stores at least one of instructions or data executable by the at least one processor for implementing a method that may include determining or identifying at least one problem associated with a built environment, determining or identifying at least one indicator associated with the identified problem, and determining or identifying at least one potential intervention based on the identified indicator, wherein the potential intervention can reduce prevalence of the at least one problem in the built environment.

In some embodiments, a system may include at least one processor, and at least one non-transitory processor-readable medium communicatively coupled to the at least one processor and which stores at least one of instructions or data executable by the at least one processor for implementing a method. The method may include determining or identifying at least one problem associated with a person, determining or identifying at least one indicator associated with the identified problem, and determining or identifying at least one potential intervention based on the identified indicator, wherein the at least one potential intervention can reduce the prevalence of the at least one problem for the person.

The teachings herein may incorporate or be used in combination with the teachings from international application no. PCT/US2016/013215, titled Systems, Methods and Articles for Monitoring and Enhancing Human Wellness that was filed Jan. 13, 2016, international application no. PCT/20U.S.17/48382 titled Systems, Methods and Articles for Enhancing Wellness Associated with Habitable Environments that was filed on Aug. 24, 2017, U.S. application Ser. No. 14/012,444, titled Systems, Methods and Articles for Enhancing Wellness Associated with Habitable Environments filed on Aug. 28, 2013, and U.S. application Ser. No. 15/249,184, titled Methods for Enhancing Wellness Associated with Habitable Environments filed Aug. 26, 2016, all of which are incorporated herein by reference.

DETAILED DESCRIPTION

A habitable or other built environment, such as, for example, a physical surrounding, structure, or other space that serves as the settings for human activity, influences human health and human behavior. In some embodiments, the systems and methods described herein are intended to improve human health and/or well-being through the built environment using an approach that attempts to tailor or select one or more interventions for specific buildings, locations, and/or populations. In some embodiments, the described systems and methods are intended to improve human health and well-being for one or more people, a neighborhood or other community, such as, for example, using an approach that attempts to tailor or select one or more interventions for the one or more people, neighborhood or other community, etc., regardless of whether or not the one or more people, neighborhood or other community, etc., or the one or more interventions, are associated with a built environment.

There are many ways that a person or a group of people may be associated with a habitable or other built environment. This includes, but is not limited to, the person or the group of people is working in a built environment, living in a built environment, visiting a built environment, passing by or through a built environment, being in or in proximity to a built environment, entering or leaving a built environment, and/or governing, owning or managing a built environment.

Similar to the above, there are many ways that a person or a group of people may be associated with a neighborhood or other community. This includes, but is not limited to, the person or the group of people is working in a neighborhood or other community, living in a neighborhood or other community, visiting a neighborhood or other community, passing by or through a neighborhood or other community, being in or in proximity to a neighborhood or other community, entering or leaving a neighborhood or other community and/or governing, owning or managing a neighborhood or other community. A neighborhood or other community may include all or parts of a city, county, country, region, residential area, manufacturing area, office area, sports related area, mixed use area, etc.

There also are many ways that a neighborhood or other community may be associated with a built environment, such as by having the built environment in, accessible to, or used by the neighborhood or other community or one or more people in or otherwise associated with the neighborhood or other community.

A habitable or other built environment or a neighborhood or other community may take many forms and designs, may be used for one or more uses, may be constructed from one or more materials, and may be associated with one or more people or groups of people. In some embodiments, a habitable or other built environment or a neighborhood or other community may be or include some or all of one or more of the following: a school, classroom(s), a gymnasium, business office(s), an office building, a single family home, a hotel, hotel room(s), a motel, motel room(s), an inn, lounge area(s), nightclub(s), theatre(s) including movie theater(s), an apartment building, apartment(s), research facility/ies, darkroom(s), drawing room(s), lab(s), a prison or prison cell(s), jail(s), library/ies, courtroom(s), a museum, gallery/ies, art studio(s), hallway(s), kennel(s), boardroom(s), locker room(s), shower(s), laundry room(s), a laundromat, wash room(s), training room(s), mail room(s), a post office, lunch room(s), kitchen(s), bed room(s), guest room(s), loft(s), a library, vestibule(s), a nursery, a day care facility, an elder care facility, a utility room, closet, reception area(s), dining area(s), storage facility/ies, storage area(s), a police station, a fire station, conference room(s), control room(s), cabin(s), ballroom(s), assembly room(s), boiler room(s), a chapel, cell(s), a newsroom, mudroom, a wine cellar, studio(s), clean room(s), show room(s), a porch, sitting room(s), a solarium, pantry/ies, nursing room(s), a conservatory, a church, recovery room(s), hospital room(s), a hospital, a temple, a lodge, a den, a foyer, an engine room, arena, castle, convention center, dormitory/ies, a drawing room, emergency room(s), fitting room(s), a cloakroom, chamber(s), a lobby, an attic, military facility/ies, a parking garage, a stairway, an underground bunker, a sport venue, manufacturing facility/ies, testing facility/ies, a train station, a bus station, store(s), a mall, an airport, a barn, a shed, a restaurant, a bar, a cafe, diner, an exercise facility, a barber shop, a beauty salon, a changing or dressing room, a bath room, a spa, a television studio or station, a radio studio or station, a recording studio, a game room, or other occupiable space or facility.

Health can be defined as a state of balance between physical, mental, and social states in the absence of illness and can be a component of well-being that is comprised of both mental or psychological aspects (e.g., stress and anxiety levels, coping mechanisms) and physical or physiological aspects or indicators (e.g., blood pressure, cholesterol levels). Health can be measured through a physical assessment (e.g., an annual physical) and a psychological assessment or work-up (e.g., a mental health assessment), and the health of a person typically changes over time. Well-being can be defined, at least in part, by a person's attitude or subjective perception towards his or her physical, mental, and social conditions and can be characterized through scales of life satisfaction, happiness, and prosperity. Although health factors can contribute to a person's well-being, other factors (e.g., life circumstances) can contribute as well. Well-being often is measured through surveys and a person's well-being may change over time.

In some embodiments, an intervention may include a set of one or more actions aimed at impacting health and well-being, as well as comfort and satisfaction outcomes in a built environment, and/or for a person or group of people, for a neighborhood or other community, etc., who or which may or may not be associated with one or more built environments. Interventions often fall in one of two main categories: 1) design (capital), which includes, but is not limited to, technology, products, furniture, aesthetic elements (e.g., paintings or pictures on walls, wall color, fixture choices, furniture design, decorations, etc.) and engineering designs that make up the physical surroundings or influence the physical state and function of a built environment and/or one or more people who may or may not be associated with a built environment, and 2) policies (operational), which include, but are not limited to, regulations, guidelines, preferences, and encouraged practices aimed at increasing the prevalence of positive behaviors (e.g., biking to work, smoking cessation, healthy eating, and social interaction, among others), and/or to decrease the prevalence of negative behaviors (i.e., smoking, high sugar diet, lack of exercise, and lack of cleanliness, among others). Policies may or may not be associated with a specific built environment, person, group of people, neighborhood, or other community. Some of the primary output metrics used in the disclosed systems, methods and articles include: 1) Disability-Adjusted Life Years (DALY), 2) Years Lived with Disability (YLD), 3) Days of Comfort Lost (DCL), and 4) Amenity Satisfaction (%). More specifically, in some embodiments the disclosed systems and methods can provide an interdisciplinary approach to benchmarking, ranking and prioritizing potential interventions that takes into account demographics (e.g., age, gender, race/culture), geography, health and other priorities, group affiliation, and the availability, feasibility, and expected efficacy of options and other interventions for improving health and well-being and creating other benefits. In some embodiments, the disclosed systems and methods may be useful to a diverse group of stakeholders, including, but not limited to, architects, interior designers, health scientists, insurance personnel, and regulatory agencies, for identifying and comparing interventions based on their top concerns (e.g., health needs, preference, efficacy, efficiency, cost, benefit provided, duration or scope of benefit provided, cost, cost-effectiveness, etc.).

In some embodiments, an intervention may be or include one or more built environment design or policy strategies or attributes that aim to impact one or more problems in a built environment or otherwise reduce the occurrence or ramifications of the one or more problems. Individual interventions, or sets of one or more interventions, may vary in their cost, feasibility, implementability, time required for implementation, effectiveness, etc., and may be ranked in accordance with one or more of these or other factors.

In some embodiments, indirect or complex relationships between one or more interventions or between one or more inventions and a problem (e.g., sit-stand desk's often weak ability to improve a user's overall physical activity level) may be address such that the impacts or outcomes of one or more interventions may be synergistically combined to more effective address a problem. For example, a sit-stand desk, along with a treadmill, a walkable design in a built environment, and safe and accessible stairways, when combined, may present a more effective approach to improving the user's health and activity levels where the problem is identified as occupants of the built environment not getting enough exercise or not having suitable access to exercise related amenities.

As used herein a problem may include, for example, an issue related to a built environment and may be internal or external to that built environment or a human issue related to a particular individual's health and wellness. Further, the indicators discussed herein may relate to a cause of the problem or a metric related thereto. By one approach, this metric is measurable to provide a sense or scope of the problem. While the measurable metric related to the problem may indicate a scope of the problem, this indicator may not indicate causation (though certain indicators may clearly illustrate causation regarding a problem), and therefore, the intervention(s), which typically relate to the cause of the problem, may be more difficult to parse, and therefore, require examination and ranking of several potential and/or recommended intervention(s). There are a number of different approaches to ranking potential interventions, as discussed below.

A lack of health or well-being (which may be a problem) created by or otherwise associated with a built environment, a community, a person, or group of people may result from many things, such as one or more of the following: presence of particulate matter at a level of PM2.5, presence of certain plant-based particulate, presence of certain animal-based particulate, presence of certain pest-based particulate, presence of certain bacteria, viruses, fungi or mold, presence of particulate matter at a level of PM10, presence of certain ozone, radon, benzene, carbon dioxide, carbon monoxide, or nitrogen dioxide, presence of diesel exhaust particulate matter, presence of lead or mercury particulates, presence of formaldehyde, presence of certain inorganic chemicals, presence of certain organic chemicals, presence of certain microorganisms, presence of tobacco smoke, presence of benz[a]pyrene, presence of certain disinfectants, presence of certain disinfectant byproducts, presence of certain ultrafine particulate, and presence of certain radionuclide. For example, the problem may be a lack of suitable air quality within an office, home, hotel, store, or other habitable space, or the presence of a particular VOC, mold, particulate matter, smoke, etc., within an office, home, restaurant, school, or other habitable space.

In other examples, a problem associated with a built environment, a person, a group of people, a neighborhood, or other community, etc., may be or include one or more of the following: availability, or lack thereof, or quality of water in the built environment; availability, or lack thereof, or quality of beverage(s) in the built environment; availability, or lack thereof, or quality of food in the built environment; availability, or lack thereof, or quality of healthy food in the built environment; availability, or lack thereof, or quality of exercise related amenities or design features in the built environment; availability, or lack thereof or quality of exercise equipment in the built environment; availability, or lack thereof, or quality of medical equipment in the built environment; disease, discomfort, disability or dissatisfaction of one or more people associated with the built environment; or a medical or health condition or one of more people associated with the built environment.

In some embodiments, a current policy or a lack of a current policy may create a problem associated with a built environment, person, group of people, neighborhood, or other community, etc. The policy may be, include or otherwise relate to: a leave policy, vacation policy, remote work policy, insurance policy, travel policy, spending policy, gift policy, trade policy, review policy, promotion policy, sick policy, management policy, approval policy, approvable spend policy, independent contractor policy, employee policy, use of company resources policy, human resources policy, security policy, privacy policy, intellectual property policy, compliance policy, financial policy, unfair practices policy, child day care policy, or a legal policy, among others. It is also possible that the problem may be the availability (or lack thereof), applicability, quality, effectiveness, consistency, or usability of one or more policies.

In some embodiments, identifying or otherwise determining at least one indicator associated with at least one problem in a built environment or associated with a person, group of people, neighborhood, or other community, etc. may include one or more of the following: accessing a database of potential indicators of one or more problems, assessing a database of actual, potential or expected problems associated with the built environment (e.g., if the built environment uses a specific type of flooring, lumber, tiles, etc., and such materials tend to outgas or emit certain particulates, gases, or VOCs, a potential problem may be created), accessing a database of actual, potential or expected problems associated with at least one person associated with the built environment (e.g., does a person frequently increase the air temperature in the built environment due to being cold, did a person change the lighting in the built environment, does the person have a disability), conducting a poll or survey related to at least one problem or potential problem (e.g., does a particular problem occur, how serious is a particular problem, what is the short-term or long-term impact of a particular problem), conducting a literature review associated with at least one problem or potential problem (e.g., the likelihood, impact or severity of a particular problem such as occurrence of a specific VOC or other material occurring in a particular type, design or location of a habitable environment), conducting or analyzing research regarding at least one indicator or potential indicator, ranking a plurality of indicators or potential indicators, ranking a relevance of a plurality of indicators or potential indicators to the at least one problem, determining a relevance of at least one indicator or potential indicator to the at least one problem, selecting at least one indicator from a plurality of potential indicators, determining a causal relationship between at least one indicator and the at least one problem, and convening an expert panel to deliberate at least one potential indicator of the at least one problem (which may include scoring or ranking one or more indicators on the effectiveness, applicability, strength of a causal relationship to one or more interventions or problems, impact of an intervention associated with an indicator, quality, implementability of an intervention related to an indicator, relevance, feasibility or effectiveness of an intervention associated with an indicator, cost of measuring or otherwise determining, etc., of one or more indicators).

In some embodiments, an intervention for a built environment, a person, group of people, neighborhood, or other community, etc. may include or be related to a reduction or other change in one or more of the following: PM2.5 level, presence of at least one plant-based particulate, presence of at least one animal-based particulate, presence of at least one pest-based particulate, presence of bacteria, presence of at least one virus, fungi, or mold, PM10 level, ozone level, radon level, benzene level, carbon dioxide level, carbon monoxide level, nitrogen dioxide level, diesel exhaust particulate matter, lead particulate level, mercury particulate level, formaldehyde level, presence of at least one inorganic chemical, presence of at least one organic chemical, at least one microorganism, presence of tobacco smoke, presence of benz[a]pyrene, presence of at least one disinfectant, presence of at least one disinfectant byproduct, presence of an ultrafine particulate, and presence of at least one radionuclide.

In some embodiments, an intervention for a built environment, a person or group associated with the built environment, a community or neighborhood that includes the built environment may include or be related to the addition or implementation of, change to, or removal of one or more of the following: a smoking ban in at least part of the built environment, a healthy entrance to at least part of the built environment, a cleaning protocol implementable in at least part of the built environment, pesticide use in at least a part of the built environment, materials used in at least part of the built environment, moisture management in at least a part of the built environment, pest control measures used in at least a part of the built environment, combustion minimization measures used in at least a part of the built environment, toxic material reduction measures used in at least a part of the built environment, material safety measures used in at least a part of the built environment, antimicrobial measures used in at least part of the built environment, ventilation effectiveness in at least a part of the built environment, ventilation control capabilities in at least a part of the built environment, agricultural contaminant management in a least a part of the built environment, organic contaminant management in at least a part of the built environment, inorganic contaminant management in at least a part of the built environment, agricultural contaminant management in at least part of the built environment, volatile organic compound (VOC) management in at least a part of the built environment, air filtration in at least a part of the built environment, air flush management in at least a part of the built environment, air purification in at least a part of the built environment, microbe control in a least a part of the built environment, mold control in at least a part of the built environment, water quality in at least a part of the built environment, air quality in at least a part of the built environment, a water additive in at least a part of the built environment, use of cleanable equipment in at least a part of the built environment, use of cleaning equipment in at least a part of the built environment, cleaning materials in at least a part of the built environment, use of at least one operable window in at least a part of the built environment, use of direct source ventilation in at least a part of the built environment, use of displacement ventilation in at least a part of the built environment, at least one outdoor air system or device connected to at least a part of the built environment, window size in at least a part of the built environment, window location in at least a part of the built environment, window transmittance in at least a part of the built environment, window shading in a least a part of the built environment, electric light control in at least a part of the built environment, lamp shielding in at least a part of the built environment, lamp quality in at least a part of the built environment, lamp positioning in at least a part of the built environment, light positioning in at least a part of the built environment, light quality in at least a part of the built environment, light temperature in at least a part of the built environment, light type in at least a part of the built environment, temperature control capability in at least a part of the built environment, humidity in at least a part of the built environment, humidity control capability in at least a part of the built environment, surface reflectivity in at least a part of the built environment, color rendering index in at least a part of the built environment, workstation design in at least a part of the built environment, air flow speed in at least a part of the built environment, air flow direction in at least a part of the built environment, signal to noise ratio in at least a part of the built environment, sound reverberation time in at least a part of the built environment, noise or sound level in at least a part of the built environment, noise or sound pressure in at least a part of the built environment, aesthetics of at least a part of the built environment, a view from at least a part of the built environment, size of at least a part of the built environment, access to and proximity of transportation from at least a part of the built environment, quality of transportation available from at least a part of the built environment, and ambient decibel level in at least a part of the built environment.

In some embodiments, a potential intervention may include or be related to the availability of, or providing more of, at least one of the following: food (healthy and/or unhealthy), fruits, vegetables, whole grain food, nuts, seeds, milk, red meat, processed meat, water, beverages, sweetened beverages, unsweetened beverages, low fiber foods, high fiber foods, foods with high sodium, foods with low sodium, foods with high trans-fat, foods with low trans-fat, foods with low omega-3 fat, foods with high omega-3 fat, high calorie foods, low calorie foods, sugar, sugar substitutes, sweeteners, low calcium foods, high calcium foods, foods with monounsaturated fatty acid, foods with polyunsaturated fatty acid, high protein foods, and low protein foods. Food availability may be determined based on whether or not the food is available in a built environment (or portions thereof), easily accessible to a built environment, or otherwise accessible or available to one or more people, neighborhoods, or other communities, who may or may not be associated with a built environment.

In some embodiments, a potential intervention may include or be related to the availability of water in a built environment or otherwise available to a person or group of people; availability of at least one beverage in a built environment or otherwise available to a person or group of people; availability of food in the built environment; availability of healthy food in the built environment or otherwise available to a person or group of people; availability of exercise equipment in the built environment or otherwise available to a person or group of people; availability of medical equipment in the built environment or otherwise available to a person or group of people; one or more policies associated with a built environment, a person, a group of people, or a neighborhood or other community; or one or more policies, goals, needs, characteristics, problems, etc., associated with one or more people who may or may not be associated with a built environment.

In some embodiments, a potential intervention for a built environment may include or be related to one or more of the following: changing indoor environmental quality (IEQ) in at least part of the built environment; changing a comfort feature in at least part of the built environment; raising, reducing, or changing the air temperature in at least part of the built environment; changing air quality in at least part of the built environment; reducing humidity in at least part of the built environment; increasing availability of biophilia in at least part of the built environment; increasing quality of biophilia in at least part of the built environment; changing air purification capability in at least part of the built environment; improving water quality in at least part of the built environment; changing water filter capability in at least part of the built environment; changing water quality control capability in at least part of the built environment; changing air quality control capability in at least part of the built environment; changing air temperature control capability in at least part of the built environment; changing air filter capability in at least part of the built environment; changing food availability in at least part of the built environment; improving food quality in at least part of the built environment; improving water availability in at least part of the built environment; changing food availability in at least part of the built environment; changing beverage availability in at least part of the built environment; changing a configuration of at least part of the built environment; changing at least one amenity available in the built environment; changing an acoustic related feature in at least part of the built environment; reducing noise in at least part of the built environment; changing at least one piece of furniture in the built environment; removing at least one piece of furniture in the built environment; removing a surface coating present in at least part of the built environment; removing a material type from at least part of the built environment; changing a material used in at last part of the built environment; adding at least one amenity available in the built environment; changing at least one amenity available in the built environment; removing at least one amenity available in the built environment; improving an ergonomic feature of the built environment; adding an ergonomic feature to the built environment; improving physical comfort for at least one person who may occupy at least a part of the built environment; changing at least one air flow pattern in at least part of the built environment; changing air flow control capability in at least part of the built environment; reducing average air particle count in at least part of the built environment; reducing the prevalence of at least one particle type of a certain size in at least part of the built environment; reducing the prevalence of at least one particle type below a designated size in at least part of the built environment; reducing the prevalence of at least one kind of material in at least part of the built environment; increasing light availability in at least part of the built environment; changing a light pattern in at least part of the built environment; changing a light temperature in at least part of the built environment; changing light availability in at least part of the built environment; changing light control capability in at least part of the built environment; changing a window size in the built environment; changing a window transparency in the built environment; installing a window in the built environment; changing a feature in the built environment; adding a feature in the built environment; removing a policy associated with the built environment; changing a policy associated with the built environment; and/or adding a policy associated with the built environment.

In some embodiments, one or more potential interventions may be ranked and such ranking may be subject to or otherwise based on one or more of the following: disability adjusted life years, years lived with disability, days of comfort lost, amenity satisfaction, or disability adjusted life years created or reduced by, or otherwise associated with, at least one potential intervention, years lived with disability created or reduced by, or otherwise associated with, at least one potential intervention, days of comfort lost created or reduced by, or otherwise associated with, at least one potential intervention, amenity satisfaction created or reduced by, or otherwise associated with, at least one potential intervention, the relevance to a person or a group of people associated with a built environment, effectiveness of at least two potential interventions regarding one or more problems, efficiency of at least two potential interventions regarding one or more problems, duration of at least two potential interventions regarding one or more problems, cost of at least two potential interventions regarding one or more problems, feasibility of at least two potential interventions regarding one or more problems, effectiveness of at least two potential interventions regarding one or more problem, feasibility or implementability of at least two potential interventions regarding one or more problems within a given time period, physical comfort of at least one person who may or may not be associated with a built environment, a change in work satisfaction of at least one person who may or may not be associated with a built environment, a change in at least one environmental condition in a built environment or impacting a person or a group of people, characteristic of at least one person or a group of people who may be impacted by at one or more potential interventions, a change in the number of people that would be impacted by at least two potential interventions for one or more problems, number of problems that would be reduced or otherwise impacted by at least two potential interventions, and/or reduction created by or the impact of one or more potential interventions in solving or helping to resolve a problem with or for a built environment, person, group of people, neighborhood or other community, among others.

In some embodiments, the systems or methods may include sending, accessing, receiving, and/or analyzing data associated with one or more of the following: one or more people or groups of people (such as, for example, by receiving health data from wearable devices, such as smartwatches that track, for example, heart rate, steps, temperature, oxygen-levels, and/or other health-related aspects), a neighborhood or other community; a plurality of geographic locations; a plurality of potential interventions; a plurality of potential interventions, wherein at least two of the plurality of potential interventions are usable in a plurality of geographic locations and/or for one or more people; a plurality of potential interventions, wherein at least two of the plurality of potential interventions are usable in a built environment or for a person or group of people; a plurality of potential interventions that may decrease the prevalence of disease associated with a built environment and/or one or more people; a plurality of potential interventions that may decrease the prevalence of disability associated with a built environment; a plurality of potential interventions that may decrease the prevalence of discomfort associated with a built environment and/or one or more people; a plurality of potential interventions that may decrease the prevalence of dissatisfaction associated with a built environment and/or one or more people, a person, a group of people or a neighborhood or other community; a plurality of current, expected, or desired uses of a built environment; a plurality of materials usable in a built environment; a plurality of materials used in a built environment; a plurality of materials usable or used in furniture; a plurality of sensors associated with a built environment; a group of people a community or neighborhood; a characteristic of a person, a group of people, a neighborhood or other community; one or more built environments; one or more devices associated with a person, worn by a person, or carried by a person; and/or a plurality of devices associated with a person associated with a built environment, worn by a person associated with a built environment, or carried by a person associated with a built environment.

For example, by one approach, the data from a plurality of wearable devices (worn by different individuals that may occupy a built space at a different times) may be analyzed to identify problems with a built environment based on the indicators that are measured by the devices. In one illustrative approach, a wearable or electronic user device may be periodically queried to request feedback from occupants in the built environment (such as, for example, to query occupants about comfort and/or alertness, among others). In operation, the wearable devices typically transmit related data from the wearable devices to a control circuit of the intervention assessment system. In one illustrative approach, the wearer of the device is typically registered with the intervention assessment system so that data obtained from the wearable device may be analyzed relative the individual's baseline or other personal data, such as, for example, age, medical history, or occupation.

Other data may be obtained, for example, from additional sensors within and around the built environment, such as, for example, carbon monoxide detector(s), particulate sensor(s), movement sensor(s), and/or light sensors, among numerous others. These sensors may be, for example, associated with ventilation or remediation systems, HVAC systems, lighting controls, and/or stand-alone sensors, such as, for example, the wearable sensors, desk-top sensors and/or wall-mounted sensors, among others.

In some embodiments, the disclosed systems and methods can assist health-related decision making, whereby recommendations can be driven by data in addition to evidence-based best practices, the integration of the strongest and up-to-date science-based evidence, expert opinion, client values/concerns, and/or other factors. Furthermore, in some approaches, such systems and methods can use at least three complementary systems for: 1) ranking environmental conditions (e.g., thermal comfort, acoustic, light, water quality, air quality, etc.) in relation to physical comfort, 2) identifying the workplace amenities that contribute most to employee satisfaction under various budget scenarios, and 3) evaluating the efficacy of interventions based on relevance, implementability, effectiveness, efficiency, duration, impact, feasibility, and cost.

Examples of Potential Applications

Corporate Wellness
Pharmaceuticals
Health Insurance
Dental Insurance
Vision Insurance
Life Insurance
Actuarial Science
Urban Planning
Product Standards
Wellness services vs others (including preventative approaches and pharma)
Supplements
Therapies (physical, psychological)
Ratings for health service companies (hospitals, assisted living facilities, hospices)
Algorithms for building automation systems
Mobile Apps
Life Coaching
Electronic medical records integration with behavior and environmental exposure
Taxation and subsidies
Local, regional, national, etc. policy development and implementation In some embodiments, one or more characteristics of one or more built environments or one or more people may be identified or otherwise determined or used. Such characteristics may be or include one or more of the following: location of a built environment; availability of water in a built environment; availability of at least one beverage in a built environment; availability of food in a built environment; availability of healthy food in a built environment; availability of exercise equipment in a built environment; availability of medical equipment in a built environment; a climate condition for a built environment; an environmental condition within a built environment; a desired environmental condition within a built environment; a quality of a built environment; a design of a built environment; a current policy associated with a built environment; a desired policy for a built environment; an amenity available at a built environment; a desired amenity for a built environment; one or more people or groups of people associated with a built environment; age of a built environment; an owner of a built environment; an occupier of a built environment; a desired occupant of a built environment; a current feature of a built environment; a desired feature of a built environment; a maintenance history of a built environment; a current use of a built environment; an expected use of a built environment; a history of use of a built environment; a desired use of a built environment; a goal of a current owner of a built environment; a goal of a current manager of a built environment; a goal of a current occupier of a built environment; a goal of an expected occupier of a built environment; and a regulation that may apply to a built environment.

In some embodiments, one or more characteristics or problems of or associated with a person or a group of people may be identified or otherwise determined or used. Such characteristics or problems may include or be related to one or more of the following: age of the person; average age of the group; association of the person with a built environment; association of the group with a built environment; occupation of the person; employer of the person; a policy or desired policy associated with the person or group of people; employment status of the person; employment history of the person; location of the person; a goal or need of the person; current health of the person; future travel plan of the person; travel history of the person; travel history of the group; medical history of the person; marital status of the person; marital history of the person; family size of the person; family history of the person; schedule of the person; gender of the person; gender ratio of the group; race of the person; education level of the person; social status or popularity of the person or group; hobby or interests of the person or group; political or other views or opinion of the person or group; affiliation of the person or group; average education level of the group; nationality of the person; a personal need of the person; a desired characteristic of the person; a desired characteristic of the group; a health condition of the person; and a health assessment of the group.

As suggested above, in some embodiments, one or more sensors may be used in, around, or otherwise associated with a built environment, a person, group of people, neighborhood, or other community, etc. Such a sensor may be or include, for example, a biometric sensor (such as those associated with personal wearable devices), an air quality sensor, a temperature sensor, a humidity sensor to detect at least one air quality parameter, an audio transducer to detect ambient noise or other sound levels, a motion detector, and a light sensor to detect at least one of a light level or a color index of light.

In some embodiments, a sensor may be associated with a person, wherein the sensor includes one or more of the following: a biometric sensor, a location detector, temperature sensor operable to detect a temperature of the person or the environment the person is in, a scale operable to detect a weight of the person, a heart rate sensor operable to detect a heart rate of the person, a blood oxygen sensor operable to detect a level of blood oxygen of the person, a respiratory cycle sensor operable to detect at least one characteristic of a respiratory cycle of the person, and an electroencephalography sensor operable to detect at least one brainwave pattern of the person, and a sensor capable of collecting wellness or other data from the person.

Indoor environmental quality (IEQ) and non-salary workplace benefits (e.g., amenities such as health insurance, subsidized gym memberships, sit-stand desks, ergonomic features, vacation policies, food availability, accessibility to transit, etc.) are important determinants of health, comfort and well-being. However, there is a lack of evidence for prioritizing efforts to improve IEQ and for selecting the amenities that will be available in a workplace or other built environments. The current evidence base is scattered across multiple different domains, including the peer-reviewed scientific literature, white papers, and public and private datasets (published and unpublished). Further, the evidence available is inconsistent in scope (e.g., addresses selected IEQ parameters or workplace amenities). The disclosed systems and methods address this gap in knowledge by using processes to identify and rank IEQ parameters and workplace amenities, accounting for geographic, social, and economic differences, so that solutions and interventions can be prioritized according to unique needs, preferences, and priorities. In some embodiments, the systems and methods may use one or more of the following:

a. Health metrics (DALY, YLD)
b. Satisfaction metrics (DCL, % satisfied)
c. Intervention evaluation, ranking or prioritization
d. Data ingestion and hosting
e. Databases for building performance and behavioral registries
f. Internal and external interfaces
g. Publications
h. Surveys or polls In some embodiments, the disclosed systems and methods may provide an approach to improving human health and well-being through the built environment or separately from the built environment using data in combination with scientifically-based evidence to tailor intervention and other recommendations to diverse locations and populations worldwide. The output estimates derived from data models can be continuously refined and updated, as data capture and data quality grow over time.

Accordingly, these teachings may be used to determine how to fill-in gaps in the scientific literature, especially as they relate to practical applications. For example, in some configurations, by receiving real-time data, such as, for example, personal data, environmental data, and feedback from individuals, the intervention assessment system can analyze the practical application of suggestions in the literature to identify, for example, best-practices or viable cost-saving alternatives.

In some embodiments, the disclosed systems and methods may be used to identify new factors that impact health and well-being, establish protocols to measure health and well-being outcomes, and establish a systematic approach to evaluating efforts to improve those outcomes. They also can serve as a decision support tool for efficient resource allocation and prioritization.

In some embodiments, the disclosed systems and methods may use new metrics to quantify the amount of benefit gained that can be attributed to specific IEQ conditions, workplace amenities, problems and potential interventions, such as those described below.

Physical Comfort Metric Weighting

The purpose of Physical Comfort Metric Weighting is to list and rank order the preference of indoor environmental quality (IEQ) related comfort conditions in the workplace. The physical comfort weights are used to derive a new metric called Days of Comfort Lost (DCL). DCL is a metric that quantifies the amount of time, in days, an individual is in a state of discomfort.

Physical Comfort Metric Weights and their use to derive DCL are both new features. The use of DCL as a measure of physical comfort is based on the disability-adjusted life years (DALY), a measure of overall disease burden developed by the Global Burden of Disease (GBD) study put out by the Institute for Health Metrics and Evaluation (IHME), one of the most established and comprehensive worldwide epidemiological studies to date.

Physical Comfort Weights are analogous to Disability Weights developed by the Global Burden of Disease (GBD) study, which are widely used to quantify loss of healthy life and overall disease burden. Physical Comfort Weights represent the magnitude of comfort loss associated with a given IEQ factor. Physical Comfort Weights are values anchored between 0 and 1, with O being the equivalent to an individual deciding that they "do not want to work in the workplace" given the IEQ factor, and 1 being equivalent to an individual deciding that the IEQ factor "does not cause any distraction in the workplace."

The principles behind Physical Comfort Metric Weighting are based on Disability Weighting in the Global Burden of Disease (GBD) study. The conceptual and methodological basis for Physical Comfort Metric Weighting (i.e., large-scale, paired comparison surveys on IEQ preferences, Thurstone re-scaling, etc.) to quantify comfort states is based on the same as that of Disability Weights in the GBD, which are widely used and well-established to describe and quantify different health states. These methods allow for disability weights to be generated for diverse groups and populations, taking into account geographic location and age and gender distributions.

In some embodiments, Physical Comfort Metric Weighting can include one or more of the following:

a. IEQ conditions are identified through literature review and randomly selected to be included in a survey of paired comparisons to list and rank preferences of IEQ conditions.

b. The survey is distributed to diverse populations of workers of different ages, gender, occupation, and geographic location worldwide. IEQ conditions are described in lay terms for general understanding and presented in pairs; respondents are asked to choose which IEQ parameter would cause them greater discomfort in a workplace setting.

c. The survey results are analyzed using the Thurstone scale to generate Physical Comfort Weights, relative weights ranging between O and 1 for each IEQ factor.

Workplace Amenity Satisfaction Weighting

The purpose of Workplace Amenity Satisfaction Weighting is to identify the amenities that contribute most to workplace satisfaction, under different budget scenarios, and derive the cost-effectiveness of each amenity's contribution to overall workplace satisfaction. By one approach, Workplace Amenity Satisfaction Weights are used to derive the output metric Amenity Satisfaction (%).

In some embodiments, Workplace Amenity Satisfaction Weighting can include one or more of the following:
 a. A list of amenities commonly found in the workplace setting.
 b. A survey administered to a diverse population of workers to measure the marginal utility functions (and the corresponding variance) of each amenity across different ages, gender, occupation, and geographic location.
 c. Amenity prices and consumer purchasing power are measured by industry, employer size, and location.
 d. Indifference curves are derived for different amenity combinations.

Intervention Evaluation

The purpose of Intervention Evaluation is to create systematic criteria for gathering and reporting data evaluating the effectiveness of interventions that impact all well-being outcomes. By one approach, Intervention Evaluation is a systematic assessment of intervention strength, in terms of causality and efficacy, in order to compare and rank interventions.

In some embodiments, Intervention Evaluation can include one or more of the following:
a. Literature reviews that may be conducted to assess the causal strength of select factors associated with health and well-being outcomes, and to evaluate the evidence on the causal link between an intervention and its effects.
b. A survey of one or more occupants of a built environment, employers associated with the built environment, etc.
c. A panel of one or more experts that develops a set of guidelines for evaluating interventions based on relevance and/or significance, effectiveness, efficiency, impact, implementability, and sustainability, as well as context, cost, and feasibility.
Based on the findings of the literature reviews and panel of one or more experts, an appropriate rating or score indicative of overall efficacy is assigned to each intervention.

In some embodiments, particularly where a built environment is an office or other workplace, measurements or other metrics that are not directly health related may be used. For example, physical comfort and job satisfaction may be used to analyze a problem, indicators, or potential interventions to one or more problems for the built environment or one or more people associated with the built environment.

Physical comfort, the sense of physical ease and freedom from unwanted distraction, annoyance and pain, often depends upon differences in physiology, health status and preference. Accordingly, comfort is a subjective and relative state of body and mind.

Within a built environment that is a professional workplace, physical comfort may be one contributor to overall occupant well-being. To quantify the amount of comfort gained or lost due to specific indoor conditions, the impact metric Days of Comfort Lost (DCL) can be used and is an extension of a popular measure used in building science comfort research, measured in the % of occupants satisfied times the duration of that satisfaction in days.

Using a metric to measure physical comfort enables the benchmarking and comparison of levels of discomfort across people and time. The use of DCLs as a measure of physical comfort is related to the disability-adjusted life years (DALY), a measure of overall disease burden developed for the Global Burden of Disease (GBD) Study. DCLs represent the magnitude of comfort loss that can be linked to discrete indoor environmental quality measurements. The unit of the Days of Comfort Lost impact metric therefore may be the time weighted dissatisfaction with one or more indoor environmental quality parameters: thermal comfort, acoustic comfort, perceived air quality, and visual comfort.

Job satisfaction can be thought of as overall judgment of a person's experiences within a workplace and can be informed by both cognitive and affective responses. Many people spend a substantial amount of time at work, and work for a significant portion of their lives. The jobs people hold and the built environments they work in may be one of the most important determinants of their overall well-being.

Job satisfaction can be measured for the purpose of individuals' professional development and the betterment of an organization's policies and practices. Several factors influence job satisfaction, including work-life balance, job meaningfulness, relationship with management, company culture, benefits and amenities, and the quality of the physical work environment. Job satisfaction can be evaluated through self-report measures, like the Job Descriptive Index (JOI).

Job satisfaction can be evaluated through self-report, observational, implicit attitude, and physiological measures. Self-report measures, such as the Job Descriptive Index (JOI), Minnesota Satisfaction Questionnaire (MSQ), and Index of Organizational Reactions (IOR), often are used because of their acceptance as valid psychometric tools and administration ease (e.g., convenience, cost). Observational, implicit attitude, and psychological measures can be used in combination with self-report measures because they may provide further insight into one or more peoples' experiences that may not be revealed through self-reported job satisfaction.

Thermal environment often may be one of the highest contributing factors to overall occupant satisfaction in a built environment. Office workers who are satisfied with their thermal environment often are more productive in the workplace. In contrast, thermal discomfort is known to play a role in sick building syndrome symptoms and other conditions, which may similarly cause decreases in productivity.

Thermal comfort is the subjective evaluation of satisfaction with thermal surroundings. There often is a high degree of variance among individual responses to thermal conditions, but there are two primary groups of factors that directly affect thermal comfort, namely environmental factors (conditions of the thermal environment) and personal factors. Two personal factors (metabolic rate and clothing insulation) and four environmental factors (temperature, humidity, draught and temperature uniformity) often are of significant importance in evaluating problems for a built environment and potential interventions.

Metabolic rate can vary substantially by age and gender, and naturally throughout the day based on circadian patterns and behavior. It also varies by the size, composition and timing of recent meals, and exercise. Clothing insulation, which also tends to vary predictably with gender, is also one of the primary forms of interventions for addressing suboptimal environmental thermal conditions, and so may not considered a mediating factor for predicting thermal comfort.

Indoor air humidity (often measured and reported as relative humidity-RH) is the ratio of the amount of water vapor in the air to the amount of water vapor that the air could hold at a specific temperature and pressure. At high humidity levels, the air has close to the maximum water vapor that it can hold, so evaporation, and therefore heat loss, is decreased. On the other hand, dry environments (usually below 30%) are also uncomfortable because of their effect on the mouth, nose, eyelids, lungs, stomach, etc.

Temperature is easily a component of thermal comfort. Too high or too low temperatures often will lead to complaints among occupants and may significantly affect occupants' satisfaction and comfort feeling. In thermal comfort at two main temperature types may be used:

(1) indoor air temperature: the average temperature of the air surrounding the occupant. Measurements take place at the ankle, waist and head levels, which vary for seated or standing occupants; and (2) radiant temperature: the amount of radiant heat transferred from a surface, depending on the material's ability to absorb or emit heat, or its emissivity.

When information on radiant temperature are not available, its value can b assumed to be equal to the indoor air temperature.

The unwanted local cooling of the body caused by air movement is defined as draught. People are often are likely to feel a draught on uncovered body parts such as their head, neck, shoulders, ankles, feet, and legs, but the sensation also depends on the airvelocity, temperature, metabolic rate and clothing.

Indoor exposure to air pollutants often causes very significant damage to a person's health and in addition to that it impacts occupants comfort feeling. Perceived Air Quality (PAQ) is a condition of mind that expresses satisfaction with the indoor air quality (IAQ) and often is assessed by subjective evaluation. PAQ can be expressed as the percentage of dissatisfied, i.e., people predicted to perceive the air as being unacceptable. Ventilation may be a necessary intervention to remove indoor generated pollutants from indoor air or dilute their concentration to acceptable levels. A ventilation rate below 10 μs per person may be associated with a significantly worse prevalence of one or more health or PAQ outcomes. Indicators or causes of bad PAQ may include high humidity levels, odor, stuffiness and dust and inventions directed to removing them may be used with a built environment may be used to address them.

Odor is a quality of gases, liquids, or particles that stimulates the olfactory organ and can come from natural things, such as plants, flowers, animals, outdoor air, etc. They also come from man-made chemicals or substances, such as furniture, paintings, etc. Often, people make assumptions about the quality of their indoor air based on what they smell or whether anyone complains about odors. An unpleasant odor may be caused by one or more volatilized chemical compounds (VOCs). Sometimes an unpleasant odor comes from specific chemicals (often man-made) that can negatively affect occupants' satisfaction and comfort with the PAQ. There also are several chemical based pollutants, for example carbon monoxide or radon, that are odorless. It can happen that these chemicals can cause a person to feel sick or uncomfortable before even noticing any source of odor in the air.

Stuffiness is the perception of indoor air in poorly ventilated spaces. Perception of stuffiness is affected by several other air quality issues, such as high humidity level, accumulation of odor or high occupancy that is reflected in concentration level of CO.

Dust generally consists of small particles suspended in the air, furniture, chemicals, aerosols, outdoor air, and particles from the occupants themselves. In an occupational settings or other workplace focused built environment, these sources of particulate matter may be important because they relate to a wide range of health diseases and dissatisfaction with the perceived air quality. Inhalable particulate fraction is that fraction of a dust that can be breathed into the nose or mouth. Thoracic particulate fraction is that fraction of dust that can penetrate the head airways and enter the airways of lung. Respirable particulate fraction is a fraction of inhaled particles that penetrate beyond to the occupants' alveoli region. Other dust characteristics besides their composition and aerodynamic diameter can be important in dust control. Occupants of a built environment may find it difficult to detect small particles, and although these have an important impact on health, larger particles often contribute more to perception of indoor air quality.

Noise, a component of acoustic comfort, often may be a prevalent source of annoyance and dissatisfaction in offices or other workplaces, and can lead to the problem of increased stress for occupants of the office. The major sources of noise in a workplace are employee activities, the sound generated by building system, and outdoor events. Often, maintaining speech privacy may be at least as important to occupants as reduction in unwanted noise. In modern building design, acoustics rarely receive the same level of architectural or engineering attentions as thermal, ventilation and other considerations.

For listeners, speech privacy is the inability of an unintentional listener to understand another person's conversation. For speakers, speech privacy is the ability to hold a private conversation in workplace. Because the sound transport in workplace is mutual direction in most of the time, a high speech privacy for listeners is considered to be equivalent high for speakers.

Background noise may be another problem in a built environment and is the accumulation of all noise (unwanted or unintended sound) which is audible to the human ear. Sources of noise in an office environment are HVAC/R system, building equipment, outdoor noise, etc.

Acoustic comfort may be realizable when the workplace provides interventions via the use of appropriate design of acoustic environment to support different styles of work in different spaces, including interaction confidentiality and concentrative work.

In addition to noise, light can profoundly influence health and well-being or the occupant of a built environment. The way the indoor lighting environments are designed not only impacts a person's ability to perform visual tasks, but it also affects comfort, mood, and a wide range of physiological and psychological functions that influence our cognition and sleep quality. Visual comfort is a subjective condition caused by an individual's experience with the visual environment and may impacted by the physiology of the eye, the amount of light, its distribution in space, and its spectral power distribution.

Different approaches can be used to evaluate and address visual comfort for occupants of a built environment under a variety of scenarios. Total amount of light, glare, uniformity of light, and the color, or spectral-power of light can all contribute to the overall subjective evaluation of visual comfort.

People often are prone to preferring natural daylight over artificial sources as objects appear more vibrant and colorful under sunlight and electrical light is not able to reproduce the full spectrum of sunlight. Not all electrical light is created equal. For example, modern high-quality LEDs can perform much better than older fluorescent fixtures. Therefore, in addition to the strength of a light source, the quality and type of lighting provided also contributes to visual comfort and may be taken into account as problems and potential interventions are being evaluated.

Figure 4:
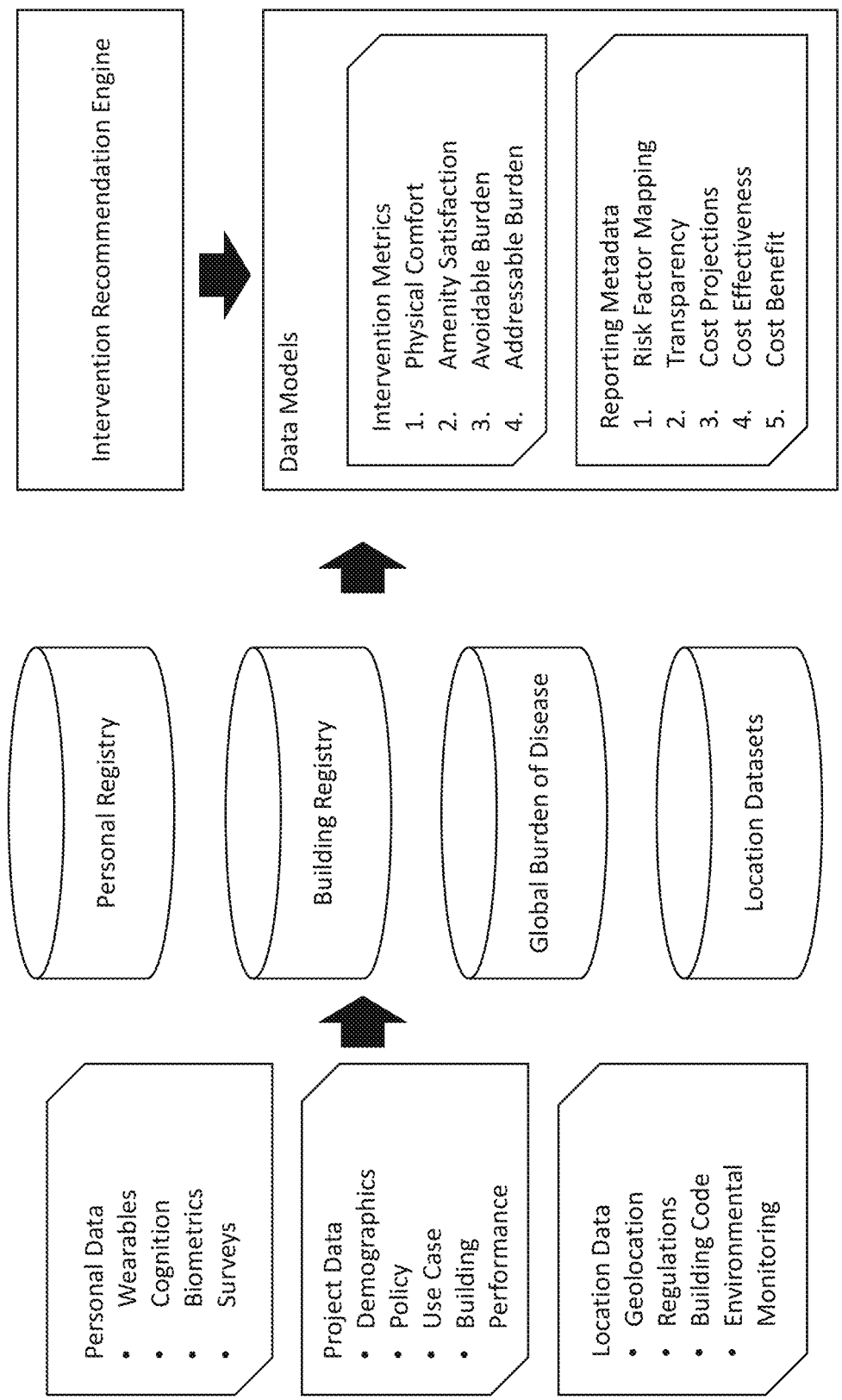
FIG. 4 is a schematic diagram illustrating an intervention assessment system in accordance with some embodiments.

FIG. 4 illustrates an example data infrastructure for a system for assessing optional interventions within a high-level data-flow framework, demonstrating the relationship between major data sources, data repositories, data models and data outputs. In the left column of FIG. 4, raw or processed data is illustrated as being ingested into a set of registries administered by, for example, third-party data partners. Each data repository then can contribute its processed, structured or unstructured, anonymized data and meta-data into a master data-model environment which may be used in evaluating the project impact, cost, value, etc. of one or more interventions. The data model environment processes this data according to its correction and meta-regression algorithms, generating output metric estimates. As illustrated in FIG. 4, and as discussed in more detail below, many types of data may be usable in determining and evaluating one or more particular problems associated with a built environment or one or more people associated with the built environment, as well as one or more inventions that may be available or usable to address the problems. Different data sets may be available and used for analyzing and measuring different interventions, indicators, problems, etc. associated with one or more multiple built environments, one or more people, one or more groups of people, etc. In determining one or more interventions for one or more problems associated with a built environment, it should be noted that built environments may be in different locations and have different topologies, uses, occupant demographics, occupant health or biometric information, amenity availability, building code requirements, building performance requirements, GBD related data, budgets, intervention availability, etc., thus data from different data sets may be used and different data sets may be accessed.

Figure 5:
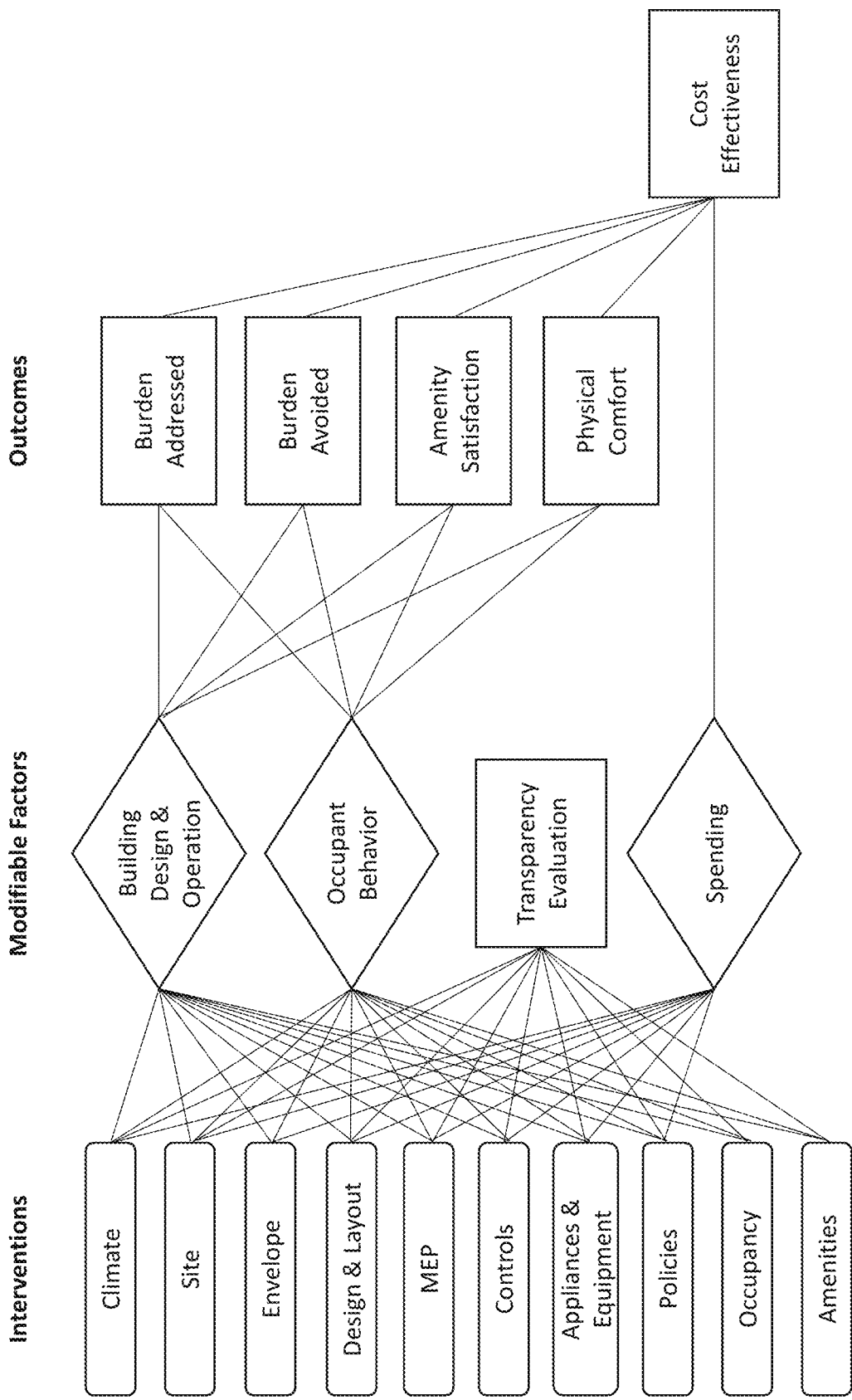
FIG. 5 is a schematic diagram in accordance with some embodiments.

FIG. 5. is an entity diagram representing the relationship between the four classes of data or impact metrics in the data model that may be used to analyze problems and solutions related to a built environment. Several different kinds of interventions for built environments are indicated in FIG. 5, such as environmental and climate, envelope, mechanical engineering and plumbing (MEP), policy, design and layout, occupancy, location/site, and amenity availability or quality related interventions that may apply to a built environment.

Interventions may impact one or more modifiable factors or problems in a many-to-many relationship. In some embodiments, modifiable factors or problems may be divided into two top-level categories, building design & operations, and occupant behavior. A generally recognized third category, metabolism and genetics, is excluded from FIG. 5 but can be incorporated into the model if desired and adequate data is available. A transparency evaluation also might be conducted to help determine the level of awareness that might result from an intervention or the implementation of an intervention or to make sure that the value, cost, and ramifications of the intervention are more fully understood and taken into account. In some embodiments, a transparency evaluation may be used in selecting one or interventions to a problem or factors occurring in or related to a built environment.

The modifiable factor or problem categories may be further subdivided into lower level factors or problems (not shown in FIG. 5), one or more of which may have a one-to-many relationship with causes of the factors or problems, and a known, expected, or predicted outcome value in one or more of the four major impact metrics or outcomes (e.g., burden addressed, burden avoided, amenity satisfaction, physical comfort). The cost associated with each intervention or the implementation of each intervention in a built environment may be used in the calculation of the cost-effectiveness of an intervention with regard to an outcome of interest for the built environment.

Figure 6:
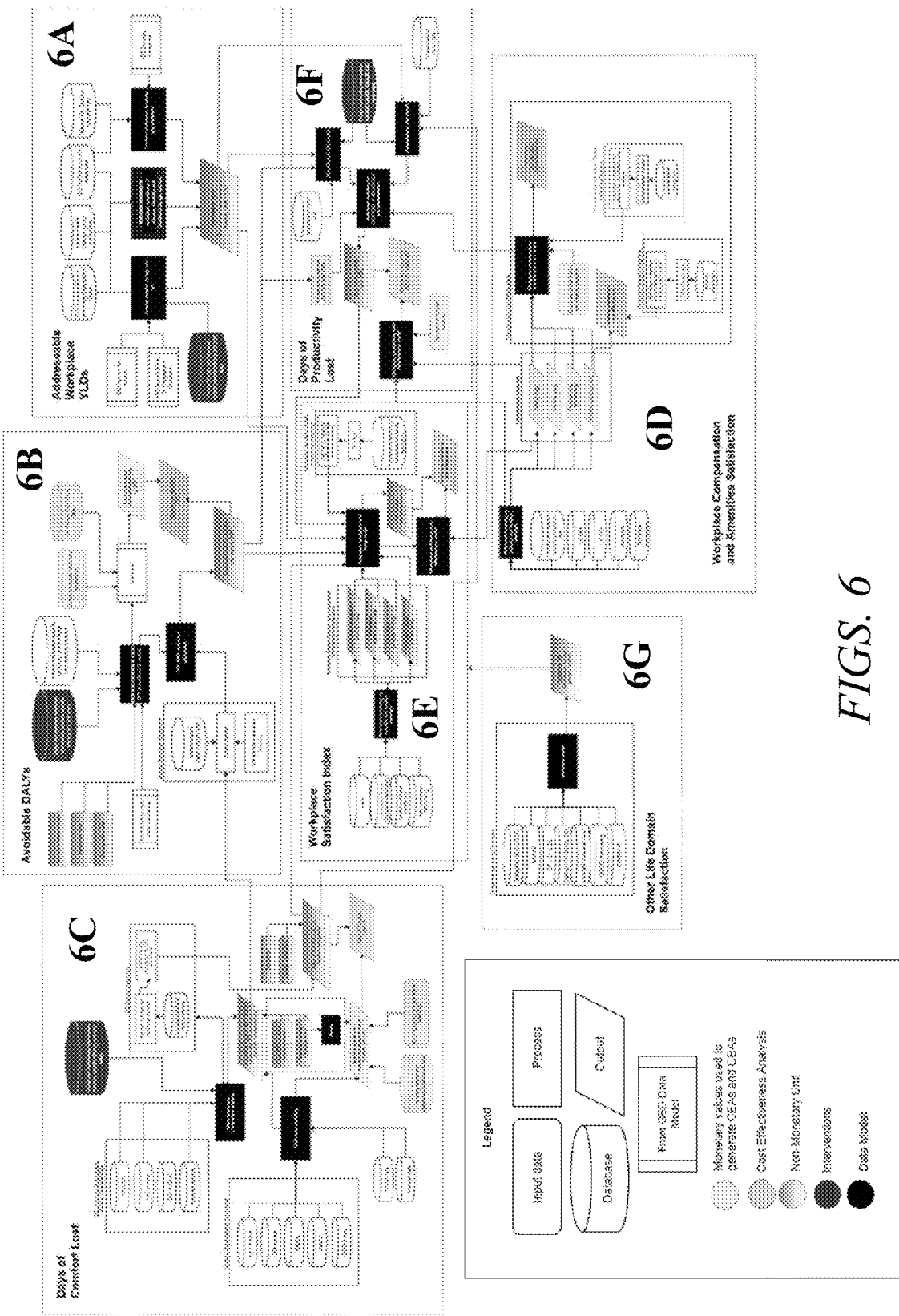
FIG. 6 is a schematic diagram illustrating an intervention assessment system in accordance with some embodiments.

FIG. 6 is a schematic diagram illustrating a potential entity relationship representing a data model framework or system for calculating multiple outcome metrics. In FIG. 6, four entities are represented: databases, inputs, processes and outputs. Databases can house data and other information that may be used in models to generate one or more outputs. In some embodiments, the system may be able to generate estimates for each outcome metric, for any age, gender and location, based on all existing, available data (databases). Where data is missing for a particular age, gender and location, modeled outputs based from the most relevant available sources will be used. Dynamic input data can also be incorporated into the system to help enable outputs to be updated more frequently to help provide more accurate outputs, etc.

In some embodiments, inputs can contain data on interventions, intervention sets, problems, indicators, or expected or potential outcomes. For example, assume that the owner of project X for a built environment (which may be part or all of one or more buildings) decides to use the system illustrated in FIG. 6 to generate estimates for the rate of Days of Comfort Lost (DCL) or other impact metric and the owner provides input data on project X's location, some of the attributes of the built environment, and some basic demographic information of the occupants of the built environment. In response, the system may produce a best estimate of the DCLs based on the input data; and later, the owner may take detailed IEQ measurements in some or all of the built environment for project X and provide them back the system, which can then provide a more accurate DCL value with the new, project X specific information. Note that outputs of "upstream" model components may become inputs in the calculation of other "downstream" metrics. For instance, estimates of physical comfort loss may be used to measure or predict satisfaction and productivity loss.

FIGS. 6A-6G illustrate portions of FIG. 6 to more clearly illustrate the details thereof for some embodiments. The flow charts show are for illustration purposes only, and different ways of using data and determining impacts of one or more problems associated with a built environment may be used. As will be shown in FIGS. 6A-6G, data from many different sources may be used, collected, analyzed, modeled, etc. in assessing potential problems, indicators, and interventions associated with a built environment or one or more people associated with the built environment.

Figure 6A:
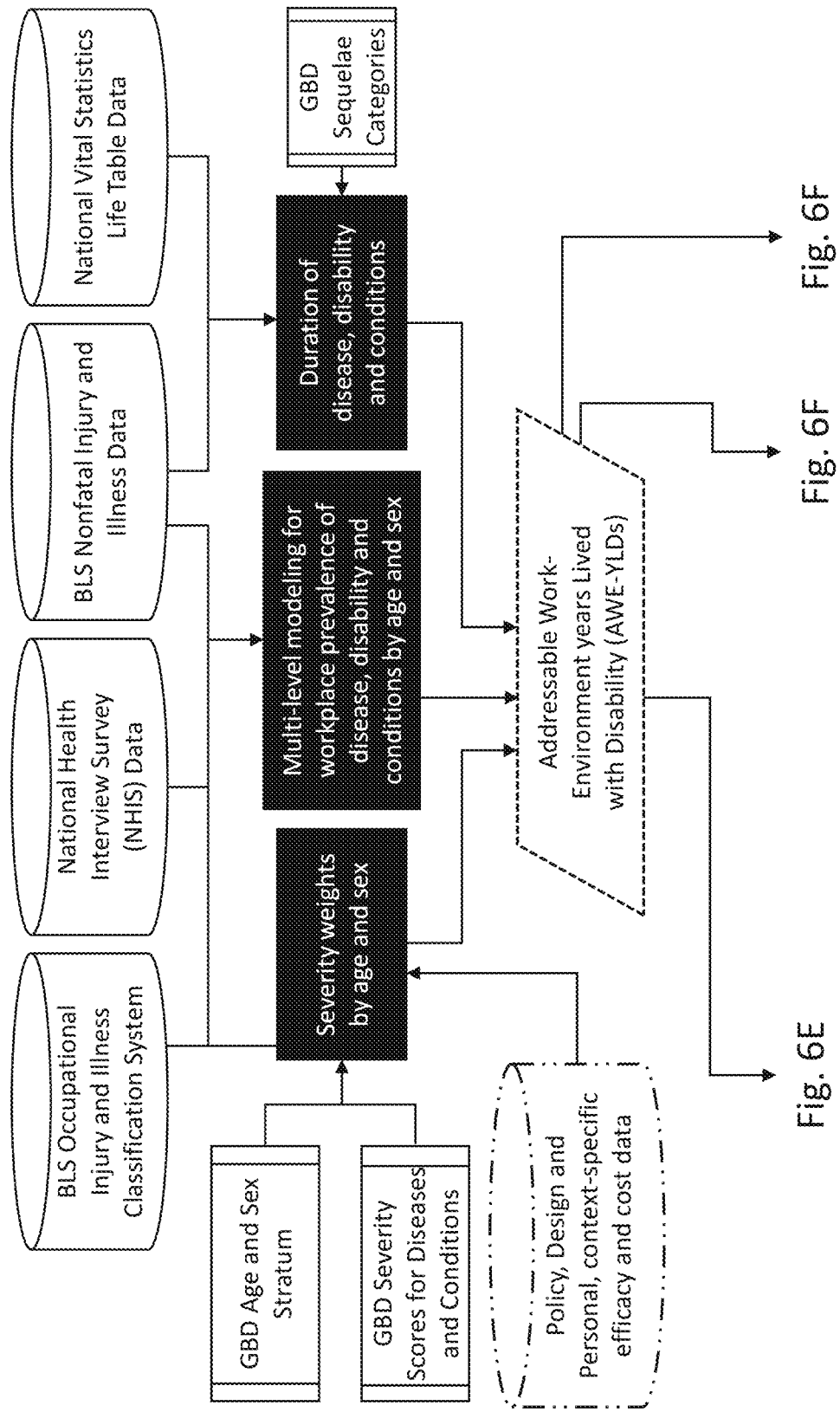
FIG. 6A is a flow chart of a portion of FIG. 6 in accordance with some embodiments.

FIG. 6A is a flow chart illustrating one way in which addressable burden for a built environment might be determined. Specifically, FIG. 6A illustrates potential data sources and main data models that may be involved in calculating Addressable Work-Environment Years lived with Disability (AWE-YLDs). The data sources may consist of nationally representative surveys, occupational surveys, and life statistics, as well as context-specific information on intervention efficacy and cost. Information may come from many sources, such as the U.S. Bureau of Labor Statistics (BLS), National Health Institute Survey (NHIS), U.S. National Institute of Health, IHME, Global Burden of Disease (GBD) data or databases, World Bank, UNICEF, national, local, or employer polices or other polices related to a built environment or one or more people, the World Health Organization (WHO), the United Nations, other national, regional, or local related databases, etc. Models or other computation or analysis components or systems may be used to determine such things as the severity or ramifications of one or more problems by occupant demographic (e.g., age, gender, health condition), the potential prevalence and duration of one or more diseases, disabilities, other health conditions, etc. for a person or group of people, some or all of which then may get used to determine AWE-YLD for a built environment or one or more people associated with the built environment. In some embodiments, addressable burdens can include such things as lower back pain, migraines, hearing loss, anemia, depressive disorder, diabetes, neck pain, musculoskeletal disorder, anxiety disorder, injuries from falls, etc.

At some point, most people will experience some degree of disability, either short- or long-term. As societies age, the burden of disease due to disability will be greater than the burden of disease due to premature death, calling for a greater emphasis on addressing existing health conditions than premature death. The quantity of "disability" that can be made more livable or of higher quality through one or more solutions is measured in Years Lived with Disability (YLDs). Unlike the Avoidable burden metric, the goal of the Addressable Burden metric is not to prevent or avoid diseases from happening in the future—it is to measure the quality of life for those already afflicted. YLDs may be used measure the prevalence of existing diseases, disabilities and injuries, and their associated disability-weightings; and these causes of disease may be used to determine or analyze the Addressable Burden impact metric for a built environment.

Modifiable problems for a built environment may include potentially-modifiable behaviors or conditions that tend to increase the likelihood of a person experiencing an adverse health event. Three major classes of risk factors include behavioral, metabolic, and environmental related elements. Problems factors are potentially modifiable via the use of one or more interventions and therefore are amenable to intervention, e.g. smoking as a risk factor for lung cancer. An exception is the class of metabolic risk factors, which are biological metrics, e.g., blood pressure; these are essentially indicators of early-stage disease and are typically amenable to medical-based treatment and extreme lifestyle intervention.

Figure 6B:
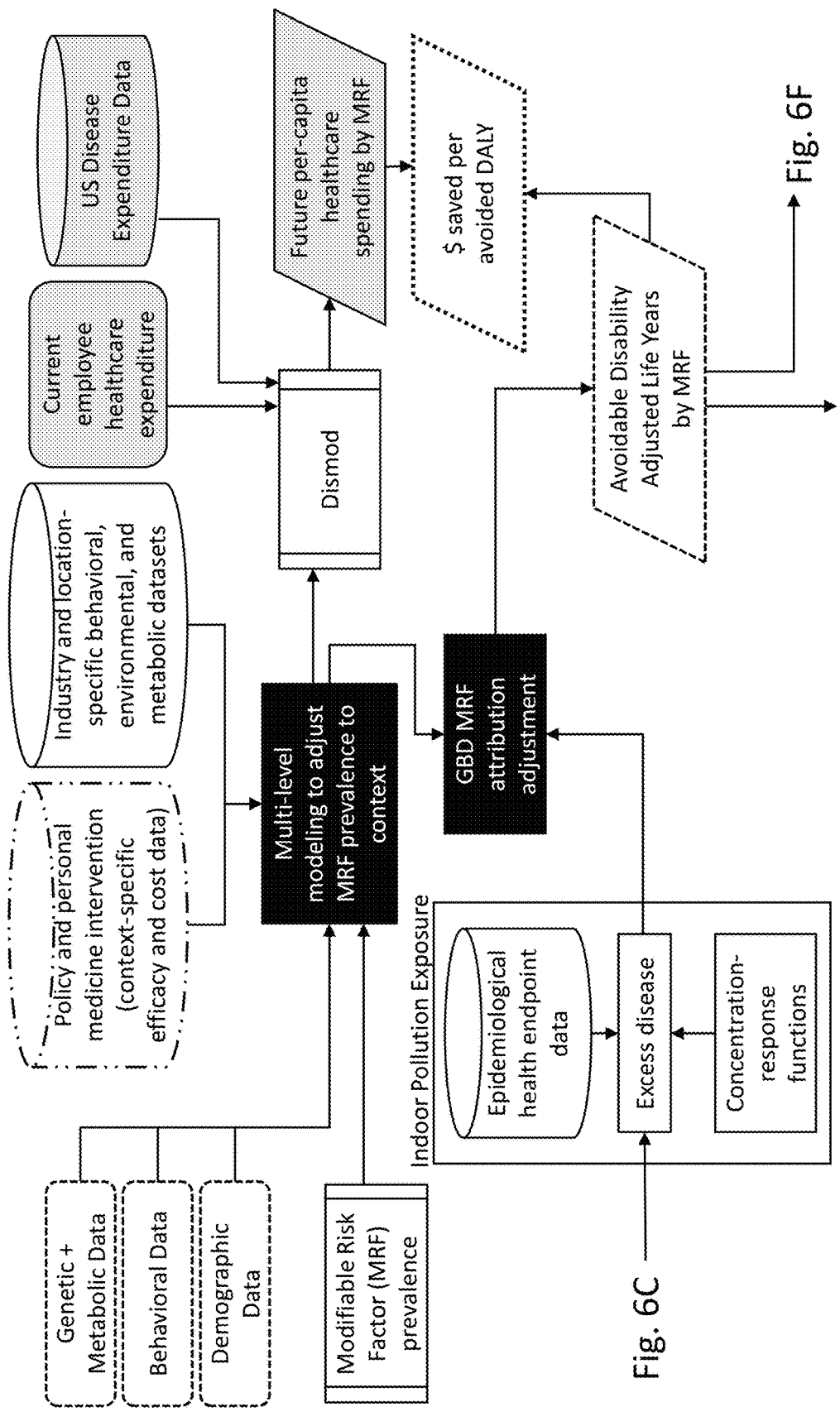
FIG. 6B is a flow chart of a portion of FIG. 6 in accordance with some embodiments.

FIG. 6B is an example flow chart illustrating the data sources and main data models that are involved in calculating Avoidable Burden (DALYs). The data sources consist of nationally representative surveys, occupational surveys, and life statistics, as well as context-specific information on intervention efficacy and cost. Avoidable burdens can include things such as the presence of ambient particulate matter, unsafe water and sanitation conditions, alcohol and drug use, being underweight, iron deficiency, dietary risk factors (e.g., diet low in fruit or vegetables, high sodium or high sugar diet), smoking, etc.

Further, FIG. 6B illustrates potential data sources and main data models that may be used or involved in calculating Avoidable Burden (DALYs) related to a built environment or to one or more people associated with the built environment. In a manner similar to what was discussed in regards to FIG. 6A, in some embodiments data sources may include nationally or regionally representative surveys, occupational surveys, and life statistics, as well as context-specific information on potential intervention efficacy and cost. Other data sources may include information related to policies, current healthcare expenditures, personal medical and behavioral information, potential or expected future healthcare spending (which may be tied specifically to one or more risk factors or problems), GBD driven data related to diseases and risk factors or problems, etc., some or all of which may be used to populate a disease model (Dismod) and to determine Avoidable DALYs associated with specific risk factors of other problems associated with the built environment or one or more people associated with the built environment. Avoidable burdens can include things such as the presence of ambient particulate matter, unsafe water and sanitation conditions, alcohol and drug use, being underweight, iron deficiency, dietary risk factors (e.g., diet low in fruit or vegetables, high sodium or high sugar diet), smoking, etc.

Figure 6C:
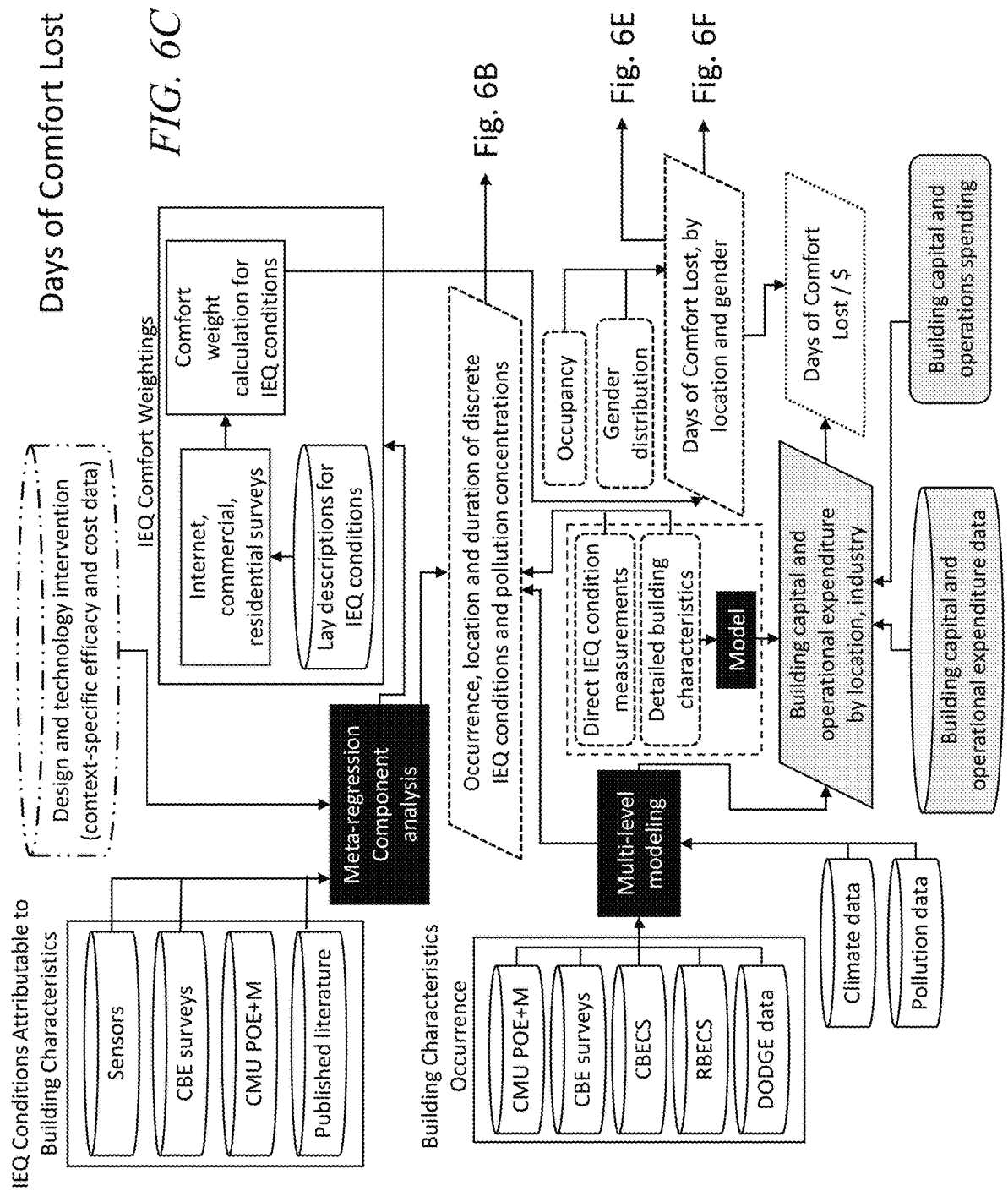
FIG. 6C is a flow chart of a portion of FIG. 6 in accordance with some embodiments.

FIG. 6C illustrates an example flow chart showing one example of potential aspects of physical comfort based on or determined from one or more existing datasets, which can be used to build models linking building characteristics with physical comforts for a built environment or one or more people associated with the built environment. In a manner similar to what was discussed in regards to FIGS. 6A and 6B, in some embodiments data sources may include nationally or regionally representative surveys, occupational surveys, and life statistics, as well as context-specific information on potential intervention efficacy and cost. Other data sources may include information related to climate data, pollution data, characteristics related to the built environment (e.g., data from surveys conducted by the Center for the Built Environment (CBE), data from Commercial Buildings Energy Consumption (CBECS) survey, DODGE construction industry data, Carnegie Mellon University (CMU) conducted post occupancy evaluations (POE)), scientific literature databases, etc. Indoor environmental quality (IEQ) data related to the built environment from sensors or databases also may be used along with information regarding the design and operation of the built environment, potential interventions for the built environment, location of the built environment, occupancy information, in one or more models to systems to compute days of comfort lost associated with the built environment or one or more people associated with the built environment.

Figure 6D:
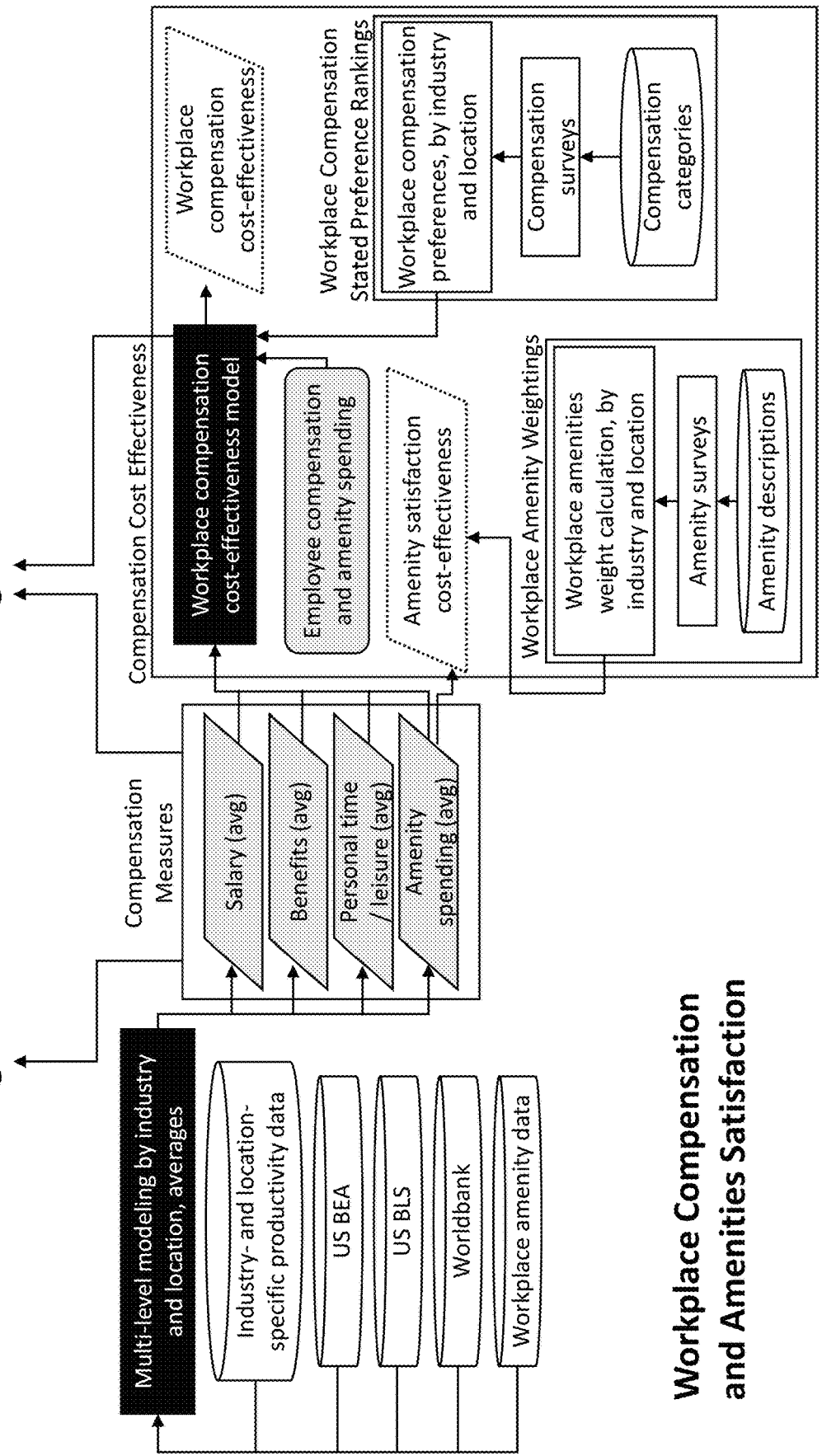
FIG. 6D is a flow chart of a portion of FIG. 6 in accordance with some embodiments.

FIG. 6D illustrates an example flow chart for assessing amenity satisfaction for a built environment or for one or more people associated with the built environment. This flow chart is similar to FIGS. 6A, 6B and 6C and may include or use data from a number of datasets, such as the U.S. Bureau of Economic Analysis (US BEA), U.S. Bureau of Labor Statistics (U.S. BLS), the Worldbank, amenity availability and quality data for the built environment, compensation measures (e.g., salary, benefits, vacation time, amenity spending) for one or more people associated with the built environment, employee surveys, industry surveys, location based information, etc. to compute work space amenities satisfaction and compensation for the built environment or one or more people associated with the built environment. For example, the flow chart illustrates that certain compensation measures, such as salary, benefits, personal time or leisure time, and amenity spending, may be analyzed to determine the workplace compensation cost-effectiveness.

Figure 6E:
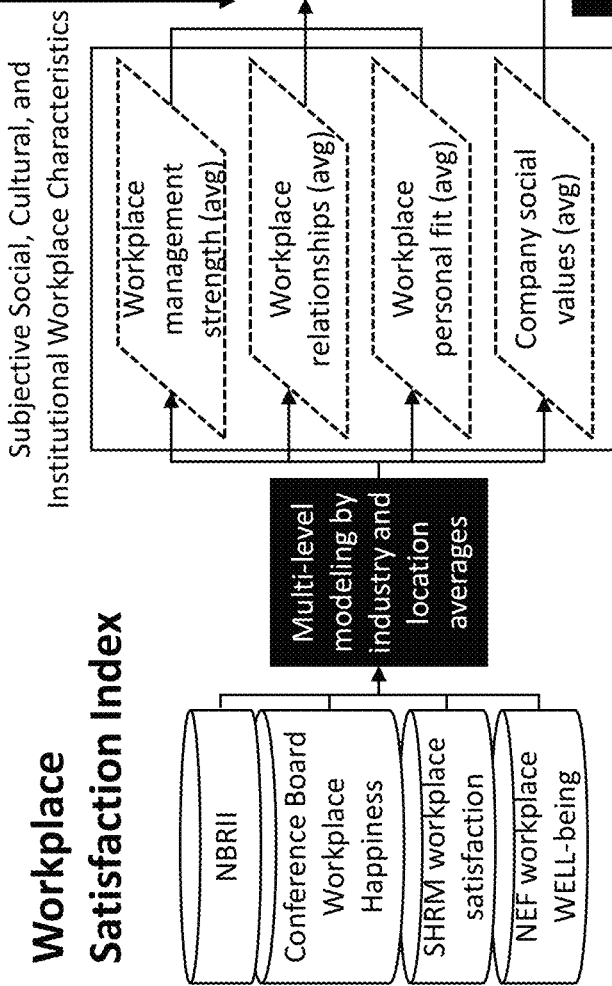
FIG. 6E is a flow chart of a portion of FIG. 6 in accordance with some embodiments.
Figure 6E:
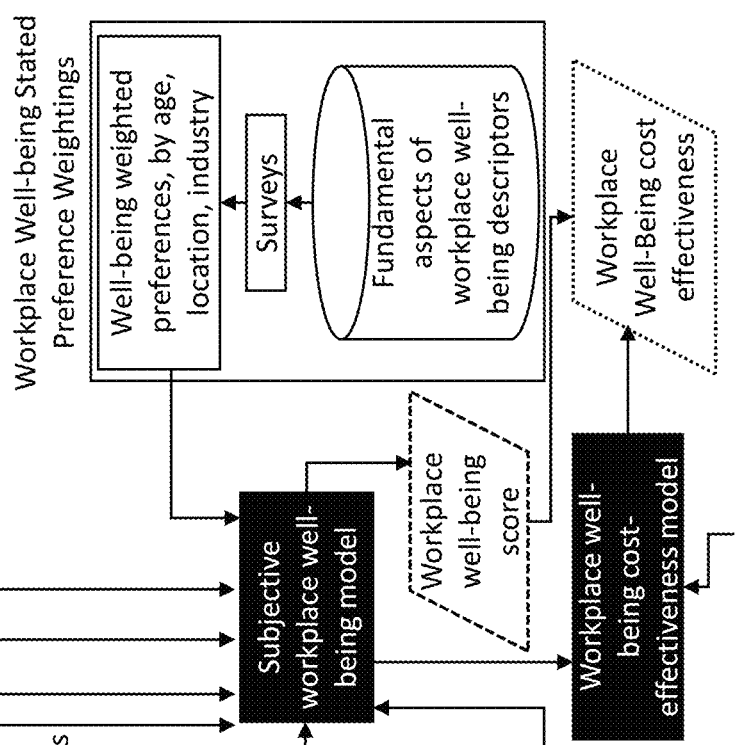
Figure 6E:

FIG. 6E is an example flow chart for assessing or analyzing workplace satisfaction or productivity as it relates to a built environment or one or more people associated with a built environment. In operation, the system herein attempts to increase certain aspects illustrated, such as employee productivity and return on investment and decrease other aspects, such as days of productivity lost (DPL) and/or days of comfort lost. This flow chart is similar to FIGS. 6A, 6B, 6C and 6D and may include or use data from a number of datasets, such as data collected or provided by the National Business Research Institute (NBRI), Society for Human Resource Management (SHRM), New Economics Foundation (NEF), etc., along with demographic data and surveys and other tools to measure or determine workplace management strength, workplace relationships, company social values, workplace personal fit, workplace well-being score and cost-effectiveness for a built environment or one or more people associated with the built environment.

Figure 6F:
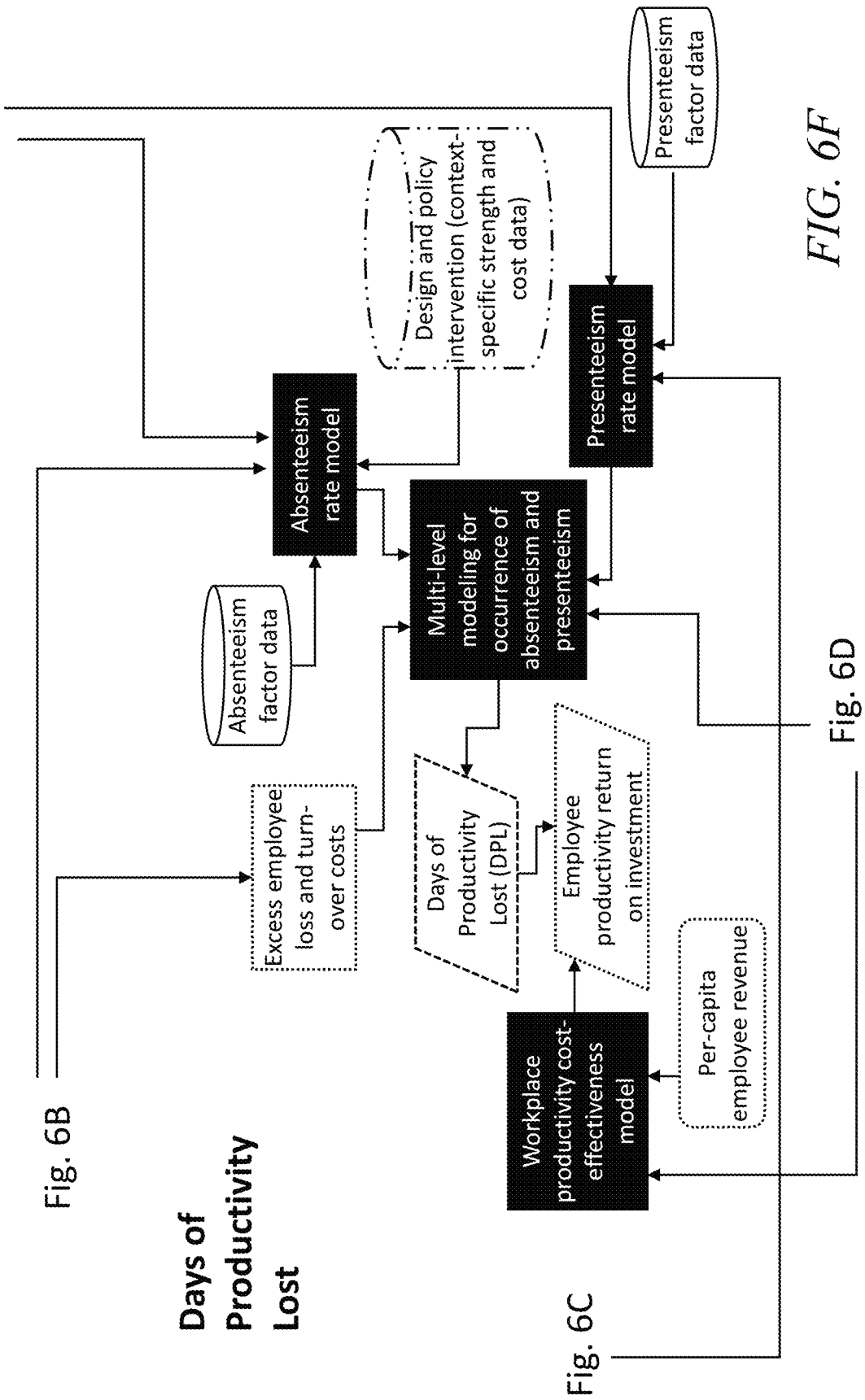
FIG. 6F is a flow chart of a portion of FIG. 6 in accordance with some embodiments.

FIG. 6F is an example flow chart for assessing or analyzing productivity as it relates to a built environment or one or more people associated with a built environment. In some embodiments, there may be an attempt to improve certain aspects associate with a built environment or one or more people associated with the built environment, such as employee productivity and return on investment, and decrease other aspects, such as days of productivity lost (DPL) and/or days of comfort lost. This flow chart is similar to FIGS. 6A, 6B, 6C, 6D and 6E and may include or use data from a number of datasets, such as data related to employee presenteeism and absenteeism, policy availability and quality, employee retention, turn-over and cost, etc.

Figure 6G:
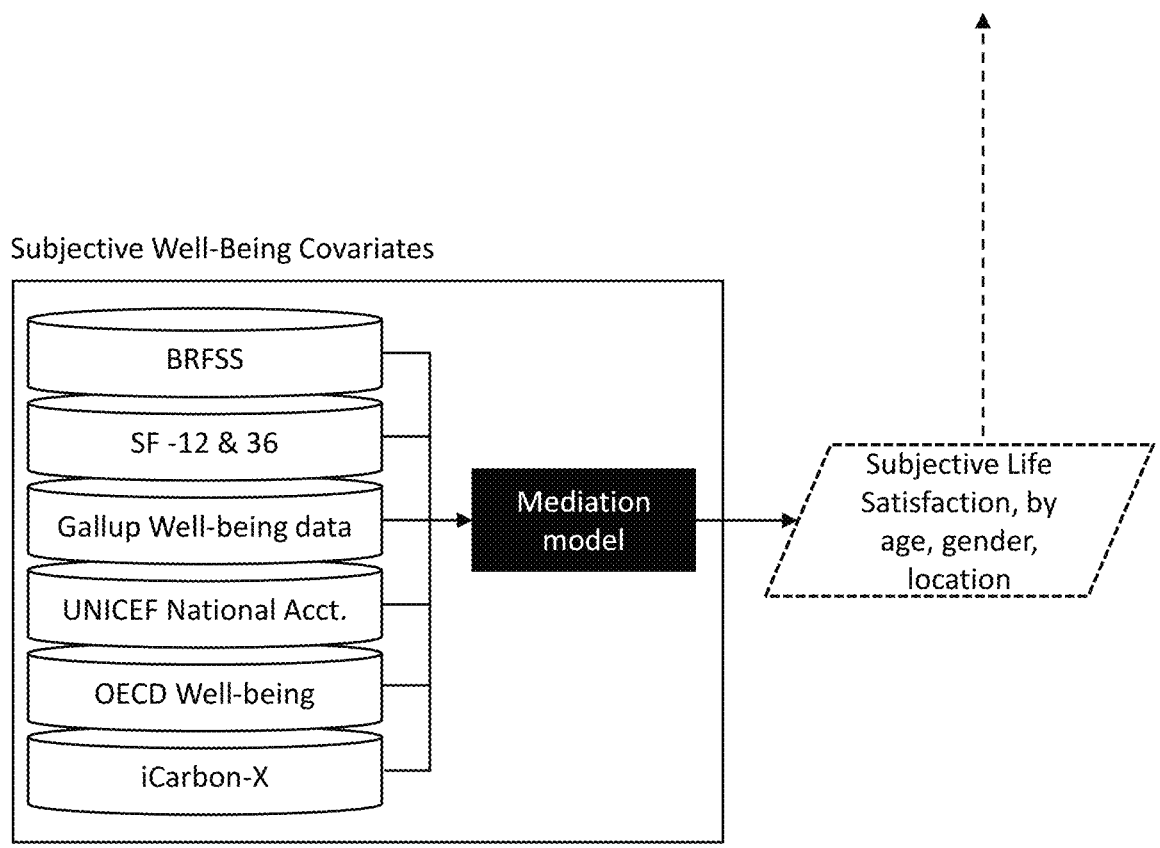
FIG. 6G is a flow chart of a portion of FIG. 6 in accordance with some embodiments.

FIG. 6G is an example flow chart for assessing or analyzing life domain satisfaction as it relates to a built environment or one or more people associated with a built environment. This flow chart is similar to FIGS. 6A, 6B, 6C, 6D, 6E and 6F and may include or use data from a number of datasets, such as data provided or used by the Behavioral Risk Factor Surveillance System (BRFSS), UNICEF, Organization for Economic Cooperation and Development (OECD), iCarbon-X, Gallup, Optum (e.g., its SF-8, SF-12, and SF-36 surveys) to determine or analyze by demographic (e.g., age, location, gender, health condition) or other variable the subjective life satisfaction associated with a built environment or one or more people associated with a built environment.

Figure 6H:
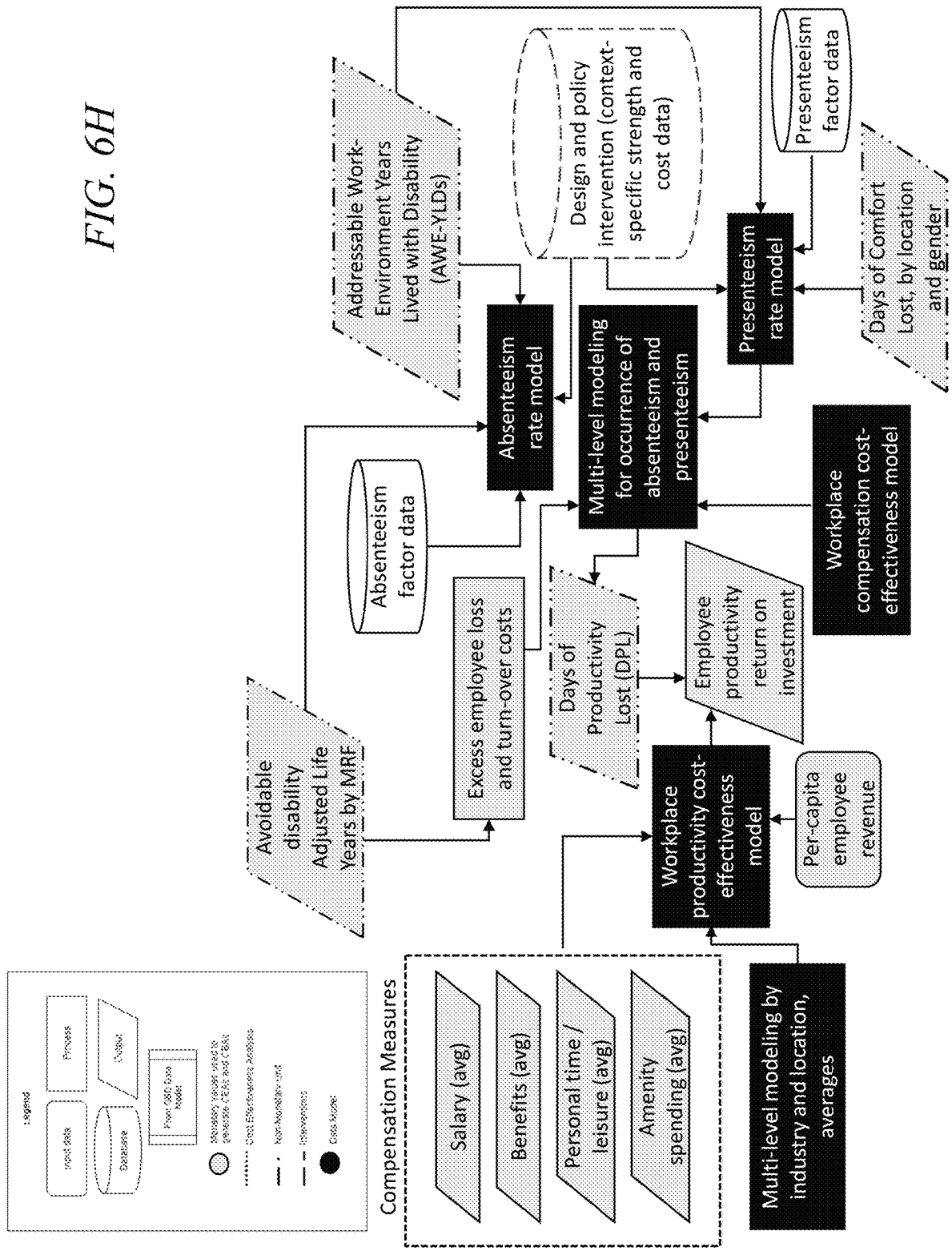
FIG. 6H is a flow chart in accordance with some embodiments.

FIG. 6H illustrates a flow chart for assessing amenity satisfaction. For example, the flow chart illustrates that certain compensation measures, such as salary, benefits, personal time or leisure time, and amenity spending, are analyzed to determine the workplace compensation cost-effectiveness. Further, FIG. 6H is an example flow chart for assessing or analyzing productivity, presenteeism and absenteeism as they relate to a built environment or one or more people associated with a built environment. This flowchart is similar to FIGS. 6A, 6B, 6C, 6D, 6E, 6F and 6G and may include or use many different kinds of data from many sources, such as salary, benefits, amenity spending, personal time availability, per-capita employee revenue, employee ROI, built environment design and operation, policy availability and quality, problems impacting presenteeism and absenteeism, etc., for determining or analyzing presenteeism, absenteeism or productivity associated with a built environment or one or more people associated with a built environment.

FIG. 1 illustrates an exemplary smart building system 100 with a built structure 150 for sheltering occupants with environmentally-controllable zones 153a-d and sensors 110a-d installed in the different environmentally-controllable zones 153a-d. The sensors 110 detect a variety of information about the environment including, for example, the temperature, the lighting intensity and wavelength, and the air quality. The system of FIG. 1 may be employed to automatically adjust environmental parameters in response to measurements from installed sensors and wearable sensors in the built structure 150. As used herein, a built structure 150 includes a building or similar structure, such as a vessel or plane, that provides the occupants thereof protection from the elements and includes walls and also often includes a roof, floors, doors or other openings for ingress and egress.

As shown, the sensors 110 are generally installed in a variety of locations within the built structure 150. If the built structure has different zones, similar to the environmentally-controllable zones 153a-d shown in FIG. 1, at least one sensors 110 is generally located in each of the controllable zones 153a-d. As noted above, the sensors 110 may detect, for example, lighting intensity and wavelength, ambient temperature, and air quality. As used herein, air quality typically includes the air-born contents of the air. In other embodiments, the sensors 110 also may be configured to detect humidity levels and air flow, among other aspects.

As illustrated, one or more occupants 126 may have one or more of a variety of wearable devices associated therewith having wearable sensors 108. As used herein, a sensor may be wearable both in the temporary sense and the permanent sense. That is, for example, the wearable sensors 108 may include, for example, fitness trackers, hear rate monitors, breathing rate monitors, sweat and body temperature monitors, smart glasses, and smart watches, among other devices, and it also may include more permanently wearable sensors, such as, for example, a pacemaker or continuous glucose monitor or blood sugar level or blood oxygen saturation level monitor. Further, the wearable sensor 108 may be both external or internal to the occupant 126. In addition, the wearable sensor 108 may include multiple wearable sensors for a single occupant 126. By one approach, the wearable sensor 108 associated with an occupant of the built structure 150 is configured to detect, for example, biometric information of the associated occupant, ambient lighting levels proximate the associated occupant, ambient temperature levels proximate the associated occupant, and/or ambient air quality levels proximate the associated occupant. By measuring the proximate lighting, temperature, and air quality levels of or nearby the associated occupant, the wearable sensor 108 is typically measuring these metrics or parameters within several feet of the occupant and within the same room, space, or zone as the occupant.

To ensure proper operation of the built structure 150, the control circuit 102 may reference a built environment operational database 106 having target operational parameters for at least one of a lighting level, a temperature level, and an air quality metric or indicator. These databases 106 may include a built environment specification database 116 and a built environment historical and/or operational database 112. These databases 116 may be generated by or with help from building operations management, architects, systems engineers, among others.

In addition to sending instructions to the built structure environmental system 130 regarding temperature, light, or air levels, the control circuit 102 also may send instructions to the system 130 or other devices (such as through the Internet of things) that permit the system 100 to automatically initiate other devices or activities. For example, if the wearable 108 detects that an occupant has high blood glucose levels when the occupant is at their home (their primary built structure 150), the refrigerator screen may display suggested high-fiber foods and the water cooler may poor the occupant a glass of water. In another example, if the wearable detects that you have woken up for the day, the control circuit 102 may send instructions for the coffee machine to begin brewing coffee.

The built structure 150 also may have a building or built structure environmental control system 130 configured to adjust at least one of lighting levels, temperature levels, or air quality levels. By one approach, these include, for example, an air remediation system, a lighting system 136, HVAC system 138, and/or a water system 140.

In addition, in some embodiments, the environmental control system 130 may also include an audio system 144 and/or Internet of things (IoT) devices 146, such as, for example, a smart coffee maker, camera, oven, fan, light, moving vacuum, music player, sound generator, mirror, sound inhibitor or masker, mobile device, television, workout equipment, and a refrigerator, among other options. By one approach, if the wearable sensor 108 of an occupant detects an elevated stress level, the audio system 144 may being playing relaxing music and/or the lighting system 136 may dim the lights. In another approach, a wearable sensor 108 that detects inactivity for a prolonged period while the occupant has the television on (which may be detected because the wearable is linked to the television or the television is linked to the remediation and control system 133 as an IoT device), the control circuit 102 may send a message to the television to be displayed, including, for example, a suggestions to walk around or displaying the amount of time that has elapsed since the television was turned on and activity or movement had stopped.

As noted, the systems herein may incorporate a variety of IoT devices 146 connected thereto and a variety of wearable sensors 108. Accordingly, the wearable sensor 108 may be configured to detect that an occupant is cold or hot by detecting a change in an occupant's skin temperature and the control circuit 102 may respond by instructing the HVAC system 138 to increase or decrease the air temperature to address the change in the occupant's skin temperature. In yet another example, the wearable device 108 may detect whether an occupant is dehydrated and the control circuit 102 may instruct the refrigerator or other water system 140 to pour the occupant a glass of water to encourage hydration.

In one illustrative approach, the wearable sensor 108 may detect physical activity, such as for example, exertion on an exercise machine, by detecting an increase heart rate, breathing rate, seating, and/or increased body temperature. In one illustrate approach, upon receipt of this information, the control circuit 102 instructs the HVAC system 138 to increase ventilation and/or air conditioning rate. The control circuit 102 also may instruct the audio system 144 to play up-tempo or more energetic music.

In an office environment, the wearable sensor 108 may detect that you have been inactive and looking at your display screen for 30 minutes, and the control circuit 102 may prompt you to look away from the screen, such as, for example, at a distance of more than 100 yards and/or out the window, to relax the occupant's eye muscles. Similarly, in one embodiment, the wearable sensor 108 may monitor the occupant's blood oxygen saturation, and upon detecting a low oxygen saturation, the control circuit 102 may instruct the wearable sensor 108 to vibrate and display a prompt to the occupant regarding going outdoor to get fresh air or instruct the HVAC system 138 to increase ventilation.

As illustrated in FIG. 1, the systems in the built structure 150, the database(s) 106, and the control circuit 102, may be communicatively coupled, either directly or indirectly, such as over one or more distributed communication networks 118, which may include, for example, LAN, WAN, Internet, cellular, Wi-Fi, and other such communication networks or combinations of two or more of such networks.

While the control circuit 102, in communication with the sensors (110, 108), database(s) 106, and the environmental control system 130, is illustrated external to the built structure 150, the control circuit 102 also may reside within or at the built structure 150. The control circuit, in one approach, is configured to receive sensor measurements from at least one of the plurality of sensors, receive sensor measurements from the at least one wearable sensor, determine whether the received sensor measurements fall within the target operational parameter of the built environment, and upon detection that at least one of the received sensor measurements falls out of the target operational parameters, instruct the built structure environmental control system to adjust associated lighting level, temperature level, or air quality level.

With the information provided to it, the control circuit 102 also may detect actionable biometric parameters (or even actionable biometric patterns, overtime) for individual occupants in the space. More specifically, the system 100 may include an occupant database 106 with occupant profiles that may include biometric information associated with occupants. With this information, the control circuit 102 may compare received sensor measurements from the wearable sensor with the occupant of the wearable sensor to detect actionable biometric parameters of the associated occupant. With this information, the control circuit is configured to instruct the built structure environmental control system to adjust at least one of lighting levels, temperature levels, or air quality levels upon detection of an actionable biometric parameter.

In some configurations, the occupant database 114 includes an occupant health database of profiles such that the control circuit queries the occupant health database prior to sending instructions to the built structure environmental control system to determine adjustment parameters.

In one embodiment, the system 100, upon detection of an actionable biometric pattern the control circuit may query the occupant regarding an alertness level via an interface of an end user device associated with the occupant. In some configurations, the end user device might be incorporated into wearable device (including one that might incorporate a wearable sensor 108).

In one illustrative example, the actionable biometric pattern may include lack of movement, movement below a certain threshold, breathing below a certain threshold, heart-rate below a certain threshold, among other indicators. In some approaches, the control circuit 102 receives an alertness level parameter from the end user device and compares the received alertness level parameter to the occupant profile associated with the occupant associated with the wearable sensor. Further, upon detection that the received alertness level parameter is below or outside a baseline associated with the occupant, the control circuit 102 compares the target operational parameters with the received measurements from the plurality of sensors and outdoor sensors and identifies one or more lighting level, temperature, or air quality adjustments to implement. By being outside of a baseline associated with the occupant, the control circuit 102 determines that the measurements do not comport with a baseline standard or threshold and are non-compliant, either in respect to a particular occupant via the occupant profile or in comparison to a preferred standard more generally for humans or a person of a particular age, weight, height, and/or gender, among other traits.

The adjustments or interventions are typically related to the actionable biometric parameter or pattern, though may be indirectly related. For example, the system 100, upon detection of such an actionable biometric patter may adjust lighting, temperature, air quality via, changing electrochromatic glass of a window proximate the occupant associated with the wearable sensor, changing a window shade of a window proximate the occupant associated with the wearable sensor, changing an electrical lighting setting of a light source proximate the occupant associated with the wearable sensor, changing a temperature setting of a heating, ventilation, and air conditioning (HVAC) system, and/or changing an air flow setting of an HVAC system.

As noted above, the systems herein provide environment customization options for occupants of the space. To that end, the system 100 may include an occupant database 114 that has personal target building parameters therein. Further, the control circuit 102 is further configured to determine whether the received sensor measurements fall within the personal target building parameters in addition to the target operational parameters. When the measurements fall outside of the personal target building parameters, the control circuit 102 may instruct the environmental control system 130 to adjust the parameters in the vicinity of the occupant, which may be determined by locations services associated with the user device and/or the occupant's wearable devices or from other system sensors. More particularly, in one illustrative approach, the control circuit 102 is configured to receive location information from the wearable sensor and determine which of the plurality of environmentally-controllable zones the occupant is occupying. Further, the control circuit 102 is configured to instruct the building environment control system 130 to adjust at least one of the lighting levels, the temperature level, and the air quality metric or indicator within one of the plurality of environmentally-controllable zones where the occupant is occupying.

As described herein, the building or built structure environmental control system 130 typically includes at least one of an electric lighting system 136 with lights 137, windows 140 with, for example, electrochromatic glass or window shades 142, a heating, ventilation, and air conditioning (HVAC) system 138, and/or a water system 140.

The built environment 150, shown in FIG. 1, has the sun 144 disposed overhead. Further, it illustrates that the sun 144 will move about the built structure 150, and this often occurs while occupants are within the space. The movement of the sun 144 (along with other weather events) may change the needs and/or wants of the occupants of the built space 150. For example, while the sun 144 is advancing on its path through the sky the sun's rays may begin to warm or shine in a bothersome manner for one or more occupants. The sensors 110 within the built structure and the wearable sensors 108 can detect the change and then the control circuit 102 may send instructions to the environmental control system 130 to address the change, such as, for example, by changing the amount of light that can shine through the window 140 by, for example, changing the electrochromatic glass 141 to darken as shown in window 143, or alternatively, to lower a shade 142 over all or a portion of the window 140. In yet another configuration, the control circuit 102 will instruct the lighting system 136 to lower the intensity of the artificial light and/or the HVAC system 138 to decrease the heat or increase the cool air.

The system 100 may automatically adjust the environmental control system 130 in the space to ensure that the occupants therein are not inconvenienced or bothered by the external changes to the built environment 150.

While these teachings are able to individually tailor the space for individual occupants, they also may protect occupants from outdoor toxins, allergies, or other unwanted substances. For example, in some embodiments, the control circuit 102 obtains an outdoor temperature level and an outdoor air quality metric or indicator. With this information, the control circuit 102 compares the outdoor air quality metric or indicator with the sensor measurements received to determine whether to recirculate air within the built structure.

Further, in some configurations, the control circuit 102 compares changes in the outdoor temperature level and the outdoor air quality metric or indicator over time to determine whether to instruct the built structure environmental control system to adjust at least one of the lighting level, the temperature level, or the air quality levels in anticipation an associated indoor change to these parameters to retain the parameters within the target operational parameters.

While the control circuit 102 may obtain outdoor data from weather or other databases, in some configurations, the system 100 includes one or more outdoor sensors configured to detect the outdoor temperature level and the outdoor air quality metric or indicator and provide that information to the control circuit 102.

The environmentally-controllable zones, as illustrated in FIG. 1, might be, for example, floors of a building such that the plurality of environmentally-controllable zones do not overlap with one another. In yet another configuration, the environmentally-controllable zones may be rooms or areas within floor. While the environmentally-controllable zones are generally indoor spaces, in some configurations, they may include partial outdoor area or ingress and egress areas.

In addition to a smart building, these teachings may be incorporated into a variety of structures that provide shelter to occupants and have environmentally-controllable capabilities. In one example, an apparatus for use in a built structure may include a plurality of sensors configured to be disposed in an environmentally-controllable built environment, a built environment operational database having target operational parameters for at least one of lighting, a temperature, and air quality, an occupant database with occupant profiles having associated biometric information and personal target building parameters, and a control circuit in communication with the plurality of sensors, wearable sensor, the built environment operational database, and the occupant database. In operation, the control circuit is configured to receive sensor measurements from the plurality of sensors and from wearable sensors associated with occupants of the built structure, determine whether the received sensor measurements fall within the target operational parameters and the personal target building parameters for the occupants of a zone in the environmentally-controllable built environment, and sending instructions to adjust at least one of associated lighting level, associated temperature level, or associated air quality level associated with the zone in the environmentally-controllable built environment.

Figure 2:
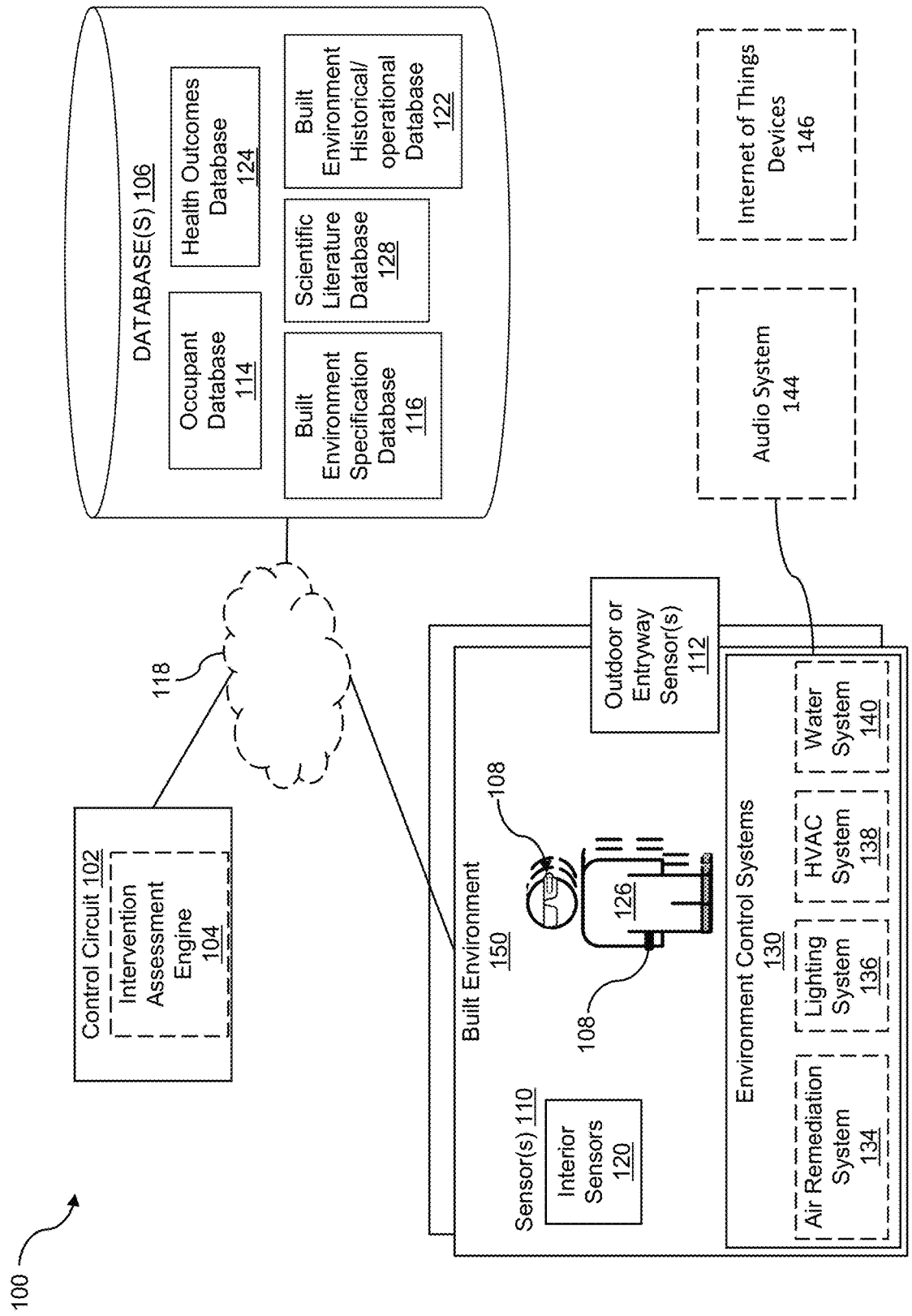
FIG. 2 is another block diagram of an exemplary smart building system in accordance with some embodiments.

FIG. 2 illustrates an intervention assessment system 200. By one approach, the intervention assessment system 200 includes a control circuit 202 (which may include an intervention assessment engine 204), one or more databases 206, a built environment 250, and sensors 210 associated therewith. In operation, the control circuit 202 may assist with ascertaining and remediating problems with numerous built environments 250. This may be particularly desirable for built environments having a location near one another, such that the control circuit 202 may analyze data from another nearby location to check for similarities or differences in sensors readings.

By one approach, the sensors 210 include stand-alone interior sensors 220, sensors 234 associated with an environment control system 230, or sensors 212 disposed outside of the built environment 250 or adjacent an entry thereto. The built environment 250 may have one or more environment control systems 230 associated therewith including, for example, ventilation systems, lighting systems, and sound systems with speakers, among others. As noted above, the sensors 210 may include, for example, those associated with occupants or users 226, such as, for example wearable devices including, e.g., fitness and/or health trackers, smartwatches, and smart glasses, among others.

The databases 206, illustrated in FIG. 2, include an individual user database 214, a health outcomes database 224, a built environment specification database 216, a scientific literature database 228, and a built environment historical/operational database 222. In other intervention assessment systems additional (or fewer) databases may be employed.

As illustrated in FIG. 2, the various devices of system 200 may communicate directly or indirectly, such as over one or more distributed communication networks, such as network 218, which may include, for example, LAN, WAN, Internet, cellular, Wi-Fi, and other such communication networks or combinations of two or more of such networks.

In one illustrative configuration, an occupant 226 may be using a wearable device 208, such as smart glasses, which may periodically measure ambient light and use a speaker and microphone to query the wearer about his or her alertness or comfort. The control circuit 202 and/or the individual user database 214 may receive these measurements. The control circuit 202 (along with the intervention assessment engine 204) may monitor these readings or indicators to identify any issues. In one illustrate example, if the control circuit 202 identifies a decrease in ambient lighting, along with a decrease in heart rate and/or a decrease in reported occupant 226 alertness, the control circuit 202 may determine that an increase in light is desirable. The control circuit 202 may then (either automatically or upon confirmation from the occupant(s)) instruct the built environment, via the environment control systems 230, to address the lack of light, such as, for example, by increasing the artificial light or raising blinds.

Alternatively, the control circuit 202, via the intervention assessment engine 204, may propose several interventions so that the occupant may select one or more interventions. For example, if the lighting is dim and the occupant alertness is low, the intervention assessment engine 204 may propose one or more of: increasing light intensity of the artificial light sources in proximity to the occupant, raising blinds, playing up-tempo music through speakers or headphones, raising the occupants desk to a standing position, and/or recommending the occupant have a meal or beverage, among other proposed interventions. In some configurations, the intervention assessment engine 204 ranks proposed interventions and presents them in order of preference. Further, in some embodiments, the intervention assessment system 204 may present a cost associated and/or impact assessment, along with the proposed intervention to occupants, which may assist the occupant with a decision in those regards. Alternatively, in some embodiments, individual users 226 may have a standing instruction such that, for example, when his or her heart rate is low and lighting is low between the hours of 9 am and 5 pm, that a particular song be played and/or a reminder to stand or move around is presented to the occupant.

In one illustrative approach, a smart building may be monitored by installed sensors and wearable sensors, such that the control circuit, along with the databases (such as health outcomes and scientific literature), may be used to identify problems and interventions and to rank or index potential interventions to find a suitable intervention or remediation. FIG. 1 illustrates that one smart building system that may include an environmentally-controllable built structure 150, a plurality of installed sensors 110 configured to detect environmental parameters in an interior of the built structure (e.g., interior sensors 120 and/or exterior/outdoor or entryway sensors 112), a plurality of wearable sensors 108 associated with occupants of the built structure, a building environmental control system 130, a built environment operational database 122 with target operational parameters for areas within the built environment 150, and an intervention assessment engine 104.

By one approach, the intervention assessment engine 104 may analyze the status of spaces in the building and relevant databases of information and instructions to determine how to proceed. In some embodiments, the intervention assessment engine 104 receives sensor measurements from the plurality of sensors and the plurality of wearable sensors, determines whether the received sensor measurements fall within the target operational parameters, and (upon detection that at least one of the received sensor measurements falls outside of the target operational parameters) analyze a health outcomes database and/or a scientific literature database to identify a plurality of potential interventions. In operation, the intervention assessment engine 104 may index or rank these potential interventions based on effectiveness, implementability, feasibility, timelines, and expense to identified a preferred intervention. Further, the intervention assessment engine 104 may instruct the built environmental control systems to adjust one of a lighting, temperature, or air quality based on the preferred intervention identified. In addition to (or in place of the above) a health outcome database 124 and/or a scientific literature database 128 may be used to assist with determining what intervention may be proceeded, some embodiments may use occupant profiles in an occupant database 114 to be referenced by the intervention assessment engine 104 to determine what adjustments or remediation to conduct.

As suggested above, a number of databases may be accessed to determine how the system 100 responds to particular measurements obtained. In some configurations, there may be conflicting interventions or adjustments requested and a hierarchical rankings may be employed to determine how the building systems respond. For example, once the system has referenced the databases 106 to identify building targets and personal targets, the control circuit 102 may rank or index options or interventions. The system 100, in some configurations, includes a plurality of sensors 120 (detecting light, temperature, and/or air quality) associated with environmentally-controllable zones, a wearable sensor 108 (detecting biometric information, ambient light, ambient temperature, and/or ambient air quality) associated with an occupant of the indoor environment, a building environmental control system configured to adjust lighting, temperature, and/or air quality, and a control circuit in communication with the database and the sensors. By one approach, the control circuit obtains a first set of rules that identify a target operational parameter for lighting, temperature, and air quality in a building, obtains a second set of rules that identify a personal target parameter for the occupant, determines a location of the occupant within the indoor environment, receives sensor measurements from the plurality of sensors and the wearable sensors, determines whether the sensor measurements are outside of the target operational parameters and the personal target parameter, and obtains a third set of rules that identify adjustment options and an associated adjustment index associated with each of the adjustment options. With this information, the control circuit 102 may instruct the building environmental control system to adjust the lighting, temperature, and/or the air quality pursuant to a preferred adjustment option based on the associated adjustment index.

By one approach, the smart building system includes a plurality of wearable sensors that are associated multiple occupants and an occupant database with occupant profiles with associated personal target building parameters. With numerous occupants, the chances increase that occupants in a space will have conflicting target parameters. To resolve these conflicts, the control circuit 102 may determine that multiple occupants are in one of the environmentally-controlled zones and upon detection of multiple occupants in the one of the environmentally-controlled zones, determine whether the personal building target parameters overlap or are in conflict with one another. With this information, the control circuit 102, upon detection of conflicting personal building target parameters of multiple occupants in a single environmentally-controlled zone, may analyze a ranking of the occupants, the associated personal target building parameters, and an occupant status. This permits remediation based on hierarchical ranking, which may be based on occupant status, such as, for example whether or not the occupant is a guest, individual status of organizational members, or imperative status, among others.

Figure 7:
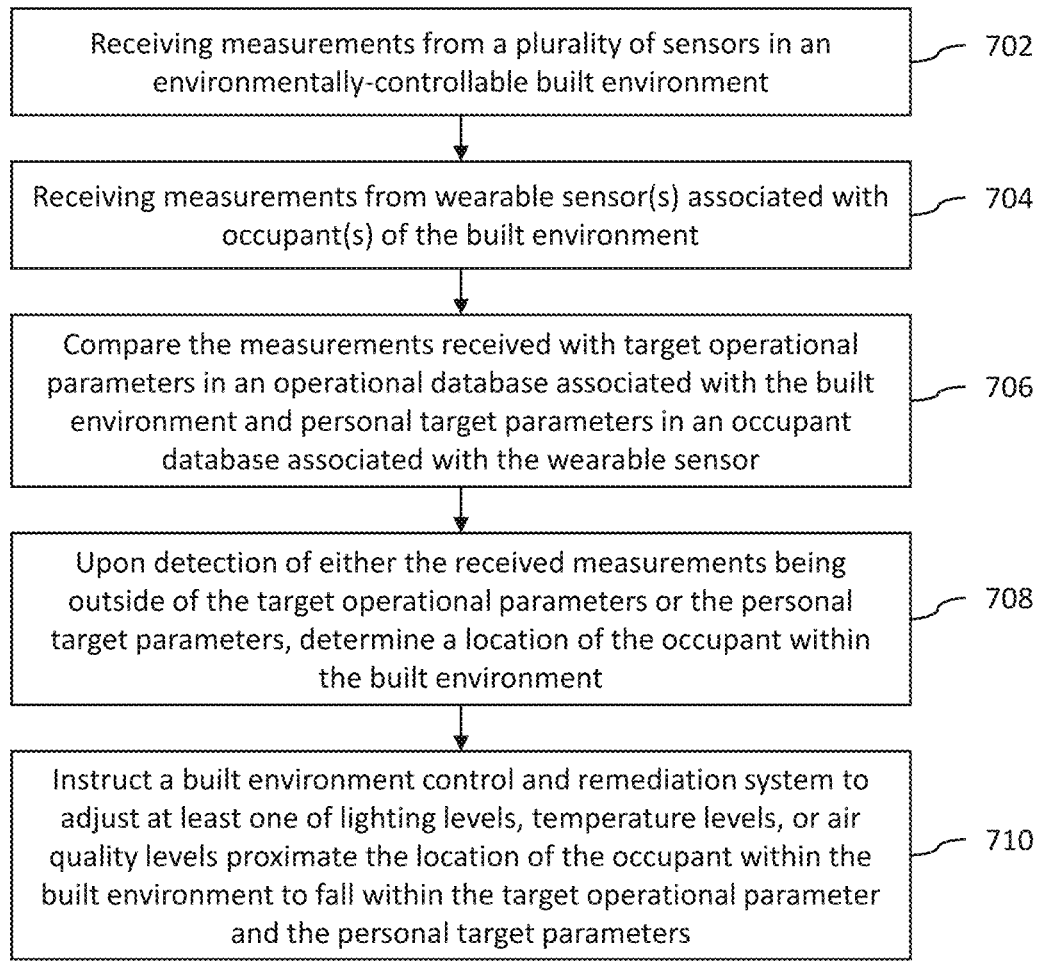
FIG. 7 is an exemplary flow diagram of a method in accordance with some embodiments.

FIG. 7 illustrates a method 700 of regulating an occupied space. The method 700 includes, as shown, receive 702 measurements from a plurality of sensors in an environmentally-controllable built environment, receive 704 measurements from a wearable sensor associated with an occupant of the built environment, compare 706 the measurements received with target operational parameters in an operational database associated with the built environment and personal target parameters in an occupant database associated with the wearable sensor associated with the occupant, and upon detection of either the received measurements being outside of the target operational parameters or the personal target parameters, determine 708 a location of the occupant within the built environment. The method 700 also instructs 710 a built environmental control system to adjust at least one of lighting levels, temperature levels, or air quality levels proximate the location of the occupant within the built environment to fall within the target operational parameter and the personal target parameters.

Figure 3:
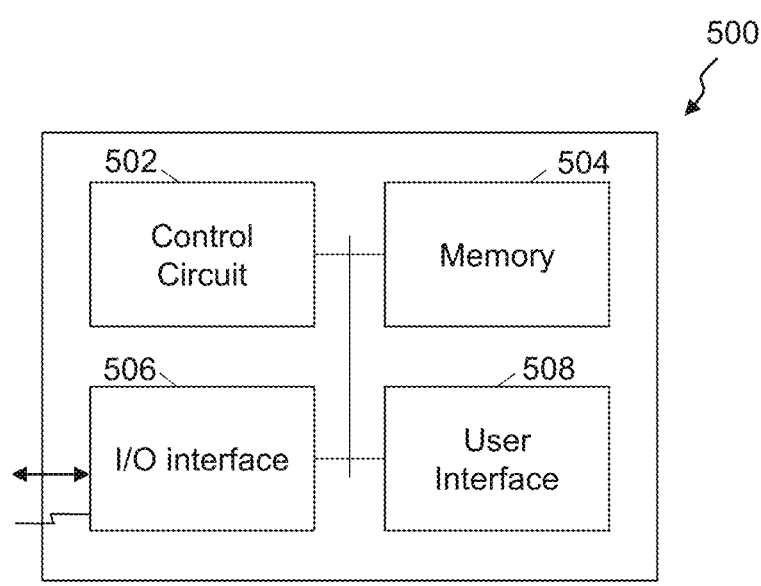
FIG. 3 is an exemplary system for use in implementing systems, apparatuses, devices, methods, techniques, and the like for delivering products to customers in accordance with some embodiments

The methods, techniques, systems, devices, services, servers, sources and the like described herein may be utilized, implemented and/or run on many different types of devices and/or systems. Referring to FIG. 3, there is illustrated a system 500 that may be used for any such implementations, in accordance with some embodiments. One or more components of the system 500 may be used to implement any system, apparatus or device mentioned above, or parts of such systems, apparatuses or devices, such as for example any of the above or below mentioned control circuits, electronic user devices, sensor(s), databases, parts thereof, and the like. However, the use of the system 500 or any portion thereof is not required.

By way of example, the system 350 may include one or more control circuits 502, memory 504, input/output (I/O) interface 506, and/or user interface 508. The control circuit 502 typically comprises one or more processors and/or microprocessors. The memory 504 stores the operational code or set of instructions that is executed by the control circuit 502 and/or processor to implement the functionality of the systems and devices described herein, parts thereof, and the like. In some embodiments, the memory 504 may also store some or all of particular data that may be needed to analyze built environments, individuals associated therewith, and potential interventions.

It is understood that the control circuit 502 and/or processor may be implemented as one or more processor devices as are well known in the art. Similarly, the memory 504 may be implemented as one or more memory devices as are well known in the art, such as one or more processor readable and/or computer readable media and can include volatile and/or nonvolatile media, such as RAM, ROM, EEPROM, flash memory and/or other memory technology. Further, the memory 504 is shown as internal to the system 500; however, the memory 504 can be internal, external or a combination of internal and external memory. The system 500 also may include a database (not shown in FIG. 3) as internal, external, or a combination of internal and external to the system 500. Additionally, the system typically includes a power supply (not shown), which may be rechargeable, and/or it may receive power from an external source. While FIG. 6 illustrates the various components being coupled together via a bus, it is understood that the various components may actually be coupled to the control circuit 502 and/or one or more other components directly.

Generally, the control circuit 502 and/or electronic components of the system 500 can comprise fixed-purpose hard-wired platforms or can comprise a partially or wholly programmable platform. These architectural options are well known and understood in the art and require no further description here. The system and/or control circuit 502 can be configured (for example, by using corresponding programming as will be well understood by those skilled in the art) to carry out one or more of the steps, actions, and/or functions described herein. In some implementations, the control circuit 502 and the memory 504 may be integrated together, such as in a microcontroller, application specification integrated circuit, field programmable gate array or other such device, or may be separate devices coupled together.

The I/O interface 506 allows wired and/or wireless communication coupling of the system 500 to external components and/or or systems. Typically, the I/O interface 506 provides wired and/or wireless communication (e.g., Wi-Fi, Bluetooth, cellular, RF, and/or other such wireless communication), and may include any known wired and/or wireless interfacing device, circuit and/or connecting device, such as but not limited to one or more transmitter, receiver, transceiver, etc.

The user interface 510 may be used for user input and/or output display, such as, for example, the wearable devices described above. Further, the user interface 510 may include, for example, any known input devices, such one or more buttons, knobs, selectors, switches, keys, touch input surfaces, audio input, and/or displays, etc. Additionally, the user interface 510 include one or more output display devices, such as lights, visual indicators, display screens, etc. to convey or request information to or from a user, such as but not limited to communication information, instructions regarding remediating an issue within a built environment, status information, notifications, errors, conditions, comfort or alertness query, and/or other such information. Similarly, the user interface 510 in some embodiments may include audio systems that can receive audio commands or requests verbally issued by a user, and/or output audio content, alerts and the like.

By one approach, a method for determining an intervention, includes, for example, determining a problem associated with a built environment, determining an indicator associated with the problem, and determining a potential intervention based on the indicator. The method also may include sending signal(s) indicative of one or more problems, one or more potential interventions, and/or ranking of the potential interventions or remediation options.

In operation, the potential intervention reduces the prevalence or severity of the problem with the built environment. For example, a user with an intervention assessment system installed in their home, by one approach, may receive a signal indicative of an indicator on a personal electronic device (e.g., a mobile telephone, fitness tracker, or smartwatch) about an elevated level of particulate in an area of a home, the personal electronic device may also then present one or more options for remediation (e.g., potential interventions) including, for example, sending instructions regarding operation of certain remediation devices or notifying a remediation specialist.

In this example, the user receives both a signal indicative of the indicator and a signal regarding potential interventions. In some embodiments, the user also may receive from the system a recommendation for which of the potential interventions to pursue. More particularly, the system may provide a ranking of the plurality of potential interventions. The ranking may be based, at least in part, on one or more of disability adjusted life years, years lived with disability, days of comfort lost, amenity satisfaction, and/or workplace amenity satisfaction for a person associated with the built environment, among other factors. In some configurations, the ranking is based on at least two of these aspects. Further, these aspects, such as, for example, disability adjusted life years, years lived with disability, days of comfort lost, and amenity satisfaction may be given based on their association with the potential interventions. In this manner, the system may rank potential interventions, in part, upon a relevance to a person associated with the built environment, effectiveness of at least two of the plurality of potential interventions, cost of materials associated with the at least two of the plurality of interventions, design changes needed to a built environment, efficiency of at least two of the plurality of potential interventions, cost of at least two of the plurality of potential interventions, feasibility of at least two of the plurality of potential interventions, implementability of at least two of the plurality of potential interventions within a given time period, physical comfort of at least one person associated with the built environment, work satisfaction of at least one person associated with the built environment, at least one environmental condition in the built environment, and/or number of people that would be impacted by at least two of the plurality of potential interventions.

Upon receipt of the signals regarding potential interventions and optionally a recommendation, the intervention assessment system is configured adjust an environmental condition in the built environment. In some configuration, this is done in response to receipt of a selection submitted at a personal electronic device and in other configurations, the adjustment may occur automatically, such as, for example, when a user is unavailable to provide instructions. For example, a user may not be interested in deciding what or whether to remediate certain issues and may provide instructions to the system to pursue intervention if the cost is below a certain threshold and according to the ranking of potential interventions. This may include, for example, adjusting an environmental condition in the built environment or an amenity associated with the built environment based on the potential intervention or the ranking thereof and/or adjusting a policy associated with the built environment based on the potential intervention or the ranking thereof. Further, the method also may include sending a signal indicative of an adjustment of an environmental condition, amenity, and/or policy adjustment in the built environment based on the potential intervention and/or the ranking thereof.

Generally, the ranking may be based, in part, on a likelihood of potential intervention(s) to reduce prevalence of the at least one problem. In this manner, the ranking may take into consideration the effectiveness of each of the potential interventions. Further, the ranking also may be based on an indicator to predict effectiveness of a potential intervention in reducing the problem. Similarly, the ranking may be based in part on effectiveness of each of the plurality of potential interventions in impacting an outcome of interest related to the at least one problem.

As illustrated herein, there are a myriad of potential interventions that one might consider. Thus, the intervention assessment system can assist with ranking a plurality of potential interventions. Further, the system may be configured to send a signal indicative of the at least one problem, such as, for example to a personal electronic device. The signal sent may indicative of one or more indicators and also may include one or more potential interventions, such as those recommended by the intervention assessment system. In this manner, a user can receive information on the problem, data on the problem as illustrated by the indicator, and one or more potential interventions, which may be accompanied by a recommendation for remediation.

By one approach, the method includes determining potential intervention(s) applicable to a particular person, wherein the intervention, if implemented, may help improve the person's health. A number of health indicators or measures are described herein.

In addition to numerous potential interventions, the system and methods described herein may identify a plurality of problems as well. These problems, like the potential interventions, may be ranked. Accordingly, in one approach, the system and methods prioritize the plurality of problems associated with the built environment. Further, the method may select one of the plurality of problems to be addressed or for some remediation.

As mentioned above, the system and method determine an indicator associated with a problem and for some, may determine determining a plurality of indicators associated with each of the one or more problems. Further, the system and method, in some approaches, ranks the plurality of indicators associated with the problem(s) such that the system and method prioritize and/or select an indicator associated with a problem.

As implied above, when the methods and systems herein determine a potential intervention associated with an indicator, a plurality of potential interventions associated with the indicator may be identified. Further, the potential interventions associated with the indicator may be ranked and prioritized for selection.

As used herein, the problem may relate to, for example, one or more of the following: PM2.5 level, plant-based particulate, animal-based particulate, pest-based particulate, bacteria, virus, fungi, mold, PM10 level, ozone level, radon level, benzene level, carbon dioxide level, carbon monoxide level, nitrogen dioxide level, diesel exhaust particulate matter, lead particulate level, mercury particulate level, formaldehyde level, as well as the presence of certain inorganic chemical(s), certain organic chemical(s), microorganism(s), tobacco smoke, benz[a]pyrene, certain disinfectant(s), certain disinfectant byproduct(s), ultrafine particulate, and certain radionuclides.

In some embodiments, the problem may relate to, for example, the presence or availability of water, beverages, food including healthy food, exercise equipment, and medical equipment in the built environment. Further, the problem may be specifically related to the occupant of the space, such as, for example related to disease, disability, discomfort, or dissatisfaction for a person associated with the built environment. In this manner, an individual with certain medical conditions, upon entering a space with an intervention assessment system, may receive an indicator on a personal electronic device about issues related to certain foods or beverages that are to be ingested or avoided. In this manner, the problem would be related to a medical or health condition of at least one person associated with the built environment. Further, the indicator of the intervention assessment system may accordingly relate to the presence or availability of the water, beverages, food including healthy food, exercise equipment, and medical equipment in the built environment A myriad of different medical or health conditions may be targeted with these teachings including, problems related to or the occurrence of, for example, hearing loss, tuberculosis, HIV/AIDS, diarrheal disease, intestinal infectious disease, lower respiratory infection, upper respiratory infection, otitis media, meningitis, encephalitis, diphtheria, whooping cough, tetanus, measles, varicella and herpes zoster, malaria, Chagas disease, Leishmaniasis, African trypanosomiasis, schistosomiasis, cysticercosis, cystic echinococcosis, lymphatic filariasis, onchocerciasis, trachoma, dengue, yellow fever, rabies, intestinal nematode infections, food-borne trematodiases, leprosy, Ebola, tropical diseases, maternal hemorrhage, maternal sepsis and other maternal infections, maternal hypertensive disorders, maternal obstructed labor, maternal abortive outcome, maternal disorder, neonatal preterm birth complications, neonatal encephalopathy due to birth asphyxia and trauma, neonatal sepsis and other neonatal infections, hemolytic disease and other neonatal jaundice, neonatal disorder, protein-energy malnutrition, iodine deficiency, vitamin A deficiency, iron-deficiency anemia, nutritional deficiency, sexually transmitted diseases excluding HIV, hepatitis, infectious disease, lip and oral cavity cancer, nasopharynx cancer, pharynx cancer, esophageal cancer, stomach cancer, colon and rectum cancer, liver cancer, gallbladder and biliary tract cancer, pancreatic cancer, larynx cancer, tracheal, bronchus, and lung cancer, malignant skin melanoma, non-melanoma skin cancer, breast cancer, cervical cancer, uterine cancer, ovarian cancer, prostate cancer, testicular cancer, kidney cancer, bladder cancer, brain and nervous system cancer, thyroid cancer, mesothelioma, Hodgkin lymphoma, non-Hodgkin lymphoma, multiple myeloma, cancer, leukemia, neoplasms, rheumatic heart disease, ischemic heart disease, cerebrovascular disease, hypertensive heart disease, cardiomyopathy and myocarditis, atrial fibrillation and flutter, peripheral vascular disease, endocarditis, cardiovascular and circulatory disease, chronic obstructive pulmonary disease, skin burn, skin disease, bone disease, bone fracture, bone breakage, skin fungus, hair loss, ingrown fingernail, ingrown toenail, pneumoconiosis, asthma, interstitial lung disease and pulmonary sarcoidosis, chronic respiratory diseases, cirrhosis due to hepatitis B, cirrhosis due to hepatitis C, cirrhosis due to alcohol use, cirrhosis, peptic ulcer disease, gastritis and duodenitis, appendicitis, paralytic ileus and intestinal obstruction, inguinal, femoral, and abdominal hernia, inflammatory bowel disease, vascular intestinal disorders, gallbladder and biliary diseases, pancreatitis, digestive disease, Alzheimer's disease and other dementias, Parkinson's disease, epilepsy, multiple sclerosis, motor neuron disease, migraine, tension-type headache medication overuse headache, neurological disorder, schizophrenia, alcohol use disorder, alcoholism, drug use disorders, drug use, depression, depressive disorder, bipolar disorder, anxiety disorder, eating disorder, autistic spectrum disorder, attention-deficit/hyperactivity disorder, conduct disorder, idiopathic intellectual disability, mental and substance use disorder, diabetes mellitus, acute glomerulonephritis, chronic kidney disease, urinary disease, male infertility, gynecological disease, hemoglobinopathies and hemolytic anemia, endocrine, metabolic, blood, and immune disorder, rheumatoid arthritis, osteoarthritis, headache, low back pain, neck pain, gout, musculoskeletal disorder, congenital anomaly, skin and subcutaneous disease, sense organ disease, oral disorders, road injury, other transport injury, fall, drowning, exposure to fire, heat, or hot substances, poisoning, blood loss, exposure to mechanical forces, adverse effect of medical treatment, animal contact or exposure, foreign body contact or exposure, exposure to forces of nature, unintentional injury, intentional injury, stress, morale, level and type of physical activity, thyroid condition, anxiety, motion sickness, dizziness, memory loss, kidney stone, heart condition, lung condition, kidney condition, blood clot, rash, burn, flu, infection, bladder control, upset stomach, injury, disease, eye problem, ear problem, throat problem, nose problem, mouth problem, skeletal problem, and interpersonal violence.

In some embodiments, the problems associated with the built environments may relate to or result from, for example, one or more policies (or lack thereof) associated with a person or group associated with the built environment (or portion thereof). Such policies may include, for example, a leave policy, vacation policy, remote work policy, insurance policy, travel policy, spending policy, gift policy, trade policy, review policy, promotion policy, sick policy, management policy, approval policy, approvable spend policy, independent contractor policy, employee policy, use of company resources policy, human resources policy, security policy, privacy policy, intellectual property policy, compliance policy, financial policy, unfair practices policy, child day care policy, or legal policy. As implied, the lack of a policy or the policy itself may create an issue so that the potential intervention relates to or involves creating or modifying a policy, such as one of those mentioned herein. Accordingly, the potential intervention may relate to a policy associated with the built environment and/or associated with a person associated with the built environment. In addition to the policies mentioned above, these may include, for example, a home insurance policy, renter insurance policy, car insurance policy, rental policy, volunteer policy, pet policy, and/or legal policy.

While the problems attendant built environments can be varied, so too can the interventions to address them. Indeed, while some interventions may remediate a problem entirely, others may only partially address a problem. Thus, the intervention assessment system typically tracks measurable improvement of a problem. Indeed, the indicators used by the intervention assessment system are typically indicative of the intervention (or potential intervention) to reduce the impact of the problem, which may be of particular interest for solutions that do not entirely remediate a problem. As used herein, the indicators may be similar to the problems themselves. For example, the indicators may include particulate levels, breathable toxins, and other toxins including those mentioned above. Similarly, the indicator (and indeed, the potential intervention) may relate to the medical or health condition associated with a person or persons associated with the built environment, similar to the medical or health conditions listed above. Furthermore, the potential interventions also may relate to fully or partially remediating the offending particulate, toxins, or other issues described herein.

Further, in operation, the indicators (and indeed, the potential interventions) may relate to a number of aspects related to the built environment or a portion thereof including the presence or lack therefor of, for example, a smoking ban, a healthy entrance, a cleaning protocol, pesticide use, materials (such as building materials), moisture management pest control measures, combustion minimization measures, toxic material reduction measures, material safety measures, antimicrobial measures, ventilation effectiveness, ventilation control capabilities, agricultural contaminant management, organic contaminant management, inorganic contaminant management, agricultural contaminant management, volatile organic (VOC) compound management, air filtration, air flush management, air purification, microbe control, mold control, water quality, air quality, a water additive, cleanable equipment, cleaning equipment, cleaning materials, one or more operable window, direct source ventilation, displacement ventilation, at least one outdoor air system or device, window size, window location, window transmittance, window shading, electric light control, lamp shielding, lamp quality, lamp positioning, light positioning, light, light temperature, light type, temperature control capability, humidity and humidity control capability, surface reflectivity, color rendering index, workstation design, air flow speed, air flow direction, signal to noise ratio, sound reverberation time, noise or sound level, noise or sound pressure, aesthetics, a view, size, access to and proximity of transportation, quality of transportation available thereto, and ambient decibel level in at least a part of the built environment.

As noted above, the lack of food, especially healthy food, may raise issues in certain built environments. By one approach, the potential interventions may include, for example, the presence or availability of water, beverages, food including healthy food, exercise equipment, and medical equipment in the built environment. Therefore, any potential interventions may involve, for example, the presence or availability of, food including, for example, fruits, vegetables, whole grains, nuts, seeds, milk, red meat, processed meat, water, beverage, sweetened beverage, unsweetened beverage, low-fiber food, high-fiber food, food with high sodium, food with low sodium, food with high trans-fat, food with low trans-fat, foods low in omega-3 fats, food high in omega-3 fats, high-calorie food, low-calorie food, sugar, sugar substitute, sweetener, low calcium food, high calcium food, food with monounsaturated fatty acid, food with polyunsaturated fatty acid, high protein food, and low protein food.

In operation, the intervention assessment system analyzes aspects and determines one or more indicator associated with one or more problems. By one approach, the intervention assessment system, for example, accesses a database of potential indicators, assesses a database of problems associated with built environment(s), accesses a database of problems associated with at least one person associated with the built environment, conducts a survey related to the built environment and/or problems, conducts a poll related to at least one problem and/or the built environment, conducts a literature review (which may be associated with built environments), conducts research regarding indicator(s), ranks a plurality of indicators, ranks a relevance of a plurality of indicators regarding the problem(s), determines a relevance of at least one indicator to the problem(s), selects indicator(s) from a plurality of potential indicators, determines a causal relationship between indicator(s) and the at least one problem, and convenes an expert panel to deliberate at least potential indicator of the at least one problem.

As used herein the built environment may include, for example, a school, class room, gymnasium, business office, office building, single family home, hotel, hotel room, motel, motel room, theatre, movie theater, apartment building, apartment, research facility, darkroom, drawing room, lab, prison, jail, library, courtroom, museum, gallery, art studio, hallway, kennel, boardroom, locker room, shower, laundry room, laundromat, wash room, training room, mail room, post office, lunch room, kitchen, bed room, guest room, loft, library, vestibule, nursery, day care facility, elder care facility, utility room, reception area, dining area, storage facility, storage area, police station, fire station, conference room, control room, cabin, ballroom, assembly room, boiler room, chapel, cell, newsroom, mud room, wine cellar, studio, clean room, show room, porch, sitting room, solarium, pantry, nursing room, conservatory, church, recovery room, hospital room, hospital, temple, lodge, den, foyer, engine room, dormitory, drawing room, emergency room, fitting room cloakroom, chamber, lobby, attic, military facility, parking garage, stairway, underground bunker, sport venue, manufacturing facility, testing facility, train station, bus station, store, mall, airport, barn, shed, restaurant, bar, cafe, diner, exercise facility, barber shop, beauty salon, changing or dressing room, bath room, spa, post office, or other occupiable space or facility.

The intervention assessment system identifying and addressing the problems, indicators, and potential interventions, may execute a number of operations including, for example, changing indoor environmental quality, changing a comfort feature, raising air temperature, reducing air temperature, changing air temperature, changing air quality, reducing humidity, increasing availability of biophilia, increasing quality of biophilia, changing air purification capability, improving water quality, changing water filter capability, changing water quality control capability, changing air quality control capability, changing air temperature control capability, changing air filter capability, changing food availability, improving food quality, improving water availability, changing food availability, changing beverage availability, changing a configuration, changing at least one amenity available, changing an acoustic related feature, reducing noise, changing at least one piece of furniture, removing at least one piece of furniture, removing a surface coating present, removing a material type from at least part of the built environment, changing a material used in at last part of the built environment, adding at least one amenity available, changing at least one amenity available, removing at least one amenity available, improving an ergonomic feature of the built environment, adding an ergonomic feature to the built environment, improving physical comfort for at least one person who may occupy at least a part of the built environment, changing at least one air flow pattern, changing air flow control capability, reducing average air particle count, reducing prevalence of at least one particle type of a certain size, reducing prevalence of at least one particle type below a designated size, reducing prevalence of at least one kind of material, increasing light availability, changing a light pattern, changing a light temperature, changing light availability, changing light control capability, changing a window size, changing a window transparency, installing a window, changing a feature, adding a feature, removing a policy associated with the built environment, changing a policy associated with the built environment, and/or adding a policy associated with the built environment or a portion thereof.

In one illustrative approach, the optional potential intervention is selected or ranked, based, in part upon at least one of a strength of the relationship between an indicator and a potential intervention, the ability of an indicator to predict that the potential intervention will resolve a particular problem, geographic location of the built environment, an amount of time a person is expected to be present in the built environment, a period of time a person is expected to be present in the built environment, an amount of time a group of people is expected to be present in the built environment, a period of time a group of people is expected to be present in the built environment, design of the built environment, a physical feature of the built environment, a demographic of people who may be present in the built environment, a cost associated with a potential intervention, data received from at least one sensor positioned within the built environment, global burden of disease related data, a budget associated with the built environment, a maintenance schedule associated with the built environment, a maintenance history associated with the built environment, an operational history associated with the built environment, an occupancy history associated with the built environment, occurrence of pollution in the built environment, location of pollution in the built environment, duration of pollution in the built environment, results of a survey, results of an experiment, results of a laboratory test, results of a use test, results of a medical exam, results of a prior implementation of or a change in a particular intervention, results of a prior implementation of or a change in an intervention in the built environment, results of an inspection of the built environment, results of an audit related to the built environment, information regarding employee compensation preferences, information regarding employee amenity preferences, information regarding amenity cost-effectiveness, information regarding employee satisfaction, information regarding employee comfort, information regarding location specific productivity data, information regarding industry specific productivity data, information regarding at least one modifiable risk factor, behavioral data, genetic data, demographic data, healthcare expenditure data, information regarding workplace prevalence of disease, disability and conditions, a health assessment of a person associated with the built environment, a characteristic of a person associated with the built environment, a characteristic of people who may be present in the built environment at a designated time, a desired change for the built environment, a required change for the built environment (such as a change in zoning laws), a regulation applicable to the built environment, a configuration of at least part of the built environment, availability of at least one amenity in the built environment, environmental condition(s) in the built environment (or portion thereof), an intended use of the built environment (or portion thereof), and an analysis of health of a person associated with the built environment. The potential intervention may be selected based upon, for example, expected change in comfort for the person arising from implementation of or a change in the at least one potential intervention, potential change in comfort for the person arising from implementation of or a change in the at least one potential intervention, potential change in health for the person arising from implementation of or a change in the at least one potential intervention, potential change in disability for the person arising from implementation of or a change in the at least one potential intervention, potential change in amenity satisfaction for the person arising from implementation of or a change in the at least one potential intervention, potential change in disability adjusted life years for the person arising from implementation of or a change in the at least one potential intervention, potential change in years lived with disability for the person arising from implementation of or a change in the at least one potential intervention, potential change in days of comfort lost for the person arising from implementation of or a change in the at least one potential intervention, expected change in comfort a group of people arising from implementation of or a change in the at least one potential intervention, potential change in comfort for a group of people arising from implementation of or a change in the at least one potential intervention, potential change in health for a group of people arising from implementation of or a change in the at least one potential intervention, potential change in disability for a group of people arising from implementation of or a change in the at least one potential intervention, potential change in amenity satisfaction for a group of people arising from implementation of or a change in the at least one potential intervention, potential change in disability adjusted life years for a group of people arising from implementation of or a change in the at least one potential intervention; potential change in years lived with disability for a group of people arising from implementation of or a change in the at least one potential intervention, and potential change in days of comfort lost for a group of people arising from implementation of or a change in the at least one potential intervention.

In operation, the intervention assessment system and methods associated therewith may include maintaining or updating a variety of data as the science relating to or the understanding of the built environment expands. For example, the method may include maintaining data associated with the built environment including maintaining, accessing, receiving, sending, and/or analyzing data about the built environment, data about at least one person associated with the built environment, data about a plurality of people associated with the built environment, data about at least one problem associated with the built environment, data about at least one potential problem that may impact the built environment, data about at least one indicator of a problem associated with the built environment, data about at least one indicator of a potential problem that may impact the built environment, data associated with a plurality of geographic locations, data associated with a plurality of potential interventions, data associated with a plurality of potential interventions (wherein at least two of the plurality of potential interventions is usable in a plurality of geographic locations), data associated with a plurality of potential interventions (wherein at least two of the plurality of potential interventions is usable in the built environment), data associated with a plurality of potential interventions that may decrease prevalence of disease associated with the built environment, data associated with a plurality of potential interventions that may decrease prevalence of disability associated with the built environment, data associated with a plurality of potential interventions that may decrease prevalence of discomfort associated with the built environment, data associated with a plurality of potential interventions that may decrease prevalence of dissatisfaction associated with the built environment, data associated with a plurality of uses of the built environment, data associated with a plurality of materials usable in the built environment, data associated with a plurality of materials used in the built environment, data associated with a plurality of materials usable in furniture, data received from a plurality of sensors associated with the built environment, data received from a plurality of sensors associated with a built environment, and/or data received from a plurality of devices associated with a person associated with the built environment, worn by a person associated with the built environment, or carried by a person associated with the built environment.

By one approach, the intervention assessment system and the methods related thereto analyze the individuals associated with the built environment and how those individuals use the built environment. For example, the system may analyze or determine how long a particular person is expected to occupy the built environment for a first period of time and/or a second period of time. In another approach, the system receives a signal indicative of the periods of time. With this information, the system may analyze or receive, for example, a start or end date or time for the first period, a length of the first period, a characteristic of the first period, a requirement for starting the first period, a requirement for ending the first period, an event that triggers a start of the first period, and, an event that triggers an end of the first period.

Further, to associate this information, the system and methods may determine a characteristic of the particular person or the identity of the person. Accordingly, the system and methods may receive a signal indicative of an individual or a characteristic of the person. For example, the system may receive or determine characteristic(s) including an age of the person, an average age of a group of people, the age distribution of a group of people, a characteristic of a group of people (which may be associated with the built environment), occupation of the person, employer of the person, employment status of the person, employment history of the person, location of the person, a goal of the person, current health of the person, future travel plan of the person, travel history of the person, medical history of the person, marital status of the person, marital history of the person, family size of the person, family history of the person, schedule of the person, gender of the person, gender ratio of a group of people that includes the person, gender ratio of a group of people that includes the person (which may be associated with the built environment), race of the person, education level of the person, average education level of a group of people that includes the person, nationality of the person, a personal need of the person, a desired characteristic of the person, a desired characteristic of a group of people that includes the person, a desired characteristic of a group of people that includes the person (which may be associated with the built environment), a health condition of the person, a health assessment of a group of people that includes the person, a health assessment of a group of people that includes the person (which may be associated with the built environment), and a health assessment of the one person.

In addition to determining and receiving information about the people (including identifying individuals), the systems and methods herein also may receive signals indicative of or determine characteristics of a particular built environment including, for example, location of the built environment, availability of water in the built environment, beverage availability of the built environment, availability of food (including healthy food) in the built environment, availability of exercise equipment in the built environment, availability of medical equipment in the built environment, aclimate condition for the built environment, an environmental condition within the built environment, a desired environmental condition within the built environment, quality of the built environment, design of the built environment, a current policy associated with the built environment, a desired policy for the built environment, an amenity available at the built environment, a desired amenity for the built environment, age of the built environment, an owner of the built environment, an occupier of the built environment, a desired occupant of the built environment, a current feature of the built environment, a desired feature of the built environment, a current use of the built environment, an expected use of the built environment, a desired use of the built environment, a goal of a current owner of the built environment, a goal of a current manager of the built environment, a goal of a current occupier of the built environment, a goal of an expected occupier of the built environment, and/or a regulation that may apply to the built environment.

To facilitate the systems and methods described herein, sensors are typically employed to receive and send data. In one embodiment, the sensors include, for example, an air quality sensor, a temperature sensor, a humidity sensor to detect at least one air quality parameter, an audio transducer to detect ambient sound levels, a motion detector, and/or a light sensor to detect at least one of a light level or a color index of light, among others. Further, information from the sensor may be used to determine one or more potential interventions.

In some approaches, the potential interventions include a relationship between an indicator and an intervention. In this manner, where the modifying a relationship between an indicator and an intervention is based at least in part on ability of the at least one intervention to resolve the at least one problem.

To facilitate remediation or improvement of a built environment, the methods and systems herein typically determine a relationship (or several aspects of the relationship) between an indicator and an intervention. Thus, in some approaches, the system and methods modify a relationship between the indicator and the problem. Further, modifying a relationship between an indicator and a problem is typically based (at least in part) on an ability of an intervention to resolve the a problem.

The methods and systems also typically determine a relationship (or several aspects of the relationship) between an indicator and a problem. Further, the more accurately the relationships are ascertained, typically, the better the outcomes.

In certain approaches, a method for determining an intervention typically includes determining one or more problems associated with a built environment, determining a plurality of indicators associated with the problems, and determining at least one potential intervention based on the plurality of indicators, where the at least one potential intervention reduces prevalence of at least one of the problems in the built environment. By some approaches, the method includes ranking and selecting potential interventions based at least in part on disability adjusted life years, years lived with disability, days of comfort lost, and/or amenity satisfaction.

In other approaches, a method for determining intervention includes determining at least one problem associated with a built environment, determining a plurality of indicators associated with the at least one problem, selecting at least one of the plurality of indicators, and determining at least one potential intervention based on the at least one of the plurality of indicators, wherein the at least one potential intervention can reduce the prevalence of the at least one problem in the built environment.

In yet other configurations, a method for determining interventions includes determining at least one problem associated with a built environment, determining at least one indicator associated with the at least one problem, and determining a plurality of potential interventions based on the at least one of the plurality of indicators, wherein each of the at plurality of interventions can reduce prevalence of the at least one problem in the built environment.

By some approaches, a method for determining an intervention includes determining at least one problem associated with a built environment, determining at least one indicator associated with the at least one problem, determining a plurality of potential interventions based on the at least one of the plurality of indicators, wherein each of the at plurality of interventions can reduce prevalence of the at least one problem in the built environment, ranking the plurality of potential interventions, and selecting at least one of the plurality of potential interventions based at least in part on the ranking. In such a configuration, the ranking of potential interventions is based at least in part on the likelihood of each of the plurality of potential interventions to reduce prevalence of the at least one problem, the effectiveness of each of the plurality of potential interventions in reducing the at least one problem, the ability of the at least one indicator to predict effectiveness of at least one of the plurality of interventions in reducing the at least one problem, the effectiveness of each of the plurality of interventions in impacting an outcome of interest related to the at least one problem, the environmental conditions in the built environment, and/or the amenities available in the built environment. In some configurations, the ranking occurs based on the relevance to a person associated with the built environment, the effectiveness of at least two of the plurality of potential interventions, the efficiency of at least two of the plurality of potential interventions, the cost of at least two of the plurality of potential interventions, the feasibility of at least two of the plurality of potential interventions, the implementability of at least two of the plurality of potential interventions within a given time period, and the number of people that would be impacted by at least two of the plurality of potential interventions.

By yet other approaches, a method for determining an intervention includes, for example, determining at least one problem associated with a built environment, determining at least one indicator associated with the at least one problem, determining a plurality of potential interventions based on the at least one of the plurality of indicators, wherein each of the at plurality of interventions can reduce prevalence of the at least one problem in the built environment, prioritizing the plurality of potential interventions, and selecting at least one of the plurality of potential interventions based at least in part on the prioritizing of the plurality of potential interventions.

In some embodiments, a method for determining an intervention includes determining a plurality of problems associated with a built environment, selecting one of the plurality of problems, determining at least one indicator associated with the one of the plurality of problems, determining a plurality of potential interventions based on the one of the plurality of indicators (wherein each of the at plurality of interventions can reduce prevalence of the at least one problem in the built environment), prioritizing the plurality of potential interventions, and selecting at least one of the plurality of potential interventions based at least in part on the prioritizing of the plurality of potential interventions.

In other embodiments, a method for determining an intervention includes determining a plurality of problems associated with a built environment, selecting one of the plurality of problems, determining at least one indicator associated with the one of the plurality of problems, determining a plurality of potential interventions based on the one of the plurality of indicators, wherein each of the at plurality of interventions can reduce prevalence of the at least one problem in the built environment, ranking the plurality of potential interventions, and selecting at least one of the plurality of potential interventions based at least in part on the ranking of the plurality of potential interventions.

In yet other embodiments, a method for determining an intervention includes determining a plurality of problems associated with a built environment, ranking the plurality of problems, selecting one of the plurality of problems based at least in part on the ranking, determining at least one indicator associated with the one of the plurality of problems, determining a plurality of potential interventions based on the one of the plurality of indicators, wherein each of the at plurality of interventions can reduce prevalence of the at least one problem in the built environment, ranking the plurality of potential interventions, and selecting at least one of the plurality of potential interventions based at least in part on the ranking of the plurality of potential interventions. In such a configuration, the method may rank the plurality of problems by prioritizing them and rank the plurality of potential interventions by prioritizing the potential interventions.

By one approach, a method for determining an intervention includes determining a plurality of problems associated with a built environment, ranking the plurality of problems, selecting one of the plurality of problems based at least in part on the ranking, determining a plurality of indicators associated with the one of the plurality of problems, ranking the plurality of indicators, selecting one of the plurality of indicators based at least in part on the ranking, determining a plurality of potential interventions based on the one of the plurality of indicators, wherein each of the at plurality of potential interventions can reduce prevalence of the at least one problem in the built environment, ranking the plurality of potential interventions, and selecting at least one of the plurality of potential interventions based at least in part on the ranking of the plurality of potential interventions.

Figure 8:
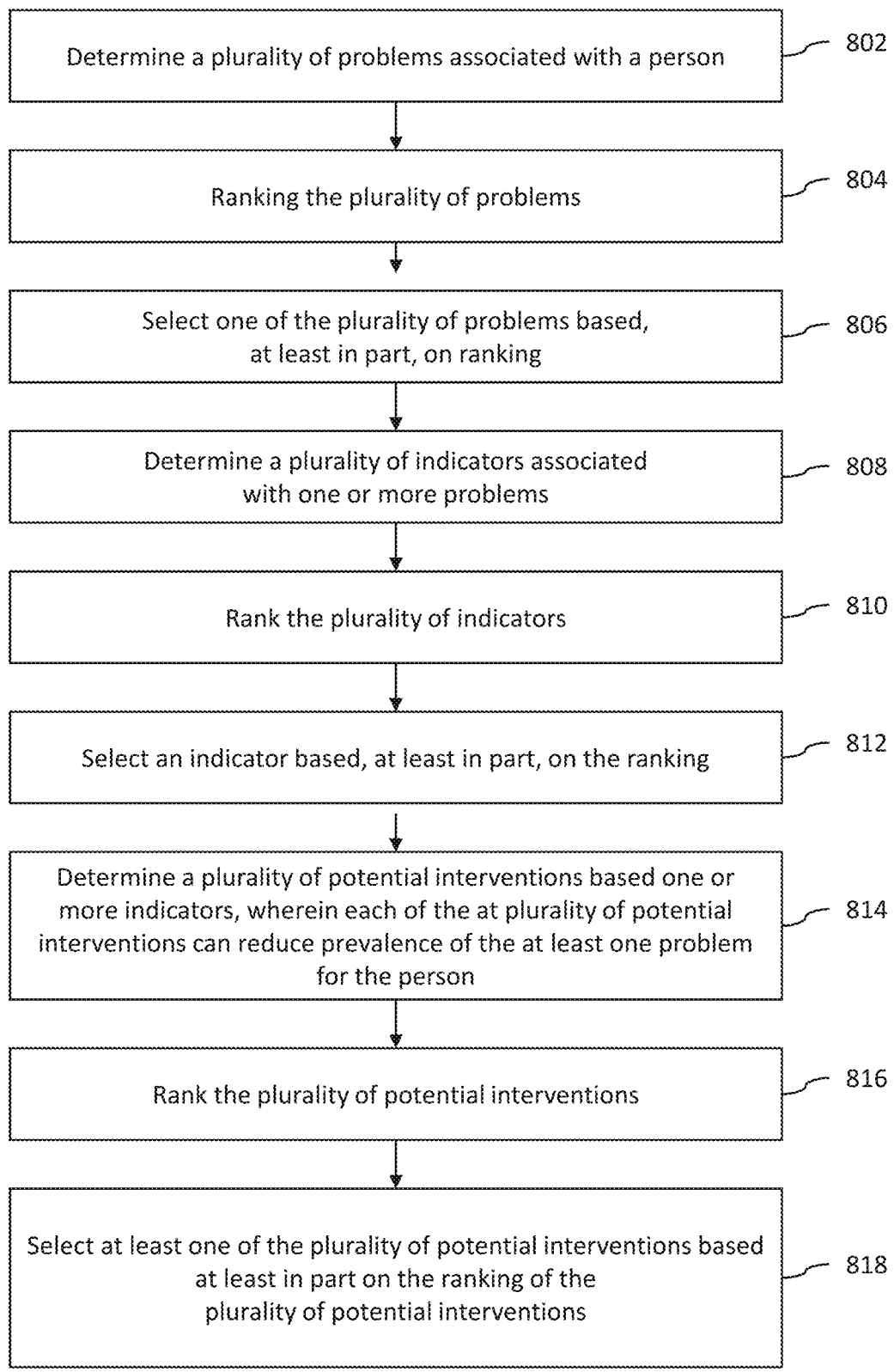
FIG. 8 is an exemplary flow diagram of another method in accordance with some embodiments.

FIG. 8 illustrates a method 800 of determining one or more interventions.

Multiple potential interventions may be referred to as an intervention set or group. In some embodiments, an intervention set is a bundled set or group of related or unrelated interventions, which together, have a positive impact on a risk factor, cause of a health burden, or one or more other problems associated with a built environment. An intervention set might not include all potential interventions that may be applicable for a given problem in a built environment. In some embodiments, multiple interventions may work synergistically, and a fully-implemented intervention set represents a comprehensive solution to addressing its target risk factor or other problem associated with a built environment. Thus, to obtain a full score or other ranking for an intervention set, all of its component interventions should be achieved or be achievable. In some embodiments, there may be some interventions for addressing a problem in a built environment that may be mutually exclusive if they are in a single intervention set. In such situations, choosing one potential intervention may exclude the option of pursuing one or more other potential interventions.

The method 800 includes, as shown, determine 802 a plurality of problems associated with a person or a built environment, rank 804 the plurality of problems, select 806 one of the plurality of problems based, at least in part, upon the ranking, determine 808 a plurality of indicators associated with one or more problems, rank 810 the plurality of indicators, select 812 an indicator based, at least in part, on the ranking, determine 814 a plurality of potential interventions based one or more indicators, wherein each of the plurality of potential interventions can reduce the prevalence of the at least one problem for the person, rank 816 the plurality of potential interventions, and select 818 at least one of the plurality of potential interventions based at least in part on the ranking of the plurality of potential interventions.

As previously discussed above, in some embodiments, determining a problem with a built environment or a person associated with a built environment may include obtaining, analyzing or using data regarding the location of the built environment. For example, pollution levels or other air quality indicators, GBD related data or findings resulting therefore, in the country or city where the built environment is located may be used, etc. Alternatively, or in addition, genetic, biometric, or other health related data associated with the person may be obtained from a database or a wearable or other device associated with the person and used to determine a health, wellness or other problem associated with the person. Surveys or polls of one or more people also may be used. Environmental data related to a built environment that the person is in, will be in, or has been in, such as air quality data, temperature data, policy information, lighting design, layout or design information, material information, water quality data, availability or quality of certain amenities (e.g., exercise equipment, healthy foods) may be used to identify or determine one or more problems associated with the person or the built environment. Such environmental data may come from a wearable or other device associated with the user or one or more sensors or other devices located in the built environment. In some embodiments, determining 802 one or more problems with a person or a built environment may include determining such problems at or over different periods of time, from different sources, etc., determining different causes of problems, determining different types of problems, etc. As one alternative to 802, only one problem associated with a person or a built environment may be determined or used.

Ranking 804 a plurality of problems may be done in different ways, such as by ranking problems by avoidable burden, addressable burden, days of comfort lost, other impact metric, GBD estimates or findings, other health or wellness impacts, cost impacts, size of impacted population or groups, long term impacts of the problems, likelihood in growth of the problems or negative impacts of the problems, population type (e.g., children, older adults) most or least impacted by the problems, findings from surveys of experts or other people, findings from literature or other reviews, other subjective or objective measures of impact or severity of the problems, etc. In some embodiments, such ranking 804 may be optional or not used.

In one illustrative approach, the control circuit is configured to determine avoidable burden, addressable burden, days of comfort lost, and/or employee satisfaction as they pertain to one or more particular occupants. Further, this may be determined or analyzed for one or more of the environmentally-controllable zones or spaces within the built environment or structure.

In some embodiments, problems may be ranked by more than one factor, and different weightings may be given to different factors in such ranking. For example, expected long term negative impacts or growth in impacts of problems on people may be weighted more heavily than current negative impacts of the problems. As another example, avoidable burdens associated with the problems may be weighted more than addressable burdens associated with the problems. As a further example, size of impacted population from a problem and expected growth of the problem may be weighted more than the cost impacts of the problem.

Selecting 806 one of such problems identified in 802 may be done solely or partially based on the ranking of the problems, or along with one or more other factors. In some embodiments, such selecting 806 may be optional or not used, particularly if only one problem is identified or otherwise determined in 802.

Determining 808 a plurality of indicators associated with one or more problems may be helpful when the causes of the problems are not known or are not completely known. Thus, an indicator may help identify one or more potential interventions based on the relationship of the indicator to one or more problems and the relationship of the indicator to one or more potential interventions. For example, air quality within a built environment may be influenced by the type of filters used in an HVAC system, the frequency of changing such filters, the frequency of air remediation within the built environment, the location of the built environment (e.g., is it in a location that has significant external air pollution), the use of the built environment (e.g., a restaurant may have lower air quality due to the cooking of food within the restaurant, a home or office may have lower air quality if someone within the home smokes), VOCs that might be created by materials used or located within the built environment, adjacency of the built environment to a manufacturing facility or coal burning facility. Different indicators may help identify the potential source or cause of the air quality problem. For example, information from one or more external sensors may help determine that air quality within a built environment is due at least in part to the external air quality, particulates in the outside air, gases or other materials in the outside air, etc. Information from one or more internal air quality sensors may help determine that some of the particulates, gases or other materials from the outside air are making it into the interior of the built environment, are present in some portions of the built environment, etc. Information from a wearable device associated with a person may indicate that the person's breathing rate changes or that the person tends to cough when the person is in particular parts of the built environment, which may indicate that the air remediation or air quality in these parts of the built environment is not adequate. Temperature sensors within the built environment may indicate that some portions of the built environment are hotter than other portions, may be too hot or too cold for general human comfort, etc. Other sensors within the built environment may indicate that VOCs are more prominent in some portions of the built environment. In some embodiments, determining 808 one or more indicators may be optional or not conducted. In some embodiments, an indicator may be indicative of more than one problem associated with a person or a built environment. In some embodiments, determining 808 one or more indicators may be limited to or include determining one or more indicators associated with a single determined problem.

Ranking 810 a plurality of indicators may be done in different ways, such as by ranking indicators based on the strength of the known or believed relationship between an indicator and a particular problem or an impact metric or other score relation to a particular problem, the quality of the sensors or other devices used to identify the problem, the quality of a database or other information resource used to identify a problem or an indicator, the quality of scientific understanding of the problem or the relationship between the problem and the indicator, etc.

In some embodiments, indicators may be ranked by more than one factor, and different weightings may be given to different factors in such ranking. For example, an indicator having a higher causal link to a problem may be weighted higher than an indicator having a lower causal link to the problem. A reading from a higher quality sensor or wearable device may be weighted to be a higher indicator than a reading from a lower quality sensor or wearable device. A reading from a sensor located in one portion of a built environment may be weighted higher than a reading from a sensor located in a different portion of the built environment. Information from a more recently updated database of scientific or research findings may be weighted higher than information from a less frequently or less recently updated database.

Selecting 812 one of such indicators identified in 808 may be done solely or partially based on the ranking 810 of the indicators, or along with one or more other factors. In some embodiments, such selecting 812 may be optional or not used, particularly if only one indicator is identified or otherwise determined in 808.

Determining 814 one or more interventions may be or may not be based on the indicators determined in 808 or one or more of the problems identified in 802. An invention for a problem should help directly or indirectly relieve, reduce or remove the problem or the negative impacts of the problem for a person or a built environment. As previously discussed above, an intervention may be or include many things, including but not limited to the addition of, change to, or removal of many things, such as the design of a built environment, an amenity available to a person or within a built environment, an environmental control device (e.g., lighting device, air remediation or purification device) within a built environment, a policy change related to the person or the built environment, a cleaning device, process or material used within the built environment, a material or piece of furniture used within the built environment, food or water available within the built environment or to the person, etc.

As suggested above, potential interventions may be ranked in 816 based at least in part on at least one of the following: relevance to a person or a group of people, relevance to a built environment, effectiveness of at least two of the plurality of potential interventions, efficiency of at least two of the plurality of potential interventions, cost of at least two of the plurality of potential interventions, feasibility of at least two of the plurality of potential interventions, implementability of at least two of the plurality of potential interventions within a given time period, physical comfort of the person, work satisfaction of the person, at least one environmental condition in the built environment, and number of people that would be impacted by at least two of the plurality of potential interventions. As noted above, the problems can relate, for example, to a disease, disability, discomfort, dissatisfaction for the person, and/or a medical or health condition of a person.

As another example of ranking of two or more interventions, interventions may be ranked according to a number of things, such as analytical soundness, measurability, relevance, cost, feasibility, effectiveness, and relationship to each other. For example, expert consultation, scientific literature, or a database may be sought for ranking potential inventions on a scale from 1 to 5. As there may be more than one expert rating each intervention, the ranking of different experts can be averaged using the following formula:

$$x = 1/K[Xij1 + Xij2 + \ldots + XijK]$$

where, Xijs is the ranking value of an intervention j with respect to any parameter used for evaluating an intervention i by decision makers. (i=1, 2, ..., n), U=1, 2, ..., m), (s=1, 2, ..., K).

In some embodiments, ranking of interventions may be based further on cost, feasibility and effectiveness using a five point scale.

| Cost | Feasibility | Effectiveness |
|---|---|---|
| 1 - not viable | 1 - not feasible | 1 - not effective |
| 2 - very expensive | 2 - low feasibility | 2 - low effectiveness |
| 3 - neither expensive nor inexpensive | 3 - neither feasible nor infeasible | 3 - neither effective nor ineffective |
| 4 - affordable | 4 - feasible | 4 - effective |
| 5 - very affordable | 5 - highly feasible | 5 - very effective |

Cost may be an estimate of the rough order of magnitude cost of implementing the intervention. Effectiveness may be the extent to which an intervention is likely to be successful in addressing a problem on its own. Feasibility may be the extent to which an intervention is easy to implement based on the availability of vendors, materials, etc. and the expertise needed or readily available for implementing the intervention.

Ranking of an intervention may then be created by aggregating the scores of the intervention as follows:

$$II = W1 \text{Effectiveness} + W2 \text{Feasibility; or}$$

$$II = W1 \text{Effectiveness} + W2 \text{Feasibility} + W3 \text{Cost};$$

or using some other formula.
where W1, W2, W3 represent the relative weights of effectiveness, feasibility, and cost, respectively for the intervention. The mean weight of all of them then determines the intervention index (11) or score for the intervention.

Once an 11 score is calculated for each potential intervention, the 11 score may be used to prioritize or otherwise rank the identified interventions for a problem associated with a built environment, person, group of people, etc.

In some embodiments, rankings may done on intervention sets, where each intervention set includes one or more potential interventions for a problem. One or more of the interventions may be included in one or more of the intervention sets, but generally each intervention set may contain a different grouping of interventions.

Rankings of intervention sets may place different weightings on each intervention, as an arithmetic aggregation of group of interventions which assumes full compensability of the interventions and thus equal weight of each intervention, likely would be a misrepresentation of the overall strength of a intervention set.

For instance, non-implementation of some interventions may not be completely compensated by implementing other inventions. This is because the nature of the association between some of the interventions within an intervention set is expected to be synergistic, such that dropping one or more interventions from the intervention set may have a multiplier effect on the computed ranking score for the intervention set. Also, interventions within an intervention set may not expected to be preferentially independent, i.e., a given subset of the interventions may be more critical in addressing a problem as compared to a complementary set of interventions. This implies that the trade-off ratio between any two interventions may be independent of the values of the remaining interventions. To account for the lack of preferential independence between interventions in an intervention set, interventions which are synergistically more tied to each other may form separate intervention sets for a feature.

In some embodiments, interventions within an intervention set may partially or fully dependency on each other. To calculate a ranking score for these intervention sets, relative partial dependency weights may be assigned to each intervention included in the intervention set. When aggregating the individual intervention II or other scores, the substitution rates among the interventions within the bundle may be equal to the weights of the interventions up to the multiplicative coefficient. However, given the complexity of computing partial dependency between each pair of interventions, these weights may symbolize the partial dependency between each intervention and the score for the intervention set. When 11 or other scores are aggregated using these weights, a TII (Total Intervention Index) score for the intervention set can be used reflect the synergistic effect of the interventions within the intervention set, such that dropping one or more interventions from the intervention set would have a multiplier effect on the computed TII score. To account for this multiplicative effect, the intervention set score may be calculated as:

$$TIIk = Wa * IIa + Wb * IIb + Wc * IIc \ldots + Wn * IIn$$

where TIIk refers to the total intervention set index of the kth intervention set; and IIn refers to II for the nth intervention, and Wa, Wb, ... Wn are weightings.

Once the PII for an intervention set is calculated, relevancy indicators may be weighted and use to calculate the Adjusted Intervention set Index (AII) or score. The AII score may be calculated using an algorithm with equal weight assigned to both PII score and the relevancy indicators. The relevancy indicators may be contextual variables that determine the overall suitability and likelihood of success of an intervention set for a problem. There could be one or more relevancy indicators associated with every factor and the AII may change as each additional relevancy indicator is applied. In some embodiments, relevancy indicators may be broadly categorized into:

Adaptability: the ease with which an intervention set can be adapted used in a specific context, for example, the size, design, type, or expect use of a built environment, a new built environment versus renovation or an existing built environment, etc.

Compatibility: the overall prowess of an intervention set in addressing a problem.

Exposure: the extent to which an intervention set facilitates reduced exposure to a problem.

In some embodiments, only the adaptability and compatibility scores are weighted to compute the AII. The exposure indicator may be weighted at a later stage. The intervention set adaptability and compatibility scores may be determined through a combination of objective evaluation of the context and subjective expert judgement. These may be rated on a 1-5 point ordinal scale as outlined below.

| Adaptability | Compatibility |
|---|---|
| 1 - not adaptable | 1 - not compatible |
| 2 - very unadaptable | 2 - very incompatible |
| 3 - moderately adaptable | 3 - moderately compatible |
| 4 - reasonably adaptable | 4 - reasonably compatible |
| 5 - easily adaptable | 5 - very compatible |

One potential way for computing AII is:

$$AIIk = WFTIIk + WCComp + WAAdap$$

where AIIk refers to the adjusted intervention set Index for the kth intervention set; WF is the weight assigned to the total intervention set score for the kth intervention set; WC refers to the weight assigned to the compatibility score of the kth intervention set; and WA refers to the weight assigned to adaptability score of the kth intervention set.

In some embodiments after AII is calculated, a third relevancy indicator such as exposure may be used in determining an intervention set impact value (IIV). The exposure may enable a determination of the proportion of the intervention set that can be addressed as a result of direct deployment of the intervention set for addressing a problem. This is in turn may be determined by the duration of time for which one or more potential beneficiaries are exposed to the intervention set. The exposure values may be static and based on where a built environment falls on a spectrum of factor exposure distribution. For instance, a built environment may be categorized as office, residential and community projects and the exposure values may be calculated as:

Exposure Value$k$=Average hours per week exposed to $Kth$ feature/Total hours in the week In some embodiments, each problem's impact on a person or a built environment may be captured by one of the four distinct impact metrics (IM) previously discussed above.
Avoidable Burden (AvB)
Addressable burden (AbB)
Days of Comfort Lost (DCL)
Employee Satisfaction (EmSat)

In some embodiment, an assumption may be made that each independent intervention or intervention set addresses only one problem. An IIV (Intervention Impact Value) may be computed for each problem by multiplying the metric score affected by each problem by the AII and the exposure values of the intervention or intervention set. An impact of the intervention or intervention set on health and wellness of the beneficiaries of the intervention or intervention set may be computed as follows.

$$IIVki = AFIki * Expki * IMi$$

where IIVki is the Intervention Impact Value of the kth intervention or intervention set designed to address the $k^{th}$ problem; IMi is the Impact Metric of the $i^{th}$ problem; AIIki is the adjusted intervention index of the kth intervention or intervention set addressing the $i^{th}$ problem and Expk is the extent to which the kth intervention or intervention set reduces exposure to the $i^{th}$ problem.

In some embodiments, problems may be prioritized (e.g., in AvB and AdB metrics) to be addressed via intervention or intervention set application based on the amount of burden the problems contribute to, in relation to total burden, in a specific country. GBD data for the most recent available year may be used, using DALYs and YLDs as metrics of quantification to make these determinations.

In some embodiments, there may be some overlap in intervention sets across some of the problems identified or selected. These overlaps might make room for synergies between these intervention sets which shall be accounted for in an estimation of a Project Impact Index (PII). Once the IIVs have been calculated to compute PII, the following actions may be taken:

Identify one or more problems that influence the same Impact Metric (IM);

Make the intervention or intervention set selection for each problem and use a statistically accurate way to aggregate IIVs for the selected problems; and Repeat this process for each of the four IMs.

The above steps may provide us four distinct total adjusted IM scores, each measured in a different unit. The computed impact metrics can then be normalized for final aggregation to estimate the PII as a composite index.

$$PII = W_1 \text{ IM } AdB_t + W_2 \text{ IM}AvB_t + W_3 \text{IMDCL}_t + W_4 \text{IMEmSa}_t + W_5 FoC$$

where W symbolizes the weight assigned to each adjusted total impact metric.

To calculate the weight for each Impact Metric (IM), in some embodiments, a default (global) weight for each metric may be determined or established. The total metric score should sum to 100%. As one example, the AdB and AvB scores may be assigned a 50% combined weight. Employee Satisfaction and Comfort may both be set at 20%, and other problems of concern are set at 10%. The sum of YLDs and DALYs in AdB and AvB at the global level can be used to determine how to divide the 50% combined weight to each:

$$W1_g = 0.5 * AdB_g / (AdB_g + AvB_g) = 12.6\%$$

$$W2_g = 0.5 * AvB_g / (AdB_g + AvB_g) = 37.4\%$$

$$W3_g = 20\%$$

$$W4_g = 20\%$$

$$W5_g = 10\%$$

Next, relative weights for individual countries can be established.

In some embodiments, a country's relative combined value of AdB and AvB can be weighed against the global average. If the country's combined AdB and AvB is larger than the global average, interventions or intervention sets related to health may be given higher priority.

If the country's combined AdB and AvB is smaller than the global average, interventions or intervention sets related to metrics of Comfort and Satisfaction may be given a relatively higher priority. Their values for a country X may be calculated as follows:

$$W1x + 2x = 0.5 * (AdB_x + AvB\ x)/(AdBg + AvBg)$$

$$W1x = W1x + 2x * AdBx / (AdBx + AvBx)$$

$$W2x = W1x + 2x * AvB_x / (AdB_x + AvB\ x)$$

The remaining three metric categories can then be adjusted as needed. Each may expand or contract linearly to account for the change in W1x+2x as follows:

$$W3x=(1-W1x+2x)*W3g/(W3g+W4g+Wsg)$$

$$W4x=(1-W1x+2x)*W4g/(W3g+W4g+Wsg)$$

$$Wsx=(1-W1x+2x)*Wsg/(W3g+W4g+Wsg)$$

In some embodiments, a more objective and statistically astute approach may be used. For example, as a preliminary step for the computation, data diagnostics can be done to understand the functional form of each relevancy indicator for an intervention or intervention set and the associations between different relevancy indicators for an intervention or intervention set. Alternatively, correlation coefficients between proposed independent relevancy indicators for an intervention or intervention set can provide insight into the associations between the relevancy indicators. For example, if the correlation between any two relevancy indicators for an intervention or an intervention set was found to be too high (defined based on a predetermined threshold), those indicators may be combined to form one relevancy indicator. If the relevancy indicators for an intervention or an intervention set are recorded as categorical/ordinal variables, they might be transformed using the Alternating Least Squares Optimal Scaling (ALSOS) methodology. Subsequently, weights may be statistically determined via methods such as Principal Component Analysis (PCA) to determine the linear combination of criteria that captures most of the variation of the underlying data. As a result, an indicator recommendation index as below may be used:

$$IRI=61Cost+62Effectiveness+63Feasibility$$

The coefficients {31, {32 & {33 may replace the subjectively determined weights created by experts or other means and represent the relative weights of IRI constructs. The resultant IRI calculations are then be normalized and rescaled to generate scores between 0 and 100 for each intervention or intervention set.

After ranking 816 one or more potential interventions or intervention sets is completed, one or more of the potential interventions or interventions set may be selected 818 and partially or fully implemented to help remove, reduce or otherwise address one or more of the problems identified in 802 or ranked in 804.

Figure 9:
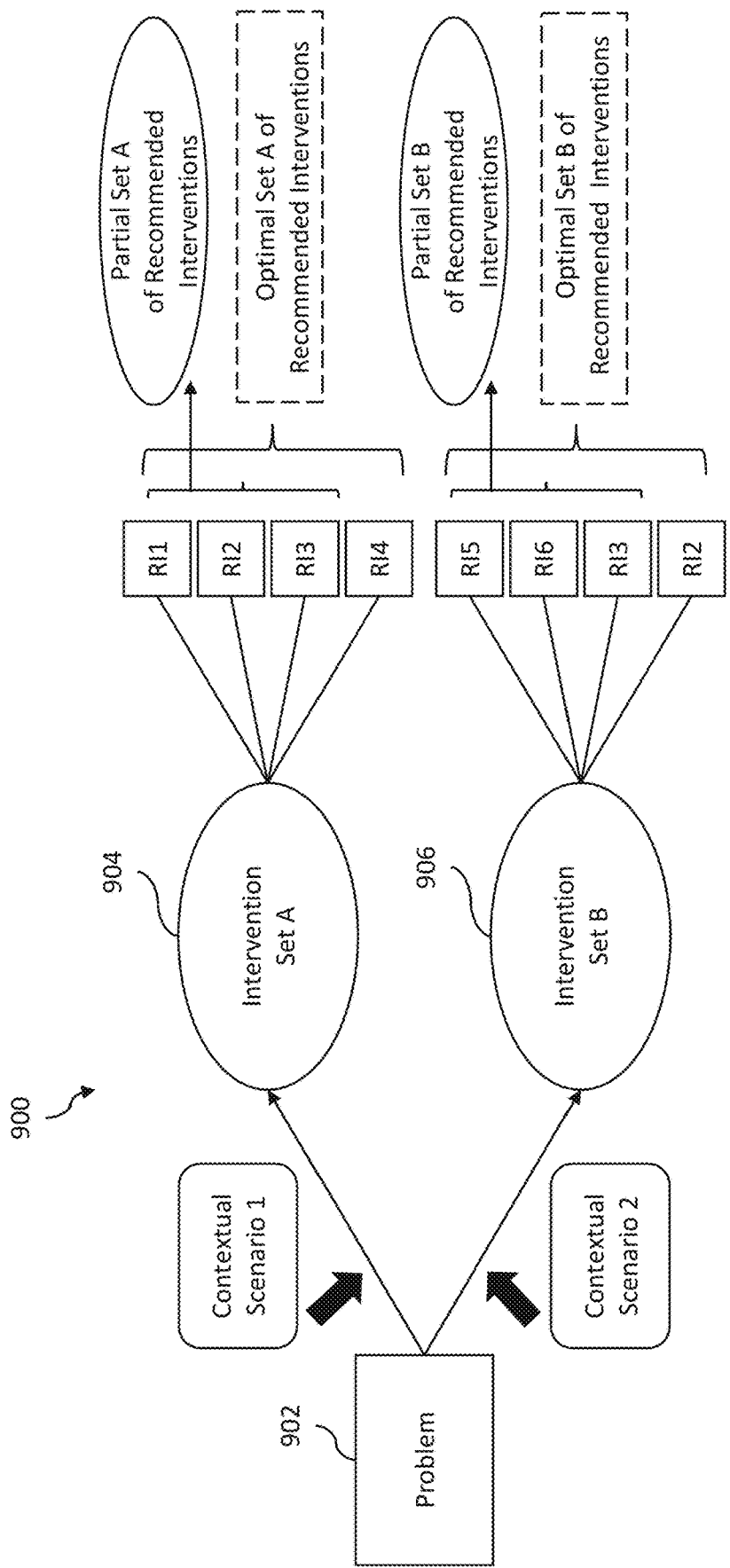
FIG. 9 is a schematic diagram in accordance with some embodiments.

Now referring to FIG. 9, a further example 900 a of problem and intervention or intervention set determination for a built environment is provided. For a problem 902, one or more interventions or intervention sets 904, 906 may be determined. The problem 902 may be or relate to the presence of particulate matter, bad or incomplete lighting, high noise or other sound levels, high temperature readings, etc., within a built environment or a portion of the built environment as determined by one or more sensors in the built environment. Other problems may be the lack of quality water, sanitation facilities, a sick leave policy, comfortable furniture, healthy snacks or other food, etc. within the built environment or a portion of the built environment. In some embodiments, problems may be measured in DALYs or other metric.

The interventions or intervention sets 904, 906 may differ in the types, scopes, complexity, feasibility, effectiveness, cost of the inventions included in them. For example, intervention set A may include recommended interventions RI1, RI2, RI3 and RI4 while intervention set B may include recommended interventions RI2, RI3, RI5 and RI6. Different recommended interventions may be the result of different contextual issues or scenarios related to the built environment. For example, risk of exposure to poor air quality or other pollution within an office is proportional to the amount of time spent in the office by a number of people. Thus, contextual scenario 1 may relate to an office wherein only two people are working an average of five hours a day while contextual scenario 2 may relate to an office wherein twenty people are working an average of ten hours a day. Other contextual differences may relate to differences in the air quality external to the built environment, as external air may be brought into the office via an HVAC system or other air handling system, thus impacting the air quality within the office. Other contextual differences may relate to the number of people who smoke in the office, the existence or non-existence of a non-smoking policy, the existence or non-existence of a dedicated smoking area, etc.

Different intervention sets 904, 906 may be measured by the intervention impact values or adjusted intervention set index as previously discussed above where the different recommended interventions RI1, RI2, RI3, RI4, RI5 and RI6 are weighted or the intervention sets 904, 906 are weighted. Weights use might be based on the different context scenarios as other factors such as effectiveness, feasibility cost and time to implement one or more of the recommended interventions RI1, RI2, RI3, RI4, RI5 and RI6 or partial subsets of the recommended interventions.

Figure 10:
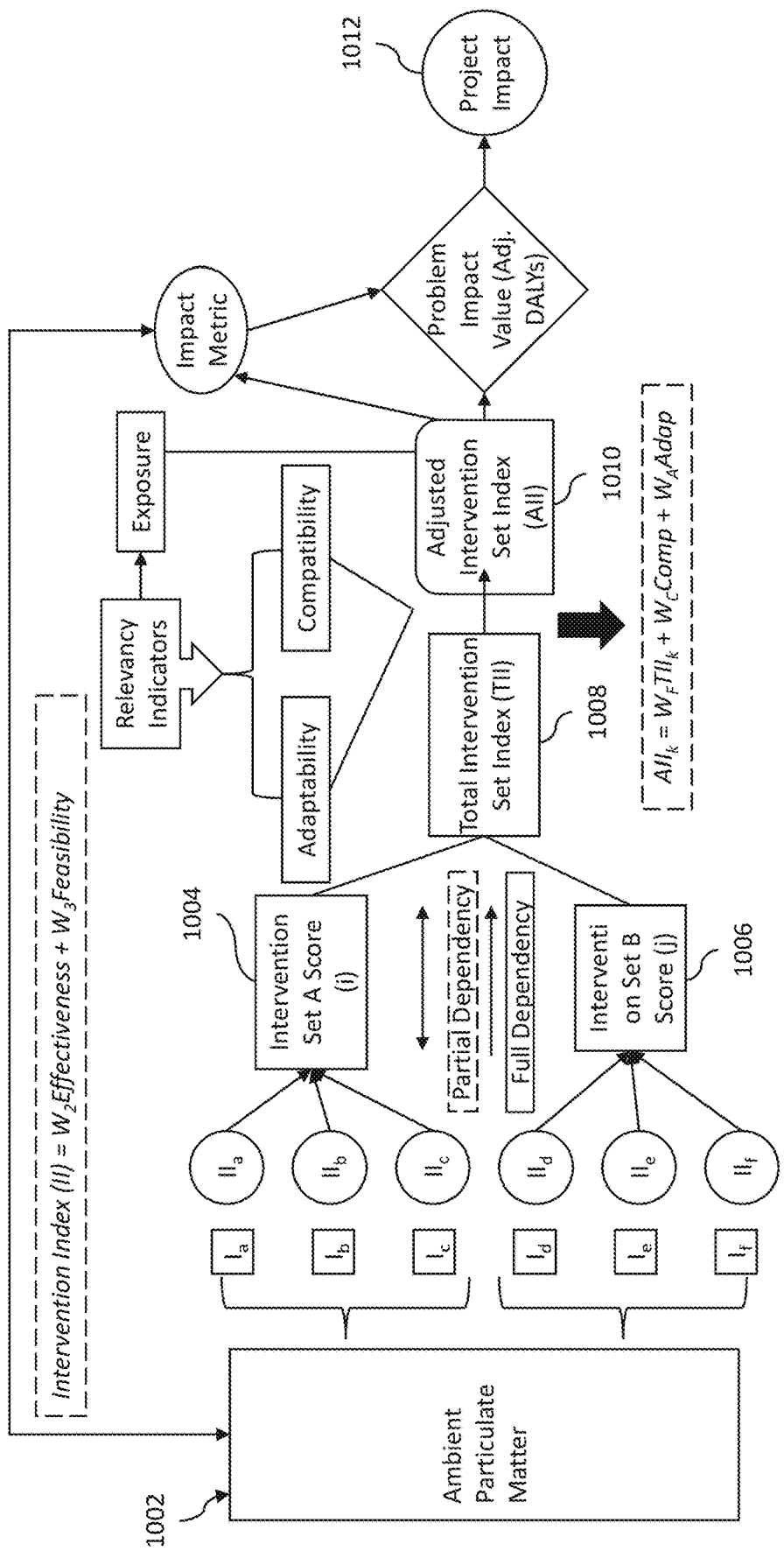
FIG. 10 is a schematic diagram in accordance with some embodiments.

Now referring to FIG. 10, a further detailed example is provided wherein a problem 1002 of ambient particulate matter in a built environment exists and potential interventions Ia, Ib, Ie, Id, Ie and If are available. Intervention indexes IIa, IIb, Iie, IId, Iie and IIf may be determined for each intervention for each of the potential interventions Ia, Ib, Ie, Id, Ie and If respectively to generate intervention set scores 1004, 1006. A total invention set index score 1008 may be computed and along with compatibility and adaptability relevancy indicators used to determine 1010 adjusted intervention set index for each potential intervention set. Impact metrics measured in DALYs may then be used to determine 1012 project impact index PII. The impact metrics may be based on the original problem 1002 of ambient particulate matter in the built environment.

Figure 11:
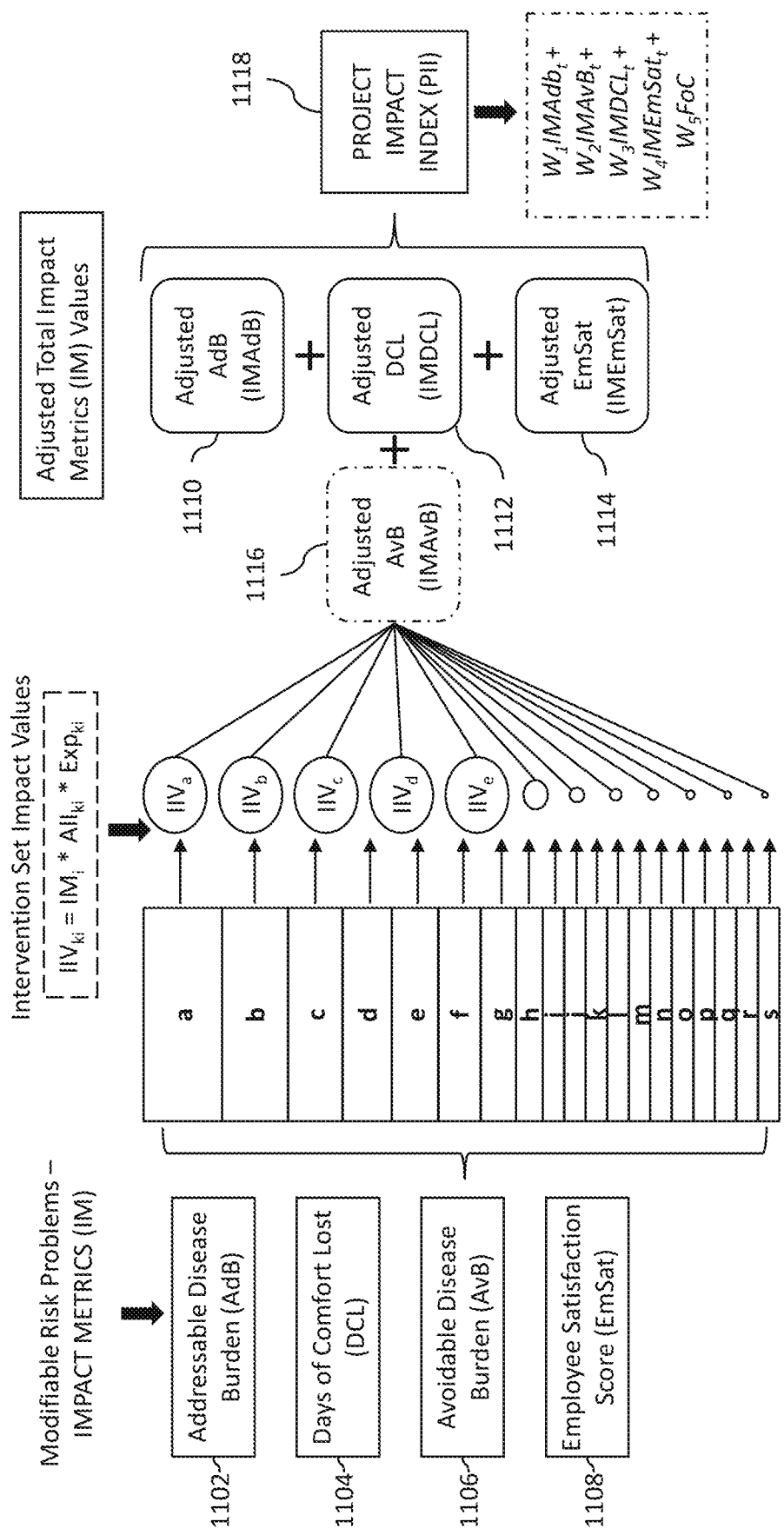
FIG. 11 is a schematic diagram in accordance with some embodiments.

Now referring to FIG. 11, a collection of impact metrics 1102, 1104, 1106, 1108 may be used to create a number of intervention sets a, b, c, d, . . . , r, s. Invention set impact values IIV may be then be determined for each of the intervention sets, which are then used with the Adjusted AdB 1110, Adjusted DCL 1112, Adjusted EmSat 1114 and Adjusted AvB 116 scores to determine project impact index 1118. The adjusted Adb, DCL, EmSat and AVB scores may result from weighting of the different scores as part of computing the project impact index (PII) score 1118.

In some configurations, a method for determining an intervention or an intervention set includes determining at least one problem associated with a built environment and determining at least one potential intervention based on the at least one problem, wherein the at least one potential intervention can reduce prevalence of the at least one problem in the built environment.

As a further example, the presence of an ambient particulate matter may be a problem associated with a built environment or a person who is associated with the built environment. Ambient particulate matter is a leading risk factor for death and disability worldwide. It is associated with multiple adverse health outcomes, including cardiovascular disease (i.e., ischemic heart disease and cerebrovascular disease), chronic obstructive pulmonary disease, lower respiratory infections, tracheal, bronchus, and lung cancer.

The GBD defines exposure to ambient particulate matter pollution as the population-weighted annual average mass concentration of particles with an aerodynamic diameter less than 2.5 micrometers (PM2.5) in a cubic meter of air. PM2.5 measurements are usually reported in μg/m 3. Data used to estimate exposure to ambient air pollution can be drawn from multiple sources, including satellite observations of aerosols in the atmosphere, ground measurements, chemical transport model simulations, population estimates and land-use data. The modelling approach used in the GBD is known as the Data Integration Model for Air Quality (DIMAQ). This approach is set within a Bayesian framework, and estimates exposure and the associated uncertainty on a high resolution grid covering the entire world.

In addition to the harmful impacts on physical health, PM2.5 also can adversely impact visibility, mood (i.e., mental health), traffic safety, construction, economy, and nature. Further economic losses can come from lost economic productivity resulting from: (1) pollution-related disease and premature death; and (2) the cost of environmental degradation. These costs often go largely unseen, because they are spread over sizable populations and many years, and may be so significant that they can distort health system spending and the growth prospects of entire countries. Fortunately, ambient air pollution often can be controlled using technical, institutional, and policy tools that have already been developed and proven effective in countries and cities around the world with varying levels of income.

If ambient particulate matter pollution is a problem associated with a built environment or a person associated with the built environment, potential inventions include the planting of more trees and the use of filters to keep the particulate matter external to the built environment from coming into the interior of the built environment. For example, particle filtration units (PFUs) for dwellings and buildings; oxidative particle filters for diesel vehicles reduce particles but produce N02, bio-mimic anti PM2.5 mask, and polyacrylonitrile (PAN) transparent air filters might be used. Electronic air cleaners and panel filters can be used in air handling units. At a personal level, a standalone air purifier also may be used. Air with a built environment might be ventilated or remediated at an increase rate or frequency to remove particulates from the air in the built environment. An electrostatic precipitator may be combined with a bag filter to facilitate hybrid particulate capture.

In ranking potential interventions to the problem of ambient particulate matter pollution, variables taken into account may include one or more of the following:

Building Level Interventions:
   Annual average ambient PM2.5 concentration
   Age distribution of the population
   Cost of ventilation filters at appropriate MERV level
   Number of ventilation filters needed
   Cost to install and maintain ventilation filters
   Cost to install and maintain the ventilation system
   Cost to build an indoor area with filtered air
   Cost of an education program related to health and air quality
   Number of persons interested in education on health and air quality
   Cost of disposable respirators
   Number of disposable respirators needed
   Cost of standalone air purifiers
   Number of standalone air purifiers needed
   Cost of entrance track-off systems
   Number of entrance track-off systems needed
   Cost of new appropriate materials
   Cost to replace existing materials with new appropriate materials
   Number of materials needing replacement with appropriate materials
   Cost of cleaning products with minimal emissions
   Number of cleaning products with minimal emissions needed
   Frequency needed to replace cleaning products
   Cost to build an appropriate storage for cleaning products
   Cost to maintain appropriate storage for cleaning products
   Cost to change building orientation, layout, and/or location
   Cost of delaying occupancy per day Personal Level Interventions:
   Age distribution of the population
   Cost to build an indoor area with filtered air
   Cost of an education program related to health and air quality
   Number of persons interested in education on health and air quality
   Cost of disposable respirators
   Number of disposable respirators needed
   Cost of standalone air purifiers
   Number of standalone air purifiers needed
   Cost to build an outdoor air quality monitoring system
   Cost to maintain an outdoor air quality monitoring system
   Cost of entrance track-off systems
   Number of entrance track-off systems needed
   Cost of new appropriate materials
   Cost to replace existing materials with new appropriate materials
   Number of materials needing replacement with appropriate materials
   Cost of cleaning products with minimal emissions
   Number of cleaning products with minimal emissions needed
   Frequency needed to replace cleaning products
   Cost to build an appropriate storage for cleaning products
   Cost to maintain appropriate storage for cleaning products
   Number of storage areas needed for cleaning products As another example of a problem associated with a built environment and a person, unsafe drinking water, sanitation and hygiene often are problems in many settings. Poor sanitation and contaminated water are also linked to transmission of diseases such as cholera, dysentery, hepatitis A, and typhoid fever.

Improving handwashing and handwashing facilities, as well as knowledge of the importance of and how to improve handwashing, often can reduce the problems associated with poor sanitation and may reduce the incidence of diarrhea. Providing soap and hygiene education, as well as implementing policies regular communication related to hygiene requirements, also may act as an intervention. The costs and benefits of the provision of soap and hygiene education for people associated with a built environment, which may be used in the ranking of interventions, may vary depending on the number of people impacted, the ages of the people, the number of training sessions and trainers needed, the cost of providing different cleaning agents and the amounts thereof, the cost of equipment needed as well as the cost of its installation and maintenance, the cost of available water sources, the cost of creating clean water for washing, etc.

Unsafe sanitation associated with the built environment may result from the toilet types used at the built environment, the quality of sewer connections and water used in such toilets, etc. Interventions may include improving the sanitation facilities, improving the water supply to the facilities, increasing the number of toilets, making sure toilet paper is available, increasing the number of private toilets, etc. The costs and benefits associated with these interventions, which may be used in the ranking of the interventions may be based on many factors, such as the number of people the built environment is serving, the ages of the people, the cost of providing toilet paper and soap, the cost of new or replacement toilets, the cost of staffs needed to keep the sanitation facilities clean and usable, the cost of water, etc.

Improving water quality for a built environment might include improving water quality at the source of the water via chlorination, biosand, ceramic and other filters, etc., while improving the quality of the water at the point-of-use may include using chlorination, flocculation, filtration, solar disinfection, etc. The cost of such interventions may depend on many factors, such as the cost of disinfectants, filters, water transportation, water containers, coagulants, etc. as well as the amount of water used and the contaminants targeted for removal.

As a further example of a problem that may be associated with a person associated with a built environment, one or more people occupying the built environment may suffer from lower back pain in one or both lower limbs. Mild lower back pain may be described as a person who has some difficulty dressing, standing, and lifting things due to the back pain. Moderate back pain may be described as a person who has difficultly dressing, sitting, standing, walking and lifting things due to the back pain. Severe lower back pain without leg pain may be described as a person who has difficulty dressing, sitting, standing, walking and lifting things and often sleeps poorly and is worried. Severe lower back pain also may create less enjoyment in life.

Potential interventions to help a person address their lower back pain may include providing a heat wrap, facilitating acupuncture or massage treatment, providing yoga or tai chi classes, providing mindfulness and stress reduction amenities, providing furniture that may reduce the lower back pain, providing a modified work schedule or policy, etc. The interventions may be ranked on many variables, such as the number of people associated with the built environment that need or want the intervention, the cost per intervention, the average time an item related to an invention lasts, the severity of the lower back pain, the frequency at which treatments or classes are provided, the cost of accommodating a modified work schedule, etc.

As a further example of a problem that may be associated with a person associate with a built environment, one or more people who work in an office may suffer from migraines, a class of often disabling headache disorders characterized by recurrent unilateral pulsatile headaches. Potential interventions that may relate to reducing the occurrence of such migraines include making accommodations to limit light triggered migraines (e.g., removing or disabling overhead fluorescent lighting), making accommodations for noise triggered migraines (e.g., moving an employee to a low traffic area, providing noise cancelling headphones), making accommodations for a smell or fragrance triggered migraine (e.g., moving an employee to an area where fragrances are not as strong, reducing the fragrances worn by other employees), providing a dark secluded room for use by an employee when experiencing a migraine, providing a flexible leave or remote working policy for employees that suffer from migraines, etc.

Interventions related to the problem of migraines can be ranked on many variables, such as the number of people impacted, the number and severity of migraines among affected employees, the cost of alternative lamps and other workspace accommodations, the cost of or time needed for building a dedicated dark room, the cost of or time needed to implement a flexible work policy, etc.

As another example, a problem associated with a built environment may involve injuries related to falls in which a person comes to rest involuntarily on the ground, a floor or other lower level. Falls and fall-related injuries, although usually nonfatal, still represent a significant health and safety issue for people of all ages. A wide range of injuries can result from a fall, depending on the height and setting of the fall, and the age, gender and fitness of the individual experiencing the fall. Injuries may be to the neck, nose, eyes, head, thorax, abdomen, lower back, lumbar spine, pelvis, shoulder and upper arm, elbow and forearm, wrist, hands, fingers, feet, legs, toes, ankle, etc.

Interventions related to reducing the problems of falls include many things, such as improving the lighting, adding more handrails to stairs or to both sides of the stairs, providing passenger loading and unloading zones, changing heights of gates and railings along walkways and decks, reducing the incline of slopes or ramps that people walk on, adding grab bars in rest rooms, increasing the fitness level of people to help reduce the occurrence of falls, reducing the slipperiness of floors, reducing access to areas where falls are more likely to occur, increasing safety training to employees working in areas where falls are more likely to occur, etc.

As another example, assume that an office is located in Beijing China, and that the owners or operations are dealing with the following limitations and problems: poor air quality, low physical activity of employees in the office, poor lighting conditions in the office, and a total budget to address these problems of $10,000.

Examining the health loss rankings (using DALY values) due to modifiable risk factors and existing illnesses at a national level for this office shows that ambient particulate matter pollution is the leading environmental risk factor for health associated with 1,623 DALYs per 100,000 individuals in 2016. Physical activity of the employees is less important, and poor lighting is not associated with health outcomes in the database used. Surveying the employees might provide further information to rank perceived problems and to better weigh the problem of poor air quality (a scale could be used to rank them among the other problems) and determine whether it is a problem that should be addressed first. In this example, a survey essentially serves as a validation method. Other factors that may be taken into consideration when ranking the problems are: cost (cost of installation of an intervention to address the problem, maintenance fees), time needed to install the intervention, and perceived value of the intervention. A problem ranking score might be created by the following:

Problem ranking score=health outcome*$X1$ +cost*$X2$ +satisfaction*$X3$ where X1, X2 and N are the weights of the different outcomes, which may be determined by a survey of the occupants, the employer, the owner of the building space, government regulations, or another way. Indicators used to assess air quality in the office can include measurements of: PM2.5, PM10, CO2, and TVOC. PM2.5 might be selected due to greater health outcomes associated with its exposure, and it is a less expensive method of monitoring compared to the other indicators. A ranking score for the indicators may be determined by the following:

Indicator ranking score=health outcome*$Y1$ +cost*$Y2$ +satisfaction*$Y3$ where Y1, Y2 and y3 are the weights associated with the different indicator sub-elements.

For problems associated with the presence of PM2.5, interventions may include

In-duct filtration: often more expensive and harder to install and maintain but it looks better aesthetically, is better integrated into the whole building infrastructure, and is more efficient at removing PM2.s.

Stand-alone filtration: often less effective and cheaper, but often looks poorer aesthetically.

Increased ventilation rate: often less effective, cheaper, and higher energy costs.

Tightened envelope for the built environment: often the most effective intervention, but may cost a lot if a building containing the built environment is old.

Based on these factors related to the interventions and the budget of $10,000, the interventions may be ranked on effectiveness, cost, time to implementation, feasibility, etc. Alternatively, an intervention ranking score may be computed as follows:

Intervention ranking score=health outcome*$Z1$ +cost*$Z2$ +satisfaction*$Z3$ where Z1, Z2 and Z3 are the weights of the different intervention sub-elements.

In one illustrative approach, a method of operation in a system (which includes at least one processor, at least one non-transitory processor-readable medium communicatively coupled to the at least one processor and which stores at least one of instructions or data executable by the at least one processor) includes determining at least one problem associated with a built environment and determining at least one potential intervention based on the at least one problem, wherein the at least one potential intervention can reduce prevalence of the at least one problem in the built environment.

In another illustrative approach, a method of operation in a system (which includes at least one processor, at least one non-transitory processor-readable medium communicatively coupled to the at least one processor and which stores at least one of instructions or data executable by the at least one processor) includes determining at least one problem associated with a built environment, determining at least one indicator associated with the at least one problem, and determining at least one potential intervention based on the at least one indicator, wherein the at least one potential intervention can reduce prevalence of the at least one problem in the built environment.

In yet another illustrative approach, a method of operation in a system (which includes at least one processor, at least one non-transitory processor-readable medium communicatively coupled to the at least one processor and which stores at least one of instructions or data executable by the at least one processor) includes determining at least one problem associated with a person, determining at least one indicator associated with the at least one problem, and determining at least one potential intervention based on the at least one indicator, wherein the at least one potential intervention can reduce prevalence of the at least one problem for the person.

In one embodiment, a method for determining an intervention or an intervention set includes determining at least one problem associated with a person, determining at least one indicator associated with the at least one problem, and determining at least one potential intervention based on the at least one indicator, wherein the at least one potential intervention can reduce prevalence of the at least one problem for the person. Further, the method may determine a built environment associated with the person, such as having an association as a result of at least one of the following: working in the built environment, living in the built environment, visiting the built environment, being in the built environment, entering the built environment, and leaving the built environment. In such a configuration, the method also may customize the at least one potential intervention for the built environment or the persons involved. By one approach, the problem and/or the potential intervention relates to at least one of: a policy associated with the built environment or an environmental condition associated with the built environment. As suggested above, potential interventions may be ranked based at least in part on at least one of the following: relevance to the person, relevance to the built environment, effectiveness of at least two of the plurality of potential interventions, efficiency of at least two of the plurality of potential interventions, cost of at least two of the plurality of potential interventions, feasibility of at least two of the plurality of potential interventions, implementability of at least two of the plurality of potential interventions within a given time period, physical comfort of the person, work satisfaction of the person, at least one environmental condition in the built environment, and number of people that would be impacted by at least two of the plurality of potential interventions. As noted above, the problems can relate, for example, to a disease, disability, discomfort, dissatisfaction for the person, and/or a medical or health condition of a person.

In some embodiments, the systems and methods may send a signal or otherwise communicate at least one potential intervention to a person, receive a signal regarding an intervention selection, and implementing the at least one potential intervention. To assist with selection, the system and methods herein may rank potential interventions based at least in part on at least one of the following: disability adjusted life years, years lived with disability, days of comfort lost, and amenity satisfaction. In such a configuration, the system and method may determine a state of the person's health at a first time and at a second time, wherein the second time is after the first time and after an intervention has been implemented in a built environment associated with the person. By one approach, the method measures or determines a difference of the person's health from the first time to the second time, such as, for example, a state of the person's comfort at a first time and a state of the person's comfort at a second time after which an intervention has been implemented in a built environment. This also may be applied to a state of a person's amenity satisfaction. Further, these teachings may be applied to a group of people associated with a built environment. Further, the data may be obtained from accessing data received from devices or sensors associated with or worn by individuals of the group. The sensors may include, for example, a biometric sensor, temperature sensor operable to detect a temperature of the person, a scale operable to detect a weight of the person, a heart rate sensor operable to detect a heart rate of the person, a blood oxygen sensor operable to detect a level of blood oxygen of the person, a respiratory cycle sensor operable to detect at least one characteristic of a respiratory cycle of the person, and an electroencephalography sensor operable to detect at least one brainwave pattern of the person, and/or a sensor capable of collecting wellness data from the person, among others. In other configurations, the sensor includes at least one of: an air quality sensor, a temperature sensor, a humidity sensor to detect at least one air quality parameter, an audio transducer to detect ambient sound levels, a motion detector, and a light sensor to detect at least one of a light level or a color index of light.

By one approach, a method for determining an intervention includes determining at least one problem associated with a person and determining at least one potential intervention based on the at least one problem, wherein the at least one potential intervention can reduce prevalence of the at least one problem for the person.

By another approach, a method for determining an intervention includes determining a plurality of problems associated with a person, ranking the plurality of problems, selecting one of the plurality of problems based at least in part on the ranking, determining a plurality of indicators associated with the one of the plurality of problems, ranking the plurality of indicators, selecting one of the plurality of indicators based at least in part on the ranking, determining a plurality of potential interventions based on the one of the plurality of indicators, wherein each of the at plurality of potential interventions can reduce prevalence of the at least one problem for the person, ranking the plurality of potential interventions, and selecting at least one of the plurality of potential interventions based at least in part on the ranking of the plurality of potential interventions.

In some configurations, a method of operation in a system (which includes at least one processor, at least one non-transitory processor-readable medium communicatively coupled to the at least one processor and which stores at least one of instructions or data executable by the at least one processor) includes determining at least one problem associated with a person, determining at least one indicator associated with the at least one problem, and determining at least one potential intervention based on the at least one indicator, wherein the at least one potential intervention can reduce prevalence of the at least one problem for the person.

In one illustrative system, a processor and a non-transitory processor-readable medium communicatively coupled to the at least one processor execute instructions for determining at least one problem associated with a built environment, determining at least one indicator associated with the at least one problem, and determining at least one potential intervention based on the at least one indicator, wherein the at least one potential intervention can reduce prevalence of the at least one problem in the built environment. In some configurations, the system includes a storage subsystem, wherein the storage subsystem includes data regarding at least one of the following: information regarding the built environment, information regarding a plurality of built environments, information regarding at least one policy associated with the built environment, information regarding at least one regulation associated with the built environment, information regarding at least one environmental condition for the built environment, a plurality of indicators, a plurality of indicators associated with the at least one problem, a plurality of interventions, a plurality of interventions associated with the built environment, a plurality of problems associated with at least one built environment, a plurality of problems associated with the built environment, a plurality of indicators associated with a least one problem associated with the built environment, a plurality of interventions associated with at least one problem associated with the built environment, information regarding at least one person associated with the built environment, information provided by a device associated with at least one person associated with the built environment, information regarding at least one sensor associated with the built environment, and information from at least one sensor associated with the built environment. In other configurations, a storage subsystem includes data regarding at least one of the following location of the built environment, availability of water in the built environment, availability of at least one beverage in the built environment, availability of food in the built environment, availability of healthy food in the built environment, availability of exercise equipment in the built environment, availability of medical equipment in the built environment, a climate condition for the built environment, an environmental condition within the built environment, a desired environmental condition within the built environment, quality of the built environment, design of the built environment, a current policy associated with the built environment, a desired policy for the built environment, an amenity available at the built environment, a desired amenity for the built environment, age of the built environment, an owner of the built environment, an occupier of the built environment, a desired occupant of the built environment, a current feature of the built environment, a desired feature of the built environment, design of the built environment, a current use of the built environment, an expected use of the built environment, a desired use of the built environment, a goal of a current owner of the built environment, a goal of a current manager of the built environment, a goal of a current occupier of the built environment, a goal of an expected occupier of the built environment, and a regulation that may apply to the built environment.

In one illustrative approach, the system including at least one processor, at least one non-transitory processor-readable medium communicatively coupled to the at least one processor and which stores at least one of instructions or data executable by the at least one processor for implementing a method, the method including determining at least one problem associated with a built environment and determining at least one potential intervention associated with the at least one problem, wherein the at least one potential intervention can reduce prevalence of the at least one problem in the built environment.

In another illustrative approach, a system including at least one processor, at least one non-transitory processor-readable medium communicatively coupled to the at least one processor and which stores at least one of instructions or data executable by the at least one processor for implementing a method, the method including, for example, determining at least one problem associated with a person, determining at least one indicator associated with the at least one problem, and determining at least one potential intervention based on the at least one indicator, wherein the at least one potential intervention can reduce prevalence of the at least one problem for the person. The system also may include a storage subsystem, wherein the storage subsystem includes data such as, for example, an age of a person, average age of a group of people that includes the person, average age of a group of people that includes the person and is associated with a built environment, age distribution of a group of people that includes the person, age distribution of a group of people that includes the person and is associated with a built environment, a characteristic of a group of people that includes the person, a characteristic of a group of people that includes the at person and is associated with a built environment, occupation of the person, employer of the person, employment status of the person, employment history of the person, location of the person, a goal of the person, current health of the person, future travel plan of the person, travel history of the person, medical history of the person, marital status of the person, marital history of the person, family size of the person, family history of the person, schedule of the person, gender of the person, gender ratio of a group of people that includes the person, gender ratio of a group of people that includes the person and is associated with a built environment, race of the person, education level of the person, average education level of a group of people that includes the person, nationality of the person, a personal need of the person, a desired characteristic of the person, a desired characteristic of a group of people that includes the person, a desired characteristic of a group of people that includes the at least one person and is associated with a built environment, a health condition of the person, a health assessment of a group of people that includes the person, a health assessment of a group of people that includes the person and is associated with the built environment, and a health assessment of the person.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

We claim:

1. A method for determining an intervention, comprising the steps of:
   receiving, at a server computing device measurements from a plurality of sensors in an environmentally-controllable built environment that includes an occupied space;
   receiving, at the server computing device, measurements from a wearable sensor associated with an occupant of the environmentally-controllable built environment;
   comparing, via the server computing device, the measurements received with target operational parameters from an operational database associated with the environmentally-controllable built environment and personal target parameters from an occupant database associated with the wearable sensor associated with the occupant;
   identifying a plurality of problems associated with the environmentally-controllable built environment;
   ranking the plurality of problems;
   wherein the ranking of the plurality of problems is based at least in part on avoidable burden, addressable burden, days of comfort lost, or employee satisfaction associated with the plurality of problems and is further based at least in part on a potential interventions' ability to change avoidable burden, addressable burden, days of comfort lost, or employee satisfaction associated with each of the plurality of problems;
   selecting one of the plurality of problems based at least in part on the ranking of the plurality of problems;
   determining a plurality of indicators associated with the one of the plurality of problems;
   ranking the plurality of indicators;
   selecting one of the plurality of indicators based at least in part on the ranking of the plurality of indicators;
   determining a plurality of potential interventions for the environmentally-controllable built environment based on the one of the plurality of indicators, wherein each of the plurality of potential interventions can reduce prevalence of the one of the plurality of problems with the environmentally-controllable built environment;
   ranking the plurality of potential interventions based, at least in part, on at least one of feasibility, implementability, time required for implementation, effectiveness, or an impact on at least one person;
   selecting at least one of the plurality of potential interventions based at least in part on the ranking of the plurality of potential interventions; and
   sending a signal to implement the at least one of the plurality of potential interventions to perform a control action in the environmentally-controllable built environment, the control action including at least one of adjusting at least one lighting level, ambient temperature level, or air quality level.

2. The method of claim 1, further comprising implementing at least one of the plurality of potential interventions in the environmentally-controllable built environment, wherein the step of implementing at least one of the plurality of potential interventions in the environmentally-controllable built environment includes changing an environmental condition in at least a portion of the environmentally-controllable built environment.

3. The method of claim 1 further comprising:
   determining that multiple occupants are in a single zone of the environmentally-controllable built environment;
   upon detection of the multiple occupants in the single zone, determining whether the personal target parameters overlap; and
   upon detection of conflicting personal target parameters of the multiple occupants in the single zone, analyze a ranking of the multiple occupants, the associated personal target building parameters, and an occupant status.

4. The method of claim 1 further comprising:
   upon detection of either the received measurements being outside of the target operational parameters or the personal target parameters, determining a location of the occupant within the environmentally-controllable built environment; and
   instructing a built environmental control system to adjust at least one of lighting levels, temperature levels, or air quality levels proximate the location of the occupant within the environmentally-controllable built environment to fall within the target operational parameter and the personal target parameters, wherein the target operational parameters are established in order to address at least one of the following for the occupied space: avoidable burden; addressable burden; days of comfort lost; or employee satisfaction.

5. The method of claim 1, wherein the plurality of sensors in the environmentally-controllable built environment includes at least one light sensor to detect at least one of a light level or a color index of light.

6. The method of claim 5, wherein the at least one of the plurality of potential interventions includes the addition of, change to, or removal of a lighting device within the environmentally-controllable built environment.

7. The method of claim 5, wherein the at least one of the plurality of potential interventions includes changing an electrical lighting setting of a light source, changing electrochromatic glass of a window, or changing a window shade of a window proximate the occupant.

8. The method of claim 5, wherein at least one of the plurality of problems relates to incomplete or poor lighting as determined by the at least one light sensor.

9. The method of claim 1, wherein the plurality of sensors in the environmentally-controllable built environment includes at least one of an air quality sensor, a temperature sensor, or a humidity sensor to detect at least one air quality parameter.

10. The method of claim 9, wherein the at least one of the plurality of potential interventions includes the addition of, change to, or removal of an air remediation device or an air purification device within the environmentally-controllable built environment.

11. The method of claim 9, wherein the at least one of the plurality of potential interventions includes changing a temperature setting or an air flow setting of a heating, ventilation, and air conditioning system.

12. The method of claim 9, wherein at least one of the plurality of problems relates to the presence of particulate matter or poor air quality as determined by the air quality sensor or high temperature as determined by the temperature sensor.

13. A smart building system comprising:
- a plurality of sensors in a built environment that includes an occupied space;
- at least one wearable sensor associated with an occupant of the built environment;
- an operational database associated with the built environment;
- an occupant database associated with the at least one wearable sensor associated with the occupant; and
- a server computing device, the server computing device in communication with the plurality of sensors, the at least one wearable sensor, the operational database, and the occupant database, the server computing device configured to:
  - receive measurements from the plurality of sensors in the built environment;
  - receive measurements from the at least one wearable sensor;
  - compare the measurements received with target operational parameters from the operational database and personal target parameters from the occupant database;
  - identify a plurality of problems associated with the built environment;
  - rank the plurality of problems;
  - wherein the ranking of the plurality of problems is based at least in part on avoidable burden, addressable burden, days of comfort lost, or employee satisfaction associated with the plurality of problems and is further based at least in part on a potential interventions' ability to change avoidable burden, addressable burden, days of comfort lost, or employee satisfaction associated with each of the plurality of problems;
  - select one of the plurality of problems based at least in part on the ranking of the plurality of problems;
  - determine a plurality of indicators associated with the one of the plurality of problems;
  - rank the plurality of indicators;
  - select one of the plurality of indicators based at least in part on the ranking of the plurality of indicators;
  - determine a plurality of potential interventions for the built environment based on the one of the plurality of indicators, wherein each of the plurality of potential interventions can reduce prevalence of the at least one problem with the built environment;
  - rank the plurality of potential interventions based, at least in part, on at least one of feasibility, implementability, time required for implementation, effectiveness, or an impact on at least one person;
  - select at least one of the plurality of potential interventions based at least in part on the ranking of the plurality of potential interventions; and
  - send a signal to implement the at least one of the plurality of potential interventions to perform a control action in the built environment, the control action including at least one of adjusting at least one lighting level, ambient temperature level, or air quality level.

14. The smart building system of claim 13, wherein the server computing device is further configured to implement at least one of the plurality of potential interventions in the built environment, wherein implementing at least one of the plurality of potential interventions in the built environment includes changing an environmental condition in at least a portion of the built environment.

15. The smart building system of claim 13, wherein the server computing device is further configured to:
- determine that multiple occupants are in a single zone of the built environment;
- upon detection of the multiple occupants in the single zone, determine whether the personal target parameters overlap; and
- upon detection of conflicting personal target parameters of the multiple occupants in the single zone, analyze a ranking of the occupants, the associated personal target building parameters, and an occupant status.

16. The smart building system of claim 13, wherein the server computing device is further configured to:
- upon detection of either the received measurements being outside of the target operational parameters or the personal target parameters, determine a location of the occupant within the built environment; and
- instruct a built environmental control system to adjust at least one of lighting levels, temperature levels, or air quality levels proximate the location of the occupant within the built environment to fall within the target operational parameter and the personal target parameters, wherein the target operational parameters are established in order to address at least one of the following for the occupied space: avoidable burden; addressable burden; days of comfort lost; or employee satisfaction.

* * * * *